United States Patent
Colloca

(10) Patent No.: US 11,859,199 B2
(45) Date of Patent: *Jan. 2, 2024

(54) ADENOVIRAL VECTORS WITH TWO EXPRESSION CASSETTES ENCODING RSV ANTIGENIC PROTEINS OR FRAGMENTS THEREOF

(71) Applicant: GLAXOSMITHKLINE BIOLOGICALS SA, Rixensart (BE)

(72) Inventor: Stefano Colloca, Rome (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 563 days.

This patent is subject to a terminal disclaimer.

(21) Appl. No.: 16/756,380

(22) PCT Filed: Oct. 16, 2018

(86) PCT No.: PCT/EP2018/078212
§ 371 (c)(1),
(2) Date: Apr. 15, 2020

(87) PCT Pub. No.: WO2019/076882
PCT Pub. Date: Apr. 25, 2019

(65) Prior Publication Data
US 2021/0189422 A1 Jun. 24, 2021

Related U.S. Application Data

(60) Provisional application No. 62/572,951, filed on Oct. 16, 2017.

(51) Int. Cl.
*C12N 15/00* (2006.01)
*C12N 15/86* (2006.01)
*A61K 39/235* (2006.01)

(52) U.S. Cl.
CPC ............ *C12N 15/86* (2013.01); *A61K 39/235* (2013.01); *C12N 2710/10343* (2013.01); *C12N 2710/16121* (2013.01); *C12N 2830/48* (2013.01)

(58) Field of Classification Search
None
See application file for complete search history.

(56) References Cited

U.S. PATENT DOCUMENTS

2010/0143304 A1* 6/2010 Lowenstein ............. C12N 7/00
435/456

FOREIGN PATENT DOCUMENTS

| JP | 2017-523139 A | 8/2017 |
|----|---------------|--------|
| WO | WO 2006/106002 A2 | 11/2005 |

(Continued)

OTHER PUBLICATIONS

Jin et al., "Identification of Novel Insertion Sites in the Ad5 Genome That Utilize the Ad Splicing Machinery for Therapeutic Gene Expression," Molecular Therapy, vol. 12, No. 6: 1052-1063 (Year: 2005).*

(Continued)

*Primary Examiner* — M Franco G Salvoza
(74) *Attorney, Agent, or Firm* — Birch, Stewart, Kolasch & Birch, LLP

(57) ABSTRACT

An adenoviral vector comprising two expression cassettes, wherein each expression cassette comprises a transgene and a promoter, and wherein each transgene encodes an RSV antigenic protein or a fragment thereof.

18 Claims, 25 Drawing Sheets

Specification includes a Sequence Listing.

(i)

(ii)

(iii)

(56) References Cited

FOREIGN PATENT DOCUMENTS

| WO | 2010086189 A2 | 8/2010 | |
|---|---|---|---|
| WO | 2012021730 A2 | 2/2012 | |
| WO | 2012089833 A2 | 7/2012 | |
| WO | WO-2015189425 A1 * | 12/2015 | ............ A61K 39/12 |
| WO | 2017017049 A1 | 2/2017 | |

OTHER PUBLICATIONS

International Search Report and Written Opinion for corresponding International Application No. PCT/EP2018/078212, dated Dec. 5, 2018 (17 pages).
Pierantoni et al., "Mucosal delivery of a vectored RSV vaccine is safe and elicits . . . ", Molecular Therapy—Methods & Clinical Develop, Jan. 2015, p. 2329-0501, vol. 2.
Li et al., "Modified recombinant adenoviruses increase porcine circovirus 2 capsid protein expression . . . ", Acta Virologica, 2016, p. 271-280, vol. 60, No. 03.
Small et al., "Construction and characterization of E1- and E3—deleted adenovirus vectors . . . ", Human Gene Therapy, 2014, p. 328-338, vol. 25, No. 4.
Anurag et al., "Maternal immunization with chimpanzee adenovirus expressing RSV fusion protein . . . ", Vaccine, Aug. 2014, p. 5761-5768, vol. 32, No. 43.
U.S. Appl. No. 16/756,377, filed Apr. 15, 2020.
International Search Report and Written Opinion for corresponding International Application No. PCT/EP2018/078210, dated Nov. 28, 2018 (15 pages).

* cited by examiner (i)

(ii)

(iii)

(a)

(b)

(c)

SEQUENCE LISTING

<160> NUMBER OF SEQ ID NOS: 12

<210> SEQ ID NO 1
<211> LENGTH: 37830
<212> TYPE: DNA
<213> ORGANISM: Chimpanzee adenovirus

```
<400> SEQUENCE: 1
catcatcaat aatatacctt attttggatt gaagccaata tgataatgag atgggcggcg      60
cggggcggga ggcgggtccg ggggcgggcc ggcgggcggg gcggtgtggc ggaagtggac     120
tttgtaagtg tggcggatgt gacttgctag tgccgggcgc ggtaaaagtg acgttttccg     180
tgcgcgacaa cgcccacggg aagtgacatt tttcccgcgg ttttttaccgg atgttgtagt    240 gaatttgggc gtaaccaagt aagatttggc cattttcgcg ggaaaactga acgggggaag    300
tgaaatctga ttaatttcgc gttagtcata ccgcgtaata tttgtcgagg gccgagggac     360
tttggccgat tacgtggagg actcgcccag gtgttttttg aggtgaattt ccgcgttccg     420
ggtcaaagtc tccgttttat tattatagtc agctgacgcg gagtgtattt ataccctctg     480
atctcgtcaa gtggccactc ttgagtgcca gcgagtagag ttttctcctc tgccgctctc     540
cgctccgctc cgctcggctc tgacaccggg gaaaaaatga gacatttcac ctacgatggc     600
ggtgtgctca ccggccagct ggctgctgaa gtcctggaca ccctgatcga ggaggtattg     660
gccgataatt atcctccctc gactccttttt gagccaccta cacttcacga actctacgat    720
ctggatgtgg tggggcccag cgatccgaac gagcaggcgg tttccagttt ttttccagag    780
tccatgttgt tggccagcca ggaggggtc gaacttgaga cccctcctcc gatcgtggat      840
tcccccgatc cgccgcagct gactaggcag cccgagcgct gtgcgggacc tgagactatg    900
ccccagctgc tacctgaggt gatcgatctc acctgtaatg agtctggttt tccacccagc     960
gaggatgagg acgaagaggg tgagcagttt gtgttagatt ctgtggaaca acccgggcga    1020
ggatgcaggt cttgtcaata tcaccggaaa aacacaggag actcccagat tatgtgttct    1080
ctgtgttata tgaagatgac ctgtatgttt atttacagta agtttatcat ctgtgggcag    1140
gtgggctata gtgtgggtgg tggtcttttgg ggggtttttt aatatatgtc aggggttatg   1200
ctgaagactt ttttattgtg attttttaaag gtccagtgtc tgagcccgag caagaacctg   1260
aaccggagcc tgagccttct cgccccagga gaaagcctgt aatcttaact agacccagcg    1320
caccggtagc gagaggcctc agcagcgcgg agaccaccga ctccggtgct tcctcatcac    1380 cccggagat tcacccccctg gtgccccctgt gtcccgttaa gcccgttgcc gtgagagtca   1440
gtgggcggcg gtctgctgtg gagtgcattg aggacttgct ttttgattca caggaacctt    1500
tggacttgag cttgaaacgc cccaggcatt aaacctggtc acctgactg aatgagttga    1560 cgcctatgtt tgcttttgaa tgacttaatg tgtatagata ataaagagtg agataatgtt   1620
ttaattgcat ggtgtgttta acttgggcgg agtctgctgg gtatataagc ttccctgggc    1680
taaacttggt tacacttgac ctcatggagg cctgggagtg tttggagaac tttgccggag    1740
ttcgtgcctt gctggacgag agctctaaca atacctcttg gtggtggagg tatttgtggg    1800
gctctcccca gggcaagtta gtttgtagaa tcaaggagga ttacaagtgg gaatttgaag    1860
agcttttgaa atcctgtggt gagctattgg attctttgaa tctaggccac caggctctct    1920
tccaggagaa ggtcatcagg actttggatt ttttccacacc ggggcgcatt gcagccgcgg   1980 ttgctttttct agcttttttg aaggatagat ggagcgaaga gacccacttg agttcgggct    2040
acgtcctgga ttttctggcc atgcaactgt ggagagcatg atcagacac aagaacaggc    2100 tgcaactgtt gtcttccgtc cgcccgttgc tgattccggc ggaggagcaa caggccgggt    2160
cagaggaccg ggcccgtcgg gatcggagg agagggcacc gaggccgggc gagaggagcg    2220
cgctgaacct gggaaccggg ctgagcggcc atccacatcg ggagtgaatg tcgggcaggt    2280
ggtggatctt tttccagaac tgcggcggat tttgactatt agggaggatg ggcaatttgt    2340
```

```
taagggtctt aagagggaga gggggcttc tgagcataac gaggaggcca gtaatttagc    2400
ttttagcttg atgaccagac accgtccaga gtgcatcact tttcagcaga ttaaggacaa    2460
ttgtgccaat gagttggatc tgttgggtca gaagtatagc atagagcagc tgaccactta    2520
ctggctgcag ccgggtgatg atctggagga agctattagg gtgtatgcta aggtggccct    2580
gcggcccgat tgcaagtaca agctcaaggg gctggtgaat atcaggaatt gttgctacat    2640
ttctggcaac gggcggagg tggagataga gaccgaagac agggtggctt tcagatgcag    2700
catgatgaat atgtggccgg gggtgctggg catggacggg gtggtgatta tgaatgtgag    2760
gttcacgggg cccaacttta acggcacggt gtttttgggg aacaccaacc tggtcctgca    2820
cggggtgagc ttctatgggt ttaacaacac ctgtgtggag gcctggaccg atgtgaaggt    2880
ccgcggttgc gccttttatg gatgttggaa ggccatagtg agccgcccta agagcaggag    2940
ttccattaag aaatgcttgt ttgagaggtg caccttgggg atcctggccg agggcaactg    3000
cagggtgcgc cacaatgtgg cctccgagtg cggttgcttc atgctagtca agagcgtggc    3060
ggtaatcaag cataatatgg tgtgcggcaa cagcgaggac aaggcctcac agatgctgac    3120
ctgcacggat ggcaactgcc acttgctgaa gaccatccat gtaaccagcc acagccggaa    3180
ggcctggccc gtgttcgagc acaacttgct gaccccgctgc tccttgcatc tgggcaacag    3240
gcgggggtg ttcctgccct atcaatgcaa ctttagtcac accaagatct tgctagagcc    3300
cgagagcatg tccaaggtga acttgaacgg ggtgtttgac atgaccatga agatctggaa    3360
ggtgctgagg tacgacgaga ccaggtcccg gtgcagaccc tgcgagtgcg ggggcaagca    3420
tatgaggaac cagcccgtga tgctggatgt gaccgaggag ctgaggacag accacttggt    3480
tctggcctgc accagggccg agtttggttc tagcgatgaa gacacagatt gaggtgggtg    3540
agtgggcgtg gcctggggtg gtcatgaaaa tatataagtt gggggtctta gggtctcttt    3600
atttgtgttg cagagaccgc cggagccatg agcgggagca gcagcagcag cagtagcagc    3660
agcgccttgg atggcagcat cgtgagccct tatttgacga cgcggatgcc ccactgggcc    3720
gggggtgcgtc agaatgtgat gggctccagc atcgacggcc gacccgtcct gcccgcaaat    3780
tccgccacgc tgacctatgc gaccgtcgcg gggacgccgt tggacgccac cgccgccgcc    3840
gccgccaccg cagccgcctc ggccgtgcgc agcctggcca cggactttgc attcctggga    3900
ccactggcga caggggctac ttctcgggcc gctgctgccg ccgttcgcga tgacaagctg    3960
accgccctgc tggcgcagtt ggatgcgctt actcgggaac tgggtgacct ttctcagcag    4020
gtcatgcccc tgcgccagca ggtctcctcc ctgcaagctg gcgggaatgc ttctcccaca    4080
aatgccgttt aagataaata aaaccagact ctgtttggat taaagaaaag tagcaagtgc    4140
attgctctct ttatttcata attttccgcg cgcgatagcc cctagaccag cgttctcggt    4200
cgttgagggt gcggtgtatc ttctccagga cgtggtagag gtggctctgg acgttgagat    4260
acatgggcat gagcccgtcc cggggtggga ggtagcacca ctgcagagct tcatgctccg    4320
gggtggtgtt gtagatgatc cagtcgtagc aggagcgctg gcatggtgc ctaaaaatgt    4380
ccttcagcag caggccgatg ccaggggga ggcccttggt gtaagtgttt acaaaacggt    4440
taagttggga agggtgcatt cggggagaga tgatgtgcat cttggactgt attttttagat    4500
tggcgatgtt tccgcccaga tcccttctgg gattcatgtt gtgcaggacc accagtacag    4560
tgtatccggt gcacttgggg aatttgtcat gcagcttaga gggaaaagcg tggaagaact    4620
tggagacgcc tttgtggcct cccagatttt ccatgcattc gtccatgatg atggcaatgg    4680
```

```
gcccgcggga ggcagcttgg gcaaagatat ttctggggtc gctgacgtcg tagttgtgtt    4740
ccagggtgag gtcgtcatag gccatttta caaagcgcgg gcggagggtg cccgactggg    4800
ggatgatggt cccctctggc cctggggcgt agttgccctc gcagatctgc atttcccagg    4860
ccttaatctc ggaggggga atcatatcca cctgcgggc gatgaagaaa acggtttccg    4920 gagccggga gattaactgg gatgagagca ggtttctaag cagctgtgat tttccacaac    4980
cggtgggccc ataaataaca cctataaccg gttgcagctg gtagtttaga gagctgcagc    5040
tgccgtcgtc ccggaggagg ggggccacct cgttgagcat gtccctgacg cgcatgttct    5100
ccccgaccag atccgccaga aggcgctcgc cgcccaggga cagcagctct tgcaaggaag    5160
caaagttttt cagcggcttg aggccgtccg ccgtgggcat gtttttcagg gtctggctca    5220
gcagctccag gcggtcccag agctcggtga cgtgctctac ggcatctcta tccagcatat    5280
ctcctcgttt cgcgggttgg ggcgactttc gctgtagggc accaagcggt ggtcgtccag    5340
cggggccaga gtcatgtcct tccatgggcg caggtcctc gtcagggtgg tctgggtcac    5400
ggtgaagggg tgcgctccgg gctgagcgct tgccaaggtg cgcttgaggc tggttctgct    5460
ggtgctgaag cgctgccggt cttcgccctg cgcgtcggcc aggtagcatt tgaccatggt    5520
gtcatagtcc agccctccg cggcgtgtcc cttggcgcgc agcttgccct tggaggtggc    5580
gccgcacgag gggcagagca ggctcttgag cgcgtagagc ttggggggcga ggaagaccga    5640 ttcggggag taggcgtccg cgccgcagac cccgcacacg gtctcgcact ccaccagcca    5700
ggtgagctcg gggcgcgccg ggtcaaaaac caggtttccc ccatgctttt tgatgcgttt    5760
cttacctcgg gtctccatga ggtggtgtcc ccgctcggtg acgaagaggc tgtccgtgtc    5820
tccgtagacc gacttgaggg gtcttttctc caggggggtc cctcggtctt cctcgtagag    5880
gaactcggac cactctgaga cgaaggcccg cgtccaggcc aggacgaagg aggctatgtg    5940
ggaggggtag cggtcgttgt ccactagggg gtccaccttc tccaaggtgt gaagacacat    6000
gtcgccttcc tcggcgtcca ggaaggtgat tggcttgtag gtgtaggcca cgtgaccggg    6060
ggttcctgac gggggggtat aaaaggggt gggggcgcgc tcgtcgtcac tctcttccgc    6120
atcgctgtct gcgagggcca gctgctgggg tgagtattcc ctctcgaagg cgggcatgac    6180
ctccgcgctg aggttgtcag tttccaaaaa cgaggaggat ttgatgttca cctgtcccga    6240
ggtgatacct ttgagggtac ccgcgtccat ctggtcagaa acacgatct tttttattgtc    6300 cagcttggtg gcgaacgacc cgtagagggc gttggagagc agcttggcga tggagcgcag    6360
ggtctggttc ttgtccctgt cggcgcgctc cttggccgcg atgttgagct gcacgtactc    6420
gcgcgcgacg cagcgccact cggggaagac ggtggtgcgc tcgtcgggca ccaggcgcac    6480
gcgccagccg cggttgtgca gggtgaccag gtccacgctg gtggcgacct cgccgcgcag    6540
gcgctcgttg gtccagcaga acggccgcc cttgcgcgag cagaagggg gcaggggtc    6600 gagctgggtc tcgtccgggg gtccgcgtc cacggtgaaa accccggggc gcaggcgcgc    6660
gtcgaagtag tctatcttgc aaccttgcat gtccagcgcc tgctgccagt cgcgggcggc    6720
gagcgcgcgc tcgtaggggt tgagcggcgg gccccagggc atgggggtggg tgagtgcgga    6780 ggcgtacatg ccgcagatgt catagacgta gaggggctcc cgcaggaccc cgatgtaggt    6840
ggggtagcag cggccgccgc ggatgctggc gcgcacgtag tcatacagct cgtgcgaggg    6900
ggcgaggagg tcggggccca ggttggtgcg gcgggggcgc tccgcgcgga agacgatctg    6960
cctgaagatg gcatgcgagt tggaagagat ggtggggcgc tggaagacgt tgaagctggc    7020
gtcctgcagg ccgacggcgt cgcgcacgaa ggaggcgtag gagtcgcgca gcttgtgtac    7080
```

```
cagctcggcg gtgacctgca cgtcgagcgc gcagtagtcg agggtctcgc ggatgatgtc   7140
atatttagcc tgccccttct ttttccacag ctcgcggttg aggacaaact cttcgcggtc   7200
tttccagtac tcttggatcg ggaaaccgtc cggttccgaa cggtaagagc ctagcatgta   7260
gaactggttg acggcctggt aggcgcagca gcccttctcc acggggaggg cgtaggcctg   7320
cgcggccttg cggagcgagg tgtgggtcag ggcgaaggtg tccctgacca tgactttgag   7380
gtactggtgc ttgaagtcgg agtcgtcgca gccgccccgc tcccagagcg agaagtcggt   7440
gcgcttcttg gagcgggggt tgggcagagc gaaggtgaca tcgttgaaga ggattttgcc   7500
cgcgcggggc atgaagttgc gggtgatgcg gaagggcccc ggcacttcag gcggttgtt    7560 gatgacctgg gcggcgagca cgatctcgtc gaagccgttg atgttgtggc ccacgatgta   7620
gagttccagg aagcggggcc ggcccttac ggtgggcagc ttctttagct cttcgtaggt    7680
gagctcctcg ggcgaggcga ggccgtgctc ggccagggcc cagtccgcga ggtgcgggtt   7740
gtctctgagg aaggacttcc agaggtcgcg ggccaggagg tctgcaggc ggtctctgaa    7800 ggtcctgaac tggcggccca cggccatttt tcgggggtg atgcagtaga aggtgagggg    7860
gtcttgctgc cagcggtccc agtcgagctg cagggcgagg tcgcgcgcgg cggtgaccag   7920
gcgctcgtcg cccccgaatt tcatgaccag catgaagggc acgagctgct ttccgaaggc   7980
ccccatccaa gtgtaggtct ctacatcgta ggtgacaaag aggcgctccg tgcgaggatg   8040
cgagccgatc gggaagaact ggatctcccg ccaccagttg gaggagtggc tgttgatgtg   8100
gtggaagtag aagtcccgtc gccgggccga acactcgtgc tggcttttgt aaaagcgagc   8160
gcagtactgg cagcgctgca cgggctgtac ctcatgcacg agatgcacct ttcgcccgcg   8220
cacgaggaag ccgaggggaa atctgagccc cccgcctggc tcgcggcatg gctggttctc   8280
ttctactttg gatgcgtgtc cgtctccgtc tggctcctcg aggggtgtta cggtggagcg   8340
gaccaccacg ccgcgcgagc cgcaggtcca gatatcggcg cgcggcggtc ggagtttgat   8400
gacgacatcg cgcagctggg agctgtccat ggtctggagc tcccgcggcg gcggcaggtc   8460
agccgggagt tcttgcaggt tcacctcgca gagtcgggcc agggcgcggg gcaggtctag   8520
gtggtacctg atctctaggg gcgtgttggt ggcggcgtcg atggcttgca ggagcccgca   8580
gccccggggg gcgacgacgg tgccccgcgg ggtggtggtg gtggtggcgg tgcagctcag   8640
aagcggtgcc gcgggcgggc ccccggaggt agggggggct ccggtcccgc gggcagggc    8700 ggcagcggca cgtcggcgtg gagcgcgggc aggagttggt gctgtgcccg gaggttgctg   8760
gcgaaggcga cgacgcggcg gttgatctcc tggatctggc gcctctgcgt gaagacgacg   8820
ggcccggtga gcttgaacct gaaagagagt tcgacagaat caatctcggt gtcattgacc   8880
gcggcctggc gcaggatctc ctgcacgtct cccgagttgt cttggtaggc gatctcggcc   8940
atgaactgct cgatctcttc ctcctggagg tctccgcgtc cggcgcgttc cacggtggcc   9000
gccaggtcgt tggagatgcg ccccatgagc tgcgagaagg cgttgagtcc gccctcgttc   9060
cagactcggc tgtagaccac gccccctgg tcatcgcggg cgcgcatgac cacctgcgcg    9120
aggttgagct ccacgtgccg cgcgaagacg gcgtagttgc gcagacgctg aagaggtag    9180 ttgagggtgg tggcggtgtg ctcggccacg aagaagttca tgacccagcg gcgcaacgtg   9240
gattcgttga tgtcccccaa ggcctccagc cgttccatgg cctcgtagaa gtccacggcg   9300
aagttgaaaa actgggagtt gcgcgccgac acggtcaact cctcctccag aagacggatg   9360
agctcggcga cggtgtcgcg cacctcgcgc tcgaaggcta tggggatctc ttcctccgct   9420
```

```
agcatcacca cctcctcctc ttcctcctct tctggcactt ccatgatggc ttcctcctct   9480
tcggggggtg gcggcggcgg cggtggggga ggggcgctc tgcgccggcg gcggcgcacc    9540
gggaggcggt ccacgaagcg cgcgatcatc tccccgcggc ggcggcgcat ggtctcggtg   9600 acggcgggc cgttctcccg ggggcgcagt tggaagacgc cgccggacat ctggtgctgg    9660
ggcgggtggc cgtgaggcag cgagacggcg ctgacgatgc atctcaacaa ttgctgcgta   9720
ggtacgccgc cgagggacct gagggagtcc atatccaccg gatccgaaaa cctttcgagg   9780
aaggcgtcta accagtcgca gtcgcaaggt aggctgagca ccgtggcggg cggcgggggg   9840 tgggggagt gtctggcgga ggtgctgctg atgatgtaat tgaagtaggc ggacttgaca    9900
cggcggatgg tcgacaggag caccatgtcc ttgggtccgg cctgctggat gcggaggcgg   9960
tcggctatgc cccaggcttc gttctggcat cggcgcaggt ccttgtagta gtcttgcatg   10020 agccttttcca ccggcacctc ttctccttcc tcttctgctt cttccatgtc tgcttcggcc  10080
ctggggcggc gccgcgcccc cctgcccccc atgcgcgtga ccccgaaccc cctgagcggt   10140
tggagcaggg ccaggtcggc gacgacgcgc tcggccagga tggcctgctg cacctgcgtg   10200
agggtggttt ggaagtcatc caagtccacg aagcggtggt aggcgcccgt gttgatggtg   10260
taggtgcagt tggccatgac ggaccagttg acggtctggt ggcccggttg cgacatctcg   10320
gtgtacctga gtcgcgagta ggcgcgggag tcgaagacgt agtcgttgca agtccgcacc   10380
aggtactggt agcccaccag gaagtgcggc ggcggctggc ggtagagggg ccagcgcagg   10440
gtggcggggg ctccggggc caggtcttcc agcatgaggc ggtggtaggc gtagatgtac     10500
ctggacatcc aggtgatacc cgcggcggtg gtggaggcgc gcgggaagtc gcgcacccgg   10560
ttccagatgt tgcgcagggg cagaaagtgc tccatggtag gcgtgctctg tccagtcaga   10620
cgcgcgcagt cgttgatact ctagaccagg gaaaacgaaa gccggtcagc gggcactctt   10680
ccgtggtctg gtgaatagat cgcaagggta tcatggcgga gggcctcggt tcgagccccg   10740
ggtccgggcc ggacggtccg ccatgatcca cgcggttacc gcccgcgtgt cgaacccagg   10800
tgtgcgacgt cagacaacgg tggagtgttc cttttggcgt ttttctggcc gggcgccggc   10860
gccgcgtaag agactaagcc gcgaaagcga aagcagtaag tggctcgctc cccgtagccg   10920
gagggatcct tgctaagggt tgcgttgcgg cgaaccccgg ttcgaatccc gtactcgggc   10980
cggccggacc cgcggctaag gtgttggatt ggcctccccc tcgtataaag accccgcttg   11040
cggattgact ccggacacgg ggacgagccc ctttttatttt tgctttcccc agatgcatcc   11100
ggtgctgcgg cagatgcgcc ccccgcccca gcagcagcaa caacaccagc aagagcggca   11160
gcaacagcag cgggagtcat gcagggcccc ctcacccacc ctcggcgggc cggccacctc   11220
ggcgtccgcg gccgtgtctg gcgcctgcgg cggcggcggg gggccggctg acgacccccga  11280 ggagccccg cggcgcaggg ccagacacta cctggacctg gaggagggcg agggcctggc    11340
gcggctgggg gcgccgtctc ccgagcgcca cccgcgggtg cagctgaagc gcgactcgcg   11400
cgaggcgtac gtgcctcggc agaacctgtt cagggaccgc gcgggcgagg agcccgagga   11460
gatgcgggac aggaggttca gcgcagggcg ggagctgcgg caggggctga accgcgagcg   11520
gctgctgcgc gaggaggact ttgagcccga cgcgcggacg gggatcagcc ccgcgcgcgc   11580
gcacgtggcg gccgccgacc tggtgacggc gtacgagcag acggtgaacc aggagatcaa   11640
cttccaaaag agtttcaaca accacgtgcg cacgctggtg gcgcgcgagg aggtgaccat   11700
cgggctgatg cacctgtggg actttgtaag cgcgctggtg cagaaccccca acagcaagcc   11760 tctgacggcg cagctgttcc tgatagtgca gcacagcagg gacaacgagg cgtttaggga   11820
```

```
cgcgctgctg aacatcaccg agcccgaggg tcggtggctg ctggacctga ttaacatcct    11880
gcagagcata gtggtgcagg agcgcagcct gagcctggcc gacaaggtgg cggccatcaa    11940
ctactcgatg ctgagcctgg gcaagtttta cgcgcgcaag atctaccaga cgccgtacgt    12000
gcccatagac aaggaggtga agatcgacgg ttttacatg cgcatggcgc tgaaggtgct    12060
caccctgagc gacgacctgg gcgtgtaccg caacgagcgc atccacaagg ccgtgagcgt    12120
gagccggcgg cgcgagctga gcgaccgcga gctgatgcac agcctgcagc gggcgctggc    12180
gggcgccggc agcggcgaca gggaggcgga gtcctacttc gatgcggggg cggacctgcg    12240
ctgggcgccc agccggcggg ccctggaggc cgcggggtc cgcgaggact atgacgagga    12300
cggcgaggag gatgaggagt acgagctaga ggagggcgag tacctggact aaaccgcggg    12360
tggtgtttcc ggtagatgca agacccgaac gtggtggacc cggcgctgcg ggcggctctg    12420
cagagccagc cgtccggcct taactcctca gacgactggc gacaggtcat ggaccgcatc    12480
atgtcgctga cggcgcgtaa cccggacgcg ttccggcagc agccgcaggc caacaggctc    12540
tccgccatcc tggaggcggt ggtgcctgcg cgctcgaacc ccacgcacga aaggtgctg    12600 gccatagtga acgcgctggc cgagaacagg gccatccgcc cggacgaggc cgggctggtg    12660
tacgacgcgc tgctgcagcg cgtggcccgc tacaacagcg gcaacgtgca gaccaacctg    12720
gaccggctgg tggggacgt gcgcgaggcg gtggcgcagc gcgagcgcgc ggatcggcag    12780
ggcaacctgg gctccatggt ggcgctgaat gccttcctga gcacgcagcc ggccaacgtg    12840 ccgcggggggc aggaagacta caccaacttt gtgagcgcgc tgcggctgat ggtgaccgag    12900
accccccaga gcgaggtgta ccagtcgggc ccggactact tcttccagac cagcagacag    12960
ggcctgcaga cggtgaacct gagccaggct ttcaagaacc tgcggggggct gtggggcgtg    13020 aaggcgccca ccggcgaccg ggcgacggtg tccagcctgc tgacgcccaa ctcgcgcctg    13080
ctgctgctgc tgatcgcgcc gttcacggac agcggcagcg tgtcccggga cacctacctg    13140
gggcacctgc tgaccctgta ccgcgaggcc atcgggcagg cgcaggtgga cgagcacacc    13200
ttccaggaga tcaccagcgt gagccgcgcg ctggggcagg aggacacgag cagcctggag    13260
gcgactctga actacctgct gaccaaccgg cggcagaaga ttccctcgct gcacagcctg    13320
acctccgagg aggagcgcat cttgcgctac gtgcagcaga gcgtgagcct gaacctgatg    13380
cgcgacgggg tgacgcccag cgtggcgctg gacatgaccg cgcgcaacat ggaacccggc    13440
atgtacgccg cgcaccggcc ttacatcaac cgcctgatgg actacctgca tcgcgcggcg    13500
gccgtgaacc ccgagtactt taccaacgcc atcctgaacc cgcactggct cccgccgccc    13560
gggttctaca gcgggggctt cgaggtcccg gagaccaacg atggcttcct gtgggacgac    13620
atggacgaca gcgtgttctc cccgcggccg caggcgctgg cggaagcgtc cctgctgcgt    13680
cccaagaagg aggaggagga ggaggcgagt cgccgccgcg gcagcagcgg cgtggcttct    13740
ctgtccgagc tgggggcggc agccgccgcg cgccccgggt ccctgggcgg cagccccttt    13800
ccgagcctgg tggggtctct gcacagcgag cgcaccaccc gccctcggct gctgggcgag    13860
gacgagtacc tgaataactc cctgctgcag ccggtgcggg agaaaaacct gcctcccgcc    13920 ttcccccaaca acgggataga gagcctggtg acaagatga gcagatggaa gacctatgcg    13980
caggagcaca gggacgcgcc tgcgctccgg ccgcccacgc ggcgccagcg ccacgaccgg    14040
cagcgggggc tggtgtggga tgacgaggac tccgcggacg atagcagcgt gctgacctg    14100 ggagggagcg gcaacccgtt cgcgcacctg cgcccccgcc tggggaggat gttttaaaaa    14160
```

|  |  |
|---|---|
| aaaaaaaaaa aagcaagaag catgatgcaa aaattaaata aaactcacca aggccatggc | 14220 |
| gaccgagcgt tggtttcttg tgttcccttc agtatgcggc gcgcggcgat gtaccaggag | 14280 |
| ggacctcctc cctcttacga gagcgtggtg ggcgcggcgg cggcggcgcc ctcttctccc | 14340 |
| tttgcgtcgc agctgctgga gccgccgtac gtgcctccgc gctacctgcg gcctacgggg | 14400 |
| gggagaaaca gcatccgtta ctcggagctg gcgcccctgt tcgacaccac ccggggtgtac | 14460 |
| ctggtggaca caagtcggc ggacgtggcc tccctgaact accagaacga ccacagcaat | 14520 |
| tttttgacca cggtcatcca gaacaatgac tacagcccga gcgaggccag cacccagacc | 14580 |
| atcaatctgg atgaccggtc gcactggggc ggcgacctga aaaccatcct gcacaccaac | 14640 |
| atgcccaacg tgaacgagtt catgttcacc aataagttca aggcgcgggt gatggtgtcg | 14700 |
| cgctcgcaca ccaaggaaga ccgggtggag ctgaagtacg agtgggtgga gttcgagctg | 14760 |
| ccagagggca actactccga gaccatgacc attgacctga tgaacaacgc gatcgtggag | 14820 |
| cactatctga aagtgggcag gcagaacggg gtcctggaga gcgacatcgg ggtcaagttc | 14880 |
| gacaccagga acttccgcct gggggctggac cccgtgaccg ggctggttat gcccggggtg | 14940 |
| tacaccaacg aggccttcca tcccgacatc atcctgctgc ccggctgcgg ggtggacttc | 15000 |
| acttacagcc gcctgagcaa cctcctgggc atccgcaagc ggcagcccttt ccaggagggc | 15060 |
| ttcaggatca cctacgagga cctggagggg ggcaacatcc ccgcgctcct cgatgtggag | 15120 |
| gcctaccagg atagcttgaa ggaaaatgag gcgggacagg aggataccgc ccccgccgcc | 15180 |
| tccgccgccg ccgagcaggg cgaggatgct gctgacaccg cggccgcgga cggggcagag | 15240 |
| gccgaccccg ctatggtggt ggaggctccc gagcaggagg aggacatgaa tgacagtgcg | 15300 |
| gtgcgcggag acaccttcgt cacccggggg gaggaaaagc aagcggaggc cgaggccgcg | 15360 |
| gccgaggaaa agcaactggc ggcagcagcg cggcggcgcg cgttggccgc ggcggaggct | 15420 |
| gagtctgagg ggaccaagcc cgccaaggag cccgtgatta agcccctgac cgaagatagc | 15480 |
| aagaagcgca gttacaacct gctcaaggac agcaccaaca ccgcgtaccg cagctggtac | 15540 |
| ctggcctaca actacggcga cccgtcgacg ggggtgcgct cctggaccct gctgtgcacg | 15600 |
| ccggacgtga cctgcggctc ggagcaggtg tactggtcgc tgcccgacat gatgcaagac | 15660 |
| cccgtgacct tccgctccac gcggcaggtc agcaacttcc cggtggtggg cgccgagctg | 15720 |
| ctgcccgtgc actccaagag cttctacaac gaccaggccg tctactccca gctcatccgc | 15780 |
| cagttcacct ctctgaccca cgtgttcaat cgctttcctg agaaccagat tctggcgcgc | 15840 |
| ccgcccgccc ccaccatcac caccgtcagt gaaaacgttc ctgctctcac agatcacggg | 15900 |
| acgctaccgc tgcgcaacag catcggagga gtccagcgag tgaccgttac tgacgccaga | 15960 |
| cgccgcacct gcccctacgt ttacaaggcc ttgggcatag tctcgccgcg cgtcctttcc | 16020 |
| agccgcactt tttgagcaac accaccatca tgtccatcct gatctcaccc agcaataact | 16080 |
| ccggctgggg actgctgcgc gcgcccagca agatgttcgg aggggcgagg aagcgttccg | 16140 |
| agcagcaccc cgtgcgcgtg cgcgggcact tccgcgcccc ctggggagcg cacaaacgcg | 16200 |
| gccgcgcggg gcgcaccacc gtggacgacg ccatcgactc ggtggtggag caggcgcgca | 16260 |
| actacaggcc cgccggtctct accgtggacg cggccatcca gaccgtggtg cggggcgcgc | 16320 |
| ggcggtacgc caagctgaag agccgccgga agcgcgtggc ccgccgccac cgccgccgac | 16380 |
| cggggccgc cgccaaacgc gccgccgcgg ccctgcttcg ccgggccaag cgcacgggcg | 16440 |
| gccgcgccgc catgagggcc gcgcgccgct tggccgccgg catcaccgcc gccaccatgg | 16500 |
| cccccgtac ccgaagacgc gcggccgccg ccgccgccgc cgccatcagt gacatggcca | 16560 |

```
gcaggcgccg gggcaacgtg tactgggtgc gcgactcggt gaccggcacg cgcgtgcccg    16620
tgcgcttccg ccccccgcgg acttgagatg atgtgaaaaa acaacactga gtctcctgct    16680
gttgtgtgta tcccagcggc ggcggcgcgc gcagcgtcat gtccaagcgc aaaatcaaag    16740
aagagatgct ccaggtcgtc gcgccggaga tctatgggcc cccgaagaag gaagagcagg    16800
attcgaagcc ccgcaagata aagcgggtca aaagaaaaa gaaagatgat gacgatgccg     16860
atggggaggt ggagttcctg cgcgccacgg cgcccaggcg cccggtgcag tggaagggcc    16920
ggcgcgtaaa gcgcgtcctg cgccccggca ccgcggtggt cttcacgccc ggcgagcgct    16980
ccacccggac tttcaagcgc gtctatgacg aggtgtacgg cgacgaagac ctgctggagc    17040
aggccaacga gcgcttcgga gagtttgctt acgggaagcg tcagcgggcg ctggggaagg    17100
aggacctgct ggcgctgccg ctggaccagg gcaaccccac ccccagtctg aagcccgtga    17160
ccctgcagca ggtgctgccg agcagcgcac cctccgaggc gaagcggggt ctgaagcgcg    17220
agggcggcga cctggcgccc accgtgcagc tcatggtgcc caagcggcag aggctggagg    17280
atgtgctgga gaaaatgaaa gtagaccccg gtctgcagcc ggacatcagg gtccgcccca    17340
tcaagcaggt ggcgccgggc ctcggcgtgc agaccgtgga cgtggtcatc cccaccggca    17400 actccccgc cgccgccacc actaccgctg cctccacgga catggagaca cagaccgatc     17460
ccgccgcagc cgcagccgca gccgccgccg cgacctcctc ggcggaggtg cagacggacc    17520
cctggctgcc gccggcgatg tcagctcccc gcgcgcgtcg cgggcgcagg aagtacggcg    17580
ccgccaacgc gctcctgccc gagtacgcct tgcatccttc catcgcgccc acccccggct    17640
accgaggcta tacctaccgc ccgcgaagag ccaagggttc cacccgccgt ccccgccgac    17700
gcgccgccgc caccacccgc cgccgccgcc gcagacgcca gcccgcactg gctccagtct    17760
ccgtgaggaa agtggcgcgc gacggacaca ccctggtgct gcccagggcg cgctaccacc    17820
ccagcatcgt ttaaaagcct gttgtggttc ttgcagatat ggccctcact tgccgcctcc    17880
gtttcccggt gccgggatac cgaggaggaa gatcgcgccg caggaggggt ctggccggcc    17940
gcggcctgag cggaggcagc cgccgcgcgc accggcggcg acgcgccacc agccgacgca    18000
tgcgcggcgg ggtgctgccc ctgttaatcc ccctgatcgc cgcggcgatc ggcgccgtgc    18060
ccgggatcgc ctccgtggcc ttgcaagcgt cccagaggca ttgacagact tgcaaacttg    18120
caaatatgga aaaaaaacc ccaataaaaa agtctagact ctcacgctcg cttggtcctg    18180
tgactatttt gtagaatgga agacatcaac tttgcgtcgc tggccccgcg tcacggctcg    18240
cgcccgttcc tgggacactg gaacgatatc ggcaccagca acatgagcgg tggcgccttc    18300
agttggggct ctctgtggag cggcattaaa agtatcgggt ctgccgttaa aaattacggc    18360
tcccgggcct ggaacagcag cacgggccag atgttgagag acaagttgaa agagcagaac    18420
ttccagcaga aggtggtgga gggcctggcc tccggcatca cggggtggt ggacctggcc     18480 aaccaggccg tgcagaataa gatcaacagc agactggacc cccggccgcc ggtggaggag    18540
gtgccgccgg cgctggagac ggtgtccccc gatgggcgtg gcgagaagcg cccgcggccc    18600
gatagggaag agaccactct ggtcacgcag accgatgagc cgccccgta tgaggaggcc      18660 ctgaagcaag gtctgccac cacgcggccc atcgcgccca tggccaccgg ggtggtgggc     18720
cgccacaccc ccgccacgct ggacttgcct ccgcccgccg atgtgccgca gcagcagaag    18780
gcggcacagc cggcccgcc cgcgaccgcc tcccgttcct ccgccggtcc tctgcgcgcg     18840
gcggccagcg gccccgcgg gggggtcgcg aggcacggca actggcagag cacgctgaac    18900
```

```
agcatcgtgg gtctggggggt gcggtccgtg aagcgccgcc gatgctactg aatagcttag    18960
ctaacgtgtt gtatgtgtgt atgcgcccta tgtcgccgcc agaggagctg ctgagtcgcc    19020
gccgttcgcg cgcccaccac caccgccact ccgcccctca agatggcgac cccatcgatg    19080
atgccgcagt ggtcgtacat gcacatctcg ggccaggacg cctcggagta cctgagcccc    19140
gggctggtgc agttcgcccg cgccaccgag agctacttca gcctgagtaa caagtttagg    19200
aaccccacgg tggcgcccac gcacgatgtg accaccgacc ggtctcagcg cctgacgctg    19260
cggttcattc ccgtggaccg cgaggacacc gcgtactcgt acaaggcgcg gttcaccctg    19320
gccgtgggcg acaaccgcgt gctggacatg gcctccacct actttgacat ccgcggggtg    19380
ctggaccggg gtcccacttt caagccctac tctggcaccg cctacaactc cctggccccc    19440
aagggcgctc ccaactcctg cgagtgggag caagaggaaa ctcaggcagt tgaagaagca    19500
gcagaagagg aagaagaaga tgctgacggt caagctgagg aagagcaagc agctaccaaa    19560
aagactcatg tatatgctca ggctccccctt tctggcgaaa aaattagtaa agatggtctg    19620
caaataggaa cggacgctac agctacagaa caaaaaccta tttatgcaga ccctacattc    19680
cagcccgaac cccaaatcgg ggagtcccag tggaatgagg cagatgctac agtcgccggc    19740
ggtagagtgc taaagaaatc tactcccatg aaaccatgct atggttccta tgcaagaccc    19800
acaaatgcta atggaggtca gggtgtacta acggcaaatg cccagggaca gctagaatct    19860
caggttgaaa tgcaattctt ttcaacttct gaaaacgccc gtaacgaggc taacaacatt    19920
cagcccaaat tggtgctgta tagtgaggat gtgcacatgg agaccccgga tacgcaccct    19980
tcttacaagc ccgcaaaaag cgatgacaat tcaaaaatca tgctgggtca gcagtccatg    20040
cccaacagac ctaattacat cggcttcaga gacaacttta tcggcctcat gtattacaat    20100
agcactggca acatgggagt gcttgcaggt caggcctctc agttgaatgc agtggtggac    20160
ttgcaagaca gaaacacaga actgtcctac cagctcttgc ttgattccat gggtgacaga    20220
accagatact tttccatgtg gaatcaggca gtggacagtt atgacccaga tgttagaatt    20280
attgaaaatc atggaactga agacgagctc cccaactatt gtttccctct gggtggcata    20340
ggggtaactg acacttacca ggctgttaaa accaacaatg gcaataacgg ggggccaggtg    20400 acttggacaa aagatgaaac ttttgcagat cgcaatgaaa tagggggtggg aaacaatttc    20460 gctatggaga tcaaccctcag tgccaacctg tggagaaact tcctgtactc caacgtggcg    20520
ctgtacctac cagacaagct taagtacaac ccctccaatg tggacatctc tgacaacccc    20580
aacacctacg attacatgaa caagcgagtg gtggccccgg ggctggtgga ctgctacatc    20640
aacctgggcg cgcgctggtc gctggactac atggacaacg tcaaccccctt caaccaccac    20700 cgcaatgcgg gcctgcgcta ccgctccatg ctcctgggca acgggcgcta cgtgcccttc    20760
cacatccagg tgccccagaa gttctttgcc atcaagaacc tcctcctcct gccgggctcc    20820
tacacctacg agtggaactt caggaaggat gtcaacatgg tcctccagag ctctctgggt    20880
aacgatctca gggtggacgg ggccagcatc aagttcgaga gcatctgcct ctacgccacc    20940
ttcttcccca tggccacaa cacggcctcc acgctcgagg ccatgctcag gaacgacacc    21000
aacgaccagt ccttcaatga ctacctctcc gccgccaaca tgctctaccc catacccgcc    21060
aacgccacca acgtccccat ctccatcccc tcgcgcaact gggcggcctt ccgcggctgg    21120
gccttcaccc gcctcaagac caaggagacc cctcccctgg gctcgggatt cgacccctac    21180
tacacctact cgggctccat tccctacctg gacggcacct tctacctcaa ccacactttc    21240
aagaaggtct cggtcacctt cgactcctcg gtcagctggc cggggcaacga ccgtctgctc    21300
```

```
accccccaacg agttcgagat caagcgctcg gtcgacgggg agggctacaa cgtggcccag  21360
tgcaacatga ccaaggactg gttcctggtc cagatgctgg ccaactacaa catcggctac  21420
cagggcttct acatcccaga gagctacaag gacaggatgt actccttctt caggaacttc  21480
cagcccatga gccggcaggt ggtggaccag accaagtaca aggactacca ggaggtgggc  21540
atcatccacc agcacaacaa ctcgggcttc gtgggctacc tcgcccccac catgcgcgag  21600
ggacaggcct accccgccaa cttccccat ccgctcatag caagaccgc ggtcgacagc  21660 atcacccaga aaaagttcct ctgcgaccgc accctctggc gcatccctt ctccagcaac  21720 ttcatgtcca tgggtgcgct ctcggacctg ggccagaact tgctctacgc caactccgcc  21780
cacgccctcg acatgacctt cgaggtcgac cccatggacg agcccaccct tctctatgtt  21840
ctgttcgaag tctttgacgt ggtccgggtc caccagccgc accgcggcgt catcgagacc  21900
gtgtacctgc gtacgccctt ctcggccggc aacgccacca cctaaagaag caagccgcag  21960
tcatcgccgc ctgcatgccg tcgggttcca ccgagcaaga gctcagggcc atcgtcagag  22020
acctgggatg cgggccctat ttttttgggca ccttcgacaa gcgcttccct ggctttgtct  22080
ccccacacaa gctggcctgc gccatcgtca acacggccgg ccgcgagacc ggggcgtgc   22140 actggctggc cttcgcctgg aacccgcgct ccaaaacatg cttcctcttt gacccttcg   22200 gcttttcgga ccagcggctc aagcaaatct acgagttcga gtacgagggc ttgctgcgtc  22260
gcagcgccat cgcctcctcg cccgaccgct gcgtcaccct cgaaaagtcc acccagaccg  22320
tgcaggggcc cgactcggcc gcctgcggtc tcttctgctg catgtttctg cacgcctttg  22380
tgcactggcc tcagagtccc atggaccgca accccaccat gaacttgctg acggggtgc   22440 ccaactccat gctccagagc ccccaggtcg agcccaccct cgccgcaac caggagcagc   22500 tctacagctt cctggagcgc cactcgcctt acttccgccg ccacagcgca cagatcagga  22560
gggccacctc cttctgccac ttgcaagaga tgcaagaagg gtaataacga tgtacacact  22620 tttttttctca ataaatggca tcttttttatt tatacaagct ctctgggta ttcatttccc  22680 accaccaccc gccgttgtcg ccatctggct ctatttagaa atcgaaaggg ttctgccggg  22740
agtcgccgtg cgccacgggc agggacacgt tgcgatactg gtagcgggtg ccccacttga  22800
actcgggcac caccaggcga ggcagctcgg ggaagttttc gctccacagg ctgcgggtca  22860
gcaccagcgc gttcatcagg tcgggcgccg agatcttgaa gtcgcagttg ggccgccgc   22920 cctgcgcgcg cgagttgcgg tacaccgggt tgcagcactg gaacaccaac agcgccgggt  22980
gcttcacgct ggccagcacg ctgcggtcgg agatcagctc ggcgtccagg tcctccgcgt  23040
tgctcagcgc gaacggggtc atcttgggca cttgccgccc caggaagggc gcgtgccccg  23100
gtttcgagtt gcagtcgcag cgcagcggga tcagcaggtg cccgtgcccg gactcggcgt  23160
tggggtacag cgcgcgcatg aaggcctgca tctggcggaa ggccatctgg gccttggcgc  23220
cctccgagaa gaacatgccg caggacttgc ccgagaactg gttgcgggg cagctggcgt   23280 cgtgcaggca gcagcgcgcg tcggtgttgg cgatctgcac cacgttgcgc ccccaccggt  23340
tcttcacgat cttggccttg gacgattgct ccttcagcgc gcgctgcccg ttctcgctgg  23400
tcacatccat ctcgatcaca tgttccttgt tcaccatgct gctgccgtgc agacacttca  23460
gctcgccctc cgtctcggtg cagcggtgct gccacagcgc gcagcccgtg ggctcgaaag  23520
acttgtaggt cacctccgcg aaggactgca ggtaccctg caaaaagcgg cccatcatgg   23580
tcacgaaggt cttgttgctg ctgaaggtca gctgcagccc gcggtgctcc tcgttcagcc  23640
```

-continued

| | | | | |
|---|---|---|---|---|
| aggtcttgca | cacggccgcc | agcgcctcca | cctggtcggg | cagcatcttg | aagttcacct | 23700 |
| tcagctcatt | ctccacgtgg | tacttgtcca | tcagcgtgcg | cgccgcctcc | atgcccttct | 23760 |
| cccaggccga | caccagcggc | aggctcacgg | ggttcttcac | catcaccgtg | gccgccgcct | 23820 |
| ccgccgcgct | ttcgctttcc | gccccgctgt | tctcttcctc | ttcctcctct | tcctcgccgc | 23880 |
| cgcccactcg | cagcccccgc | accacggggt | cgtcttcctg | caggcgctgc | accttgcgct | 23940 |
| tgccgttgcg | cccctgcttg | atgcgcacgg | gcggggttgct | gaagcccacc | atcaccagcg | 24000 |
| cggcctcttc | ttgctcgtcc | tcgctgtcca | gaatgacctc | cggggagggg | gggttggtca | 24060 |
| tcctcagtac | cgaggcacgc | ttcttttttct | tcctgggggc | gttcgccagc | tccgcggctg | 24120 |
| cggccgctgc | cgaggtcgaa | ggccgagggc | tgggcgtgcg | cggcaccagc | gcgtcctgcg | 24180 |
| agccgtcctc | gtcctcctcg | gactcgagac | ggaggcgggc | ccgcttcttc | ggggcgcgc | 24240 |
| ggggcggcgg | aggcggcggc | ggcgacggag | acggggacga | gacatcgtcc | agggtgggtg | 24300 |
| gacggcgggc | cgcgccgcgt | ccgcgctcgg | gggtggtctc | gcgctggtcc | tcttcccgac | 24360 |
| tggccatctc | ccactgctcc | ttctcctata | ggcagaaaga | gatcatggag | tctctcatgc | 24420 |
| gagtcgagaa | ggaggaggac | agcctaaccg | ccccctctga | gccctccacc | accgccgcca | 24480 |
| ccaccgccaa | tgccgccgcg | gacgacgcgc | ccaccgagac | caccgccagt | accaccctcc | 24540 |
| ccagcgacgc | accccgctc | gagaatgaag | tgctgatcga | gcaggacccg | ggttttgtga | 24600 |
| gcggagagga | ggatgaggtg | gatgagaagg | agaaggagga | ggtcgccgcc | tcagtgccaa | 24660 |
| aagaggataa | aaagcaagac | caggacgacg | cagataagga | tgagacagca | gtcgggcggg | 24720 |
| ggaacggaag | ccatgatgct | gatgacggct | acctagacgt | gggagacgac | gtgctgctta | 24780 |
| agcacctgca | ccgccagtgc | gtcatcgtct | gcgacgcgct | gcaggagcgc | tgcgaagtgc | 24840 |
| ccctggacgt | ggcggaggtc | agccgcgcct | acgagcggca | cctcttcgcg | ccgcacgtgc | 24900 |
| cccccaagcg | ccgggagaac | ggcacctgcg | agcccaaccc | gcgtctcaac | ttctacccgg | 24960 |
| tcttcgcggt | acccgaggtg | ctggccacct | accacatctt | tttccaaaac | tgcaagatcc | 25020 |
| ccctctcctg | ccgcgccaac | cgcacccgcg | ccgacaaaac | cctgaccctg | cggcagggcg | 25080 |
| cccacatacc | tgatatcgcc | tctctggagg | aagtgcccaa | gatcttcgag | ggtctcggtc | 25140 |
| gcgacgagaa | acgggcggcg | aacgctctgc | acggagacag | cgaaaacgag | agtcactcgg | 25200 |
| gggtgctggt | ggagctcgag | ggcgacaacg | cgcgcctggc | cgtactcaag | cgcagcatag | 25260 |
| aggtcaccca | ctttgcctac | ccggcgctca | acctgccccc | caaggtcatg | agtgtggtca | 25320 |
| tgggcgagct | catcatgcgc | cgcgcccagc | ccctggccgc | ggatgcaaac | ttgcaagagt | 25380 |
| cctccgagga | aggcctgccc | gcggtcagcg | acgagcagct | ggcgcgctgg | ctggagaccc | 25440 |
| gcgaccccgc | gcagctggag | gagcggcgca | agctcatgat | ggccgcggtg | ctggtcaccg | 25500 |
| tggagctcga | gtgtctgcag | cgcttcttcg | cggaccccga | gatgcagcgc | aagctcgagg | 25560 |
| agaccctgca | ctacaccttc | cgccagggct | acgtgcgcca | ggcctgcaag | atctccaacg | 25620 |
| tggagctctg | caacctggtc | tcctacctgg | gcatcctgca | cgagaaccgc | ctcgggcaga | 25680 |
| acgtcctgca | ctccaccctc | aaagggagg | cgcgccgcga | ctacatccgc | gactgcgcct | 25740 |
| acctcttcct | ctgctacacc | tggcagacgc | ccatgggggt | ctggcagcag | tgcctggagg | 25800 |
| agcgcaacct | caaggagctg | gaaaagctcc | tcaagcgcac | cctcagggac | ctctggacgg | 25860 |
| gcttcaacga | gcgctcggtg | gccgccgcgc | tggcggacat | catctttccc | gagcgcctgc | 25920 |
| tcaagaccct | gcagcagggc | ctgcccgact | tcaccagcca | gagcatgctg | cagaacttca | 25980 |
| ggactttcat | cctggagcgc | tcgggcatcc | tgccggccac | ttgctgcgcg | ctgcccagcg | 26040 |

```
acttcgtgcc catcaagtac agggagtgcc cgccgccgct ctggggccac tgctacctct    26100
tccagctggc caactacctc gcctaccact cggacctcat ggaagacgtg agcggcgagg    26160
gcctgctcga gtgccactgc cgctgcaacc tctgcacgcc ccaccgctct ctagtctgca    26220
acccgcagct gctcagcgag agtcagatta tcggtacctt cgagctgcag ggtccctcgc    26280
ctgacgagaa gtccgcggct ccagggctga aactcactcc ggggctgtgg acttccgcct    26340
acctacgcaa atttgtacct gaggactacc acgcccacga gatcaggttc tacgaagacc    26400
aatcccgccc gcccaaggcg gagctcaccg cctgcgtcat cacccagggg cacatcctgg    26460
gccaattgca agccatcaac aaagcccgcc gagagttctt gctgaaaaag gtcgggggg    26520 tgtacctgga cccccagtcc ggcgaggagc taaacccgct accccgccg ccgccccagc    26580 agcgggacct tgcttcccag gatggcaccc agaaagaagc agcagccgcc gccgccgccg    26640
cagccataca tgcttctgga ggaagaggag gaggactggg acagtcaggc agaggaggtt    26700
tcggacgagg agcaggagga gatgatggaa gactgggagg aggacagcag cctagacgag    26760
gaagcttcag aggccgaaga ggtggcagac gcaacaccat cgccctcggt cgcagccccc    26820
tcgccggggc ccctgaaatc ctccgaaccc agcaccagcg ctataacctc cgctcctccg    26880
gcgccggcgc cacccgcccg cagacccaac cgtagatggg acaccacagg aaccggggtc    26940
ggtaagtcca agtgcccgcc gccgccaccg cagcagcagc agcagcagcg ccagggctac    27000
cgctcgtggc gcgggcacaa gaacgccata gtcgcctgct tgcaagactg cgggggcaac    27060
atctctttcg cccgccgctt cctgctattc caccacgggg tcgcctttcc ccgcaatgtc    27120
ctgcattact accgtcatct ctacagcccc tactgcagcg gcgacccaga ggcggcagcg    27180
gcagccacag cggcgaccac cacctaggaa gatatcctcc gcgggcaaga cagcggcagc    27240
agcggccagg agacccgcgg cagcagcggc gggagcggtg ggcgcactgc gcctctcgcc    27300
caacgaaccc ctctcgaccc gggagctcag acacaggatc ttccccactt tgtatgccat    27360
cttccaacag agcagaggcc aggagcagga gctgaaaata aaaaacagat ctctgcgctc    27420
cctcacccgc agctgtctgt atcacaaaag cgaagatcag cttcggcgca cgctggagga    27480
cgcggaggca ctcttcagca aatactgcgc gctcactctt aaagactagc tccgcgccct    27540
tctcgaattt aggcgggaga aaactacgtc atcgccggcc gccgcccagc ccgcccagcc    27600
gagatgagca aagagattcc cacgccatac atgtggagct accagccgca gatgggactc    27660
gcggcgggag cggcccagga ctactccacc cgcatgaact acatgagcgc gggaccccac    27720
atgatctcac aggtcaacgg gatccgcgcc cagcgaaacc aaatactgct ggaacaggcg    27780
gccatcaccg ccacgccccg ccataatctc aaccccgaa attggcccgc cgccctcgtg    27840
taccaggaaa cccccctccgc caccaccgta ctacttccgc gtgacgccca ggccgaagtc    27900
cagatgacta actcaggggc gcagctcgcg ggcggctttc gtcacggggc gcggccgctc    27960
cgaccaggta taagcacct gatgatcaga ggccgaggta tccagctcaa cgacgagtcg    28020
gtgagctctt cgctcggtct ccgtccggac ggaactttcc agctcgccgg atccggccgc    28080
tcttcgttca cgccccgcca ggcgtacctg actctgcaga cctcgtcctc ggagccccgc    28140
tccggcggca tcggaaccct ccagttcgtg gaggagttcc tgccctcggt ctacttcaac    28200
cccttctcgg gacctcccgg acgctacccc gaccagttca ttccgaactt tgacgcggtg    28260
aaggactcgg cggacggcta cgactgaatg tcaggtgtcg aggcagagca gcttcgcctg    28320
agacacctcg agcactgccg ccgccacaag tgcttcgccc gcggttctgg tgagttctgc    28380
```

```
tactttcagc tacccgagga gcataccgag gggccggcgc acggcgtccg cctgaccacc    28440
cagggcgagg ttacctgttc cctcatccgg gagtttaccc tccgtcccct gctagtggag    28500
cgggagcggg gtccctgtgt cctaactatc gcctgcaact gccctaaccc tggattacat    28560
caagatcttt gctgtcatct ctgtgctgag tttaataaac gctgagatca gaatctactg    28620
gggctcctgt cgccatcctg tgaacgccac cgtcttcacc caccccgacc aggcccaggc    28680
gaacctcacc tgcggtctgc atcggagggc caagaagtac ctcacctggt acttcaacgg    28740
cacccccttt gtggtttaca acagcttcga cggggacgga gtctccctga agaccagct    28800 ctccggtctc agctactcca tccacaagaa caccaccctc caactcttcc ctccctacct    28860
gccgggaacc tacgagtgcg tcaccggccg ctgcacccac ctcacccgcc tgatcgtaaa    28920
ccagagcttt ccgggaacag ataactccct cttccccaga acaggaggtg agctcaggaa    28980
actcccgggg gaccagggcg gagacgtacc ttcgacccct gtggggttag gattttttat    29040
taccgggttg ctggctcttt taatcaaagt ttccttgaga tttgttcttt ccttctacgt    29100
gtatgaacac ctcaacctcc aataactcta ccctttcttc ggaatcaggt gacttctctg    29160
aaatcgggct tggtgtgctg cttactctgt tgattttttt ccttatcata ctcagccttc    29220
tgtgcctcag gctcgccgcc tgctgcgcac acatctatat ctactgctgg ttgctcaagt    29280
gcaggggtcg ccacccaaga tgaacaggta catggtccta tcgatcctag gcctgctggc    29340
cctggcggcc tgcagcgccg ccaaaaaaga gattaccttt gaggagcccg cttgcaatgt    29400
aactttcaag cccgagggtg accaatgcac caccctcgtc aaatgcgtta ccaatcatga    29460
gaggctgcgc atcgactaca aaaacaaaac tggccagttt gcggtctata gtgtgtttac    29520
gcccggagac ccctctaact actctgtcac cgtcttccag ggcggacagt ctaagatatt    29580
caattacact ttccctttt atgagttatg cgatgcggtc atgtacatgt caaaacagta    29640
caacctgtgg cctccctctc cccaggcgtg tgtggaaaat actgggtctt actgctgtat    29700
ggctttcgca atcactacgc tcgctctaat ctgcacggtg ctatacataa aattcaggca    29760
gaggcgaatc tttatcgatg aaaagaaaat gccttgatcg ctaacaccgg ctttctatct    29820
gcagaatgaa tgcaatcacc tccctactaa tcaccaccac cctccttgcg attgcccatg    29880
ggttgacacg aatcgaagtg ccagtggggt ccaatgtcac catggtgggc cccgccggca    29940
attccaccct catgtgggaa aaatttgtcc gcaatcaatg ggttcatttc tgctctaacc    30000
gaatcagtat caagcccaga gccatctgcg atgggcaaaa tctaactctg atcaatgtgc    30060
aaatgatgga tgctgggtac tattacgggc agcggggaga atcattaat tactggcgac    30120 cccacaagga ctacatgctg catgtagtcg aggcacttcc cactaccacc cccactacca    30180
cctctcccac caccaccacc actactacta ctactactac tactactact actaccacta    30240
ccgctgcccg ccatacccgc aaaagcacca tgattagcac aaagcccct cgtgctcact    30300 cccacgccgg cgggcccatc ggtgcgacct cagaaaccac cgagctttgc ttctgccaat    30360
gcactaacgc cagcgctcat gaactgttcg acctggagaa tgaggatgtc cagcagagct    30420
ccgcttgcct gacccaggag gctgtggagc ccgttgccct gaagcagatc ggtgattcaa    30480
taattgactc ttcttctttt gccactcccg aatacctcc cgattctact ttccacatca    30540
cgggtaccaa agaccctaac ctctctttct acctgatgct gctgctctgt atctctgtgg    30600
tctcttccgc gctgatgtta ctggggatgt tctgctgcct gatctgccgc agaaagagaa    30660
aagctcgctc tcagggccaa ccactgatgc ccttcccta ccccccggat tttgcagata    30720
acaagatatg agctcgctgc tgacactaac cgctttacta gcctgcgctc taacccttgt    30780
```

```
cgcttgcgac tcgagattcc acaatgtcac agctgtggca ggagaaaatg ttactttcaa   30840
ctccacggcc gatacccagt ggtcgtggag tggctcaggt agctacttaa ctatctgcaa   30900
tagctccact tcccccggca tatccccaac caagtaccaa tgcaatgcca gcctgttcac   30960
cctcatcaac gcttccaccc tggacaatgg actctatgta ggctatgtac cctttggtgg   31020
gcaaggaaag acccacgctt acaacctgga agttcgccag cccagaacca ctacccaagc   31080
ttctcccacc accaccacca ccaccaccat caccagcagc agcagcagca gcagccacag   31140
cagcagcagc agattattga ctttggtttt ggccagctca tctgccgcta cccaggccat   31200
ctacagctct gtgcccgaaa ccactcagat ccaccgccca gaaacgacca ccgccaccac   31260
cctacacacc tccagcgatc agatgccgac caacatcacc cccttggctc ttcaaatggg   31320
acttacaagc cccactccaa aaccagtgga tgcggccgag gtctccgccc tcgtcaatga   31380
ctgggcgggg ctgggaatgt ggtggttcgc cataggcatg atggcgctct gcctgcttct   31440
gctctggctc atctgctgcc tccaccgcag gcgagccaga ccccccatct atagacccat   31500
cattgtcctg aaccccgata tgatgggat ccatagattg gatggcctga aaaacctact   31560 ttttctttt acagtatgat aaattgagac atgcctcgca ttttcttgta catgttcctt   31620
ctcccacctt ttctggggtg ttctacgctg gccgctgtgt ctcacctgga ggtagactgc   31680
ctctcaccct tcactgtcta cctgctttac ggattggtca ccctcactct catctgcagc   31740
ctaatcacag taatcatcgc cttcatccag tgcattgatt acatctgtgt gcgcctcgca   31800
tacttcagac accaccgca gtaccgagac aggaacattg cccaacttct aagactgctc   31860
taatcatgca taagactgtg atctgccttc tgatcctctg catcctgccc accctcacct   31920
cctgccagta caccacaaaa tctccgcgca aaagacatgc ctcctgccgc ttacccaac   31980 tgtggaatat acccaaatgc tacaacgaaa agagcgagct ctccgaagct tggctgtatg   32040
gggtcatctg tgtcttagtt ttctgcagca ctgtctttgc cctcataatc taccccact   32100 ttgatttggg atggaacgcg atcgatgcca tgaattaccc caccttttccc gcacccgaga   32160 taattccact gcgacaagtt gtacccgttg tcgttaatca acgcccccca tccctacgc   32220 ccactgaaat cagctacttt aacctaacag gcggagatga ctgacgccct agatctagaa   32280
atggacggca tcagtaccga gcagcgtctc ctagagaggc gcaggcaggc ggctgagcaa   32340
gagcgcctca atcaggagct ccgagatctc gttaacctgc accagtgcaa aagaggcatc   32400
ttttgtctgg taaagcaggc caaagtcacc tacgagaaga ccggcaacag ccaccgcctc   32460
agttacaaat tgcccaccca cgccagaag ctggtgctca tggtgggtga aatccatc   32520 accgtcaccc agcactcggt agagaccgag gggtgtctgc actccccctg tcgggtcca   32580 gaagacctct gcaccctggt aaagaccctg tgcggtctca gagatttagt cccctttaac   32640
taatcaaaca ctggaatcaa taaaagaat cacttactta aaatcagaca gcaggtctct   32700
gtccagttta ttcagcagca cctccttcc ctcctcccaa ctctggtact ccaaacgcct   32760
tctggcggca aacttcctcc acaccctgaa gggaatgtca gattcttgct cctgtccctc   32820
cgcacccact atcttcatgt tgttgcagat gaagcgcacc aaaacgtctg acgagagctt   32880
caaccccgtg taccctatg acacggaaag cggcctccc tccgtcctt tcctcacccc   32940 tccctccgtg tctcccgatg gattccaaga aagtccccc ggggtcctgt ctctgaacct   33000
ggccgagccc ctggtcactt cccacggcat gctcgccctg aaaatgggaa gtggcctctc   33060
cctggacgac gctggcaacc tcacctctca agatatcacc accgctagcc ctccccctcaa   33120
```

```
aaaaaccaag accaacctca gcctagaaac ctcatccccc ctaactgtga gcacctcagg    33180
cgccctcacc gtagcagccg ccgctcccct ggcggtggcc ggcacctccc tcaccatgca    33240
atcagaggcc cccctgacag tacaggatgc aaaactcacc ctggccacca aaggccccct    33300
gaccgtgtct gaaggcaaac tggccttgca acatcggcc ccgctgacgg ccgctgacag     33360
cagcaccctc acagtcagtg ccacaccacc ccttagcaca agcaatggca gcttgggtat    33420
tgacatgcaa gcccccattt acaccaccaa tggaaaacta ggacttaact ttggcgctcc    33480
cctgcatgtg gtagacagcc taaatgcact gactgtagtt actggccaag gtcttacgat    33540
aaacggaaca gccctacaaa ctagagtctc aggtgccctc aactatgaca catcaggaaa    33600
cctagaattg agagctgcag ggggtatgcg agttgatgca aatggtcaac ttatccttga    33660
tgtagcttac ccatttgatg cacaaaacaa tctcagcctt aggcttggac agggacccct    33720
gtttgttaac tctgcccaca acttggatgt taactacaac agaggcctct acctgttcac    33780
atctggaaat accaaaaagc tagaagttaa tatcaaaaca gccaagggtc tcatttatga    33840
tgacactgct atagcaatca atgcgggtga tgggctacag tttgactcag gctcagatac    33900
aaatccatta aaaactaaac ttggattagg actggattat gactccagca gagccataat    33960
tgctaaactg ggaactggcc taagctttga acacacaggt gccatcacag taggcaacaa    34020
aaatgatgac aagcttacct tgtggaccac accagaccca tcccctaact gtagaatcta    34080
ttcagagaaa gatgctaaat tcacacttgt tttgactaaa tgcggcagtc aggtgttggc    34140
cagcgtttct gttttatctg taaaaggtag ccttgcgccc atcagtggca cagtaactag    34200
tgctcagatt gtcctcagat ttgatgaaaa tggagttcta ctaagcaatt cttcccttga    34260
ccctcaatac tggaactaca gaaaaggtga ccttacagag ggcactgcat ataccaacgc    34320
agtgggattt atgcccaacc tcacagcata cccaaaaaca cagagccaaa ctgctaaaag    34380
caacattgta agtcaggttt acttgaatgg ggacaaatcc aaacccatga ccctcaccat    34440
taccctcaat ggaactaatg aaacaggaga tgccacagta agcacttact ccatgtcatt    34500
ctcatggaac tggaatggaa gtaattacat taatgaaacg ttccaaacca actccttcac    34560
cttctcctac atcgcccaag aataaaaagc atgacgctgt tgatttgatt caatgtgttt    34620
ctgttttatt ttcaagcaca acaaaatcat tcaagtcatt cttccatctt agcttaatag    34680
acacagtagc ttaatagacc cagtagtgca aagccccatt ctagcttata gatcagacag    34740
tgataattaa ccaccaccac caccatacct tttgattcag gaaatcatga tcatcacagg    34800
atcctagtct tcaggccgcc ccctccctcc caagacacag aatacacagt cctctccccc    34860
cgactggctt taaataacac catctggttg gtcacagaca tgttcttagg ggttatattc    34920
cacacggtct cctgccgcgc caggcgctcg tcggtgatgt tgataaactc tcccggcagc    34980
tcgctcaagt tcacgtcgct gtccagcggc tgaacctccg gctgacgcga taactgtgcg    35040
accggctgct ggacgaacgg aggccgcgcc tacaagggg tagagtcata atcctcggtc      35100
aggatagggc ggtgatgcag cagcagcgag cgaaacatct gctgccgccg ccgctccgtc    35160
cggcaggaaa acaacacgcc ggtggtctcc tccgcgataa tccgcaccgc ccgcagcatc    35220
agcttcctcg ttctccgcgc gcagcacctc acccttatct cgctcaaatc ggcgcagtag    35280
gtacagcaca gcaccacgat gttattcatg atcccacagt gcagggcgct gtatccaaag    35340
ctcatgccgg gaaccaccgc ccccacgtgg ccatcgtacc acaagcgcac gtaaatcaag    35400
tgtcgacccc tcatgaacgc gctggacaca aacattactt ccttgggcat gttgtaattc    35460
accacctccc ggtaccagat aaacctctgg ttgaacaggg caccttccac caccatcctg    35520
```

```
aaccaagagg ccagaacctg cccaccggct atgcactgca gggaacccgg gttggaacaa    35580
tgacaatgca gactccaagg ctcgtaaccg tggatcatcc ggctgctgaa ggcatcgatg    35640
ttggcacaac acagacacac gtgcatgcac tttctcatga ttagcagctc ttccctcgtc    35700
aggatcatat cccaaggaat aacccattct tgaatcaacg taaaacccac acagcaggga    35760
aggcctcgca cataactcac gttgtgcatg gtcagcgtgt tgcattccgg aaacagcgga    35820
tgatcctcca gtatcgaggc gcgggtctcc ttctcacagg gaggtaaagg gtccctgctg    35880
tacggactgc gccgggacga ccgagatcgt gttgagcgta gtgtcatgga aaagggaacg    35940
ccggacgtgg tcatacttct tgaagcagaa ccaggttcgc gcgtggcagg cctccttgcg    36000
tctgcggtct cgccgtctag ctcgctccgt gtgatagttg tagtacagcc actcccgcag    36060
agcgtcgagg cgcaccctgg cttccggatc tatgtagact ccgtcttgca ccgcggccct    36120
gataatatcc accaccgtag aataagcaac acccagccaa gcaatacact cgctctgcga    36180
gcggcagaca ggaggagcgg gcagagatgg gagaaccatg ataaaaaact ttttttaaag    36240
aatattttcc aattcttcga aagtaagatc tatcaagtgg cagcgctccc ctccactggc    36300
gcggtcaaac tctacggcca aagcacagac aacggcattt ctaagatgtt ccttaatggc    36360
gtccaaaaga cacaccgctc tcaagttgca gtaaactatg aatgaaaacc catccggctg    36420
attttccaat atagacgcgc cggcagcgtc caccaaaccc agataatttt cttctctcca    36480
gcggtttacg atctgtctaa gcaaatccct tatatcaagt ccgaccatgc caaaaatctg    36540
ctcaagagcg ccctccacct tcatgtacaa gcagcgcatc atgattgcaa aaattcaggt    36600
tcttcagaga cctgtataag attcaaaatg gaacattaa caaaaattcc tctgtcgcgc    36660
agatcccttc gcagggcaag ctgaacataa tcagacaggt ccgaacggac cagtgaggcc    36720
aaatccccac caggaaccag atccagagac cctatactga ttatgacgcg catactcggg    36780
gctatgctga ccagcgtagc gccgatgtag gcgtgctgca tgggcggcga gataaaatgc    36840
aaagtgctgg ttaaaaaatc aggcaaagcc tcgcgcaaaa aagctaacac atcataatca    36900
tgctcatgca ggtagttgca ggtaagctca ggaaccaaaa cggaataaca cacgattttc    36960
ctctcaaaca tgacttcgcg gatactgcgt aaaacaaaaa attataaata aaaaattaat    37020
taaataactt aaacattgga agcctgtctc acaacaggaa aaaccacttt aatcaacata    37080
agacgggcca cgggcatgcc ggcatagccg taaaaaaatt ggtccccgtg attaacaagt    37140
accacagaca gctccccggt catgtcgggg gtcatcatgt gagactctgt atacacgtct    37200
ggattgtgaa catcagacaa acaaagaaat cgagccacgt agcccggagg tataatcacc    37260
cgcaggcgga ggtacagcaa aacgaccccc ataggaggaa tcacaaaatt agtaggagaa    37320
aaaaatacat aaacaccaga aaaacccctgt tgctgaggca aaatagcgcc ctcccgatcc    37380 aaacaacat aaagcgcttc cacaggagca gccataacaa agacccgagt cttaccagta    37440
aaagaaaaaa gatctctcaa cgcagcacca gcaccaacac ttcgcagtgt aaaaggccaa    37500
gtgccgagag agtatatata ggaataaaaa gtgacgtaaa cgggcaaagt ccaaaaaacg    37560
cccagaaaaa ccgcacgcga acctacgccc cgaaacgaaa gccaaaaaac actagacact    37620
cccttccggc gtcaacttcc gctttcccac gctacgtcac ttccccccggt caaacaaact    37680 acatatcccg aacttccaag tcgccacgcc caaaacaccg cctacacctc cccgcccgcc    37740
ggcccgcccc cggacccgcc tcccgccccg cgccgcccat ctcattatca tattggcttc    37800
aatccaaaat aaggtatatt attgatgatg                                    37830
```

<210> SEQ ID NO 2
<211> LENGTH: 36571
<212> TYPE: DNA
<213> ORGANISM: Chimpanzee adenovirus

<400> SEQUENCE: 2

```
catcatcaat aatatacctc aaacttttgg tgcgcgttaa tatgcaaatg agctgtttga      60
atttggggat gcggggcgct gattggctgc gggagcggcg accgttaggg gcggggcggg     120
tgacgttttg atgacgtggc cgtgaggcgg agccggtttg caagttctcg tgggaaaagt     180
gacgtcaaac gaggtgtggt ttgaacacgg aaatactcaa ttttcccgcg ctctctgaca     240
ggaaatgagg tgtttctggg cggatgcaag tgaaaacggg ccattttcgc gcgaaaactg     300
aatgaggaag tgaaaatctg agtaatttcg cgtttatggc agggaggagt atttgccgag     360
ggccgagtag actttgaccg attacgtggg ggtttcgatt accgtatttt tcacctaaat     420
ttccgcgtac ggtgtcaaag tccggtgttt ttacgtaggc gtcagctgat cgccagggta     480
tttaaacctg cgctcactag tcaagaggcc actcttgagt ccagcgagt agagttttct      540 cctccgcgcc gcgagtcaga tctacacttt gaaagatgag gcacttgaga gacctgcccg     600
gtaatgtttt cctggctact gggaacgaga ttctggaatt ggtggtggac gccatgatgg     660
gtgacgaccc tcccgagccc cctaccccat ttgaggcgcc ttcgctgtac gatttgtatg     720
atctggaggt ggatgtgccc gagaacgacc ccaacgagga ggcggtgaat gatttgttta     780
gcgatgccgc gctgctggct gccgagcagg ctaatacgga ctttggctca gacagcgatt     840
cttctctcca tacccgaga cccggcagag gtgagaaaaa gatccccgag cttaaagggg     900
aagagctcga cctgcgctgc tatgaggaat gcttgcctcc gagcgatgat gaggaggacg     960
aggaggcgat tcgagctgca gcgaaccagg gagtgaaagc tgcgggcgaa agctttagcc    1020
tggactgtcc tactctgccc ggacacggct gtaagtcttg tgaatttcat cgcatgaata    1080
ctggagataa gaatgtgatg tgtgccctgt gctatatgag agcttacaac cattgtgttt    1140
acagtaagtg tgattaactt tagttgggaa ggcagagggt gactgggtgc tgactggttt    1200
atttatgtat atgtttttta tgtgtaggtc ccgtctctga cgcagatgag accccccactt    1260 cagagtgcat ttcatcaccc ccagaaattg gcgaggaacc gcccgaagat attattcata    1320
gaccagttgc agtgagagtc accgggcgga gagcagctgt ggagagtttg gatgacttgc    1380
tacagggtgg ggatgaacct ttggacttgt gtacccggaa acgccccagg cactaagtgc    1440
cacacatgtg tgtttactta aggtgatgtc agtatttata gggtgtggag tgcaataaaa    1500
tccgtgttga ctttaagtgc gtggtttatg actcaggggt ggggactgtg ggtatataag    1560
caggtgcaga cctgtgtggt cagttcagag caggactcat ggagatctgg acggtcttgg    1620
aagactttca ccagactaga cagctgctag agaactcatc ggagggagtc tcttacctgt    1680
ggagattctg cttcggtggg cctctagcta agctagtcta tagggccaag caggattata    1740
aggatcaatt tgaggatatt ttgagagagt gtcctggtat ttttgactct ctcaacttgg    1800
gccatcagtc tcactttaac cagagtattc tgagagccct tgactttttcc actcctggca    1860 gaactaccgc cgcggtagcc ttttttgcct ttatccttga caatggagt caagaaaccc    1920 atttcagcag ggattaccgt ctggactgct tagcagtagc tttgtggaga acatggaggt    1980
gccagcgcct gaatgcaatc tccggctact tgccagtaca gccggtagac acgctgagga    2040
tcctgagtct ccagtcaccc caggaacacc aacgccgcca gcagccgcag caggagcagc    2100
agcaagagga ggaccgagaa gagaacccga gagccggtct ggaccctccg gtggcggagg    2160
```

```
aggaggagta gctgacttgt ttcccgagct gcgccgggtg ctgactaggt cttccagtgg   2220
acgggagagg gggattaagc gggagaggca tgaggagact agtcacagaa ctgaactgac   2280
tgtcagtctg atgagccgca ggcgcccaga atcggtgtgg tggcatgagg tgcagtcgca   2340
ggggatagat gaggtctcgg tgatgcatga gaaatattcc ctagaacaag tcaagacttg   2400
ttggttggag cctgaggatg attgggaggt agccatcagg aattatgcca agctagctct   2460
gaagccagac aagaagtaca agattaccaa actgattaat atcagaaatt cctgctacat   2520
ttcagggaat ggggccgagg tggagatcag tacccaggag agggtggcct tcagatgctg   2580
catgatgaat atgtacccgg gggtggtggg catggaggga gtcaccttta tgaacgcgag   2640
gttcaggggc gatgggtata atggggtggt ctttatggcc aacaccaagc tgacagtgca   2700
cggatgctcc ttctttggct tcaataacat gtgcatcgag gcctgggca gtgtttcagt   2760 gaggggatgc agttttcag ccaactggat ggggtcgtg gcagaacca agagcaaggt   2820 gtcagtgaag aaatgcctgt tcgagaggtg ccacctgggg gtgatgagcg agggcgaagc   2880
caaagtcaaa cactgcgcct ctactgagac gggctgcttt gtgctgatca agggcaatgc   2940
ccaagtcaag cataacatga tctgtggggc ctcggatgag cgcggctacc agatgctgac   3000
ctgcgccggt gggaacagcc atatgctggc caccgtgcat gtgacctcgc accccgcaa   3060 gacatggccc gagttcgagc acaacgtcat gacccgctgc aatgtgcacc tgggctcccg   3120
ccgaggcatg ttcatgccct accagtgcaa catgcaattt gtgaaggtgc tgctggagcc   3180
cgatgccatg tccagagtga gcctgacggg ggtgtttgac atgaatgtgg agatgtggaa   3240
aattctgaga tatgatgaat ccaagaccag gtgccgggcc tgcgaatgcg gaggcaagca   3300
cgccaggctt cagcccgtgt gtgtggaggt gacggaggac ctgcgacccg atcatttggt   3360
gttgtcctgc aacgggacgg agttcggctc cagcggggaa gaatctgact agagtgagta   3420
gtgtttgggg gaggtggagg gcctggatga ggggcagaat gactaaaatc tgtgtttttc   3480
tgcgcagcag catgagcgga agcgcctcct ttgagggagg ggtattcagc ccttatctga   3540
cggggcgtct cccctcctgg gcgggagtgc gtcagaatgt gatgggatcc acggtggacg   3600
gccggcccgt gcagcccgcg aactcttcaa ccctgaccta cgcgaccctg agctcctcgt   3660
ccgtggacgc agctgccgcc gcagctgctg cttccgccgc cagcgccgtg cgcggaatgg   3720
ccctgggcgc cggctactac agctctctgg tggccaactc gagttccacc aataatcccg   3780
ccagcctgaa cgaggagaag ctgctgctgc tgatggccca gctcgaggcc ctgacccagc   3840
gcctgggcga gctgacccag caggttgctc agctgcaggc ggagacgcgg gccgcggttg   3900
ccacggtgaa aaccaaataa aaaatgaatc aataaataaa cggagacggt tgttgatttt   3960
aacacagagt cttgaatctt tatttgattt ttcgcgcgcg gtaggccctg gaccaccggt   4020
ctcgatcatt gagcacccgg tggatctttt ccaggacccg gtagaggtgg gcttggatgt   4080
tgaggtacat gggcatgagc ccgtcccggg ggtggaggta gctccattgc agggcctcgt   4140 gctcggggt ggtgttgtaa atcacccagt catagcaggg gcgcagggcg tggtgctgca   4200
cgatgtcctt gaggaggaga ctgatggcca cgggcagccc cttggtgtag gtgttgacga   4260
acctgttgag ctgggaggga tgcatgcggg gggagatgag atgcatcttg gcctggatct   4320
tgagattggc gatgttcccg cccagatccc gccgggggtt catgttgtgc aggaccacca   4380
gcacggtgta tccggtgcac ttggggaatt tgtcatgcaa cttggaaggg aaggcgtgaa   4440
agaatttgga gacgcccttg tggccgccca ggttttccat gcactcatcc atgatgatgg   4500
```

```
cgatgggccc gtgggcggcg gcctgggcaa agacgtttcg ggggtcggac acatcgtagt    4560
tgtggtcctg ggtgagctcg tcataggcca ttttaatgaa tttggggcgg agggtgcccg    4620
actgggggac gaaggtgccc tcgatcccgg gggcgtagtt gccctcgcag atctgcatct    4680
cccaggcctt gagctcggag ggggggatca tgtccacctg cggggcgatg aaaaaaacgg    4740 tttccgggc gggggagatg agctgcgccg aaagcaggtt ccggagcagc tgggacttgc     4800
cgcagccggt ggggccgtag atgaccccga tgaccggctg caggtggtag ttgagggaga    4860
gacagctgcc gtcctcgcgg aggaggggg ccacctcgtt catcatctcg cgcacatgca     4920
tgttctcgcg cacgagttcc gccaggaggc gctcgccccc cagcgagagg agctcttgca    4980
gcgaggcgaa gttttcagc ggcttgagcc cgtcggccat gggcattttg gagagggtct     5040
gttgcaagag ttccagacgg tcccagagct cggtgatgtg ctctagggca tctcgatcca    5100
gcagacctcc tcgtttcgcg ggttggggcg actgcgggag tagggcacca ggcgatgggc    5160
gtccagcgag gccagggtcc ggtccttcca gggtcgcagg gtccgcgtca gcgtggtctc    5220
cgtcacggtg aaggggtgcg cgccgggctg ggcgcttgcg agggtgcgct tcaggctcat    5280
ccggctggtc gagaaccgct cccggtcggc gccctgtgcg tcggccaggt agcaattgag    5340
catgagttcg tagttgagcg cctcggccgc gtggcccttg gcgcggagct tacctttgga    5400
agtgtgtccg cagacgggac agaggaggga cttgagggcg tagagcttgg gggcgaggaa    5460
gacggactcg ggggcgtagg cgtccgcgcc gcagctggcg cagacggtct cgcactccac    5520
gagccaggtg aggtcgggc ggtcggggtc aaaaacgagg tttcctccgt gcttttttgat    5580 gcgtttctta cctctggtct ccatgagctc gtgtccccgc tgggtgacaa agaggctgtc    5640
cgtgtccccg tagaccgact ttatgggccg gtcctcgagc ggggtgccgc ggtcctcgtc    5700
gtagaggaac cccgcccact ccgagacgaa ggcccgggtc caggccagca cgaaggaggc    5760
cacgtgggag gggtagcggt cgttgtccac cagcgggtcc accttctcca gggtatgcaa    5820
gcacatgtcc ccctcgtcca catccaggaa ggtgattggc ttgtaagtgt aggccacgtg    5880
accgggggtc ccggccgggg gggtataaaa gggggcgggc ccctgctcgt cctcactgtc    5940
ttccggatcg ctgtccagga gcgccagctg ttggggtagg tattccctct cgaaggcggg    6000
catgacctcg gcactcaggt tgtcagttc tagaaacgag gaggatttga tattgacggt     6060
gccgttggag acgcctttca tgagcccctc gtccatctgg tcagaaaaga cgatcttttt    6120
gttgtcgagc ttggtggcga aggagccgta gagggcgttg gagagcagct ggcgatgga     6180 gcgcatggtc tggttctttt ccttgtcggc gcgctccttg gcggcgatgt tgagctgcac    6240
gtactcgcgc gccacgcact ccattcgggg gaagacggtg gtgagctcgt cgggcacgat    6300 tctgaccccgc cagccgcggt tgtgcagggt gatgaggtcc acgctggtgg ccacctcgcc    6360
gcgcaggggc tcgttggtcc agcagaggcg cccgcccttg cgcgagcaga aggggggcag    6420
cgggtccagc atgagctcgt cggggggggtc ggcgtccacg tgaagatgc cgggcaggag    6480 ctcggggtcg aagtagctga tgcaggtgcc cagatcgtcc agcgccgctt gccagtcgcg    6540
cacggccagc gcgcgctcgt aggggctgag gggcgtgccc cagggcatgg ggtgcgtgag    6600 cgcggaggc tacatgccgc agatgtcgta gacgtagagg ggctcctcga ggacgccgat     6660
gtaggtgggg tagcagcgcc ccccgcggat gctggcgcgc acgtagtcgt acagctcgtg    6720
cgagggcgcg aggagcccg tgccgaggtt ggagcgttgc ggcttttcgg cgcggtagac     6780
gatctggcgc aagatggcgt gggagttgga ggagatggtg ggcctctgga agatgttgaa    6840
gtgggcgtgg ggcaggccga ccgagtccct gatgaagtgg gcgtaggagt cctgcagctt    6900
```

```
ggcgacgagc tcggcggtga cgaggacgtc cagggcgcag tagtcgaggg tctcttggat    6960
gatgtcgtac ttgagctggc ccttctgctt ccacagctcg cggttgagaa ggaactcttc    7020
gcggtccttc cagtactctt cgaggggaa cccgtcctga tcggcacggt aagagcccac     7080
catgtagaac tggttgacgg ccttgtaggc gcagcagccc ttctccacgg ggagggcgta    7140
agcttgcgcg gccttgcgca gggaggtgtg ggtgagggcg aaggtgtcgc gcaccatgac    7200
tttgaggaac tggtgcttga agtcgaggtc gtcgcagccg ccctgctccc agagttggaa    7260
gtccgtgcgc ttcttgtagg cggggttggg caaagcgaaa gtaacatcgt tgaagaggat    7320
cttgcccgcg cggggcatga agttgcgagt gatgcgaaa ggctggggca cctcggcccg     7380
gttgttgatg acctgggcgg cgaggacgat ctcgtcgaag ccgttgatgt tgtgcccgac    7440
gatgtagagt tccacgaatc gcgggcagcc cttgacgtgg ggcagcttct tgagctcgtc    7500
gtaggtgagc tcggcggggt cgctgagccc gtgctgctcg agggcccagt cggcgacgtg    7560
ggggttggcg ctgaggaagg aagtccagag atccacggcc agggcggtct gcaagcggtc    7620
ccggtactga cggaactgct ggcccacggc cattttttcg ggggtgacgc agtagaaggt    7680
gcgggggtcg ccgtgccagc ggtcccactt gagttggagg gcgaggtcgt gggcgagctc    7740
gacgagcggc gggtccccgg agagtttcat gaccagcatg aaggggacga gctgcttgcc    7800
gaaggacccc atccaggtgt aggtttccac atcgtaggtg aggaagagcc tttcggtgcg    7860
aggatgcgag ccgatgggga gaactggat ctcctgccac cagttggagg aatggctgtt     7920
gatgtgatgg aagtagaaat gccgacggcg cgccgagcac tcgtgcttgt gtttatacaa    7980
gcgtccgcag tgctcgcaac gctgcacggg atgcacgtgc tgcacgagct gtacctgggt    8040
tcctttgacg aggaatttca gtgggcagtg gagcgctggc ggctgcatct ggtgctgtac    8100
tacgtcctgg ccatcggcgt ggccatcgtc tgcctcgatg gtggtcatgc tgacgagccc    8160
gcgcgggagg caggtccaga cctcggctcg gacgggtcgg agagcgagga cgagggcgcg    8220
caggccggag ctgtccaggg tcctgagacg ctgcggagtc aggtcagtgg gcagcggcgg    8280
cgcgcggttg acttgcagga gcttttccag ggcgcgcggg aggtccagat ggtacttgat    8340
ctccacggcg ccgttggtgg cgacgtccac ggcttgcagg gtcccgtgcc cctggggcgc    8400
caccaccgtg ccccgtttct tcttgggcgg cggcggctcc atgcttagaa gcggcggcga    8460
ggacgcgcgc cgggcggcag gggcggctcg ggcccggag gcaggggcgg caggggcacg     8520
tcggcgccgc gcgcgggcag gttctggtac tgcgcccgga aagactggc gtgagcgacg     8580 acgcgacggt tgacgtcctg gatctgacgc ctctgggtga aggccacggg acccgtgagt    8640
ttgaacctga aagagagttc gacagaatca atttcggtat cgttgacggc ggcctgccgc    8700
aggatctctt gcacgtcgcc cgagttgtcc tggtaggcga tctcggtcat gaactgctcg    8760
atctcctcct cctgaaggtc tccgcggccg gcgcgctcga cggtggccgc gaggtcgttg    8820
gagatgcggc ccatgagctg cgagaaggcg ttcatgccgg cctcgttcca gacgcggctg    8880
tagaccacgg ctccgttggg gtcgcgcgcg cgcatgacca cctgggcgag gttaagctcg    8940
acgtggcgcg tgaagaccgc gtagttgcag aggcgctggt agaggtagtt gagcgtggtg    9000
gcgatgtgct cggtgacgaa gaagtacatg atccagcggc ggagcggcat ctcgctgacg    9060
tcgcccaggg cttccaagcg ctccatggtc tcgtagaagt ccacggcgaa gttgaaaaac    9120
tgggagttgc gcgccgagac ggtcaactcc tcctccagaa gacggatgag ctcggcgatg    9180
gtggcgcgca cctcgcgctc gaaggccccg gggggctcct cttcttccat ctcctcctcc    9240
```

```
tcttcctcct ccactaacat ctcttctact tcctcctcag gaggcggcgg cggggggaggg   9300 gccctgcgtc gccggcggcg cacgggcaga cggtcgatga agcgctcgat ggtctccccg   9360
cgccggcgac gcatggtctc ggtgacggcg cgcccgtcct cgcggggccg cagcgtgaag   9420
acgccgccgc gcatctccag gtggccgccg ggggggtctc cgttgggcag ggagagggcg   9480
ctgacgatgc atcttatcaa ttggcccgta gggactccgc gcaaggacct gagcgtctcg   9540
agatccacgg gatccgaaaa ccgctgaacg aaggcttcga gccagtcgca gtcgcaaggt   9600
aggctgagcc cggtttcttg ttcttcgggt atttggtcgg gaggcgggcg ggcgatgctg   9660
ctggtgatga agttgaagta ggcggtcctg agacggcgga tggtggcgag gagcaccagg   9720
tccttgggcc cggcttgctg gatgcgcaga cggtcggcca tgccccaggc gtggtcctga   9780
cacctgcgca ggtccttgta gtagtcctgc atgagccgct ctacgggcac gtcctcctcg   9840
cccgcgcggc cgtgcatgcg cgtgagcccg aacccgcgct gcggctggac gagcgccagg   9900
tcggcgacga cgcgctcggc gaggatggcc tgctggatct gggtgagggt ggtctggaag   9960
tcgtcgaagt cgacgaagcg gtggtaggct ccggtgttga tggtgtagga gcagttggcc  10020
atgacggacc agttgacggt ctggtggccg gggcgcacga gctcgtggta cttgaggcgc  10080
gagtaggcgc gcgtgtcgaa gatgtagtcg ttgcaggtgc gcacgaggta ctggtatccg  10140
acgaggaagt gcggcggcgg ctggcggtag agcggccatc gctcggtggc ggggcgccg   10200 ggcgcgaggt cctcgagcat gaggcggtgg tagccgtaga tgtacctgga catccaggtg  10260
atgccggcgg cggtggtgga ggcgcgcggg aactcgcgga cgcggttcca gatgttgcgc  10320
agcggcagga agtagttcat ggtggccgcg gtctggcccg tgaggcgcgc gcagtcgtgg  10380
atgctctaga catacgggca aaaacgaaag cggtcagcgg ctcgactccg tggcctggag  10440
gctaagcgaa cgggttgggc tgcgcgtgta ccccggttcg aatctcgaat caggctgag   10500 ccgcagctaa cgtggtactg gcactcccgt ctcgacccaa gcctgctaac gaaacctcca  10560
ggatacggag gcgggtcgtt ttttggcctt ggtcgctggt catgaaaaac tagtaagcgc  10620
ggaaagcggc cgcccgcgat ggctcgctgc cgtagtctgg agaaagaatc gccagggttg  10680
cgttgcggtg tgccccggtt cgagcctcag cgctcggtgc cggccggatt ccgcggctaa  10740
cgtgggcgtg gctgccccgt cgtttccaag accccttagc cagccgactt ctccagttac  10800
ggagcgagcc cctcttttc ttgtgttttt gccagatgca tcccgtactg cggcagatgc  10860
gcccccaccc tccaccacaa ccgcccctac cgcagcagca gcaacagccg gcgcttctgc  10920
ccccgcccca gcagcagcag ccagccacta ccgcggcggc cgccgtgagc ggagccggcg  10980
ttcagtatga cctggccttg gaagagggcg aggggctggc gcggctgggg gcgtcgtcgc  11040
cggagcggca cccgcgcgtg cagatgaaaa gggacgctcg cgaggcctac gtgcccaagc  11100
agaacctgtt cagagacagg agcggcgagg agcccgagga gatgcgcgcc tcccgcttcc  11160
acgcggggcg ggagctgcgg cgcggcctgg accgaaagcg ggtgctgagg gacgaggatt  11220
tcgaggcgga cgagctgacg gggatcagcc ccgcgcgcgc gcacgtggcc gcggccaacc  11280
tggtcacggc gtacgagcag accgtgaagg aggagagcaa ctttcaaaaa tccttcaaca  11340
accacgtgcg cacgctgatc gcgcgcgagg aggtgacccc tgggcctgatg cacctgtggg  11400 acctgctgga ggccatcgtg cagaaccccca cgagcaagcc gctgacggcg cagctgtttc  11460
tggtggtgca gcacagtcgg gacaacgaga cgttcaggga ggcgctgctg aatatcaccg  11520
agcccgaggg ccgctggctc ctggacctgg tgaacattct gcagagcatc gtggtgcagg  11580
agcgcgggct gccgctgtcc gagaagctgg cggccatcaa cttctcggtg ctgagcctgg  11640
```

```
gcaagtacta cgctaggaag atctacaaga ccccgtacgt gcccatagac aaggaggtga   11700
agatcgacgg gttttacatg cgcatgaccc tgaaagtgct gaccctgagc gacgatctgg   11760
gggtgtaccg caacgacagg atgcaccgcg cggtgagcgc cagccgccgg cgcgagctga   11820
gcgaccagga gctgatgcac agcctgcagc gggccctgac cggggccggg accgaggggg   11880
agagctactt tgacatgggc gcggacctgc gctggcagcc cagccgccgg gccttggaag   11940
ctgccggcgg cgtgccctac gtggaggagg tggacgatga ggaggaggag ggcgagtacc   12000
tggaagactg atggcgcgac cgtattttgg ctagatgcag caacagccac cgccgcctcc   12060
tgatcccgcg atgcgggcgg cgctgcagag ccagccgtcc ggcattaact cctcggacga   12120
ttggacccag gccatgcaac gcatcatggc gctgacgacc cgcaatcccg aagcctttag   12180
acagcagcct caggccaacc ggctctcggc catcctggag gccgtggtgc cctcgcgctc   12240
gaaccccacg cacgagaagg tgctggccat cgtgaacgcg ctggtggaga caaggccat    12300 ccgcggcgac gaggccgggc tggtgtacaa cgcgctgctg gagcgcgtgg cccgctacaa   12360
cagcaccaac gtgcagacga acctggaccg catggtgacc gacgtgcgcg aggcggtgtc   12420
gcagcgcgag cggttccacc gcgagtcgaa cctgggctcc atggtggcgc tgaacgcctt   12480
cctgagcacg cagcccgcca acgtgccccg gggccaggag gactacacca acttcatcag   12540
cgcgctgcgg ctgatggtgg ccgaggtgcc ccagagcgag gtgtaccagt cggggccgga   12600
ctacttcttc cagaccagtc gccagggctt gcagaccgtg aacctgagcc aggcttttcaa   12660 gaacttgcag ggactgtggg gcgtgcaggc cccggtcggg gaccgcgcga cggtgtcgag   12720
cctgctgacg ccgaactcgc gcctgctgct gctgctggtg gcgcccttca cggacagcgg   12780
cagcgtgagc cgcgactcgt acctgggcta cctgcttaac ctgtaccgcg aggccatcgg   12840
gcaggcgcac gtggacgagc agacctacca ggagatcacc cacgtgagcc gcgcgctggg   12900
ccaggaggac ccgggcaacc tggaggccac cctgaacttc ctgctgacca accggtcgca   12960
gaagatcccg ccccagtacg cgctgagcac cgaggaggag cgcatcctgc gctacgtgca   13020
gcagagcgtg gggctgttcc tgatgcagga gggggccacg cccagcgccg cgctcgacat   13080
gaccgcgcgc aacatggagc ccagcatgta cgcccgcaac cgcccgttca tcaataagct   13140
gatggactac ttgcatcggg cggccgccat gaactcggac tactttacca acgccatctt   13200
gaaccccgca ctggctcccgc cgcccgggtt ctacacgggc gagtacgaca tgcccgaccc   13260
caacgacggg ttcctgtggg atgacgtgga cagcagcgtg ttctcgccgc gtcccaccac   13320
caccgtgtgg aagaaagagg gcggggaccg gcggccgtcc tcggcgctgt ccggtcgcgc   13380
gggtgctgcc gcggcggtgc ccgaggccgc cagccccttt ccgagcctgc ccttttcgct   13440
gaacagcgtg cgcagcagcg agctgggtcg gctgacgcgg ccgcgcctgc tgggcgagga   13500
ggagtacctg aacgactcct tgttgaggcc cgagcgcgaa aagaacttcc ccaataacgg   13560
gatagagagc ctggtggaca agatgagccg ctggaagacg tacgcgcacg agcacaggga   13620
cgagccccga gctagcagcg caggcacccg tagacgccag cggcacgaca ggcagcgggg   13680
tctggtgtgg gacgatgagg attccgccga cgacagcagc gtgttggact tgggtgggag   13740
tggtggtggt aacccgttcg ctcacttgcg ccccgtatc gggcgcctga tgtaagaatc    13800
tgaaaaataa aaaacggtac tcaccaaggc catggcgacc agcgtgcgtt cttctctgtt   13860
gtttgtagta gtatgatgag gcgcgtgtac ccggagggtc ctcctccctc gtacgagagc   13920
gtgatgcagc aggcggtggc ggcggcgatg cagcccccgc tggaggcgcc ttacgtgccc   13980
```

```
ccgcggtacc tggcgcctac ggaggggcgg aacagcattc gttactcgga gctggcaccc    14040
ttgtacgata ccacccggtt gtacctggtg gacaacaagt cggcggacat cgcctcgctg    14100
aactaccaga cgaccacag caacttcctg accaccgtgg tgcagaacaa cgatttcacc    14160 cccacgagg ccagcaccca gaccatcaac tttgacgagc gctcgcggtg gggcggccag    14220
ctgaaaacca tcatgcacac caacatgccc aacgtgaacg agttcatgta cagcaacaag    14280
ttcaaggcgc gggtgatggt ctcgcgcaag accccccaacg gggtcacagt aacagatggt    14340
agtcaggacg agctgaccta cgagtgggtg gagtttgagc tgcccgaggg caacttctcg    14400
gtgaccatga ccatcgatct gatgaacaac gccatcatcg acaactactt ggcggtgggg    14460
cggcagaacg gggtgctgga gagcgacatc ggcgtgaagt tcgacacgcg caacttccgg    14520
ctgggctggg accccgtgac cgagctggtg atgccgggcg tgtacaccaa cgaggccttc    14580
caccccgaca tcgtcctgct gcccggctgc ggcgtggact tcaccgagag ccgcctcagc    14640
aacctgctgg gcatccgcaa gcggcagccc ttccaggagg gcttccagat cctgtacgag    14700
gacctggagg ggggcaacat ccccgcgctc ttggatgtcg aagcctacga gaaaagcaag    14760
gaggatagca ccgccgtggc taccgccgcg actgtggcag atgccactgt caccaggggc    14820
gatacattcg ccacccaggc ggaggaagca gccgccctag cggcgaccga tgatagtgaa    14880
agtaagatag ttatcaagcc ggtggagaag gacagcaagg acaggagcta caacgttcta    14940
tcggatggaa agaacaccgc ctaccgcagc tggtacctgg cctacaacta cggcgacccc    15000
gagaagggcg tgcgctcctg gacgctgctc accacctcgg acgtcacctg cggcgtggag    15060
caagtctact ggtcgctgcc cgacatgatg caagacccgg tcaccttccg ctccacgcgt    15120
caagttagca actaccggt ggtgggcgcc gagctcctgc ccgtctactc caagagcttc    15180
ttcaacgagc aggccgtcta ctcgcagcag ctgcgcgcct tcacctcgct cacgcacgtc    15240
ttcaaccgct tccccgagaa ccagatcctc gtccgcccgc ccgcgcccac cattaccacc    15300
gtcagtgaaa acgttcctgc tctcacagat cacgggaccc tgccgctgcg cagcagtatc    15360
cggggagtcc agcgcgtgac cgtcactgac gccagacgcc gcacctgccc ctacgtctac    15420
aaggccctgg gcgtagtcgc gccgcgcgtc ctctcgagcc gcaccttcta aaaaatgtcc    15480
attctcatct cgcccagtaa taacaccggt tggggcctgc gcgcgcccag caagatgtac    15540
ggaggcgctc gccaacgctc cacgcaacac cccgtgcgcg tgcgcgggca cttccgcgct    15600
ccctggggcg ccctcaaggg tcgcgtgcgc tcgcgcacca ccgtcgacga cgtgatcgac    15660
caggtggtgg ccgacgcgcg caactacacg cccgccgccg cgcccgcctc caccgtggac    15720
gccgtcatcg acagcgtggt ggccgacgcg cgccggtacg cccgcgccaa gagccggcgg    15780
cggcgcatcg cccggcggca ccggagcacc cccgccatgc gcgcggcgcg agccttgctg    15840
cgcagggcca ggcgcacggg acgcagggcc atgctcaggg cggccagacg cgcggcctcc    15900
ggcagcagca gcgccggcag gacccgcaga gcgcgcggcca ggcggcggc ggcggccatc    15960 gccagcatgt cccgccgcg gcgcggcaac gtgtactggg tgcgcgacgc cgccaccggt    16020
gtgcgcgtgc ccgtgcgcac ccgccccccct cgcacttgaa gatgctgact tcgcgatgtt    16080
gatgtgtccc agcggcgagg aggatgtcca agcgcaaata caaggaagag atgctccagg    16140
tcatcgcgcc tgagatctac ggccccgcgg cggcggtgaa ggaggaaaga aagccccgca    16200
aactgaagcg ggtcaaaaag gacaaaaagg aggaggaaga tgtggacgga ctggtggagt    16260
ttgtgcgcga gttcgccccc cggcggcgcg tgcagtggcg cgggcggaaa gtgaaaccgg    16320
tgctgcggcc cggcaccacg gtggtcttca cgcccggcga gcgttccggc tccgcctcca    16380
```

```
agcgctccta cgacgaggtg tacggggacg aggacatcct cgagcaggcg gccgagcgtc  16440
tgggcgagtt tgcttacggc aagcgcagcc gccccgcgcc cttgaaagag gaggcggtgt  16500
ccatcccgct ggaccacggc aaccccacgc cgagcctgaa gccggtgacc ctgcagcagg  16560
tgctgccgag cgcggcgccg cgccgggct  tcaagcgcga gggcggcgag gatctgtacc  16620
cgaccatgca gctgatggtg cccaagcgcc agaagctgga ggacgtgctg gagcacatga  16680
aggtggaccc cgaggtgcag cccgaggtca aggtgcggcc catcaagcag gtggccccgg  16740
gcctgggcgt gcagaccgtg gacatcaaga tccccacgga gcccatggaa acgcagaccg  16800
agcccgtgaa gcccagcacc agcaccatgg aggtgcagac ggatccctgg atgccggcgc  16860
cggcttccac caccactcgc cgaagacgca agtacggcgc ggccagcctg ctgatgccca  16920
actacgcgct gcatccttcc atcatcccca cgccgggcta ccgcggcacg cgcttctacc  16980
gcggctacag cagccgccgc aagaccacca cccgccgccg ccgtcgccgc acccgccgca  17040
gcaccaccgc gacttccgcc gccgccttgg tgcggagagt gtaccgcagc gggcgtgagc  17100
ctctgaccct gccgcgcgcg cgctaccacc cgagcatcgc catttaactc tgccgtcgcc  17160
tccttgcaga tatggccctc acatgccgcc tccgcgtccc cattacgggc taccgaggaa  17220
gaaagccgcg ccgtagaagg ctgacgggga acgggctgcg tcgccatcac caccggcggc  17280
ggcgcgccat cagcaagcgg ttgggggag  gcttcctgcc cgcgctgatc cccatcatcg  17340
ccgcggcgat cggggcgatc cccggcatag cttccgtggc ggtgcaggcc tctcagcgcc  17400
actgagacac agcttggaaa atttgtaata aaaaaatgga ctgacgctcc tggtcctgtg  17460
atgtgtgttt ttagatggaa gacatcaatt tttcgtccct ggcaccgcga cacggcacgc  17520
ggccgtttat gggcacctgg agcgacatcg gcaacagcca actgaacggg ggcgccttca  17580
attggagcag tctctggagc gggcttaaga atttcgggtc cacgctcaaa acctatggca  17640
acaaggcgtg gaacagcagc acagggcagg cgctgaggga aaagctgaaa gagcagaact  17700
tccagcagaa ggtggtcgat ggcctggcct cgggcatcaa cggggtggtg gacctggcca  17760
accaggccgt gcagaaacag atcaacagcc gcctggacgc ggtcccgccc gcggggtccg  17820
tggagatgcc ccaggtggag gaggagctgc ctcccctgga caagcgcggc gacaagcgac  17880
cgcgtcccga cgcggaggag acgctgctga cgcacacgga cgagccgccc cgtacgagg   17940 aggcggtgaa actgggtctg cccaccacgc ggcccgtggc gcctctggcc accggggtgc  18000
tgaaacccag cagcagcagc agccagcccg cgaccctgga cttgcctcca cctcgcccct  18060
ccacagtggc taagcccctg ccgccggtgg ccgtcgcgtc gcgcgccccc cgaggccgcc  18120
cccaggcgaa ctggcagagc actctgaaca gcatcgtggg tctgggagtg cagagtgtga  18180
agcgccgcct ctgctattaa agacactgt  agcgcttaac ttgcttgtct gtgtgtatat  18240
gtatgtccgc cgaccagaag gaggaggaag aggcgcgtcg ccgagttgca agatggccac  18300
cccatcgatg ctgcccccagt gggcgtacat gcacatcgcc ggacaggacg cttcggagta  18360
cctgagtccg ggtctggtgc agttcgcccg cgccacagac acctacttca gtctggggaa  18420
caagtttagg aaccccacgg tggcacccac gcacgatgtg accaccgacc gcagccagcg  18480
gctgacgctc gcgcttcgtgc ccgtggaccg cgaggacaac acctactcgt acaaagtgcg  18540
ctacacgctg gccgtgggcg acaaccgcgt gctggacatg gccagcacct actttgacat  18600
ccgcggcgtg ctggatcggg gccccagctt caaaccctac tccggcaccg cctacaacag  18660
cctggctccc aagggagcgc ccaacacctc acagtggata accaaagaca atggaactga  18720
```

-continued

```
taagacatac agttttggaa atgctccagt cagaggattg gacattacag aagagggtct    18780
ccaaatagga accgatgagt caggggtga aagcaagaaa attttgcag acaaaaccta     18840
tcagcctgaa cctcagcttg gagatgagga atggcatgat actattggag ctgaagacaa    18900
gtatggaggc agagcgctta aacctgccac caacatgaaa ccctgctatg ggtctttcgc    18960
caagccaact aatgctaagg gaggtcaggc taaaagcaga accaaggacg atggcactac    19020
tgagcctgat attgacatgg ccttctttga cgatcgcagt cagcaagcta gtttcagtcc    19080
agaacttgtt ttgtatactg agaatgtcga tctggacacc ccggatatccc acattattta   19140
caaacctggc actgatgaaa caagttcttc tttcaacttg ggtcagcagt ccatgcccaa    19200
cagacccaac tacattggct tcagagacaa ctttatcggg ctcatgtact acaacagcac    19260
tggcaatatg ggtgtactgg ccggtcaggc ctcccagctg aatgctgtgg tggacttgca    19320
ggacagaaac actgaactgt cctaccagct cttgcttgac tctctgggtg acagaaccag    19380
gtatttcagt atgtgaatc aggcggtgga cagctatgac cccgatgtgc gcattattga    19440
aaatcacggt gtggaggatg aactccccaa ctattgcttc cctttgaatg gtgtgggctt    19500
tacagataca ttccagggaa ttaaggttaa aactacaaat aacggaacag caaatgctac    19560
agagtgggaa tctgatacct ctgtcaataa tgctaatgag attgccaagg gcaatccttt    19620
cgccatggag atcaacatcc aggccaacct gtggcggaac ttcctctacg cgaacgtggc    19680
gctgtacctg cccgactcct acaagtacac gccggccaac atcacgctgc ccaccaacac    19740
caacacctac gattacatga acggccgcgt ggtggcgccc tcgctggtgg acgcctacat    19800
caacatcggg gcgcgctggt cgctggaccc catggacaac gtcaacccct tcaaccacca    19860
ccgcaacgcg ggcctgcgct accgctccat gctcctgggc aacgggcgct acgtgccctt    19920
ccacatccag gtgcccaaa agttttcgc catcaagagc ctcctgctcc tgcccgggtc    19980
ctacacctac gagtggaact tccgcaagga cgtcaacatg atcctgcaga gctccctcgg    20040
caacgacctg cgcacggacg gggcctccat cgccttcacc agcatcaacc tctacgccac    20100
cttcttcccc atggcgcaca acaccgcctc cacgctcgag gccatgctgc gcaacgacac    20160
caacgaccag tccttcaacg actacctctc ggcggccaac atgctctacc ccatcccggc    20220
caacgccacc aacgtgccca tctccatccc ctcgcgcaac tgggccgcct ccgcggatg    20280
gtccttcacg cgcctcaaga cccgcgagac gccctcgctc ggctccgggt tcgacccctca   20340
ccgtctctac tcgggctcca tcccctacct cgacggcacc ttctacctca ccacaccttt    20400
caagaaggtc tccatcacct tcgactcctc cgtcagctgg cccggcaacg accgcctcct    20460
gacgcccaac gagttcgaaa tcaagcgcac cgtcgacgga gagggtaca acgtggccca    20520
gtgcaacatg accaaggact ggttcctggt ccagatgctg gcccactaca acatcggcta    20580
ccagggcttc tacgtgcccg agggctacaa ggaccgcatg tactccttct tccgcaactt    20640
ccagcccatg agccgccagg tcgtggacga ggtcaactac aaggactacc aggccgtcac    20700
cctggcctac cagcacaaca actcgggctt cgtcggctac ctcgcgccca ccatgcgcca    20760
gggccagccc taccccgcca actaccccta cccgctcatc ggcaagagcg ccgtcgccag    20820
cgtcacccag aaaaagttcc tctgcgaccg ggtcatgtgg cgcatcccct ctccagcaa    20880
cttcatgtcc atgggcgcgc tcaccgacct cggccagaac atgctctacg ccaactccgc    20940
ccacgcgcta gacatgaatt tcgaagtcga cccatggat gagtccaccc ttctctatgt    21000
tgtcttcgaa gtcttcgacg tcgtccgagt gcaccagccc caccgcggcg tcatcgaggc    21060
cgtctacctg cgcacgccct tctcggccgg caacgccacc acctaagcct cttgcttctt    21120
```

```
gcaagatgac ggcctgtggc tccggcgagc aggagctcag ggccatcctc cgcgacctgg   21180
gctgcgggcc ctacttcctg ggcaccttcg acaagcgctt cccgggattc atggcccgc    21240 acaagctggc ctgcgccatc gtcaacacgg ccggccgcga  accgggggc gagcactggc   21300 tggccttcgc ctggaacccg cgcacccaca cctgctacct cttcgacccc ttcgggttct   21360
cggacgagcg cctcaagcag atctaccagt tcgagtacga gggcctgctg cgccgcagcg   21420
ccctggccac cgaggaccgc tgcgtcaccc tggaaaagtc cacccagacc gtgcagggtc   21480
cgcgctcggc cgcctgcggg ctcttctgct gcatgttcct gcacgccttc gtgcactggc   21540
ccgaccgccc catggacaag aaccccacca tgaacttgct gacggggtg cccaacggca    21600 tgctccagtc gccccaggtg aacccaccc tgcgccgcaa ccaggaggcg ctctaccgct    21660
tcctcaacgc ccactccgcc tactttcgct cccaccgcgc gcgcatcgag aaggccaccg   21720
ccttcgaccg catgaatcaa gacatgtaaa ctgtgtgtat gtgaatgctt tattcataat   21780
aaacagcaca tgtttatgcc accttctctg aggctctgac tttatttaga aatcgaaggg   21840
gttctgccgg ctctcggcgt gccccgcggg cagggatacg ttgcggaact ggtacttggg   21900
cagccacttg aactcgggga tcagcagctt cggcacgggg aggtcgggga acgagtcgct   21960
ccacagcttg cgcgtgagtt gcagggcgcc cagcaggtcg ggcgcggata tcttgaaatc   22020
acagttggga cccgcgttct gcgcgcgaga gttgcggtac acggggttgc agcactggaa   22080
caccatcagg gccgggtgct tcacgctcgc cagcaccgtc gcgtcggtga tgccctccac   22140
gtccagatcc tcggcgttgg ccatcccgaa gggggtcatc ttgcaggtct gccgccccat   22200
gctgggcacg cagccgggct tgtggttgca atcgcagtgc aggggggatca gcatcatctg   22260 ggcctgctcg gagctcatgc ccgggtacat ggccttcatg aaagcctcca gctggcggaa   22320
ggcctgctgc gccttgccgc cctcggtgaa gaagaccccg caggacttgc tagagaactg   22380
gttggtggcg cagccggcgt cgtgcacgca gcagcgcgcg tcgttgttgg ccagctgcac   22440
cacgctgcgc ccccagcggt tctgggtgat cttggcccgg tcggggttct ccttcagcgc   22500
gcgctgcccg ttctcgctcg ccacatccat ctcgatcgtg tgctccttct ggatcatcac   22560
ggtcccgtgc aggcaccgca gcttgccctc ggcttcggtg catccgtgca gccacagcgc   22620
gcagccggtg cactcccagt tcttgtgggc gatctgggag tgcgagtgca cgaagccctg   22680
caggaagcgg cccatcatcg cggtcagggt cttgttgctg gtgaaggtca gcgggatgcc   22740
gcggtgctcc tcgttcacat acaggtggca gatgcggcgg tacacctcgc cctgctcggg   22800
catcagctgg aaggcggact tcaggtcgct ctccacgcgg taccgctcca tcagcagcgt   22860
catgacttcc atgcccttct cccaggccga aacgatcggc aggctcaggg ggttcttcac   22920
cgttgtcatc ttagtcgccg ccgccgaggt caggggtcg ttctcgtcca gggtctcaaa    22980
cactcgcttg ccgtccttct cggtgatgcg cacggggga aagctgaagc ccacggccgc    23040
cagctcctcc tcggcctgcc tttcgtcctc gctgtcctgg ctgatgtctt gcaaaggcac   23100
atgcttggtc ttgcggggtt ctttttggg cggcagaggc ggcggcggag acgtgctggg    23160
cgagcgcgag ttctcgctca ccacgactat ttcttcttct tggccgtcgt ccagagaccac  23220 gcggcggtag gcatgcctct tctggggcag aggcggaggc gacgggctct cgcggttcgg   23280
cgggcggctg gcagagcccc ttccgcgttc ggggtgcgc tcctggcggc gctgctctga    23340
ctgacttcct ccgcggccgg ccattgtgtt ctcctaggga gcaagcatgg agactcagcc   23400
atcgtcgcca acatcgccat ctgccccgc cgccgccgac gagaaccagc agcagcagaa    23460
```

```
tgaaagctta accgccccgc cgcccagccc cacctccgac gccgcggccc cagacatgca  23520
agagatggag gaatccatcg agattgacct gggctacgtg acgcccgcgg agcacgagga  23580
ggagctggca gcgcgctttt cagccccgga agagaaccac caagagcagc cagagcagga  23640
agcagagagc gagcagagcc aggctgggct cgagcatggc gactacctga gcggggcaga  23700
ggacgtgctc atcaagcatc tggcccgcca atgcatcatc gtcaaggatg cgctgctcga  23760
ccgcgccgag gtgcccctca gcgtggcgga gctcagccgc gcctacgagc gcaacctctt  23820
ctcgccgcgc gtgcccccca agcgccagcc caacggcacc tgcgagccca cccgcgcct  23880 caacttctac ccggtcttcg cggtgcccga ggccctggcc acctaccacc tcttttttcaa  23940 gaaccaaagg atccccgtct cctgccgcgc caaccgcacc cgcgccgacg ccctgctcaa  24000
cctgggcccc ggcgcccgcc tacctgatat cgcctccttg gaagaggttc ccaagatctt  24060
cgagggtctg ggcagcgacg agactcgggc cgcgaacgct ctgcaaggaa gcggagagga  24120
gcatgagcac cacagcgccc tggtggagtt ggaaggcgac aacgcgcgcc tggcggtcct  24180
caagcgcacg gtcgagctga cccacttcgc ctacccggcg ctcaacctgc cccccaaggt  24240
catgagcgcc gtcatggacc aggtgctcat caagcgcgcc tcgcccctct cggaggagga  24300
gatgcaggac cccgagagct cggacgaggg caagcccgtg gtcagcgacg agcagctggc  24360
gcgctggctg ggagcgagta gcacccccca gagcctggaa gagcggcgca agctcatgat  24420
ggccgtggtc ctggtgaccg tggagctgga gtgtctgcgc cgcttcttcg ccgacgcgga  24480
gaccctgcgc aaggtcgagg agaacctgca ctacctcttc aggcacgggt tcgtgcgcca  24540
ggcctgcaag atctccaacg tggagctgac caacctggtc tcctacatgg gcatcctgca  24600
cgagaaccgc ctggggcaga acgtgctgca caccaccctg cgcggggagg cccgccgcga  24660
ctacatccgc gactgcgtct acctgtacct ctgccacacc tggcagacgg gcatgggcgt  24720
gtggcagcag tgcctggagg agcagaacct gaaagagctc tgcaagctcc tgcagaagaa  24780
cctgaaggcc ctgtgaccg ggttcgacga gcgcaccacc gcctcggacc tggccgacct  24840
catcttcccc gagcgcctgc ggctgacgct gcgcaacggg ctgcccgact ttatgagcca  24900
aagcatgttg caaaactttc gctctttcat cctcgaacgc tccgggatcc tgcccgccac  24960
ctgctccgcg ctgccctcgg acttcgtgcc gctgaccttc gcgagtgcc cccgccgct  25020 ctggagccac tgctacctgc tgcgtctggc caactacctg gctaccact cggacgtgat  25080 cgaggacgtc agcggcgagg gtctgctcga gtgccactgc cgctgcaacc tctgcacgcc  25140
gcaccgctcc ctggcctgca accccagct gctgagcgag acccagatca tcggcacctt  25200
cgagttgcaa ggccccggcg aggagggcaa gggggggtctg aaactcaccc cggggctgtg  25260
gacctcggcc tacttgcgca agttcgtgcc cgaggactac catcccttcg agatcaggtt  25320
ctacgaggac caatcccagc cgcccaaggc cgagctgtcg gcctgcgtca tcacccaggg  25380
ggccatcctg gcccaattgc aagccatcca gaaatcccgc caagaatttc tgctgaaaaa  25440
gggccacggg gtctacttgg accccagac cggagaggag ctcaaccca gcttcccca  25500 ggatgcccag aggaagcagc aagaagctga aagtggagct gccgctgccg ccggaggatt  25560
tggaggaaga ctgggagagc agtcaggcag aggaggagga gatggaagac tgggacagca  25620
ctcaggcaga ggaggacagc ctgcaagaca gtctggaaga cgaggtggag gaggaggcag  25680
aggaagaagc agccgccgcc agaccgtcgt cctcggcgga gaaagcaagc agcacggata  25740
ccatctccgc tccgggtcgg ggtctcggcg gccgggccca cagtaggtgg gacgagaccg  25800
ggcgcttccc gaacccccacc acccagaccg gtaagaagga gcggcaggga tacaagtcct  25860
```

```
ggcggggca  caaaaacgcc  atcgtctcct  gcttgcaagc  ctgcggggc  aacatctcct   25920 tcacccggcg  ctacctgctc  ttccaccgcg  gggtgaactt  ccccccgcaac atcttgcatt  25980 actaccgtca  cctccacagc  ccctactact  gtttccaaga  agaggcagaa  acccagcagc  26040
agcagaaaac  cagcagcagc  tagaaaatcc  acagcggcgg  cggcggcagg  tggactgagg  26100
atcgcggcga  acgagccggc  gcagacccgg  gagctgagga  accggatctt  tcccaccctc  26160
tatgccatct  tccagcagag  tcgggggcag  gagcaggaac  tgaaagtcaa  gaaccgttct  26220
ctgcgctcgc  tcacccgcag  ttgtctgtat  cacaagagcg  aagaccaact  tcagcgcact  26280
ctcgaggacg  ccgaggctct  cttcaacaag  tactgcgcgc  tcactcttaa  agagtagccc  26340
gcgcccgccc  acacacggaa  aaaggcggga  attacgtcac  cacctgcgcc  cttcgcccga  26400
ccatcatcat  gagcaaagag  attcccacgc  cttacatgtg  gagctaccag  ccccagatgg  26460
gcctggccgc  cggcgccgcc  caggactact  ccacccgcat  gaactggctc  agtgccgggc  26520
ccgcgatgat  ctcacgggtg  aatgacatcc  gcgcccgccg  aaaccagata  ctcctagaac  26580
agtcagcgat  caccgccacg  ccccgccatc  accttaatcc  gcgtaattgg  cccgccgccc  26640
tggtgtacca  ggaaattccc  cagcccacga  ccgtactact  tccgcgagac  gcccaggccg  26700
aagtccagct  gactaactca  ggtgtccagc  tggccggcgg  cgccgccctg  tgtcgtcacc  26760
gccccgctca  gggtataaag  cggctggtga  tccgaggcag  aggcacacag  ctcaacgacg  26820
aggtggtgag  ctcttcgctg  ggtctgcgac  ctgacggagt  cttccaactc  gccggatcgg  26880
ggagatcttc  cttcacgcct  cgtcaggccg  tcctgacttt  ggagagttcg  tcctcgcagc  26940
cccgctcggg  tggcatcggc  actctccagt  tcgtggagga  gttcactccc  tcggtctact  27000 tcaaccccctt  ctccggctcc  cccggccact  accggacga  gttcatcccg  aacttcgacg  27060
ccatcagcga  gtcggtggac  ggctacgatt  gaatgtccca  tggtggcgcg  gctgacctag  27120
ctcggcttcg  acacctggac  cactgccgcc  gcttccgctg  cttcgctcgg  gatctcgccg  27180
agtttgccta  ctttgagctg  cccgaggagc  acctcaggg  cccggccac  ggagtgcgga  27240 tcatcgtcga  aggggggcctc  gactccacc  tgcttcggat  cttcagccag  cgtccgatcc  27300
tggtcgagcg  cgagcaagga  cagacccgtc  tgaccctgta  ctgcatctgc  aaccaccccg  27360
gcctgcatga  aagtctttgt  tgtctgctgt  gtactgagta  taataaaagc  tgagatcagc  27420
gactactccg  gacttccgtg  tgttcctgaa  tccatcaacc  agtccctgtt  cttcaccggg  27480
aacgagaccg  agctccagct  ccagtgtaag  ccccacaaga  agtacctcac  ctggctgttc  27540
cagggctccc  cgatcgccgt  tgtcaaccac  tgcgacaacg  acggagtcct  gctgagcggc  27600
cctgccaacc  ttactttttc  caccgcaga  agcaagctcc  agctcttcca  acccttcctc  27660
cccgggacct  atcagtgcgt  ctcgggaccc  tgccatcaca  ccttccacct  gatcccgaat  27720
accacagcgt  cgctccccgc  tactaacaac  caaactaccc  accaacgcca  ccgtcgcgac  27780 cttcctctg  aatctaatac  cactaccgga  ggtgagctcc  gaggtcgacc  aacctctggg  27840
atttactacg  gcccctggga  ggtggtgggg  ttaatagcgc  taggcctagt  tgtgggtggg  27900
cttttggctc  tctgctacct  atacctccct  tgctgttcgt  acttagtggt  gctgtgttgc  27960
tggtttaaga  aatgggcag  atcacccctag  tgagctgcgg  tgtgctggtg  gcggtggtgc  28020
tttcgattgt  gggactgggc  ggcgcggctg  tagtgaagga  gaaggccgat  ccctgcttgc  28080
atttcaatcc  cgacaaatgc  cagctgagtt  ttcagcccga  tggcaatcgg  tgcgcggtgc  28140
tgatcaagtg  cggatgggaa  tgcgagaacg  tgagaatcga  gtacaataac  aagactcgga  28200
```

| | |
|---|---|
| acaatactct cgcgtccgtg tggcagcccg gggaccccga gtggtacacc gtctctgtcc | 28260 |
| ccggtgctga cggctcccog cgcaccgtga ataatacttt catttttgcg cacatgtgcg | 28320 |
| acacggtcat gtggatgagc aagcagtacg atatgtggcc ccccacgaag gagaacatcg | 28380 |
| tggtcttctc catcgcttac agcctgtgca cggtgctaat caccgctatc gtgtgcctga | 28440 |
| gcattcacat gctcatcgct attcgcccca gaaataatgc cgaaaaagag aaacagccat | 28500 |
| aacacgtttt ttcacacacc ttgttttac agacaatgcg tctgttaaat tttttaaaca | 28560 |
| ttgtgctcag tattgcttat gcctctggct atgcaaacat acagaaaacc ctctatgtag | 28620 |
| gatctgatga tacactagag ggtacccaat cacaagctag ggtttcatgg tatttttata | 28680 |
| aaagctcaga taatcctatt actctttgca aaggtgatca ggggcggaca acaaagccgc | 28740 |
| ctatcacatt tagctgtacc agaacaaatc tcacgctttt ctcaattaca aaacaatatg | 28800 |
| ctggtattta ttacagtaca aactttcata gtgggcaaga taaatattat actgttaagg | 28860 |
| tagaaaatcc taccactcct agaactacca ccaccaccac caccaccacc actactgcga | 28920 |
| agcccactaa acctaaaact accaagaaaa ccactgtgaa aactacaact agaaccacca | 28980 |
| caactacaga aaccaccacc agcacaacac ttgctgcaac tacacacaca cacactgagc | 29040 |
| taaccttaca gaccactaat gatttgatag ccctgttgca aaaggggat aacagccacca | 29100 |
| cttccaatga ggagataccc aaatccatga ttggcattat tgttgctgta gtggtgtgca | 29160 |
| tgttgatcat cgccttgtgc atggtgtact atgccttctg ctacagaaag cacagactga | 29220 |
| acgacaagct ggaacactta ctaagtgttg aatttaatt ttttagaacc atgaagatcc | 29280 |
| taggcctttt agttttttct atcattacct ctgctctatg caattctgac aatgaggacg | 29340 |
| ttactgtcgt tgtcggatca aattatacac tgaaaggtcc agcgaagggt atgctttcgt | 29400 |
| ggtattgctg gtttggaact gacactgatc aaactgagct ttgcaatgca atgaaaggtc | 29460 |
| aaataccaac ctcaaaaatt aaacataaat gcaatggtac tgacttagta ctactcaata | 29520 |
| tcacgaaatc atatgctggc agctattcat gccctggaga tgatgctgag aacatgattt | 29580 |
| tttacaaagt aactgttgtt gatcccacta ctccaccacc caccaccaca actactcaca | 29640 |
| ccacacacac agaacaaaca ccagaggcag cagaagcaga gttggccttc caggttcacg | 29700 |
| gagattcctt tgctgtcaat acccctacac ccgatcatcg gtgtccgggg ctgctagtca | 29760 |
| gcggcattgt cggtgtgctt tcgggattag cagtcataat catctgcatg ttcattttg | 29820 |
| cttgctgcta tagaaggctt taccgacaaa aatcagaccc actgctgaac ctctatgttt | 29880 |
| aatttttcc agagccatga aggcagttag cgctctagtt ttttgttctt tgattggcat | 29940 |
| tgttttttgc aatcctatta ctagagttag ctttattaaa gatgtgaatg ttactgaggg | 30000 |
| gggcaatgtg acactggtag gtgtagaggg tgctaaaaac accacctgga caaaatacca | 30060 |
| ccttgggtgg aaagatattt gcaattggag tgtcactgtg tacacatgtg agggagttaa | 30120 |
| tcttaccatt gtcaatgcca cctcagctca aaatggtaga attcaaggac aaagtgttag | 30180 |
| tgtgaccagt gatgggtatt ttacccaaca tactttatc tatgacgtta aagtcatacc | 30240 |
| actgcctacg cctagcccac ctagcaccac tacacaaaca acccacacta cacagacaac | 30300 |
| cacatacagt acatcaaatc agcctaccac cactacagca gcagaggttg ccagctcgtc | 30360 |
| tggagttcaa gtggcatttt tgttgttgcc cccatctagc agtcccactg ctattaccaa | 30420 |
| tgagcagact actgcatttt tgtccactgt cgagagccac accacagcta cctccagtgc | 30480 |
| cttctctagc accgccaatc tctcctcgct ttcctctaca ccaatcagtc ccgctactac | 30540 |
| tactaccccc gctattcttc ccactcccct gaagcaaaca gacggcggca tgcaatggca | 30600 |

```
gatcaccctg ctcattgtga tcgggttggt catcctagcc gtgttgctct actacatctt    30660
ctgccgccgc attcccaacg cgcaccgcaa gccggtctac aagcccatca ttgtcgggca    30720
gccggagccg cttcaggtgg aagggggtct aaggaatctt ctcttctctt ttacagtatg    30780
gtgattgaac tatgattcct agacaattct tgatcactat tcttatctgc ctcctccaag    30840
tctgtgccac cctcgctctg gtggccaacg ccagtccaga ctgtattggg cccttcgcct    30900
cctacgtgct ctttgccttc atcacctgca tctgctgctg tagcatagtc tgcctgctta    30960
tcaccttctt ccagttcatt gactggatct ttgtgcgcat cgcctacctg cgccaccacc    31020
cccagtaccg cgaccagcga gtggcgcagc tgctcaggct cctctgataa gcatgcgggc    31080
tctgctactt ctcgcgcttc tgctgttagt gctccccgt cccgttgacc cccggccccc    31140
cactcagtcc cccgaggagg tccgcaaatg caaattccaa gaaccctgga aattcctcaa    31200
atgctaccgc caaaaatcag acatgcatcc cagctggatc atgatcattg ggatcgtgaa    31260
cattctggcc tgcaccctca tctcctttgt gatttacccc tgctttgact ttggttggaa    31320
ctcgccagag gcgctctatc tcccgcctga acctgacaca ccaccacagc aacctcaggc    31380
acacgcacta ccaccaccac agcctaggcc acaatacatg cccatattag actatgaggc    31440
cgagccacag cgacccatgc tccccgctat tagttacttc aatctaaccg gcggagatga    31500
ctgacccact ggccaacaac aacgtcaacg accttctcct ggacatggac ggccgcgcct    31560
cggagcagcg actcgcccaa cttcgcattc gccagcagca ggagagagcc gtcaaggagc    31620
tgcaggacgg catagccatc caccagtgca agaaaggcat cttctgcctg gtgaaacagg    31680
ccaagatctc ctacgaggtc acccagaccg accatcgcct ctcctacgag ctcctgcagc    31740
agcgccagaa gttcacctgc ctggtcggag tcaaccccat cgtcatcacc cagcagtcgg    31800
gcgataccaa ggggtgcatc cactgctcct gcgactcccc cgactgcgtc cacactctga    31860
tcaagaccct ctgcggcctc cgcgacctcc tccccatgaa ctaatcaccc acttatccag    31920
tgaaataaaa aaataatcat ttgatttgaa ataaagatac aatcatattg atgatttgag    31980
tttaacaaaa ataagaatc acttacttga aatctgatac caggtctctg tccatatttt    32040
ctgccaacac cacctcactc ccctcttccc agctctggta ctgcaggccc cggcgggctg    32100
caaacttcct ccacacgctg aaggggatgt caaattcctc ctgcccctca atcttcattt    32160
tatcttctat cagatgtcca aaaagcgcgt ccgggtggat gatgacttcg accccgtcta    32220
cccctacgat gcagacaacg caccgaccgt gcccttcatc aaccccccct tcgtctcttc    32280
agatggattc caagagaagc ccctgggggt gttgtccctg cgactggccg accccgtcac    32340
caccaagaac ggggaaatca ccctcaagct gggagagggg gtggacctcg actcctcggg    32400
aaaactcatc tccaacacgg ccaccaaggc cgctgcccct ctcagttttt ccaacaacac    32460
catttccctt aacatggatc acccctttta cactaaagat ggaaaattag ccttacaagt    32520
ttctccacca ttaaatatac tgagaacaag cattctaaac acactagctt taggttttgg    32580
atcaggttta ggactccgtg gctctgcctt ggcagtacag ttagtctctc cacttacatt    32640
tgatactgat ggaaacataa agcttaccct agacagaggt ttgcatgtta caacaggaga    32700
tgcaattgaa agcaacataa gctgggctaa aggtttaaaa tttgaagatg gagccatagc    32760
aaccaacatt ggaaatgggt tagagtttgg aagcagtagt acagaaacag gtgtcgatga    32820
tgcttaccca atccaagtta aacttggatc tggcctgagc tttgacagta caggagccat    32880
aatggctggt aacaaagaag acgataaact cactttgtgg acaacacctg atccatcacc    32940
```

```
aaactgtcaa atactcgcag aaaatgatgc aaaactaaca ctttgcttga ctaaatgtgg    33000
tagtcaaata ctggccactg tgtcagtctt agttgtagga agtggaaacc taaaccccat    33060
tactggcacc gtaagcagtg ctcaggtgtt tctacgtttt gatgcaaacg gtgttctttt    33120
aacagaacat tctacactaa aaaaatactg ggggtatagg cagggagata gcatagatgg    33180
cactccatat gtcaatgctg taggattcat gcccaattta aaagcttatc caaagtcaca    33240
aagttctact actaaaaata atatagtagg gcaagtatac atgaatggag atgtttcaaa    33300
acctatgctt ctcactataa ccctcaatgg tactgatgac agcaacagta catattcaat    33360
gtcattttca tacacctgga ctaatggaag ctatgttgga gcaacatttg gagctaactc    33420
ttataccttc tcctacatcg cccaagaatg aatactgtat cccaccctgc atgcccaacc    33480
ctcccccacc tctgtctata tggaaaactc tgaaacacaa aataaaataa agttcaagtg    33540
ttttattgat tcaacagttt tacaggattc gagcagttat ttttcctcca ccctcccagg    33600
acatggaata caccaccctc tcccccgca cagccttgaa catctgaatg ccattggtga    33660
tggacatgct tttggtctcc acgttccaca cagtttcaga gcgagccagt ctcgggtcgg    33720
tcagggagat gaaaccctcc gggcactccc gcatctgcac ctcacagctc aacagctgag    33780
gattgtcctc ggtggtcggg atcacggtta tctggaagaa gcagaagagc ggcggtggga    33840
atcatagtcc gcgaacggga tcggccggtg gtgtcgcatc aggccccgca gcagtcgctg    33900
ccgccgccgc tccgtcaagc tgctgctcag ggggtccggg tccagggact ccctcagcat    33960
gatgcccacg gccctcagca tcagtcgtct ggtgcggcgg gcgcagcagc gcatgcggat    34020
ctcgctcagg tcgctgcagt acgtgcaaca caggaccacc aggttgttca acagtccata    34080
gttcaacacg ctccagccga aactcatcgc gggaaggatg ctacccacgt ggccgtcgta    34140
ccagatcctc aggtaaatca agtggcgccc cctccagaac acgctgccca tgtacatgat    34200
ctccttgggc atgtggcggt tcaccacctc ccggtaccac atcaccctct ggttgaacat    34260
gcagccccgg atgatcctgc ggaaccacag ggccagcacc gccccgcccg ccatgcagcg    34320
aagagacccc gggtcccggc aatggcaatg gaggacccac cgctcgtacc cgtggatcat    34380
ctgggagctg aacaagtcta tgttggcaca gcacaggcac acgctcatgc atctcttcag    34440
cactctcagc tcctcggggg tcaaaaccat atcccagggc acgggaaact cttgcaggac    34500
agcgaagccc gcagaacagg gcaatcctcg cacataactt acattgtgca tggacagggt    34560
atcgcaatca ggcagcaccg ggtgatcctc caccagagaa gcgcgggtct cggtctcctc    34620
acagcgtggt aaggggccg gccgatacgg gtgatggcgg gacgcggctg atcgtgttcg    34680
cgaccgtgtc atgatgcagt tgctttcgga cattttcgta cttgctgaag cagaacctgg    34740
tccgggcgct gcacaccgat cgccggcggc ggtctcggcg cttggaacgc tcggtgttga    34800
agttgtaaaa cagccactct ctcagaccgt gcagcagatc tagggcctca ggagtgatga    34860 agatccatc atgcctgatg ctctgatca catcgaccac cgtggaatgg ccagaccca    34920 gccagatgat gcaattttgt tgggtttcgg tgacggcggg ggaggaaga acaggaagaa    34980 ccatgattaa cttttaatcc aaacggtctc ggagcacttc aaaatgaagg tcgcggagat    35040
ggcacctctc gccccgctg tgttggtgga aaataacagc caggtcaaag gtgatacggt    35100
tctcgagatg ttccacggtg gcttccagca aagcctccac gcgcacatcc agaaacaaga    35160
caatagcgaa agcgggaggg ttctctaatt cctcaatcat catgttacac tcctgcacca    35220
tccccagata attttcattt ttccagcctt gaatgattcg aactagttcc tgaggtaaat    35280
ccaagccagc catgataaag agctcgcgca gagcgccctc caccggcatt cttaagcaca    35340
```

```
ccctcataat tccaagatat tctgctcctg gttcacctgc agcagattga caagcgggat    35400
atcaaaatct ctgccgcgat ccctgagctc ctccctcagc aataactgta agtactcttt    35460
catatcctct ccgaaatttt tagccatagg accccagga ataagagaag ggcaagccac     35520
attacagata aaccgaagtc cccccagtg agcattgcca aatgtaagat tgaaataagc     35580
atgctggcta gacccggtga tatcttccag ataactggac agaaaatcgg gcaagcaatt    35640
tttaagaaaa tcaacaaaag aaaaatcttc caggtgcacg tttagggcct cgggaacaac    35700
gatggagtaa gtgcaagggg tgcgttccag catggttagt tagctgatct gtaaaaaaac    35760
aaaaaataaa acattaaacc atgctagcct ggcgaacagg tgggtaaatc gttctctcca    35820
gcaccaggca ggccacgggg tctccggcgc gaccctcgta aaaattgtcg ctatgattga    35880
aaaccatcac agagagacgt tcccggtggc cggcgtgaat gattcgagaa gaagcataca    35940
cccccggaac attggagtcc gtgagtgaaa aaaagcggcc gaggaagcaa tgaggcacta    36000
caacgctcac tctcaagtcc agcaaagcga tgccatgcgg atgaagcaca aaattttcag    36060
gtgcgtaaaa aatgtaatta ctcccctcct gcacaggcag cgaagctccc gatccctcca    36120
gatacacata caaagcctca gcgtccatag cttaccgagc ggcagcagca gcggcacaca    36180
acaggcgcaa gagtcagaga aaagactgag ctctaacctg tccgcccgct ctctgctcaa    36240
tatatagccc cagatctaca ctgacgtaaa ggccaaagtc taaaaatacc cgccaaataa    36300
tcacacacgc ccagcacacg cccagaaacc ggtgacacac tcaaaaaaat acgcgcactt    36360
cctcaaacgc ccaaactgcc gtcatttccg ggttccacg ctacgtcatc aaaacacgac     36420
tttcaaattc cgtcgaccgt taaaaacgtc acccgccccg ccctaacgg tcgccgctcc     36480 cgcagccaat cagcgccccg catccccaaa ttcaaacagc tcatttgcat attaacgcgc    36540
accaaaagtt tgaggtatat tattgatgat g                                  36571

<210> SEQ ID NO 3
<211> LENGTH: 1109
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3
ggagttccgc gttacataac ttacggtaaa tggcccgcct ggctgaccgc ccaacgaccc       60
ccgcccattg acgtcaataa tgacgtatgt tcccatagta acgccaatag ggactttcca      120
ttgacgtcaa tgggtggagt atttacggta aactgcccac ttggcagtac atcaagtgta      180
tcatatgcca agtacgcccc ctattgacgt caatgacggt aaatggcccg cctggcatta      240
tgcccagtac atgaccttat gggactttcc tacttggcag tacatctacg tattagtcat      300
cgctattacc atggtcgagg tgagcccac gttctgcttc actctcccca tctcccccc       360 ctccccaccc ccaattttgt atttatttat tttttaatta ttttgtgcag cgatggggc       420 ggggggggg ggggcgcgc gccaggcggg gcggggcggg gcgaggggcg gggcggggcg       480
aggcggagag gtgcggcggc agccaatcag agcggcgcgc tccgaaagtt tccttttatg      540
gcgaggcggc ggcggcggcg gccctataaa aagcgaagcg ctccctatca gtgatagaga      600
tctccctatc agtgatagag atcgtcgacg agctcgcgg gggcgggagt cgctgcgcgc      660
tgccttcgcc ccgtgccccg ctccgccgcc gcctcgcgcc gcccgcccg gctctgactg      720
```

```
accgcgttac taaaacaggt aagtccggcc tccgcgccgg gttttggcgc ctcccgcggg    780 cgccccctc ctcacggcga gcgctgccac gtcagacgaa gggcgcagcg agcgtcctga    840
tccttccgcc cggacgctca ggacagcggc ccgctgctca taagactcgg ccttagaacc    900
ccagtatcag cagaaggaca ttttaggacg ggacttgggt gactctaggg cactggtttt    960 cttccagag agcggaacag gcgaggaaaa gtagtccctt ctcggcgatt ctgcggaggg   1020
atctccgtgg ggcggtgaac gccgatgatg cctctactaa ccatgttcat gttttctttt   1080
tttttctaca ggtcctgggt gacgaacag                                    1109
```

<210> SEQ ID NO 4
<211> LENGTH: 37559
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 4

```
catcatcaat aatataccct attttggatt gaagccaata tgataatgag atgggcggcg     60
cggggcgggg cgcggggcgg gaggcgggtt tgggggcggg ccggcgggcg gggcggtgtg    120
gcggaagtgg actttgtaag tgtggcggat gtgacttgct agtgccgggc gcggtaaaag    180
tgacgttttc cgtgcgcgac aacgccccg ggaagtgaca ttttccccgc ggttttacc     240 ggatgttgta gtgaatttgg gcgtaaccaa gtaagatttg gccattttcg cgggaaaact    300
gaaacgggga agtgaaatct gattaatttt gcgttagtca taccgcgtaa tatttgtcta    360
gggccgaggg actttggccg attacgtgga ggactcgccc aggtgttttt tgaggtgaat    420
ttccgcgttc cgggtcaaag tctgcgtttt attattatag gatatcccat tgcatacgtt    480
gtatccatat cataatatgt acatttatat tggctcatgt ccaacattac cgccatgttg    540
acattgatta ttgactagtt attaatagta atcaattacg gggtcattag ttcatagccc    600
atatatggag ttccgcgtta cataacttac ggtaaatggc ccgcctggct gaccgcccaa    660 cgaccccgc ccattgacgt caataatgac gtatgttccc atagtaacgc caatagggac    720
tttccattga cgtcaatggg tggagtattt acggtaaact gcccacttgg cagtacatca    780
agtgtatcat atgccaagta cgccccctat tgacgtcaat gacggtaaat ggcccgcctg    840
gcattatgcc cagtacatga ccttatggga ctttcctact tggcagtaca tctacgtatt    900
agtcatcgct attaccatgg tgatgcggtt ttggcagtac atcaatgggc gtggatagcg    960
gtttgactca cggggatttc caagtctcca ccccattgac gtcaatggga gtttgttttg   1020
gcaccaaaat caacgggact ttccaaaatg tcgtaacaac tccgccccat tgacgcaaat   1080
gggcggtagg cgtgtacggt gggaggtcta tataagcaga gctctcccta tcagtgatag   1140
agatctccct atcagtgata gagatcgtcg acgagctcgt ttagtgaacc gtcagatcgc   1200
ctggagacgc catccacgct gttttgacct ccatagaaga caccgggacc gatccagcct   1260
ccgcggccgg gaacggtgca ttggaacgcg gattccccgt gccaagagtg agatcttccg   1320
tttatctagg taccagatat cgccaccatg gaactgctga tcctgaaggc caacgccatc   1380
accaccatcc tgaccgccgt gaccttctgc ttcgccagcg ccagaacat caccgaggaa   1440 ttctaccaga gcacctgtag cgccgtgagc aagggctacc tgagcgccct gagaaccggc   1500
tggtacacca gcgtgatcac catcgagctg agcaacatca agaaaacaa gtgcaacggc   1560 accgacgcca agtgaagct gatcaagcag gaactggaca gtacaagaa cgccgtgacc   1620
```

```
gagctgcagc tgctgatgca gagcacccccc gccaccaaca accgggccag acgggagctg    1680
cccgggttca tgaactacac cctgaacaac gccaaaaaga ccaacgtgac cctgagcaag    1740
aagcggaagc ggcggttcct gggctttctg ctgggcgtgg gcagcgccat tgccagcggc    1800
gtggccgtgt ctaaggtgct gcacctggaa ggcgaagtga caagatcaa gagcgccctg     1860
ctgagcacca caaggccgt ggtgtccctg agcaacggcg tgagcgtgct gaccagcaag     1920
gtgctggatc tgaagaacta catcgacaag cagctgctgc ccatcgtgaa caagcagagc    1980
tgcagcatca gcaacatcga cacagtgatc gagttccagc agaagaacaa ccggctgctg    2040
gaaatcaccc gggagttcag cgtgaacgcc ggcgtgacca cccctgtgtc cacctacatg    2100
ctgaccaaca gcgagctgct gagcctgatc aacgacatgc ccatcaccaa cgaccagaaa    2160
aagctgatga caacaacgt gcagatcgtg cggcagcaga gctactccat catgtccatc     2220
atcaaagaag aggtgctggc ctacgtggtg cagctgcccc tgtacggcgt gatcgacacc    2280
ccctgctgga agctgcacac cagcccctg tgcaccacca acaccaaaga gggcagcaac     2340
atctgcctga cccggaccga cagaggctgg tactgcgaca acgccggcag cgtgtcattc    2400
tttccacagg ccgagacatg caaggtgcag agcaaccggg tgttctgcga caccatgaac    2460
agcctgaccc tgccctccga agtgaacctg tgcaacgtgg acatcttcaa ccccaagtac    2520
gactgcaaga tcatgacctc caagaccgac gtgtccagct ccgtgatcac ctccctgggc    2580
gccatcgtgt cctgctacgg caagaccaag tgcaccgcca gcaacaagaa ccgggggcatc   2640
atcaagacct tcagcaacgg ctgcgactac gtgtccaaca agggggtgga caccgtgtcc   2700
gtgggcaaca ccctgtacta cgtgaacaaa caggaaggca agagcctgta cgtgaagggc    2760
gagcccatca tcaacttcta cgaccccctg gtgttcccca cgacgagtt cgacgccagc    2820
atcagccagg tgaacgagaa gatcaaccag agcctggcct tcatccggaa gtccgacgag    2880
ctgctgcaca atgtgaatgc cggcaagtcc accaccaacc ggaagcggag agcccctgtg    2940
aagcagaccc tgaacttcga cctgctgaag ctggccggcg acgtggagag caatcccggc    3000
cctatggccc tgagcaaagt gaaactgaac gatacactga acaaggacca gctgctgtcc    3060
agcagcaagt acaccatcca gcggagcacc ggcgacagca tcgataccc caactacgac    3120
gtgcagaagc acatcaacaa gctgtgcggc atgctgctga tcacagagga cgccaaccac    3180
aagttcaccg gcctgatcgg catgctgtac gccatgagcc ggctgggccg ggaggacacc    3240
atcaagatcc tgcgggacgc cggctaccac gtgaaggcca atggcgtgga cgtgaccaca    3300
caccggcagg acatcaacgg caaagaaatg aagttcgagg tgctgaccct ggccagcctg    3360
accaccgaga tccagatcaa tatcgagatc gagagccgga agtcctacaa gaaaatgctg    3420
aaagaaatgg gcgaggtggc ccccgagtac agacacgaca gccccgactg cggcatgatc    3480
atcctgtgta tcgccgccct ggtgatcaca aagctggccg ctggcgacag atctggcctg    3540
acagccgtga tcgacggc caacaatgtg ctgaagaacg agatgaagcg gtacaagggc    3600
ctgctgccca aggacattgc caacagcttc tacgaggtgt tcgagaagta ccccactttc    3660
atcgacgtgt tcgtgcactt cggcattgcc cagagcagca ccagaggcgg ctccagagtg    3720
gagggcatct tcgccggcct gttcatgaac gcctacggcg ctggccaggt gatgctgaga    3780
tggggcgtgc tggccaagag cgtgaagaac atcatgctgg ccacgccag cgtgcaggcc    3840
gagatggaac aggtggtgga ggtgtacgag tacgcccaga agctgggcgg agaggccggc    3900
ttctaccaca tcctgaacaa ccctaaggcc tccctgctgt ccctgaccca gttcccccac    3960
```

```
ttctccagcg tggtgctggg aaatgccgcc ggactgggca tcatgggcga gtaccggggc    4020
acccccagaa accaggacct gtacgacgcc gccaaggcct acgccgagca gctgaaagaa    4080
aacggcgtga tcaactacag cgtgctggac ctgaccgctg aggaactgga agccatcaag    4140
caccagctga accccaagga caacgacgtg agctgggag gcggaggatc tggcggcgga    4200
ggcatgagca gacggaaccc ctgcaagttc gagatccggg ccactgcct gaacggcaag    4260 cggtgccact tcagccacaa ctacttcgag tggccccctc atgctctgct ggtgcggcag    4320
aacttcatgc tgaaccggat cctgaagtcc atggacaaga gcatcgacac cctgagcgag    4380
atcagcggag ccgccgagct ggacagaacc gaggaatatg ccctgggcgt ggtgggagtg    4440
ctggaaagct acatcggctc catcaacaac atcacaaagc agagcgcctg cgtggccatg    4500
agcaagctgc tgacagagct gaacagcgac gacatcaaga agctgaggga caacgaggaa    4560
ctgaacagcc ccaagatccg ggtgtacaac accgtgatca gctacattga gagcaaccgc    4620
aagaacaaca agcagaccat ccatctgctg aagcggctgc ccgccgacgt gctgaaaaag    4680
accatcaaga cacccctgga catccacaag tccatcacca tcaacaatcc caaagaaagc    4740
accgtgtctg acaccaacga tcacgccaag aacaacgaca ccacctgatg agcggccgcg    4800
atctgctgtg ccttctagtt gccagccatc tgttgtttgc ccctccccg tgccttcctt    4860 gaccctggaa ggtgccactc ccactgtcct ttcctaataa aatgaggaaa ttgcatcgca    4920
ttgtctgagt aggtgtcatt ctattctggg ggtggggtg gggcaggaca gcaaggggga    4980
ggattgggaa gacaatagca ggcatgctgg ggatgcggtg ggctctatgg ccgatcagcg    5040
atcgctgagg tgggtgagtg ggcgtggcct ggggtggtca tgaaaatata taagttgggg    5100
gtcttagggt ctctttattt tgttgcaga gaccgccgga gccatgagcg ggagcagcag    5160
cagcagcagt agcagcagcg ccttggatgg cagcatcgtg agcccttatt tgacgacgcg    5220
gatgccccac tgggccgggg tgcgtcagaa tgtgatgggc tccagcatcg acggccgacc    5280
cgtcctgccc gcaaattccg ccacgctgac ctatgcgacc gtcgcgggga cgccgttgga    5340
cgccaccgcc gccgccgccg ccaccgcagc cgcctcggcc gtgcgcagcc tggccacgga    5400 cttttgcattc ctgggaccac tggcgacagg ggctacttct cgggccgctg ctgccgccgt    5460
tcgcgatgac aagctgaccg ccctgctggc gcagttggat gcgcttactc gggaactggg    5520
tgacctttct cagcaggtca tggccctgcg ccagcaggtc tcctccctgc aagctggcgg    5580
gaatgcttct cccacaaatg ccgtttaaga taaataaaac cagactctgt ttggattaaa    5640
gaaaagtagc aagtgcattg ctctctttat ttcataattt tccgcgcgcg ataggcccta    5700
gaccagcgtt ctcggtcgtt gagggtgcgg tgtatcttct ccaggacgtg gtagaggtgg    5760
ctctggacgt tgagatacat gggcatgagc ccgtcccggg ggtggaggta gcaccactgc    5820
agagcttcat gctccggggt ggtgttgtag atgatccagt cgtagcagga gcgctgggca    5880
tggtgcctaa aaatgtcctt cagcagcagg ccgatggcca gggggaggcc cttggtgtaa    5940
gtgtttacaa aacggttaag ttgggaaggg tgcattcggg gagagatgat gtgcatcttg    6000
gactgtattt ttagattggc gatgtttccg cccagatccc ttctgggatt catgttgtgc    6060
aggaccacca gtacagtgta tccggtgcac ttggggaatt tgtcatgcag cttagaggga    6120
aaagcgtgga agaacttgga gacgcctttg tggcctccca gattttccat gcattcgtcc    6180
atgatgatgg caatgggccc gcggaggca gcttgggcaa agatatttct ggggtcgctg    6240
acgtcgtagt tgtgttccag ggtgaggtcg tcataggcca ttttttacaaa gcgcgggcgg    6300 agggtgcccg actgggggat gatggtcccc tctggccctg gggcgtagtt gccctcgcag    6360
```

```
atctgcattt cccaggcctt aatctcggag gggggaatca tatccacctg cggggcgatg    6420
aagaaaacgg tttccggagc cggggagatt aactgggatg agagcaggtt tctaagcagc    6480
tgtgattttc cacaaccggt gggcccataa ataacaccta taaccggttg cagctggtag    6540
tttagagagc tgcagctgcc gtcgtcccgg aggagggggg ccacctcgtt gagcatgtcc    6600
ctgacgcgca tgttctcccc gaccagatcc gccagaaggc gctcgccgcc cagggacagc    6660
agctcttgca aggaagcaaa gttttttcagc ggcttgaggc cgtccgccgt gggcatgttt    6720
```

```
caaactcttc gcggtctttc cagtactctt ggatcgggaa accgtccggt tccgaacggt    8760
aagagcctag catgtagaac tggttgacgg cctggtaggc gcagcagccc ttctccacgg    8820
ggagggcgta ggcctgcgcg gccttgcgga gcgaggtgtg ggtcagggcg aaggtgtccc    8880
tgaccatgac tttgaggtac tggtgcttga agtcggagtc gtcgcagccg ccccgctccc    8940
agagcgagaa gtcggtgcgc ttcttggagc gggggttggg cagagcgaag gtgacatcgt    9000
tgaagaggat tttgcccgcg cggggcatga agttgcgggt gatgcggaag gccccggca     9060 cttcagagcg gttgttgatg acctgggcgg cgagcacgat ctcgtcgaag ccgttgatgt    9120
tgtggcccac gatgtagagt tccaggaagc ggggccggcc cttacggtg gcagcttct      9180 ttagctcttc gtaggtgagc cctcgggcg aggcgaggcc gtgctcggcc agggcccagt     9240
ccgcgaggtg cggttgtct ctgaggaagg acttccagag gtcgcgggcc aggagggtct     9300
gcaggcggtc tctgaaggtc ctgaactggc ggcccacggc catttttcg ggggtgatgc     9360 agtagaaggt gagggggtct tgctgccagc ggtcccagtc gagctgcagg gcgaggtcgc    9420
gcgcggcggt gaccaggcgc tcgtcgcccc cgaatttcat gaccagcatg aagggcacga    9480
gctgctttcc gaaggccccc atccaagtgt aggtctctac atcgtaggtg acaaagaggc    9540
gctccgtgcg aggatgcgag ccgatcggga agaactggat ctcccgccac cagttggagg    9600
agtggctgtt gatgtggtgg aagtagaagt cccgtcgccg ggccgaacac tcgtgctggc    9660
ttttgtaaaa gcgagcgcag tactggcagc gctgcacggg ctgtacctca tgcacgagat    9720
gcacctttcg cccgcgcacg aggaagccga ggggaaatct gagccccccg cctggctcgc    9780
ggcatggctg gttctcttct actttggatg cgtgtccgtc tccgtctggc tcctcgaggg    9840
gtgttacggt ggagcggacc accacgccgc gcgagccgca ggtccagata tcggcgcgcg    9900
gcggtcgagg tttgatgacg acatcgcgca gctgggagct gtccatggtc tggagctccc    9960
gcggcggcgg caggtcagcc gggagttctt gcaggttcac ctcgcagagt cgggccaggg    10020
cgcggggcag gtctaggtgg tacctgatct ctaggggcgt gttggtggcg gcgtcgatgg    10080
cttgcaggag cccgcagccc cgggggggcga cgacggtgcc ccgcggggtg gtggtggtgg   10140
tggcggtgca gctcagaagc ggtgccgcgg gcgggccccc ggaggtaggg ggggctccgg    10200
tcccgcgggc aggggcggca gcggcacgtc ggcgtggagc gcgggcagga gttggtgctg    10260
tgcccggagg ttgctggcga aggcgacgac gcggcggttg atctcctgga tctggcgcct    10320
ctgcgtgaag acgacgggcc cggtgagctt gaacctgaaa gagagttcga cagaatcaat    10380
ctcggtgtca ttgaccgcgg cctggcgcag gatctcctgc acgtctcccg agttgtcttg    10440
gtaggcgatc tcggccatga actgctcgat ctcttcctcc tggaggtctc cgcgtccggc    10500
gcgttccacg gtggccgcca ggtcgttgga gatgcgcccc atgagctgcg agaaggcgtt    10560
gagtccgccc tcgttccaga ctcggctgta gaccacgccc ccctggtcat cgcgggcgcg    10620
catgaccacc tgcgcgaggt tgagctccac gtgccgcgcg aagacggcgt agttgcgcag    10680
acgctggaag aggtagttga gggtggtggc ggtgtgctcg gccacgaaga agttcatgac    10740
ccagcggcgc aacgtggatt cgttgatgtc ccccaaggcc tccagccgtt ccatggcctc    10800
gtagaagtcc acgcgcaagt tgaaaaactg ggagttgcgc gccgacacgg tcaactcctc    10860
ctccagaaga cggatgagct cggcgacggt gtcgcgcacc tcgcgctcga aggctatggg    10920
gatctcttcc tccgctagca tcaccacctc ctcctcttcc tcctcttctg gcacttccat    10980
gatggcttcc tcctcttcgg ggggtggcgg cggcggcggt gggggagggg gcgctctgcg    11040
ccggcggcgg cgcaccggga ggcggtccac gaagcgcgcg atcatctccc cgcggcggcg    11100
```

```
gcgcatggtc tcggtgacgg cgcggccgtt ctcccggggg cgcagttgga agacgccgcc    11160
ggacatctgg tgctgggcg gtggccgtg aggcagcgca acggcgctga cgatgcatct    11220
caacaattgc tgcgtaggta cgccgccgag ggacctgagg gagtccatat ccaccggatc    11280
cgaaaacctt tcgaggaagg cgtctaacca gtcgcagtcg caaggtaggc tgagcaccgt    11340
ggcgggcggc gggggtggg gggagtgtct ggcggaggtg ctgctgatga tgtaattgaa    11400
gtaggcggac ttgacacggc ggatggtcga caggagcacc atgtccttgg gtccggcctg    11460
ctggatgcgg aggcggtcgg ctatgcccca ggcttcgttc tggcatcggc gcaggtcctt    11520
gtagtagtct tgcatgagcc tttccaccgg cacctcttct ccttcctctt ctgcttcttc    11580
catgtctgct tcggccctgg ggcggcgccg cgccccctg ccccccatgc gcgtgacccc    11640
gaaccccctg agcggttgga gcagggccag gtcggcgacg acgcgctcgg ccaggatggc    11700
ctgctgcacc tgcgtgaggg tggtttggaa gtcatccaag tccacgaagc ggtggtaggc    11760
gcccgtgttg atggtgtagg tgcagttggc catgacggac cagttgacgg tctggtggcc    11820
cggttgcgac atctcggtgt acctgagtcg cgagtaggcg cgggagtcga agacgtagtc    11880
gttgcaagtc cgcaccaggt actggtagcc caccaggaag tgcggcggcg gctggcggta    11940
gaggggccag cgcagggtgg cgggggctcc ggggccagg tcttccagca tgaggcggtg    12000
gtaggcgtag atgtacctgg acatccaggt gatacccgcg gcggtggtgg aggcgcgcgg    12060
gaagtcgcgc acccggttcc agatgttgcg caggggcaga aagtgctcca tggtaggcgt    12120
gctctgtcca gtcagacgcg cgcagtcgtt gatactctag accagggaaa acgaaagccg    12180
gtcagcgggc actcttccgt ggtctggtga atagatcgca agggtatcat ggcggagggc    12240
ctcggttcga gccccgggtc cgggccggac ggtccgccat gatccacgcg gttaccgccc    12300
gcgtgtcgaa cccaggtgtg cgacgtcaga caacggtgga gtgttccttt tggcgttttt    12360
ctggccgggc gccggcgccg cgtaagagac taagccgcga agcgaaagc agtaagtggc    12420 tcgctccccg tagccggagg gatccttgct aagggttgcg ttgcggcgaa ccccggttcg    12480
aatcccgtac tcgggccggc cggacccgcg gctaaggtgt tggattggcc tcccctcgt    12540 ataaagaccc cgcttgcgga ttgactccgg acacggggac gagccccttt tatttttgct    12600
ttccccagat gcatccggtg ctgcggcaga tgcgcccccc gccccagcag cagcaacaac    12660
accagcaaga gcggcagcaa cagcagcggg agtcatgcag ggcccccctca cccaccctcg    12720 gcgggccggc cacctcggcg tccgcggccg tgtctggcgc ctgcggcggc ggcggggggc    12780
cggctgacga ccccgaggag cccccgcggc gcagggccag acactacctg gacctggagg    12840
agggcgaggg cctggcgcgg ctgggggcgc cgtctcccga gcgccacccg cgggtgcagc    12900
tgaagcgcga ctcgcgcgag gcgtacgtgc tcggcagaa cctgttcagg gaccgcgcgg    12960
gcgaggagcc cgaggagatg cgggacagga ggttcagcgc agggcgggag ctgcggcagg    13020
ggctgaaccg cgacggctg ctgcgcgagg aggactttga gcccgacgcg cggacgggga    13080
tcagccccgc gcgcgcgcac gtggcggccg ccgacctggt gacggcgtac gagcagacgg    13140
tgaaccagga gatcaacttc caaaagagtt tcaacaacca cgtgcgcacg ctggtggcgc    13200
gcgaggaggt gaccatcggg ctgatgcacc tgtgggactt tgtaagcgcg ctggtgcaga    13260
accccaacag caagcctctg acggcgcagc tgttcctgat agtgcagcac agcagggaca    13320
acgaggcgtt tagggacgcg ctgctgaaca tcaccgagcc cgaggtcggg tggctgctgg    13380
acctgattaa catcctgcag agcatagtgg tgcaggagcg cagcctgagc ctggccgaca    13440
```

```
aggtggcggc catcaactac tcgatgctga gcctgggcaa gttttacgcg cgcaagatct   13500
accagacgcc gtacgtgccc atagacaagg aggtgaagat cgacggtttt tacatgcgca   13560
tggcgctgaa ggtgctcacc ctgagcgacg acctgggcgt gtaccgcaac gagcgcatcc   13620
acaaggccgt gagcgtgagc cggcggcgcg agctgagcga ccgcgagctg atgcacagcc   13680
tgcagcgggc gctggcgggc gccggcagcg gcgacaggga ggcggagtcc tacttcgatg   13740
cgggggcgga cctgcgctgg gcgcccagcc ggcgggccct ggaggccgcg ggggtccgcg   13800
aggactatga cgaggacggc gaggaggatg aggagtacga gctagaggag ggcgagtacc   13860
tggactaaac cgcgggtggt gtttccggta gatgcaagac ccgaacgtgg tggacccggc   13920
gctgcgggcg gctctgcaga gccagccgtc cggccttaac tcctcagacg actggcgaca   13980
ggtcatggac cgcatcatgt cgctgacggc gcgtaacccg gacgcgttcc ggcagcagcc   14040
gcaggccaac aggctctccg ccatcctgga ggcggtggtg cctgcgcgct cgaacccac    14100 gcacgagaag gtgctggcca tagtgaacgc gctggccgag aacagggcca tccgcccgga   14160
cgaggccggg ctggtgtacg acgcgctgct gcagcgcgtg gcccgctaca acagcggcaa   14220
cgtgcagacc aacctggacc ggctggtggg ggacgtgcgc gaggcggtgg cgcagcgcga   14280
gcgcgcggat cggcagggca acctgggctc catggtggcc ctgaatgcct tcctgagcac   14340
gcagccggcc aacgtgccgc gggggcagga agactacacc aactttgtga gcgcgctgcg   14400
gctgatggtg accgagaccc cccagagcga ggtgtaccag tcgggcccgg actacttctt   14460
ccagaccagc agacagggcc tgcagacggt gaacctgagc caggctttca agaacctgcg   14520
ggggctgtgg ggcgtgaagg cgcccaccgg cgaccgggcg acggtgtcca gcctgctgac   14580
gcccaactcg cgcctgctgc tgctgctgat cgcgccgttc acggacagcg gcagcgtgtc   14640
ccgggacacc tacctggggc acctgctgac cctgtaccgc gaggccatcg gcaggcgca    14700 ggtggacgag cacaccttcc aggagatcac cagcgtgagc cgcgcgctgg ggcaggagga   14760
cacgagcagc ctggaggcga ctctgaacta cctgctgacc aaccggcggc agaagattcc   14820
ctcgctgcac agcctgacct ccgaggagga gcgcatcttg cgctacgtgc agcagagcgt   14880
gagcctgaac ctgatgcgcg acggggtgac gcccagcgtg gcgctggaca tgaccgcgcg   14940
caacatggaa ccgggcatgt acgccgcgca ccggccttac atcaaccgcc tgatggacta   15000
cctgcatcgc gcggcggccg tgaaccccga gtactttacc aacgccatcc tgaacccgca   15060
ctggctcccg ccgcccgggt tctacagcgg gggcttcgag gtcccggaga ccaacgatgg   15120
cttcctgtgg gacgacatgg acgacagcgt gttctccccg cggccgcagg cgctggcgga   15180
agcgtccctg ctgcgtccca agaaggagga ggaggaggag gcgagtcgcc gccgcggcag   15240
cagcggcgtg gcttctctgt ccgagctggg ggcggcagcc gccgcgcgcc ccgggtccct   15300
gggcggcagc cccttccga gcctggtggg gtctctgcac agcgagcgca ccacccgccc    15360
tcggctgctg ggcgaggacg agtacctgaa taactcccctg ctgcagccgg tgcgggagaa   15420
aaacctgcct cccgccttcc ccaacaacgg gatagagagc ctggtggaca agatgagcag   15480
atggaagacc tatgcgcagg agcacaggga cgcgcctgcg ctccggccgc ccacgcggcg   15540
ccagcgccac gaccggcagc ggggggctggt gtgggatgac gaggactccg cggacgatag   15600
cagcgtgctg gacctgggag ggagcggcaa cccgttcgcg cacctgcgcc ccgcctggg    15660 gaggatgttt taaaaaaaaa aaaaaaaagc aagaagcatg atgcaaaaat taaataaaac   15720
tcaccaaggc catggcgacc gagcgttggt ttcttgtgtt cccttcagta tgcggcgcgc   15780
ggcgatgtac caggagggac ctcctccctc ttacgagagc gtggtgggcg cggcggcggc   15840
```

```
ggcgccctct tctccctttg cgtcgcagct gctggagccg ccgtacgtgc ctccgcgcta   15900
cctgcggcct acgggggga gaaacagcat ccgttactcg gagctggcgc ccctgttcga   15960
caccacccgg gtgtacctgg tggacaacaa gtcggcggac gtggcctccc tgaactacca   16020
gaacgaccac agcaattttt tgaccacggt catccagaac aatgactaca gcccgagcga   16080
ggccagcacc cagaccatca atctggatga ccggtcgcac tggggcggcg acctgaaaac   16140
catcctgcac accaacatgc ccaacgtgaa cgagttcatg ttcaccaata agttcaaggc   16200
gcgggtgatg gtgtcgcgct cgcacaccaa ggaagaccgg gtggagctga agtacgagtg   16260
ggtggagttc gagctgccag agggcaacta ctccgagacc atgaccattg acctgatgaa   16320
caacgcgatc gtggagcact atctgaaagt gggcaggcag aacggggtcc tggagagcga   16380
catcggggtc aagttcgaca ccaggaactt ccgcctgggg ctggaccccg tgaccgggct   16440
ggttatgccc ggggtgtaca ccaacgaggc cttccatccc gacatcatcc tgctgcccgg   16500
ctgcggggtg gacttcactt acagccgcct gagcaacctc ctgggcatcc gcaagcggca   16560
gcccttccag gagggcttca ggatcaccta cgaggacctg gaggggggca acatccccgc   16620
gctcctcgat gtgaggcct accaggatag cttgaaggaa aatgaggcgg acaggagga   16680 taccgccccc gccgcctccg ccgccgccga gcagggcgag gatgctgctg acaccgcggc   16740
cgcggacggg gcagaggccg accccgctat ggtggtggag gctcccgagc aggaggagga   16800
catgaatgac agtgcggtgc gcggagacac cttcgtcacc cggggggagg aaaagcaagc   16860
ggaggccgag gccgcggccg aggaaaagca actggcggca gcagcggcgg cggcggcgtt   16920
ggccgcggcg gaggctgagt ctgaggggac caagcccgcc aaggagcccg tgattaagcc   16980
cctgaccgaa gatagcaaga agcgcagtta caacctgctc aaggacagca ccaacaccgc   17040
gtaccgcagc tggtacctgg cctacaacta cggcgacccg tcgacggggg tgcgctcctg   17100
gaccctgctg tgcacgccgg acgtgacctg cggctcggag caggtgtact ggtcgctgcc   17160
cgacatgatg caagaccccg tgaccttccg ctccacgcgg caggtcagca acttcccggt   17220
ggtgggcgcc gagctgctgc ccgtgcactc caagagcttc tacaacgacc aggccgtcta   17280
ctcccagctc atccgccagt tcacctctct gacccacgtg ttcaatcgct ttcctgagaa   17340
ccagattctg gcgcgcccgc ccgccccac catcaccacc gtcagtgaaa acgttcctgc   17400
tctcacagat cacgggacgc taccgctgcg caacagcatc ggaggagtcc agcgagtgac   17460
cgttactgac gccagacgcc gcacctgccc ctacgtttac aaggccttgg catagtctc   17520 gccgcgcgtc ctttccagcc gcactttttg agcaacacca ccatcatgtc catcctgatc   17580
tcacccagca ataactccgg ctggggactg ctgcgcgcgc ccagcaagat gttcggaggg   17640
gcgaggaagc gttccgagca gcaccccgtg cgcgtgcgcg ggcacttccg cgccccctgg   17700
ggagcgcaca aacgcggccg cgcggggcgc accaccgtgg acgacgccat cgactcggtg   17760
gtggagcagg cgcgcaacta caggcccgcg gtctctaccg tggacgcggc catccagacc   17820
gtggtgcggg gcgcgcggcg gtacgccaag ctgaagagcc gccggaagcg cgtggcccgc   17880
cgccaccgcc gccgaccgg ggcgccgcc aaacgcgccg ccgcggccct gcttcgccgg   17940
gccaagcgca cgggccgccg cgccgccatg agggccgcgc gccgcttggc cgccggcatc   18000
accgccgcca ccatggcccc ccgtacccga agacgcgcgg ccgccgccgc cgccgccgcc   18060
atcagtgaca tggccagcag gcgccggggc aacgtgtact gggtgcgcga ctcggtgacc   18120
ggcacgcgcg tgcccgtgcg cttccgcccc ccgcggactt gagatgatgt gaaaaaacaa   18180
```

```
cactgagtct cctgctgttg tgtgtatccc agcggcggcg gcgcgcgcag cgtcatgtcc    18240
aagcgcaaaa tcaaagaaga gatgctccag gtcgtcgcgc cggagatcta tgggcccccg    18300
aagaaggaag agcaggattc gaagcccgc aagataaagc gggtcaaaaa gaaaaagaaa    18360
gatgatgacg atgccgatgg ggaggtggag ttcctgcgcg ccacggcgcc caggcgcccg    18420
gtgcagtgga agggccggcg cgtaaagcgc gtcctgcgcc ccggcaccgc ggtggtcttc    18480
acgcccggcg agcgctccac ccggactttc aagcgcgtct atgacgaggt gtacggcgac    18540
gaagacctgc tggagcaggc caacgagcgc ttcggagagt ttgcttacgg gaagcgtcag    18600
cgggcgctgg ggaaggagga cctgctggcg ctgccgctgg accagggcaa ccccaccccc    18660
agtctgaagc ccgtgaccct gcagcaggtg ctgccgagca gcgcaccctc cgaggcgaag    18720
cggggtctga agcgcgaggg cggcgacctg gcgcccaccg tgcagctcat ggtgcccaag    18780
cggcagaggc tggaggatgt gctggagaaa atgaaagtag accccggtct gcagccggac    18840
atcagggtcc gccccatcaa gcaggtggcg ccgggcctcg gcgtgcagac cgtggacgtg    18900
gtcatcccca ccgcaactc ccccgccgcc gccaccacta ccgctgcctc cacgacatg    18960 gagacacaga ccgatcccgc cgcagccgca gccgcagccg ccgccgcgac ctcctcggcg    19020
gaggtgcaga cggacccctg gctgccgccg gcgatgtcag ctccccgcgc gcgtcgcggg    19080
cgcaggaagt acggcgccgc caacgcgctc ctgcccgagt acgccttgca tccttccatc    19140
gcgcccaccc ccgctaccg aggctatacc taccgcccgc gaagagccaa gggttccacc    19200
cgccgtcccc gccgacgcgc cgccgccacc acccgccgcc gccgccgcag acgccagccc    19260
gcactggctc cagtctccgt gaggaaagtg gcgcgcgacg gacacaccct ggtgctgccc    19320
agggcgcgct accaccccag catcgtttaa aagcctgttg tggttcttgc agatatggcc    19380
ctcacttgcc gcctccgttt cccggtgccg ggataccgag gaggaagatc gcgccgcagg    19440
aggggtctgg ccggccgcgg cctgagcgga ggcagccgcc gcgcgcaccg gcggcgacgc    19500
gccaccagcc gacgcatgcg cggcggggtg ctgcccctgt taatcccct gatcgccgcg    19560 gcgatcggcg ccgtgcccgg gatcgcctcc gtggccttgc aagcgtccca gaggcattga    19620
cagacttgca aacttgcaaa tatgcaaaaa aaaacccccaa taaaaaagtc tagactctca    19680
cgctcgcttg gtcctgtgac tattttgtag aatggaagac atcaactttg cgtcgctggc    19740
cccgcgtcac ggctcgcgcc cgttcctggg acactggaac gatatcggca ccagcaacat    19800
gagcggtggc gccttcagtt ggggctctct gtggagcggc attaaaagta tcgggtctgc    19860
cgttaaaaat tacggctccc gggcctggaa cagcagcacg ggccagatgt tgagagacaa    19920
gttgaaagag cagaacttcc agcagaaggt ggtggagggc ctggcctccg gcatcaacgg    19980
ggtggtggac ctggccaacc aggccgtgca gaataagatc aacagcagac tggacccccg    20040
gccgccggtg gaggaggtgc cgccggcgct ggagacggtg tccccgatg ggcgtggcga    20100 gaagcgcccg cggcccgata gggaagagac cactctggtc acgcagaccg atgagccgcc    20160
cccgtatgag gaggccctga gcaaggtct gcccaccacg cggcccatcg cgcccatggc    20220 caccgggggtg gtgggccgcc acacccccgc cacgctggac ttgcctccgc ccgccgatgt    20280
gccgcagcag cagaaggcgg cacagccggg cccgcccgcg accgcctccc gttcctccgc    20340
cggtcctctg cgccgcgcgg ccagcggccc ccgcgggggg gtcgcgaggc acggcaactg    20400
gcagagcacg ctgaacagca tcgtgggtct gggggtgcgg tccgtgaagc gccgccgatg    20460
ctactgaata gcttagctaa cgtgttgtat gtgtgtatgc gccctatgtc gccgccagag    20520
gagctgctga gtcgccgccg ttcgcgcgcc caccaccacc gccactccgc ccctcaagat    20580
```

```
ggcgacccca tcgatgatgc cgcagtggtc gtacatgcac atctcgggcc aggacgcctc    20640
ggagtacctg agccccgggc tggtgcagtt cgcccgcgcc accgagagct acttcagcct    20700
gagtaacaag tttaggaacc ccacggtggc gcccacgcac gatgtgacca ccgaccggtc    20760
tcagcgccta acgctgcggt tcattcccgt ggaccgcgag gacaccgcgt actcgtacaa    20820
ggcgcggttc accctggccg tgggcgacaa ccgcgtgctg gacatggcct ccacctactt    20880
tgacatccgc ggggtgctgg accggggtcc cactttcaag ccctactctg caccgccta    20940 caactccctg gcccccaagg gcgctcccaa ctcctgcgag tgggagcaag aggaaactca    21000
ggcagttgaa gaagcagcag aagaggaaga agaagatgct gacggtcaag ctgaggaaga    21060
gcaagcagct accaaaaaga ctcatgtata tgctcaggct cccctttctg gcgaaaaaat    21120
tagtaaagat ggtctgcaaa taggaacgga cgctacagct acagaacaaa aacctattta    21180
tgcagaccct acattccagc ccgaacccca aatcggggag tcccagtgga atgaggcaga    21240
tgctacagtc gccggcggta gagtgctaaa gaaatctact cccatgaaac catgctatgg    21300
ttcctatgca agacccacaa atgctaatgg aggtcagggt gtactaacgg caaatgccca    21360
gggacagcta gaatctcagg ttgaaatgca attcttttca acttctgaaa cgcccgtaa    21420 cgaggctaac aacattcagc ccaaattggt gctgtatagt gaggatgtgc acatggagac    21480
cccggatacg caccttttctt acaagcccgc aaaaagcgat gacaattcaa aaatcatgct    21540
gggtcagcag tccatgccca acagacctaa ttacatcggc ttcagagaca actttatcgg    21600
cctcatgtat tacaatagca ctggcaacat gggagtgctt gcaggtcagg cctctcagtt    21660
gaatgcagtg gtggacttgc aagacagaaa cacagaactg tcctaccagc tcttgcttga    21720
ttccatgggt gacagaacca gatactttc catgtggaat caggcagtgg acagttatga    21780
cccagatgtt agaattattg aaaatcatgg aactgaagac gagctcccca actattgttt    21840
ccctctgggt ggcataggg taactgacac ttaccaggct gttaaaacca acaatggcaa    21900 taacggggc caggtgactt ggacaaaaga tgaaactttt gcagatcgca atgaaatagg    21960
ggtgggaaac aatttcgcta tggagatcaa cctcagtgcc aacctgtgga gaaacttcct    22020
gtactccaac gtggcgctgt acctaccaga caagcttaag tacaacccct ccaatgtgga    22080
catctctgac aacccaaaca cctacgatta catgaacaag cgagtggtgg ccccgggct    22140 ggtggactgc tacatcaacc tgggcgcgcg ctggtcgctg gactacatgg acaacgtcaa    22200
ccccttcaac caccaccgca atgcgggcct gcgctaccgc tccatgctcc tgggcaacgg    22260
gcgctacgtg cccttccaca tccaggtgcc ccagaagttc tttgccatca gaacctcct    22320 cctcctgccg ggctcctaca cctacgagtg gaacttcagg aaggatgtca acatggtcct    22380
ccagagctct ctgggtaacg atctcagggt ggacggggcc agcatcaagt tcgagagcat    22440
ctgcctctac gccaccttct tccccatggc ccacaacacg gcctccacgc tcgaggccat    22500
gctcaggaac gacaccaacg accagtcctt caatgactac ctctccgccg ccaacatgct    22560
ctaccccata cccgccaacg ccaccaacgt ccccatctcc atccctcgc gcaactgggc    22620 ggccttccgc ggctgggcct tcacccgcct caagaccaag gagaccccct ccctgggctc    22680
gggattcgac ccctactaca cctactcggg ctccattccc tacctggacg gcaccttcta    22740
cctcaaccac actttcaaga aggtctcggt caccttcgac tcctcggtca gctggccggg    22800
caacgaccgt ctgctcaccc ccaacgagtt cgagatcaag cgctcggtcg acggggaggg    22860
ctacaacgtg gcccagtgca acatgaccaa ggactggttc ctggtccaga tgctggccaa    22920
```

```
ctacaacatc ggctaccagg gcttctacat cccagagagc tacaaggaca ggatgtactc    22980
cttcttcagg aacttccagc ccatgagccg gcaggtggtg gaccagacca agtacaagga    23040
ctaccaggag gtgggcatca tccaccagca caacaactcg ggcttcgtgg gctacctcgc    23100
ccccaccatg cgcgagggac aggcctaccc cgccaacttc ccctatccgc tcataggcaa    23160
gaccgcggtc gacagcatca cccagaaaaa gttcctctgc gaccgcaccc tctggcgcat    23220
ccccttctcc agcaacttca tgtccatggg tgcgctctcg gacctgggcc agaacttgct    23280
ctacgccaac tccgcccacg ccctcgacat gaccttcgag gtcgaccccs tggacgagcc    23340 caccttctc tatgttctgt tcgaagtctt tgacgtggtc cgggtccacc agccgcaccg    23400
cggcgtcatc gagaccgtgt acctgcgtac gcccttctcg gccggcaacg ccaccaccta    23460
aagaagcaag ccgcagtcat cgccgcctgc atgccgtcgg gttccaccga gcaagagctc    23520
agggccatcg tcagagacct gggatgcggg ccctattttt tgggcacctt cgacaagcgc    23580
ttccctggct tgtctcccc acacaagctg gcctgcgcca tcgtcaacac ggccggccgc    23640
gagaccgggg gcgtgcactg gctggccttc gcctggaacc cgcgctccaa acatgcttc    23700 ctctttgacc ccttcggctt ttcggaccag cggctcaagc aaatctacga gttcgagtac    23760
gagggcttgc tgcgtcgcag cgccatcgcc tcctcgcccg accgctgcgt caccctcgaa    23820
aagtccaccc agaccgtgca ggggcccgac tcggccgcct gcggtctctt ctgctgcatg    23880
tttctgcacg cctttgtgca ctggcctcag agtcccatgg accgcaaccc caccatgaac    23940
ttgctgacgg gggtgcccaa ctccatgctc cagagccccc aggtcgagcc caccctgcgc    24000
cgcaaccagg agcagctcta cagcttcctg gagcgccact cgccttactt ccgccgccac    24060
agcgcacaga tcaggagggc caccctcctttc tgccacttgc aagagatgca agaagggtaa    24120
taacgatgta cacacttttt ttctcaataa atggcatctt tttatttata caagctctct    24180
ggggtattca tttcccacca ccacccgccg ttgtcgccat ctggctctat ttagaaatcg    24240
aaagggttct gccgggagtc gccgtgcgcc acgggcaggg acacgttgcg atactggtag    24300
cgggtgcccc acttgaactc gggcaccacc aggcgaggca gctcggggaa gttttcgctc    24360
cacaggctgc gggtcagcac cagcgcgttc atcaggtcgg gcgccagagat cttgaagtcg    24420 cagttggggc cgccgccctg cgcgcgcgag ttgcggtaca ccgggttgca gcactggaac    24480
accaacagcg ccgggtgctt cacgctggcc agcacgctgc ggtcgagat cagctcggcg    24540 tccaggtcct ccgcgttgct cagcgcgaac ggggtcatct tgggcacttg ccgccccagg    24600
aagggcgcgt gccccggttt cgagttgcag tcgcagcgca gcgggatcag caggtgcccg    24660
tgcccggact cggcgttggg gtacagcgcg cgcatgaagg cctgcatctg gcggaaggcc    24720
atctgggcct tggcgccctc cgagaagaac atgccgcagg acttgcccga gaactggttt    24780
gcggggcagc tggcgtcgtg caggcagcag cgcgcgtcgg tgttggcgat ctgcaccacg    24840
ttgcgccccc accggttctt cacgatcttg gccttggacg attgctcctt cagcgcgcgc    24900
tgcccgttct cgctggtcac atccatctcg atcacatgtt ccttgttcac catgctgctg    24960
ccgtgcagac acttcagctc gccctccgtc tcggtgcagc ggtgctgcca cagcgcgcag    25020
cccgtgggct cgaaagactt gtaggtcacc tccgcgaagg actgcaggta cccctgcaaa    25080
aagcggccca tcatggtcac gaaggtcttg ttgctgctga aggtcagctg cagcccgcgg    25140
tgctcctcgt tcagccaggt cttgcacacg gccgccagcg cctccacctg gtcgggcagc    25200
atcttgaagt tcaccttcag ctcattctcc acgtggtact tgtccatcag cgtgcgcgcc    25260
gcctccatgc ccttctccca ggccgacacc agcggcaggc tcacggggtt cttcaccatc    25320
```

```
accgtggccg ccgcctccgc cgcgctttcg ctttccgccc cgctgttctc ttcctcttcc    25380
tcctcttcct cgccgccgcc cactcgcagc ccccgcacca cggggtcgtc ttcctgcagg    25440
cgctgcacct tgcgcttgcc gttgcgcccc tgcttgatgc gcacgggcgg gttgctgaag    25500
cccaccatca ccagcgcggc ctcttcttgc tcgtcctcgc tgtccagaat gacctccggg    25560
gagggggggt tggtcatcct cagtaccgag gcacgcttct ttttcttcct gggggcgttc    25620
gccagctccg cggctgcggc cgctgccgag gtcgaaggcc gagggctggg cgtgcgcggc    25680
accagcgcgt cctgcgagcc gtcctcgtcc tcctcggact cgagacggag gcgggcccgc    25740
ttcttcgggg gcgcgcgggg cggcggaggc ggcggcggcg acggagacgg ggacgagaca    25800
tcgtccaggg tgggtggacg gcgggccgcg ccgcgtccgc gctcggggt ggtctcgcgc     25860
tggtcctctt cccgactggc catctcccac tgctccttct cctataggca gaaagagatc    25920
atggagtctc tcatgcgagt cgagaaggag gaggacagcc taaccgcccc ctctgagccc    25980
tccaccaccg ccgccaccac cgccaatgcc gccgcgacg acgcgcccac cgagaccacc     26040
gccagtacca ccctccccag cgacgcaccc ccgctcgaga atgaagtgct gatcgagcag    26100
gacccggggtt ttgtgagcgg agaggaggat gaggtggatg agaaggagaa ggaggaggtc   26160
gccgcctcag tgccaaaaga ggataaaaag caagaccagg acgacgcaga taaggatgag    26220
acagcagtcg ggcgggggaa cggaagccat gatgctgatg acggctacct agacgtggga    26280
gacgacgtgc tgcttaagca cctgcaccgc cagtgcgtca tcgtctgcga cgcgctgcag    26340
gagcgctgcg aagtgcccct ggacgtggcg gaggtcagcc gcgcctacga gcggcacctc    26400
ttcgcgccgc acgtgccccc caagcgccgg gagaacggca cctgcgagcc caacccgcgt    26460
ctcaacttct acccggtctt cgcggtaccc gaggtgctgg ccacctacca catctttttc    26520
caaaactgca agatccccct ctcctgccgc gccaaccgca cccgcgccga caaaaccctg    26580
accctgcggc agggcgccca catacctgat atcgcctctc tggaggaagt gcccaagatc    26640
ttcgagggtc tcggtcgcga cgagaaacgg gcggcgaacg ctctgcacgg agacagcgaa    26700
aacgagagtc actcgggggt gctggtggag ctcgagggcg acaacgcgcg cctggccgta    26760
ctcaagcgca gcatagaggt cacccacttt gcctacccgg cgctcaacct gccccccaag    26820
gtcatgagtg tggtcatggg cgagctcatc atgcgccgcg cccagcccct ggccgcggat    26880
gcaaacttgc aagagtcctc cgaggaaggc ctgcccgcgg tcagcgacga gcagctggcg    26940
cgctggctgg agacccgcga ccccgcgcag ctggaggagc ggcgcaagct catgatggcc    27000
gcggtgctgg tcaccgtgga gctcgagtgt ctgcagcgct tcttcgcgga ccccgagatg    27060
cagcgcaagc tcgaggagac cctgcactac accttccgcc agggctacgt gcgccaggcc    27120
tgcaagatct ccaacgtgga gctctgcaac ctggtctcct acctgggcat cctgcacgag    27180
aaccgcctcg ggcagaacgt cctgcactcc accctcaaag gggaggcgcg ccgcgactac    27240
atccgcgact cgcctacct cttcctctgc tacacctggc agacggccat ggggtctgg     27300
cagcagtgcc tggaggagcg caacctcaag gagctggaaa agctcctcaa gcgcaccctc    27360
agggacctct ggacgggctt caacgagcgc tcggtggccg ccgcgctggc ggacatcatc    27420
tttcccgagc gcctgctcaa gaccctgcag cagggcctgc ccgacttcac cagccagagc    27480
atgctgcaga acttcaggac tttcatcctg gagcgctcgg gcatcctgcc ggccacttgc    27540
tgcgcgctgc ccagcgactt cgtgcccatc aagtacaggg agtgcccgcc gccgctctgg    27600
ggccactgct acctcttcca gctggccaac tacctcgcct accactcgga cctcatggaa    27660
```

-continued

```
gacgtgagcg gcgagggcct gctcgagtgc cactgccgct gcaacctctg cacgcccac    27720
cgctctctag tctgcaaccc gcagctgctc agcgagagtc agattatcgg taccttcgag   27780
ctgcagggtc cctcgcctga cgagaagtcc gcggctccag ggctgaaact cactccgggg   27840
ctgtggactt ccgcctacct acgcaaattt gtacctgagg actaccacgc ccacgagatc   27900
aggttctacg aagaccaatc ccgcccgccc aaggcggagc tcaccgcctg cgtcatcacc   27960
cagggcaca tcctgggcca attgcaagcc atcaacaaag cccgccgaga gttcttgctg    28020
aaaaagggtc gggggtgta cctggacccc cagtccggcg aggagctaaa cccgctaccc    28080
ccgccgccgc cccagcagcg ggaccttgct tcccaggatg gcacccagaa agaagcagca   28140
gccgccgccg ccgccgcagc catacatgct tctggaggaa gaggaggagg actgggacag   28200
tcaggcagag gaggtttcgg acgaggagca ggaggagatg atggaagact gggaggagga   28260
cagcagccta gacgaggaag cttcagaggc cgaagaggtg gcagacgcaa caccatcgcc   28320
ctcggtcgca gcccctcgc cggggcccct gaaatcctcc gaacccagca ccagcgctat    28380
aacctccgct cctccggcgc cggcgccacc cgcccgcaga cccaaccgta gatgggacac   28440
cacaggaacc ggggtcggta agtccaagtg cccgccgccg ccaccgcagc agcagcagca   28500
gcagcgccag ggctaccgct cgtggcgcgg gcacaagaac gccatagtcg cctgcttgca   28560
agactgcggg ggcaacatct ctttcgcccg ccgcttcctg ctattccacc acggggtcgc   28620
cttccccgc aatgtcctgc attactaccg tcatctctac agccctact gcagcggcga    28680
cccagaggcg gcagcggcag ccacagcggc gaccaccacc taggaagata tcctccgcgg   28740
gcaagacagc ggcagcagcg gccaggagac ccgcggcagc agcggcggga gcggtgggcg   28800
cactgcgcct ctcgcccaac gaaccctct cgacccggga gctcagacac aggatcttcc    28860
ccactttgta tgccatcttc caacagagca gaggccagga gcaggagctg aaaataaaaa   28920
acagatctct gcgctccctc acccgcagct gtctgtatca caaaagcgaa gatcagcttc   28980
ggcgcacgct ggaggacgcg gaggcactct tcagcaaaata ctgcgcgctc actcttaaag   29040
actagctccg cgcccttctc gaatttaggc gggagaaaac tacgtcatcg ccggccgccg   29100
cccagcccgc ccagccgaga tgagcaaaga gattcccacg ccatacatgt ggagctacca   29160
gccgcagatg ggactcgcgg cgggagcggc ccaggactac tccacccgca tgaactacat   29220
gagcgcggga ccccacatga tctcacaggt caacgggatc cgcgcccagc gaaaccaaat   29280
actgctggaa caggcggcca tcaccgccac gccccgccat aatctcaacc cccgaaattg   29340
gcccgccgcc ctcgtgtacc aggaaacccc ctccgccacc accgtactac ttccgcgtga   29400
cgcccaggcc gaagtccaga tgactaactc aggggcgcag ctcgcgggcg gctttcgtca   29460
cggggcgcgg ccgctccgac caggtataag acacctgatg atcagaggcc gaggtatcca   29520
gctcaacgac gagtcggtga gctcttcgct cggtctccgt ccggacggaa ctttccagct   29580
cgccggatcc ggccgctctt cgttcacgcc ccgccaggcg tacctgactc tgcagacctc   29640
gtcctcggag ccccgctccg gcggcatcgg aaccctccag ttcgtggagg agttcgtgcc   29700
ctcggtctac ttcaacccct tctcgggacc tccggacgc taccccgacc agttcattcc    29760
gaactttgac gcggtgaagg actcggcgga cggctacgac tgaatgtcag gtgtcgaggc   29820
agagcagctt cgcctgagac acctcgagca ctgccgccgc cacaagtgct tcgcccgcgg   29880
ttctggtgag ttctgctact ttcagctacc cgaggagcat accgaggggc cggcgcacgg   29940
cgtccgcctg accacccagg gcgaggttac ctgttccctc atccgggagt ttaccctccg   30000
tccctgcta gtggagcggg agcggggtcc ctgtgtccta actatcgcct gcaactgccc    30060
```

```
taaccctgga ttacatcaag atctttgctg tcatctctgt gctgagttta ataaacgctg   30120
agatcagaat ctactggggc tcctgtcgcc atcctgtgaa cgccaccgtc ttcacccacc   30180
ccgaccaggc ccaggcgaac ctcacctgcg gtctgcatcg gagggccaag aagtacctca   30240
cctggtactt caacggcacc cccttgtgg tttacaacag cttcgacggg gacggagtct   30300
ccctgaaaga ccagctctcc ggtctcagct actccatcca caagaacacc accctccaac   30360
tcttccctcc ctacctgccg ggaacctacg agtgcgtcac cggccgctgc acccacctca   30420
cccgcctgat cgtaaaccag agctttccgg gaacagataa ctccctcttc cccagaacag   30480
gaggtgagct caggaaaactc cccggggacc agggcggaga cgtaccttcg acccttgtgg   30540
ggttaggatt ttttattacc gggttgctgg ctcttttaat caaagtttcc ttgagatttg   30600
ttctttcctt ctacgtgtat gaacacctca acctccaata actctaccct tcttcggaa   30660 tcaggtgact tctctgaaat cgggcttggt gtgctgctta ctctgttgat ttttttcctt   30720
atcatactca gccttctgtg cctcaggctc gccgcctgct cgcacacat ctatatctac   30780 tgctggttgc tcaagtgcag gggtcgccac ccaagatgaa caggtacatg gtcctatcga   30840
tcctaggcct gctggccctg gcggcctgca gcgccgccaa aaaagagatt acctttgagg   30900
agcccgcttg caatgtaact ttcaagcccg agggtgacca atgcaccacc ctcgtcaaat   30960
gcgttaccaa tcatgagagg ctgcgcatcg actacaaaaa caaaactggc cagtttgcgg   31020
tctatagtgt gtttacgccc ggagacccct ctaactactc tgtcaccgtc ttccagggcg   31080
gacagtctaa gatattcaat tacactttcc cttttatga gttatgcgat gcggtcatgt   31140
acatgtcaaa acagtacaac ctgtggcctc cctctcccca ggcgtgtgtg gaaaatactg   31200
ggtcttactg ctgtatggct ttcgcaatca ctacgctcgc tctaatctgc acggtgctat   31260
acataaaatt caggcagagg cgaatcttta tcgatgaaaa gaaaatgcct tgatcgctaa   31320
caccggcttt ctatctgcag aatgaatgca atcacctccc tactaatcac caccaccctc   31380
cttgcgattg cccatgggtt gacacgaatc gaagtgccag tggggtccaa tgtcaccatg   31440
gtgggccccg ccggcaattc caccctcatg tgggaaaaat ttgtccgcaa tcaatgggtt   31500
catttctgct ctaaccgaat cagtatcaag cccagagcca tctgcgatgg gcaaaatcta   31560
actctgatca atgtgcaaat gatggatgct gggtactatt acgggcagcg gggagaaatc   31620
attaattact ggcgacccca caaggactac atgctgcatg tagtcgaggc acttcccact   31680
accaccccca ctaccacctc tcccaccacc accaccacta ctactactac tactactact   31740
actactacta ccactaccgc tgcccgccat acccgcaaaa gcaccatgat tagcacaaag   31800
ccccctcgtg ctcactccca cgccggcggg cccatcggtg cgacctcaga aaccaccgag   31860
ctttgcttct gccaatgcac taacgccagc gctcatgaac tgttcgacct ggagaatgag   31920
gatgtccagc agagctccgc ttgcctgacc caggaggctg tggagcccgt tgccctgaag   31980
cagatcggtg attcaataat tgactcttct tcttttgcca ctcccgaata ccctcccgat   32040
tctactttcc acatcacggg taccaaagac cctaacctct ctttctacct gatgctgctg   32100
ctctgtatct ctgtggtctc ttccgcgctg atgttactgg ggatgttctg ctgcctgatc   32160
tgccgcagaa agagaaaagc tcgctctcag ggccaaccac tgatgccctt ccctaccccc   32220
ccggattttg cagataacaa gatatgagct cgctgctgac actaaccgct ttactagcct   32280
gcgctctaac ccttgtcgct tgcgactcga gattccacaa tgtcacagct gtggcaggag   32340
aaaatgttac tttcaactcc acggccgata cccagtggtc gtggagtggc tcaggtagct   32400
```

```
acttaactat ctgcaatagc tccacttccc ccggcatatc cccaaccaag taccaatgca   32460
atgccagcct gttcaccctc atcaacgctt ccaccctgga caatggactc tatgtaggct   32520
atgtacccct tggtgggcaa ggaaagaccc acgcttacaa cctggaagtt cgccagccca   32580
gaaccactac ccaagcttct cccaccacca ccaccaccac caccatcacc agcagcagca   32640
gcagcagcag ccacagcagc agcagcagat tattgacttt ggttttggcc agctcatctg   32700
ccgctaccca ggccatctac agctctgtgc ccgaaaccac tcagatccac cgcccagaaa   32760
cgaccaccgc caccacccta cacacctcca gcgatcagat gccgaccaac atcacccct    32820 tggctcttca aatgggactt acaagcccca ctccaaaacc agtggatgcg gccgaggtct   32880
ccgccctcgt caatgactgg gcggggctgg gaatgtggtg gttcgccata ggcatgatgg   32940
cgctctgcct gcttctgctc tggctcatct gctgcctcca ccgcaggcga gccagacccc   33000
ccatctatag acccatcatt gtcctgaacc ccgataatga tgggatccat agattggatg   33060
gcctgaaaaa cctactttt  tcttttacag tatgataaat tgagacatgc ctcgcatttt   33120
cttgtacatg ttccttctcc caccttttct ggggtgttct acgctggccg ctgtgtctca   33180
cctggaggta gactgcctct caccccttcac tgtctacctg ctttacggat tggtcaccct   33240
cactctcatc tgcagcctaa tcacagtaat catcgccttc atccagtgca ttgattacat   33300
ctgtgtgcgc ctcgcatact tcagacacca cccgcagtac cgagacagga acattgccca   33360
acttctaaga ctgctctaat catgcataag actgtgatct gccttctgat cctctgcatc   33420
ctgcccaccc tcacctcctg ccagtacacc acaaaatctc cgcgcaaaag acatgcctcc   33480
tgccgcttca cccaactgtg gaatataccc aaatgctaca cgaaaagag  cgagctctcc   33540 gaagcttggc tgtatggggt catctgtgtc ttagtttct  gcagcactgt cttttgccctc  33600 ataatctacc cctactttga tttgggatgg aacgcgatcg atgccatgaa ttaccccacc   33660
tttcccgcac ccgagataat tccactgcga caagttgtac ccgttgtcgt taatcaacgc   33720
cccccatccc ctacgcccac tgaaatcagc tactttaacc taacaggcgg agatgactga   33780
cgccctagat ctagaaatgg acggcatcag taccgagcag cgtctcctag agaggcgcag   33840
gcaggcggct gagcaagagc gcctcaatca ggagctccga gatctcgtta acctgcacca   33900
gtgcaaaaga ggcatctttt gtctggtaaa gcaggccaaa gtcacctacg agaagaccgg   33960
caacagccac cgcctcagtt acaaattgcc cacccagcgc cagaagctgg tgctcatggt   34020
gggtgagaat cccatcaccg tcacccagca ctcggtagag accgaggggt gtctgcactc   34080
cccctgtcgg ggtccagaag acctctgcac cctggtaaag accctgtgcg gtctcagaga   34140
tttagtcccc tttaactaat caaacactgg aatcaataaa aagaatcact tacttaaaat   34200
cagacagcag gtctctgtcc agtttattca gcagcacctc cttcccctcc tcccaactct   34260
ggtactccaa acgccttctg gcggcaaact tcctccacac cctgaaggga atgtcagatt   34320
cttgctcctg tccctccgca cccactatct tcatgttgtt gcagatgaag cgcaccaaaa   34380
cgtctgacga gagcttcaac cccgtgtacc cctatgacac ggaaagcggc cctccctccg   34440 tcccttctcct caccccctccc ttcgtgtctc ccgatggatt ccaagaaagt cccccccggg  34500
tcctgtctct gaacctggcc gagccctgg  tcacttccca cggcatgctc gccctgaaaa   34560
tgggaagtgg cctctccctg gacgacgctg gcaacctcac ctctcaagat atcaccaccg   34620
ctagccctcc cctcaaaaaa accaagacca acctcagcct agaaacctca tcccccctaa   34680
ctgtgagcac ctcaggcgcc ctcaccgtag cagccgccgc tccccggcg  gtggccggca   34740 cctccctcac catgcaatca gaggcccccc tgacagtaca ggatgcaaaa ctcaccctgg   34800
```

```
ccaccaaagg ccccctgacc gtgtctgaag gcaaactggc cttgcaaaca tcggccccgc    34860
tgacggccgc tgacagcagc accctcacag tcagtgccac accacccctt agcacaagca    34920
atggcagctt gggtattgac atgcaagccc ccatttacac caccaatgga aaactaggac    34980
ttaactttgg cgctcccctg catgtggtag acagcctaaa tgcactgact gtagttactg    35040
gccaaggtct tacgataaac ggaacagccc tacaaactag agtctcaggt gccctcaact    35100 atgcacatc aggaaaccta gaattgagag ctgcaggggg tatgcgagtt gatgcaaatg     35160
gtcaacttat ccttgatgta gcttacccat ttgatgcaca aaacaatctc agccttaggc    35220
ttggacaggg acccctgttt gttaactctg cccacaactt ggatgttaac tacaacagag    35280
gcctctacct gttcacatct ggaaatacca aaaagctaga agttaatatc aaaacagcca    35340
agggtctcat ttatgatgac actgctatag caatcaatgc gggtgatggg ctacagtttg    35400
actcaggctc agatacaaat ccattaaaaa ctaaacttgg attaggactg gattatgact    35460
ccagcagagc cataattgct aaactgggaa ctggcctaag cttcgacaac acaggtgcca    35520
tcacagtagg caacaaaaat gatgacaagc ttaccttgtg gaccacacca gacccatccc    35580
ctaactgtag aatctattca gagaaagatg ctaaattcac acttgttttg actaaatgcg    35640
gcagtcaggt gttggccagc gtttctgttt tatctgtaaa aggtagcctt gcgcccatca    35700
gtggcacagt aactagtgct cagattgtcc tcagatttga tgaaaatgga gttctactaa    35760
gcaattcttc ccttgaccct caatactgga actacagaaa aggtgacctt acagagggca    35820
ctgcatatac caacgcagtg ggatttatgc ccaacctcac agcatacccca aaaacacaga    35880 gccaaactgc taaaagcaac attgtaagtc aggtttactt gaatggggac aaatccaaac    35940 ccatgacccct caccattacc ctcaatggaa ctaatgaaac aggagatgcc acagtaagca    36000
cttactccat gtcattctca tggaactgga atggaagtaa ttacattaat gaaacgttcc    36060
aaaccaactc cttcacccttc tcctacatcg cccaagaata aaaagcatga cgctgttgat    36120
ttgattcaat gtgtttctgt tttattttca agcacaacaa aatcattcaa gtcattcttc    36180
catcttagct taatagacac agtagcttaa tagacccagt agtgcaaagc cccattctag    36240
cttataacta gtggagaagt actcgcctac atggggtag agtcataatc gtgcatcagg    36300
ataggcgtgt ggtgctgcag cagcgcgcga ataaactgct gccgccgccg ctccgtcctg    36360
caggaataca acatggcagt ggtctcctca gcgatgattc gcaccgcccg cagcataagg    36420
cgccttgtcc tccgggcaca gcagcgcacc ctgatctcac ttaaatcagc acagtaactg    36480
cagcacagca ccacaatatt gttcaaaatc ccacagtgca aggcgctgta tccaaagctc    36540
atggcgggga ccacagaacc cacgtggcca tcataccaca agcgcaggta gattaagtgg    36600
cgacccctca taaacacgct ggacataaac attacctctt ttggcatgtt gtaattcacc    36660 acctccggt accatataaa cctctgatta aacatggcgc catccaccac catcctaaac    36720
cagctggcca aaacctgccc gccggctata cactgcaggg aaccgggact ggaacaatga    36780
cagtggagag cccaggactc gtaaccatgg atcatcatgc tcgtcatgat atcaatgttg    36840
gcacaacaca ggcacacgtg catacacttc ctcaggatta caagctcctc ccgcgttaga    36900
accatatccc agggaacaac ccattcctga atcagcgtaa atcccacact gcagggaaga    36960
cctcgcacgt aactcacgtt gtgcattgtc aaagtgttac attcgggcag cagcggatga    37020
tcctccagta tggtagcgcg ggtttctgtc tcaaaaggag gtagcgatc cctactgtac    37080 ggagtgcgcc gagacaaccg agatcgtgtt ggtcgtagtg tcatgccaaa tggaacgccg    37140
```

```
gacgtagtca tatttcctga agtcttagat ctctcaacgc agcaccagca ccaacacttc    37200
gcagtgtaaa aggccaagtg ccgagagagt atatatagga ataaaaagtg acgtaaacgg    37260
gcaaagtcca aaaacgcccc agaaaaaccg cacgcgaacc tacgccccga aacgaaagcc    37320
aaaaaacact agacactccc ttccggcgtc aacttccgct ttcccacgct acgtcacttg    37380
ccccagtcaa acaaactaca tatcccgaac ttccaagtcg ccacgcccaa acaccgcct    37440 acacctcccc gcccgccggc ccgccccaa accgcctcc cgccccgcgc ccgcccccgc     37500
gccgcccatc tcattatcat attggcttca atccaaaata aggtatatta ttgatgatg    37559
```

<210> SEQ ID NO 5
<211> LENGTH: 1145
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Asn Asp Met Pro Ile Thr Asn Asp Gln Lys Lys Leu
            260                 265                 270

Met Ser Asn Asn Val Gln Ile Val Arg Gln Gln Ser Tyr Ser Ile Met
        275                 280                 285
```

-continued

Ser Ile Ile Lys Glu Glu Val Leu Ala Tyr Val Val Gln Leu Pro Leu
    290                 295                 300

Tyr Gly Val Ile Asp Thr Pro Cys Trp Lys Leu His Thr Ser Pro Leu
305                 310                 315                 320

Cys Thr Thr Asn Thr Lys Glu Gly Ser Asn Ile Cys Leu Thr Arg Thr
                325                 330                 335

Asp Arg Gly Trp Tyr Cys Asp Asn Ala Gly Ser Val Ser Phe Phe Pro
            340                 345                 350

Gln Ala Glu Thr Cys Lys Val Gln Ser Asn Arg Val Phe Cys Asp Thr
        355                 360                 365

Met Asn Ser Leu Thr Leu Pro Ser Glu Val Asn Leu Cys Asn Val Asp
    370                 375                 380

Ile Phe Asn Pro Lys Tyr Asp Cys Lys Ile Met Thr Ser Lys Thr Asp
385                 390                 395                 400

Val Ser Ser Ser Val Ile Thr Ser Leu Gly Ala Ile Val Ser Cys Tyr
                405                 410                 415

Gly Lys Thr Lys Cys Thr Ala Ser Asn Lys Asn Arg Gly Ile Ile Lys
            420                 425                 430

Thr Phe Ser Asn Gly Cys Asp Tyr Val Ser Asn Lys Gly Val Asp Thr
        435                 440                 445

Val Ser Val Gly Asn Thr Leu Tyr Tyr Val Asn Lys Gln Glu Gly Lys
    450                 455                 460

Ser Leu Tyr Val Lys Gly Glu Pro Ile Ile Asn Phe Tyr Asp Pro Leu
465                 470                 475                 480

Val Phe Pro Ser Asp Glu Phe Asp Ala Ser Ile Ser Gln Val Asn Glu
                485                 490                 495

Lys Ile Asn Gln Ser Leu Ala Phe Ile Arg Lys Ser Asp Glu Leu Leu
            500                 505                 510

His Asn Val Asn Ala Gly Lys Ser Thr Thr Asn Arg Lys Arg Arg Ala
        515                 520                 525

Pro Val Lys Gln Thr Leu Asn Phe Asp Leu Leu Lys Leu Ala Gly Asp
    530                 535                 540

Val Glu Ser Asn Pro Gly Pro Met Ala Leu Ser Lys Val Lys Leu Asn
545                 550                 555                 560

Asp Thr Leu Asn Lys Asp Gln Leu Leu Ser Ser Ser Lys Tyr Thr Ile
                565                 570                 575

Gln Arg Ser Thr Gly Asp Ser Ile Asp Thr Pro Asn Tyr Asp Val Gln
            580                 585                 590

Lys His Ile Asn Lys Leu Cys Gly Met Leu Leu Ile Thr Glu Asp Ala
        595                 600                 605

Asn His Lys Phe Thr Gly Leu Ile Gly Met Leu Tyr Ala Met Ser Arg
    610                 615                 620

Leu Gly Arg Glu Asp Thr Ile Lys Ile Leu Arg Asp Ala Gly Tyr His
625                 630                 635                 640

Val Lys Ala Asn Gly Val Asp Val Thr Thr His Arg Gln Asp Ile Asn
                645                 650                 655

Gly Lys Glu Met Lys Phe Glu Val Leu Thr Leu Ala Ser Leu Thr Thr
            660                 665                 670

Glu Ile Gln Ile Asn Ile Glu Ile Glu Ser Arg Lys Ser Tyr Lys Lys
        675                 680                 685

Met Leu Lys Glu Met Gly Glu Val Ala Pro Glu Tyr Arg His Asp Ser
    690                 695                 700

```
Pro Asp Cys Gly Met Ile Ile Leu Cys Ile Ala Ala Leu Val Ile Thr
705                 710                 715                 720

Lys Leu Ala Ala Gly Asp Arg Ser Gly Leu Thr Ala Val Ile Arg Arg
            725                 730                 735

Ala Asn Asn Val Leu Lys Asn Glu Met Lys Arg Tyr Lys Gly Leu Leu
                740                 745                 750

Pro Lys Asp Ile Ala Asn Ser Phe Tyr Glu Val Phe Glu Lys Tyr Pro
            755                 760                 765

His Phe Ile Asp Val Phe Val His Phe Gly Ile Ala Gln Ser Ser Thr
770                 775                 780

Arg Gly Gly Ser Arg Val Glu Gly Ile Phe Ala Gly Leu Phe Met Asn
785                 790                 795                 800

Ala Tyr Gly Ala Gly Gln Val Met Leu Arg Trp Gly Val Leu Ala Lys
                805                 810                 815

Ser Val Lys Asn Ile Met Leu Gly His Ala Ser Val Gln Ala Glu Met
            820                 825                 830

Glu Gln Val Val Glu Val Tyr Glu Tyr Ala Gln Lys Leu Gly Gly Glu
                835                 840                 845

Ala Gly Phe Tyr His Ile Leu Asn Asn Pro Lys Ala Ser Leu Leu Ser
850                 855                 860

Leu Thr Gln Phe Pro His Phe Ser Ser Val Val Leu Gly Asn Ala Ala
865                 870                 875                 880

Gly Leu Gly Ile Met Gly Glu Tyr Arg Gly Thr Pro Arg Asn Gln Asp
                885                 890                 895

Leu Tyr Asp Ala Ala Lys Ala Tyr Ala Glu Gln Leu Lys Glu Asn Gly
            900                 905                 910

Val Ile Asn Tyr Ser Val Leu Asp Leu Thr Ala Glu Leu Glu Ala
            915                 920                 925

Ile Lys His Gln Leu Asn Pro Lys Asp Asn Val Glu Leu Gly Gly
            930                 935                 940

Gly Gly Ser Gly Gly Gly Met Ser Arg Arg Asn Pro Cys Lys Phe
945                 950                 955                 960

Glu Ile Arg Gly His Cys Leu Asn Gly Lys Arg Cys His Phe Ser His
                965                 970                 975

Asn Tyr Phe Glu Trp Pro Pro His Ala Leu Leu Val Arg Gln Asn Phe
            980                 985                 990

Met Leu Asn Arg Ile Leu Lys Ser Met Asp Lys Ser Ile Asp Thr Leu
            995                 1000                1005

Ser Glu Ile Ser Gly Ala Ala Glu Leu Asp Arg Thr Glu Glu Tyr
    1010                1015                1020

Ala Leu Gly Val Val Gly Val Leu Glu Ser Tyr Ile Gly Ser Ile
    1025                1030                1035

Asn Asn Ile Thr Lys Gln Ser Ala Cys Val Ala Met Ser Lys Leu
    1040                1045                1050

Leu Thr Glu Leu Asn Ser Asp Asp Ile Lys Lys Leu Arg Asp Asn
    1055                1060                1065

Glu Glu Leu Asn Ser Pro Lys Ile Arg Val Tyr Asn Thr Val Ile
    1070                1075                1080

Ser Tyr Ile Glu Ser Asn Arg Lys Asn Asn Lys Gln Thr Ile His
    1085                1090                1095

Leu Leu Lys Arg Leu Pro Ala Asp Val Leu Lys Lys Thr Ile Lys
    1100                1105                1110
```

```
Asn Thr Leu Asp Ile His Lys Ser Ile Thr Ile Asn Asn Pro Lys
    1115                1120                1125

Glu Ser Thr Val Ser Asp Thr Asn Asp His Ala Lys Asn Asn Asp
    1130                1135                1140

Thr Thr
    1145
```

<210> SEQ ID NO 6
<211> LENGTH: 1187
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 6

```
ccattgcata cgttgtatcc atatcataat atgtacattt atattggctc atgtccaaca      60
ttaccgccat gttgacattg attattgact agttattaat agtaatcaat tacggggtca     120
ttagttcata gcccatatat ggagttccgc gttacataac ttacggtaaa tggcccgcct     180
ggctgaccgc ccaacgaccc ccgcccattg acgtcaataa tgacgtatgt tcccatagta     240
acgccaatag ggactttcca ttgacgtcaa tgggtggagt atttacggta aactgcccac     300
ttggcagtac atcaagtgta tcatatgcca agtacgcccc ctattgacgt caatgacggt     360
aaatggcccg cctggcatta tgcccagtac atgaccttat gggactttcc tacttggcag     420
tacatctacg tattagtcat cgctattacc atggtgatgc ggttttggca gtacatcaat     480
gggcgtggat agcggtttga ctcacgggga tttccaagtc tccaccccat tgacgtcaat     540
gggagtttgt tttggcacca aaatcaacgg gactttccaa aatgtcgtaa caactccgcc     600
ccattgacgc aaatgggcgg taggcgtgta cggtgggagg tctatataag gcgaagcgct     660
ccctatcagt gatagagatc tccctatcag tgatagagat cgtcgacgag ctcgcggcgg     720
gcgggagtcg ctgcgcgctg ccttcgcccc gtgccccgct ccgccgccgc ctcgcgccgc     780
ccgccccggc tctgactgac cgcgttacta aaacaggtaa gtccggcctc cgcgccgggt     840
tttggcgcct cccgcgggcg cccccctcct cacggcgagc gctgccacgt cagacgaagg     900
gcgcagcgag cgtcctgatc cttccgcccg gacgctcagg acagcggccc gctgctcata     960
agactcggcc ttagaacccc agtatcagca gaaggacatt taggacggga cttgggtga    1020 ctctagggca ctggttttct ttccagagag cggaacaggc gaggaaaagt agtcccttct    1080
cggcgattct gcggagggat ctccgtgggg cggtgaacgc cgatgatgcc tctactaacc    1140
atgttcatgt tttctttttt tttctacagg tcctgggtga cgaacag                 1187
```

<210> SEQ ID NO 7
<211> LENGTH: 2908
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 7

```
ccattgcata cgttgtatcc atatcataat atgtacattt atattggctc atgtccaaca      60
ttaccgccat gttgacattg attattgact agttattaat agtaatcaat tacggggtca     120
ttagttcata gcccatatat ggagttccgc gttacataac ttacggtaaa tggcccgcct     180
```

-continued

```
ggctgaccgc ccaacgaccc ccgcccattg acgtcaataa tgacgtatgt tcccatagta      240
acgccaatag ggactttcca ttgacgtcaa tgggtggagt atttacggta aactgcccac      300
ttggcagtac atcaagtgta tcatatgcca agtacgcccc ctattgacgt caatgacggt      360
aaatggcccg cctggcatta tgcccagtac atgaccttat gggactttcc tacttggcag      420
tacatctacg tattagtcat cgctattacc atggtgatgc ggttttggca gtacatcaat      480
gggcgtggat agcggtttga ctcacgggga tttccaagtc tccaccccat tgacgtcaat      540
gggagtttgt tttggcacca aaatcaacgg gactttccaa aatgtcgtaa caactccgcc      600
ccattgacgc aaatgggcgg taggcgtgta cggtgggagg tctatataag cagagctctc      660
cctatcagtg atagagatct ccctatcagt gatagagatc gtcgacgagc tcgtttagtg      720
aaccgtcaga tcgcctggag acgccatcca cgctgttttg acctccatag aagacaccgg      780
gaccgatcca gcctccgcgg ccgggaacgg tgcattggaa cgcggattcc ccgtgccaag      840
agtgagatct tccgtttatc taggtaccag atatcgccac catggccctg agcaaagtga      900
aactgaacga tacactgaac aaggaccagc tgctgtccag cagcaagtac accatccagc      960
ggagcaccgg cgacagcatc gataccccca actacgacgt gcagaagcac atcaacaagc     1020
tgtgcggcat gctgctgatc acagaggacg ccaaccacaa gttcaccggc ctgatcggca     1080
tgctgtacgc catgagccgg ctgggccggg aggacaccat caagatcctg cgggacgccg     1140
gctaccacgt gaaggccaat ggcgtggacg tgaccacaca ccggcaggac atcaacggca     1200
aagaaatgaa gttcgaggtg ctgaccctgg ccagcctgac caccgagatc cagatcaata     1260
tcgagatcga gagccggaag tcctacaaga aaatgctgaa agaaatgggc gaggtggccc     1320
ccgagtacag acacgacagc cccgactgcg gcatgatcat cctgtgtatc gccgccctgg     1380
tgatcacaaa gctggccgct ggcgacagat ctggcctgac agccgtgatc agacgggcca     1440
acaatgtgct gaagaacgag atgaagcggt acaagggcct gctgcccaag gacattgcca     1500
acagcttcta cgaggtgttc gagaagtacc cccacttcat cgacgtgttc gtgcacttcg     1560
gcattgccca gagcagcacc agaggcggct ccagagtgga gggcatcttc gccggcctgt     1620
tcatgaacgc ctacgcgct ggccaggtga tgctgagatg gggcgtgctg gccaagagcg     1680
tgaagaacat catgctgggc cacgccagcg tgcaggccga gatggaacag gtggtggagg     1740
tgtacgagta cgcccagaag ctgggcggag aggccggctt ctaccacatc ctgaacaacc     1800
ctaaggcctc cctgctgtcc ctgacccagt tcccccactt ctccagcgtg gtgctgggaa     1860
atgccgccgg actgggcatc atgggcgagt accggggcac cccagaaaac caggacctgt     1920
acgacgccgc caaggcctac gccgagcagc tgaaagaaaa cggcgtgatc aactacagcg     1980
tgctggacct gaccgctgag gaactggaag ccatcaagca ccagctgaac cccaaggaca     2040
acgacgtgga gctgggaggc ggaggatctg cggcggagg catgagcaga cggaacccct      2100
gcaagttcga gatccggggc cactgcctga acggcaagcg tgccacttc agccacaact     2160 acttcgagtg gccccctcat gctctgctgg tgcggcagaa cttcatgctg aaccggatcc     2220
tgaagtccat ggacaagagc atcgacaccc tgagcgagat cagcggagcc gccgagctgg     2280
acagaaccga ggaatatgcc ctgggcgtgg tgggagtgct ggaaagctac atcggctcca     2340
tcaacaacat cacaaagcag agcgcctgcg tggccatgag caagctgctg acagagctga     2400
acagcgacga catcaagaag ctgagggaca acgaggaact gaacagcccc aagatccggg     2460
tgtacaacac cgtgatcagc tacattgaga gcaaccgcaa gaacaacaag cagaccatcc     2520
atctgctgaa gcggctgccc gccgacgtgc tgaaaagac catcaagaac accctggaca     2580
```

-continued

```
tccacaagtc catcaccatc aacaatccca agaaaagcac cgtgtctgac accaacgatc    2640
acgccaagaa caacgacacc acctgatgag cggccgcgat ctgctgtgcc ttctagttgc    2700
cagccatctg ttgtttgccc ctcccccgtg ccttccttga ccctggaagg tgccactccc    2760
actgtccttt cctaataaaa tgaggaaatt gcatcgcatt gtctgagtag tgtcattct    2820 attctggggg gtggggtggg gcaggacagc aaggggagg attgggaaga caatagcagg    2880
catgctgggg atgcggtggg ctctatgg                                      2908
```

<210> SEQ ID NO 8
<211> LENGTH: 594
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

```
Met Ala Leu Ser Lys Val Lys Leu Asn Asp Thr Leu Asn Lys Asp Gln
1               5                   10                  15

Leu Leu Ser Ser Ser Lys Tyr Thr Ile Gln Arg Ser Thr Gly Asp Ser
            20                  25                  30

Ile Asp Thr Pro Asn Tyr Asp Val Gln Lys His Ile Asn Lys Leu Cys
        35                  40                  45

Gly Met Leu Leu Ile Thr Glu Asp Ala Asn His Lys Phe Thr Gly Leu
    50                  55                  60

Ile Gly Met Leu Tyr Ala Met Ser Arg Leu Gly Arg Glu Asp Thr Ile
65                  70                  75                  80

Lys Ile Leu Arg Asp Ala Gly Tyr His Val Lys Ala Asn Gly Val Asp
                85                  90                  95

Val Thr Thr His Arg Gln Asp Ile Asn Gly Lys Glu Met Lys Phe Glu
            100                 105                 110

Val Leu Thr Leu Ala Ser Leu Thr Thr Glu Ile Gln Ile Asn Ile Glu
        115                 120                 125

Ile Glu Ser Arg Lys Ser Tyr Lys Lys Met Leu Lys Glu Met Gly Glu
    130                 135                 140

Val Ala Pro Glu Tyr Arg His Asp Ser Pro Asp Cys Gly Met Ile Ile
145                 150                 155                 160

Leu Cys Ile Ala Ala Leu Val Ile Thr Lys Leu Ala Ala Gly Asp Arg
                165                 170                 175

Ser Gly Leu Thr Ala Val Ile Arg Arg Ala Asn Asn Val Leu Lys Asn
            180                 185                 190

Glu Met Lys Arg Tyr Lys Gly Leu Leu Pro Lys Asp Ile Ala Asn Ser
        195                 200                 205

Phe Tyr Glu Val Phe Glu Lys Tyr Pro His Phe Ile Asp Val Phe Val
    210                 215                 220

His Phe Gly Ile Ala Gln Ser Ser Thr Arg Gly Gly Ser Arg Val Glu
225                 230                 235                 240

Gly Ile Phe Ala Gly Leu Phe Met Asn Ala Tyr Gly Ala Gly Gln Val
                245                 250                 255

Met Leu Arg Trp Gly Val Leu Ala Lys Ser Val Lys Asn Ile Met Leu
            260                 265                 270

Gly His Ala Ser Val Gln Ala Glu Met Glu Gln Val Val Glu Val Tyr
        275                 280                 285
```

```
Glu Tyr Ala Gln Lys Leu Gly Gly Glu Ala Gly Phe Tyr His Ile Leu
    290                 295                 300

Asn Asn Pro Lys Ala Ser Leu Leu Ser Leu Thr Gln Phe Pro His Phe
305                 310                 315                 320

Ser Ser Val Val Leu Gly Asn Ala Ala Gly Leu Gly Ile Met Gly Glu
                325                 330                 335

Tyr Arg Gly Thr Pro Arg Asn Gln Asp Leu Tyr Asp Ala Ala Lys Ala
            340                 345                 350

Tyr Ala Glu Gln Leu Lys Glu Asn Gly Val Ile Asn Tyr Ser Val Leu
        355                 360                 365

Asp Leu Thr Ala Glu Glu Leu Glu Ala Ile Lys His Gln Leu Asn Pro
    370                 375                 380

Lys Asp Asn Asp Val Glu Leu Gly Gly Gly Ser Gly Gly Gly Gly
385                 390                 395                 400

Met Ser Arg Arg Asn Pro Cys Lys Phe Glu Ile Arg Gly His Cys Leu
                405                 410                 415

Asn Gly Lys Arg Cys His Phe Ser His Asn Tyr Phe Glu Trp Pro Pro
            420                 425                 430

His Ala Leu Leu Val Arg Gln Asn Phe Met Leu Asn Arg Ile Leu Lys
        435                 440                 445

Ser Met Asp Lys Ser Ile Asp Thr Leu Ser Glu Ile Ser Gly Ala Ala
    450                 455                 460

Glu Leu Asp Arg Thr Glu Glu Tyr Ala Leu Gly Val Val Gly Val Leu
465                 470                 475                 480

Glu Ser Tyr Ile Gly Ser Ile Asn Asn Ile Thr Lys Gln Ser Ala Cys
                485                 490                 495

Val Ala Met Ser Lys Leu Leu Thr Glu Leu Asn Ser Asp Asp Ile Lys
            500                 505                 510

Lys Leu Arg Asp Asn Glu Glu Leu Asn Ser Pro Lys Ile Arg Val Tyr
        515                 520                 525

Asn Thr Val Ile Ser Tyr Ile Glu Ser Asn Arg Lys Asn Asn Lys Gln
    530                 535                 540

Thr Ile His Leu Leu Lys Arg Leu Pro Ala Asp Val Leu Lys Lys Thr
545                 550                 555                 560

Ile Lys Asn Thr Leu Asp Ile His Lys Ser Ile Thr Ile Asn Asn Pro
                565                 570                 575

Lys Glu Ser Thr Val Ser Asp Thr Asn Asp His Ala Lys Asn Asn Asp
            580                 585                 590

Thr Thr
```

<210> SEQ ID NO 9
<211> LENGTH: 3617
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 9

```
ccattgcata cgttgtatcc atatcataat atgtacattt atattggctc atgtccaaca      60
ttaccgccat gttgacattg attattgact agttattaat agtaatcaat tacggggtca     120
ttagttcata gcccatatat ggagttccgc gttacataac ttacggtaaa tggcccgcct     180
ggctgaccgc ccaacgaccc ccgcccattg acgtcaataa tgacgtatgt tcccatagta     240
```

-continued

```
acgccaatag ggactttcca ttgacgtcaa tgggtggagt atttacggta aactgcccac    300
ttggcagtac atcaagtgta tcatatgcca agtacgcccc ctattgacgt caatgacggt    360
aaatggcccg cctggcatta tgcccagtac atgaccttat gggactttcc tacttggcag    420
tacatctacg tattagtcat cgctattacc atggtgatgc ggttttggca gtacatcaat    480
gggcgtggat agcggtttga ctcacgggga tttccaagtc tccaccccat tgacgtcaat    540
gggagtttgt tttggcacca aaatcaacgg gactttccaa aatgtcgtaa caactccgcc    600
ccattgacgc aaatgggcgg taggcgtgta cggtgggagg tctatataag gcgaagcgct    660
ccctatcagt gatagagatc tccctatcag tgatagagat cgtcgacgag ctcgcggcgg    720
gcgggagtcg ctgcgcgctg ccttcgcccc gtgccccgct ccgccgccgc ctcgcgccgc    780 ccgcccggc tctgactgac cgcgttacta aaacaggtaa gtccggcctc cgcgccgggt    840
tttggcgcct cccgcgggcg cccccctcct cacggcgagc gctgccacgt cagacgaagg    900
gcgcagcgag cgtcctgatc cttccgcccg gacgctcagg acagcggccc gctgctcata    960
agactcggcc ttagaacccc agtatcagca gaaggacatt taggacggg acttgggtga   1020 ctctagggca ctggttttct ttccagagag cggaacaggc gaggaaaagt agtcccttct   1080
cggcgattct gcggagggat ctccgtgggg cggtgaacgc cgatgatgcc tctactaacc   1140
atgttcatgt tttctttttt tttctacagg tcctgggtga cgaacaggat atcgccacca   1200
tggaactgct gatcctgaag gccaacgcca tcaccaccat cctgaccgcc gtgaccttct   1260
gcttcgccag cggccagaac atcaccgagg aattctacca gagcacctgt agcgccgtga   1320
gcaagggcta cctgagcgcc ctgagaaccg gctggtacac cagcgtgatc accatcgagc   1380
tgagcaacat caaagaaaac aagtgcaacg caccgacgc caaagtgaag ctgatcaagc   1440
aggaactgga caagtacaag aacgccgtga ccgagctgca gctgctgatg cagagcaccc   1500
ccgccaccaa caaccgggcc agacgggagc tgcccggtt catgaactac accctgaaca   1560
acgccaaaaa gaccaacgtg accctgagca agaagcggaa cgcgcggttc ctgggctttc   1620
tgctgggcgt gggcagcgcc attgccagcg cgtggccgt gtctaaggtg ctgcacctgg   1680
aaggcgaagt gaacaagatc aagagcgccc tgctgagcac caacaaggcc gtggtgtccc   1740
tgagcaacgg cgtgagcgtg ctgaccagca aggtgctgga tctgaagaac tacatcgaca   1800
agcagctgct gcccatcgtg aacaagcaga gctgcagcat cagcaacatc gagacagtga   1860
tcgagttcca gcagaagaac aaccggctgc tggaaatcac ccgggagttc agcgtgaacg   1920
ccggcgtgac caccctgtg tccacctaca tgctgaccaa cagcgagctg ctgagcctga   1980
tcaacgacat gcccatcacc aacgaccaga aaaagctgat gagcaacaac gtgcagatcg   2040
tgcggcagca gagctactcc atcatgtcca tcatcaaaga agaggtgctg gcctacgtgg   2100
tgcagctgcc cctgtacggc gtgatcgaca ccccctgctg gaagctgcac accagccccc   2160
tgtgcaccac caacaccaaa gagggcagca acatctgcct gacccggacc gacagaggct   2220
ggtactgcga caacgccggc agcgtgtcat tctttccaca ggccgagaca tgcaaggtgc   2280
agagcaaccg ggtgttctgc gacaccatga acagcctgac cctgccctcc gaagtgaacc   2340
tgtgcaacgt ggacatcttc aaccccaagt acgactgcaa gatcatgacc tccaagaccg   2400
acgtgtccag ctccgtgatc acctccctgg gcgccatcgt gtcctgctac ggcaagacca   2460
agtgcaccgc cagcaacaag aaccggggca tcatcaagac cttcagcaac ggctgcgact   2520
acgtgtccaa caagggggtg gacaccgtgt ccgtgggcaa caccctgtac tacgtgaaca   2580
aacaggaagg caagagcctg tacgtgaagg gcgagcccat catcaacttc tacgaccccc   2640
```

-continued

```
tggtgttccc cagcgacgag ttcgacgcca gcatcagcca ggtgaacgag aagatcaacc    2700
agagcctggc cttcatccgg aagtccgacg agctgctgca caatgtgaat gccggcaagt    2760
ccaccaccaa ctgatgagcg gccatctaat caacctctgg attacaaaat tgtgaaaga    2820 ttgactggta ttcttaacta tgttgctcct tttacgctat gtggatacgc tgctttaatg    2880
cctttgtatc atgctattgc ttcccgtatg gctttcattt tctcctcctt gtataaatcc    2940
tggttgctgt ctctttatga ggagttgtgg cccgttgtca ggcaacgtgg cgtggtgtgc    3000
actgtgtttg ctgacgcaac ccccactggt tggggcattg ccaccacctg tcagctcctt    3060
tccgggactt tcgctttccc cctccctatt gccacggcgg aactcatcgc cgcctgcctt    3120
gcccgctgct ggacaggggc tcggctgttg ggcactgaca attccgtggt gttgtcgggg    3180
aaatcatcgt cctttccttg gctgctcgcc tgtgttgcca cctggattct gcgcgggacg    3240
tccttctgct acgtcccttc ggccctcaat ccagcggacc ttccttcccg cggcctgctg    3300
ccggctctgc ggcctcttcc gcgtcttcgc cttcgccctc agacgagtcg gatctccctt    3360
tgggccgcct ccccgcctgc ggccgcgatc tgctgtgcct tctagttgcc agccatctgt    3420
tgtttgcccc tccccgtgc cttccttgac cctggaaggt gccactccca ctgtcctttc    3480
ctaataaaat gaggaaattg catcgcattg tctgagtagg tgtcattcta ttctgggggg    3540
tggggtgggg caggacagca aggggagga ttgggaagac aatagcaggc atgctggga    3600 tgcggtgggc tctatgg                                                  3617
```

<210> SEQ ID NO 10
<211> LENGTH: 524
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175
```

```
Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
            195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
            290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn
            515                 520

<210> SEQ ID NO 11
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 11

Gly Gly Gly Ser Gly Gly Gly
1               5

<210> SEQ ID NO 12
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Gly Gly Gly Ser Gly Gly Gly Gly
1               5
```

ADENOVIRAL VECTORS WITH TWO EXPRESSION CASSETTES ENCODING RSV ANTIGENIC PROTEINS OR FRAGMENTS THEREOF

CROSS-REFERENCE TO RELATED APPLICATIONS

This application is filed pursuant to 35 U.S.C. § 371 as a United States National Phase Application of International Application No. PCT/EP2018/078212, filed 16 Oct. 2018, which claims priority to U.S. Provisional Patent Application No. 62/572,951, filed on 16 Oct. 2017, the complete contents of each of which are hereby incorporated by reference for all purposes.

SEQUENCE LISTING

The instant application contains a Sequence Listing which has been submitted electronically in ASCII format and is hereby incorporated by reference in its entirety. Said ASCII copy, created on Oct. 11, 2018, is named VU66441A_WO_SL.txt and is 178,926 bytes in size.

FIELD OF THE INVENTION

This invention is in the field of recombinant adenoviral vectors. The invention relates to an adenoviral vector comprising two expression cassettes. In particular, the invention relates to a simian adenovirus such as a chimpanzee (chimp) adenovirus comprising two expression cassettes. In the invention, each expression cassette comprises a transgene encoding at least one antigenic protein or a fragment thereof, wherein the antigenic protein encoded is derived from respiratory syncytial virus (RSV).

BACKGROUND OF THE INVENTION

Recombinant adenoviruses are useful in gene therapy and as vaccines.

Human adenoviruses have been widely used for gene transfer applications due to their large transgene capacity and ability to achieve highly efficient gene transfer in a variety of target tissues.

However, most humans are exposed to and develop immunity to human adenoviruses.

Therefore, there is a demand for vectors which effectively deliver molecules to a target and minimize the effect of pre-existing immunity to human adenovirus serotypes. Simian adenoviruses are effective in this regard; they are sufficiently closely related to human viruses to be effective in inducing immunity to delivered exogenous antigens to which humans have little or no pre-existing immunity. Therefore, viral vectors based on simian adenoviruses can provide an alternative to the use of human derived adenoviral vectors for the development of nucleic acid based vaccines.

Replication defective adenoviruses deliver their genome to the interior of a cell and, because they do not replicate, do not amplify the transgene payload. Typically, the E1 gene is replaced with a transgene cassette comprising a promoter of choice and a nucleic acid sequence corresponding to a gene or genes of interest, resulting in a replication defective recombinant virus.

There is a need in the art for improved recombinant adenoviruses.

Respiratory syncytial virus (RSV) is a highly contagious human pathogen that causes respiratory tract infections in people of all ages. During the first year of life, 50-70% of infants are infected with RSV and essentially all children have had an RSV infection by their second birthday. The risk for severe RSV associated lower respiratory tract infections (LRTI) is highest in infants below 6 months of age and is a leading cause for hospitalization. Infection with RSV does not confer full protective immunity. Symptomatic RSV re-infections are common later in life and continue throughout adulthood. These re-infections generally go undiagnosed because they usually present as common acute upper respiratory tract infections. In more vulnerable persons (e.g., immunocompromised adults or elderly), re infections can however also lead to severe disease.

To date, no vaccine is available against RSV and treatment of RSV disease is largely symptomatic and supportive care. The antiviral drug ribavirin is currently the only approved antiviral therapy for RSV treatment, but its use is restricted to severe hospitalized cases due to uncertainties regarding its efficacy, difficulty in administration (aerosol) and high cost [American Academy of Pediatrics Subcommittee on Diagnosis and Management of Bronchiolitis, 2006]. RSV-specific monoclonal antibodies (palivizumab, Synagis™, Medimmune) are indicated for the prevention of serious LRTIs requiring hospitalization caused by RSV in children at high risk for RSV disease but are not indicated or recommended in the general, healthy infant population due to high cost and the need for repeated administration.

In the late 1960s, a formalin-inactivated whole virus RSV vaccine (FI-RSV) tested in clinical trials led to more severe clinical symptoms upon subsequent natural infection with RSV in children under the age of two [Kim, 1969; Chin, 1969]). This experience has led to heightened safety concerns with pediatric RSV vaccine candidates. Since that time, several investigational vaccines have been and continue to be explored, including live attenuated viral vaccines and those based upon purified or recombinant viral proteins. However, there is not yet a licensed vaccine for the prevention of RSV disease.

SUMMARY OF THE INVENTION

The invention relates to an adenoviral vector comprising two expression cassettes, wherein each expression cassette encodes at least one RSV antigenic protein or a fragment thereof. In particular, the invention relates to a simian adenovirus, preferably a chimpanzee (chimp) adenovirus comprising two expression cassettes, wherein each expression cassette encodes at least one RSV antigenic protein or a fragment thereof. Examples of suitable chimp adenoviruses include ChAd155 and ChAd83.

The adenovirus vectors of the invention are useful as components of immunogenic compostions for the induction of an immune response in a subject, methods for their use in treatment and processes for manufacture.

The term "vector" refers to an agent (such as a plasmid or virus) that contains or carries genetic material and can be used to introduce exogenous genes into an organism. The adenoviral vector of the present invention is preferably derived from a non-human simian adenovirus, also referred to as a "simian adenovirus". Preferably, the adenoviral vector of the present invention is an adenovirus.

Each expression cassette in the adenoviral vector of the invention comprises a transgene and a promoter. A "transgene" is a nucleic acid sequence, heterologous to the vector sequences flanking the transgene, which encodes a polypeptide of interest. The nucleic acid coding sequence is operatively linked to regulatory components in a manner which permits transgene transcription, translation, and/or expression in a host cell. A "promoter" is a nucleotide sequence that permits the binding of RNA polymerase and directs the transcription of a gene. Typically, a promoter is located in a non-coding region of a gene, proximal to the transcriptional start site.

In the present invention, each expression cassette of the adenoviral vector comprises a transgene which encodes an antigenic protein or a fragment thereof derived from respiratory syncytial virus (RSV), i.e. each transgene encodes an RSV antigen or a fragment of an RSV antigen.

In other words, the recombinant adenoviral vector of the invention comprises nucleic acid sequences encoding two heterologous proteins, wherein the nucleic acid sequences are operatively linked to sequences which direct expression of said heterologous proteins in a host cell. In the invention, each heterologous protein is an antigenic protein or a fragment thereof derived from RSV. In a preferred embodiment, the heterologous proteins comprise one or more of fusion protein (F), the attachment protein (G), the matrix protein (M2) and the nucleoprotein (N) of RSV or fragments thereof.

In a preferred embodiment of the invention, the nucleic acid sequences encoding the heterologous proteins encode RSV F, M and N antigens. Most preferably, the nucleic acid sequences encode an RSV FΔTM antigen, an RSV M2-1 antigen and an N antigen.

In one preferred embodiment, one of the expression cassettes encodes an RSV F antigen, and the other expression cassette encodes a fusion protein comprising RSV M and N antigens. In particular, in this embodiment, one of the expression cassettes encodes an RSV FΔTM antigen, and the other expression cassette encodes a fusion protein comprising the RSV M2-1 and N antigens.

In adenoviral vectors of the invention, a first expression cassette is inserted in the E1 region of the virus, and a second expression cassette is inserted into a second region of the adenoviral vector.

In a simian adenoviral vector comprising two expression cassettes of the invention, a first expression cassette is inserted in the E1 region of the simian adenoviral vector, and a second expression cassette is inserted in a region of the adenoviral vector that is compatible with vector replication. A region of the adenoviral vector genome is considered "compatible with vector replication" if distruption of this region would not affect the ability of the adenoviral vector to replicate.

In an embodiment of adenoviral vectors of the invention, the first expression cassette may be inserted in the E1 region of the virus, and the second expression cassette may be inserted into the E3, HE1 or HE2 region of theadenoviral vector. As is well known in the art, the E3 genes are expressed in the early phase of transduction to prepare the host cell for viral replication. E3 is involved in immune modulation. The term "HE1" is used to describe a site located between the stop codons of L5 and E4. The term "HE2" has been used to define a site located between the end of the ITR and the cap site of E4 mRNA.

For example, in a ChAd155 adenovirus vector:
  HE1 ChAd155: insertion site between bp 34611 and 34612 of SEQ ID NO: 1.
  HE2 ChAd155: insertion site between bp 37662 and 37663 of SEQ ID NO: 1.
In another example, in a ChAd83 adenovirus vector:
  HE1 ChAd83: insertion site between bp 33535 and 33536 of SEQ ID NO: 2.
  HE2 ChAd83: insertion site between bp 36387 and 36388 of SEQ ID NO: 2.

If the first expression cassette is inserted in the E1 region of the adenoviral vector, the native E1 region is deleted. In order to increase the cloning capacity of the vector the native E3 region can be removed from the adenoviral vector. The native E3 region can be deleted from the adenoviral vector in embodiments of the invention where the second expression cassette is inserted in the E3 region, or in embodiments where the second expression cassette is not inserted into the E3 region. The insertion in HE1 or HE2 site doesn't require deletion of any specific sequence of the vector backbone.

Preferably, the second expression cassette is inserted into the HE1 or HE2 region of the adenoviral vector. Most preferably, the second expression cassette is inserted in the HE2 region of the adenoviral vector. In one embodiment, the native E3 region is deleted from the adenoviral vector to increase the cloning capacity of the vector, and the second expression cassette is inserted in the HE1 or HE2 region of the adenoviral vector.

In embodiments comprising RSV F, M and N antigens, the RSV F antigen may be encoded by either the first or second expression cassette. Similarly, the RSV M and N antigens may be encoded by the first expression cassette or the second expression cassette.

In embodiments of the invention, the first expression cassette of the adenoviral vector may comprise a human CMV or an enhanced human CMV promoter, and/or the second expression cassette may comprise a human CMV or an enhanced human CMV promoter.

In a preferred embodiment, the first and second expression cassettes comprise different promoters. For example, in one embodiment, the first expression cassette may comprise a human CMV promoter and the second expression cassette an enhanced human CMV promoter (or vice versa).

In one aspect of the invention, there is provided an adenoviral vector of the invention, wherein the first expression cassette is inserted in the E1 region of the virus, and the second expression cassette is inserted in a region of the adenoviral vector that is compatible with vector replication, wherein at least one of the first and second expression cassette comprises an enhanced CMV promoter. In some embodiments, the enhanced hCMV promoter can include a nucleic acid sequence having at least about 90%, at least about 95%, at least about 96%, at least about 97%, at least about 98%, at least about 99%, or more, sequence identity to SEQ ID NO: 6. In some embodiments, the promoter comprises or consists of a nucleic acid sequence of SEQ ID NO: 6.

Adenoviral vectors of the invention are derived from a simian adenoviral vector, for example, from chimpanzees (*Pan troglodytes*), bonobos (*Pan paniscus*), gorillas (*Gorilla gorilla*) and orangutans (*Pongo abelii* and *Pongo pygmaeus*). Chimpanzee adenoviruses include, but are not limited to AdY25, ChAd3, ChAd19, ChAd25.2, ChAd26, ChAd27, ChAd29, ChAd30, ChAd31, ChAd32, ChAd33, ChAd34, ChAd35, ChAd37, ChAd38, ChAd39, ChAd40, ChAd63, ChAd83, ChAd155, ChAd15, SadV41, sAd4310A, sAd4312, SAdV31, SAdV-A1337, ChAdOx1, ChAdOx2 and ChAd157. Preferably, the simian adenoviral vector of the invention is a ChAd83 or ChAd155 adenovirus vector, most preferably a ChAd155 adenovirus vector.

Preferably, the adenoviral vector of the invention has a seroprevalence of less than 30%, preferably less than 10% in human subjects and, most preferably, no seroprevalence in human subjects.

In a preferred embodiment, the adenoviral vector of the invention is capable of infecting a mammalian cell.

The present invention also provides a composition comprising a adenoviral vector and a pharmaceutically acceptable excipient.

In addition, the present invention provides a adenoviral vector or composition comprising such an adenoviral vector for use as a medicament, a vaccine, and/or for the therapy or prophylaxis of a disease.

The invention also provides a method of inducing an immune response in a subject comprising administering the adenoviral vector or composition to the subject.

Figure 1:
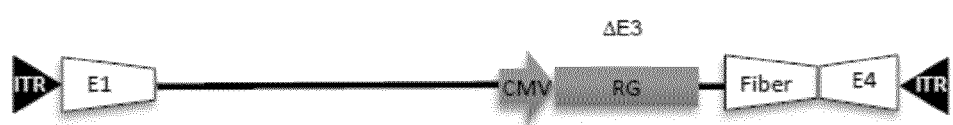
FIG. 1: Simian adenoviral constructs with a single expression cassette. Inverted terminal repeats (ITR) flank the 3' and 5' ends; E1 is the early gene 1; CMV is the cytomegalovirus promoter; CASI is the CASI promoter, RG is a model antigen, WPRE is the Woodchuck Hepatitis Postranscriptional Regulatory Element, ΔE3 denotes that the early gene 3 is deleted; fiber denotes the adenoviral gene encoding the fiber protein and E4 is the early gene 4.
Figure 1:
Figure 1:

Three different simian adenoviral vectors are shown in FIG. 1. The vector of FIG. 1(i) was constructed by inserting a transgene expression cassette in place of the E3 region of the adenoviral genome ("RC1") (top panel), the vector of FIG. 1(ii) was formed by inserting a transgene expression cassette in the HE1 region, i.e., between the stop codons of the fiber gene and the E4 region ("RC3") (middle panel), and the vector of FIG. 1(iii) was made by inserting a transgene expression cassette in the HE2 region, i.e., between the end of the ITR and the cap site of E4 mRNA ("RC2") (bottom panel).

Figure 2A:
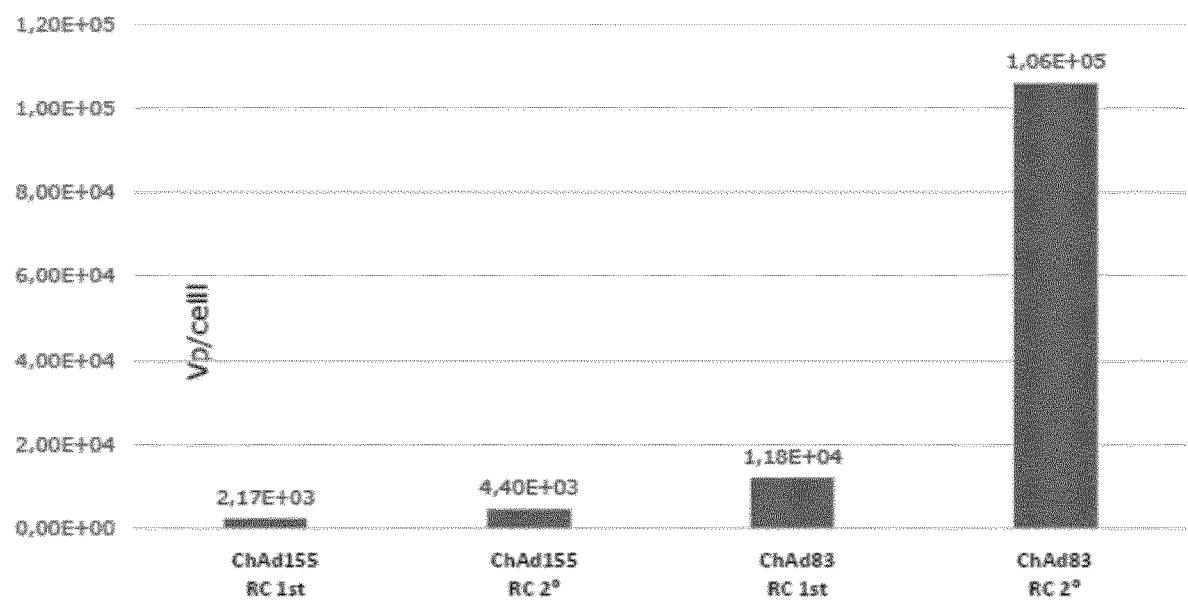

FIG. 2A: Production of ChAd155 and ChAd83 with transgene cassette inserted in E3 and HE2 sites (RC1 and RC2 vectors of FIG. 1) in a primary human cell line.

Figure 2B:
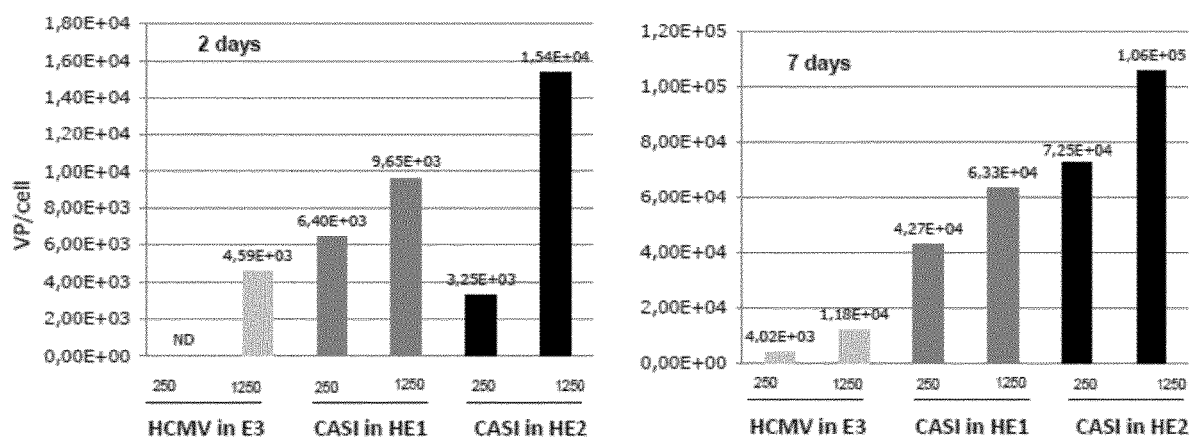

FIG. 2B: Production of ChAd83 with transgene cassette inserted in E3, HE1 and HE2 (the RC1, RC2 and RC3 vectors of FIG. 1) in a human MRC5 cell line at two and seven days post-infection. Cells were infected at multiplicities of infection of 250 and 1250.

Figure 3A:
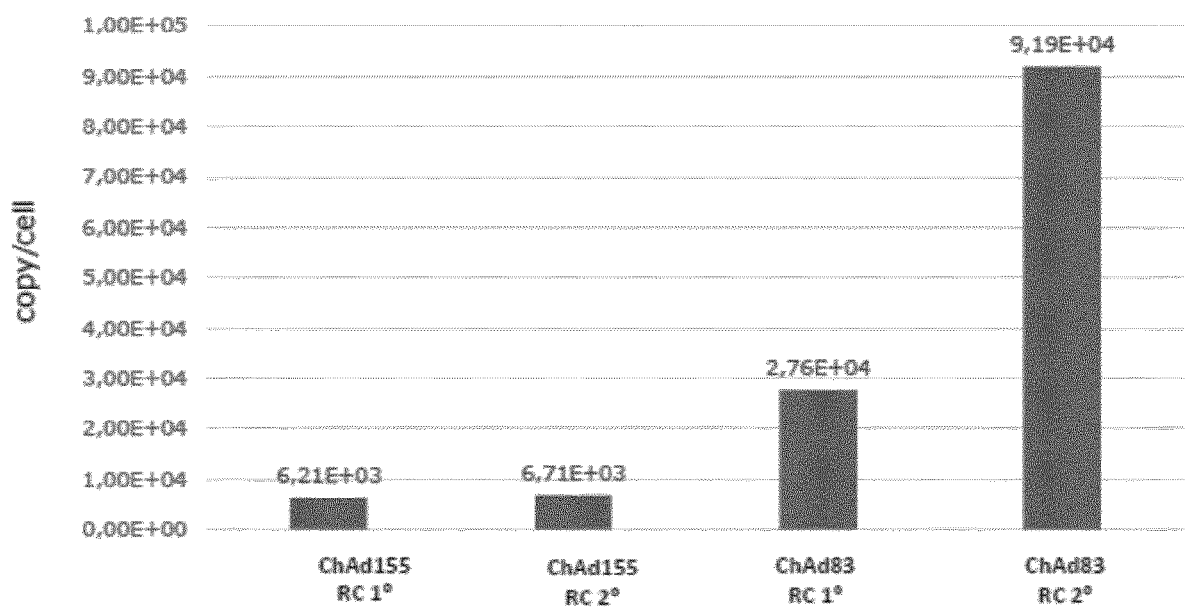

FIG. 3A: Total viral genome copy number of RC1 and RC2 vector (ChAd155 and ChAd83) of FIG. 1 in a primary human cell line.

Figure 3B:
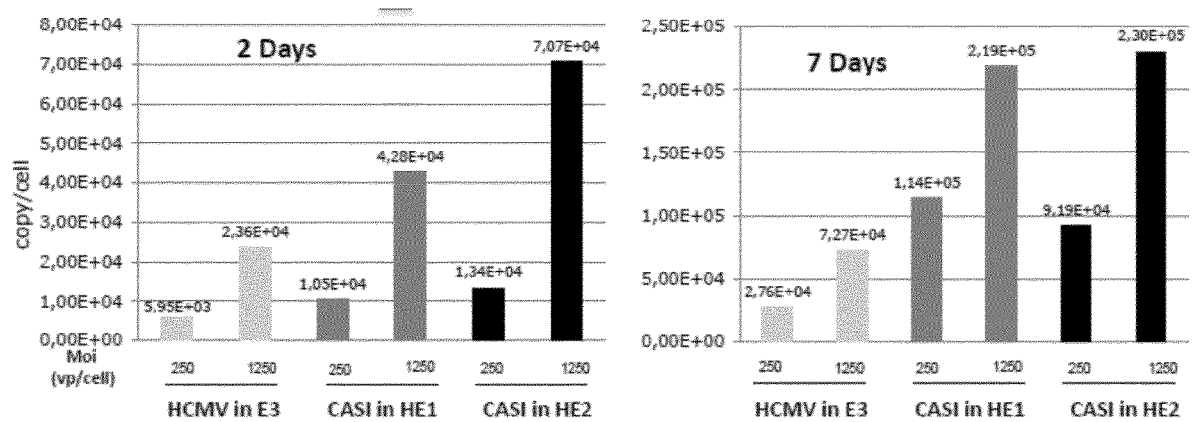

FIG. 3B: Total viral genome copy number of RC1, RC2 and RC3 versions of ChAd83 vector of FIG. 1 in a human MRC5 cell line at two and seven days post-infection. Cells were infected at multiplicities of infection of 250 and 1250.

Figure 4:
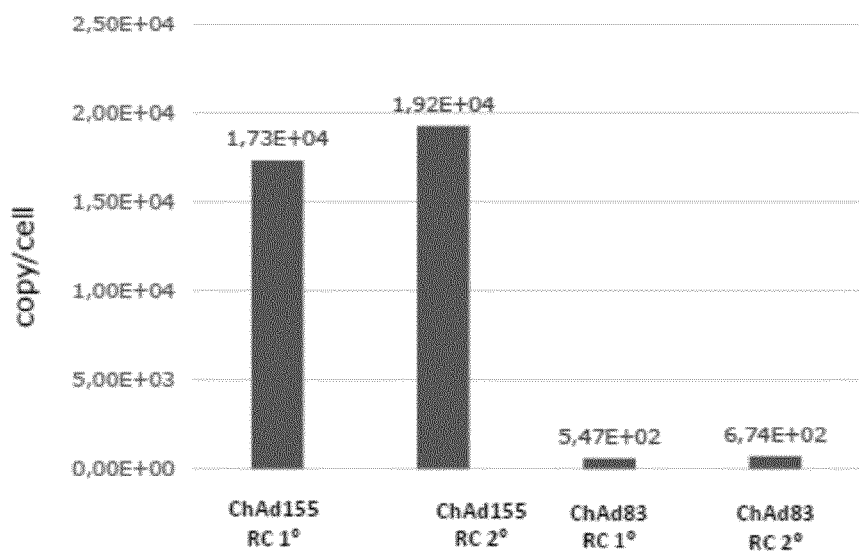
Figure 4:
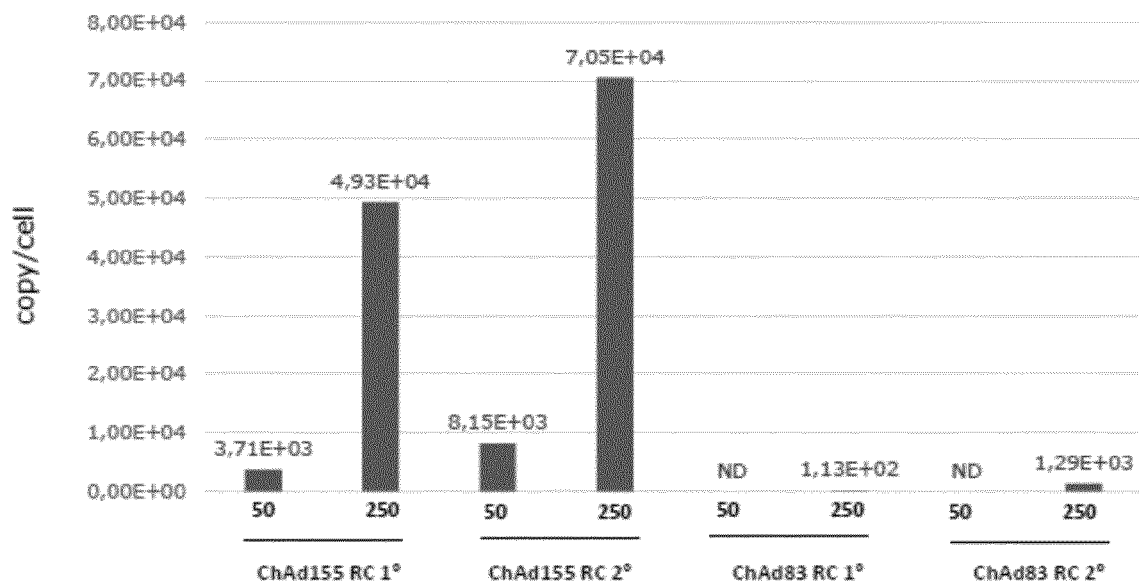

FIG. 4: Total viral genome copy number of ChAd155 RC1 and RC2 and ChAd83 RC1 and RC2 vectors of FIG. 1 in a murine cell line (FIG. 4(a), top panel) and in a non-human primate cell line (FIG. 4(b), bottom panel). Cells were infected at multiplicities of infection of 50 and 250.

Figure 5:
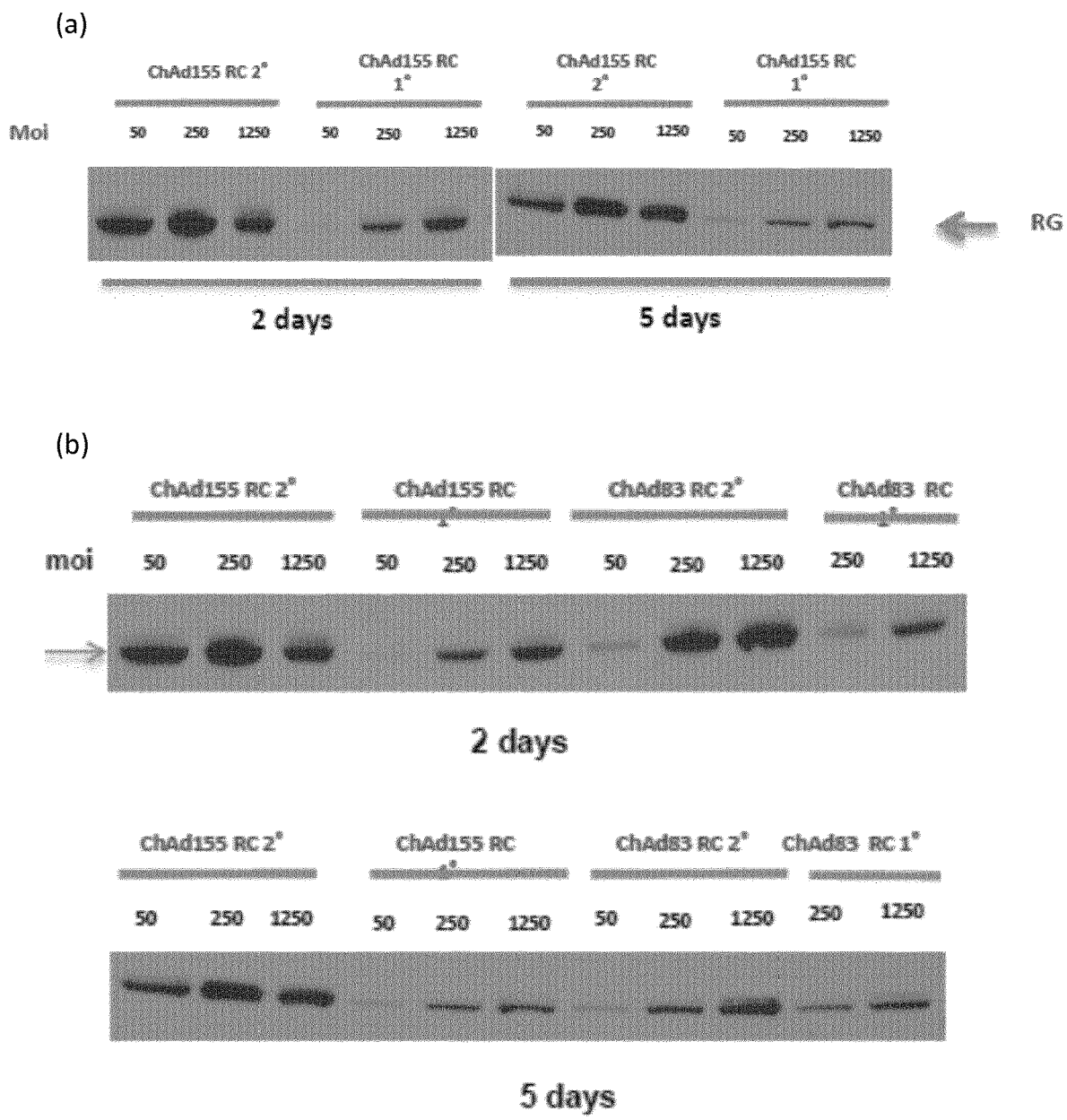
Figure 5:
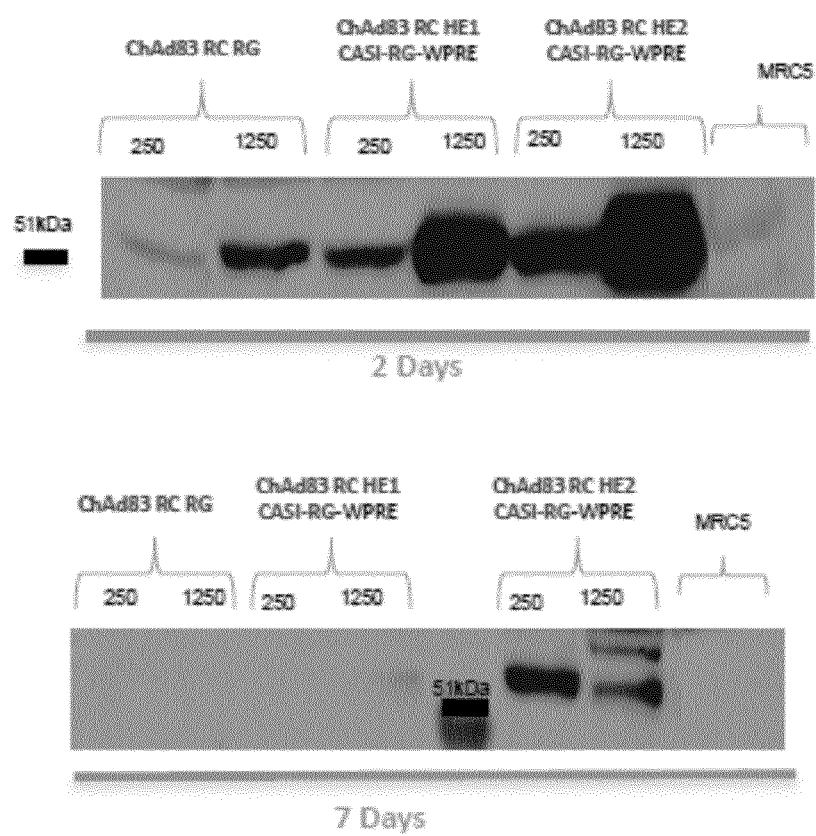

FIG. 5: Comparison of the expression levels of ChAd155 RC1 and RC2 vectors expressing a model rabies glycoprotein (RG) transgene in a murine cell line, demonstrated by western blot at two and five days post-infection (FIG. 5(a), top panel). Comparison of the expression levels of ChAd155 RC1 and RC2 vectors with ChAd83 RC1 and RC2 vectors expressing a model rabies glycoprotein (RG) transgene in a murine cell line, demonstrated by western blot at two and five days post-infection (FIG. 5(b), bottom panel). Cells were infected at multiplicities of infection of 50, 250 and 1250.

FIG. 5(c): Comparison of the expression levels of ChAd83 RC1, RC2 and RC3 vectors expressing a model rabies glycoprotein (RG) transgene in a human MRC5 cell line, demonstrated by western blot at two and seven days post-infection. Cells were infected at multiplicities of infection of 250 and 1250.

Figure 6:
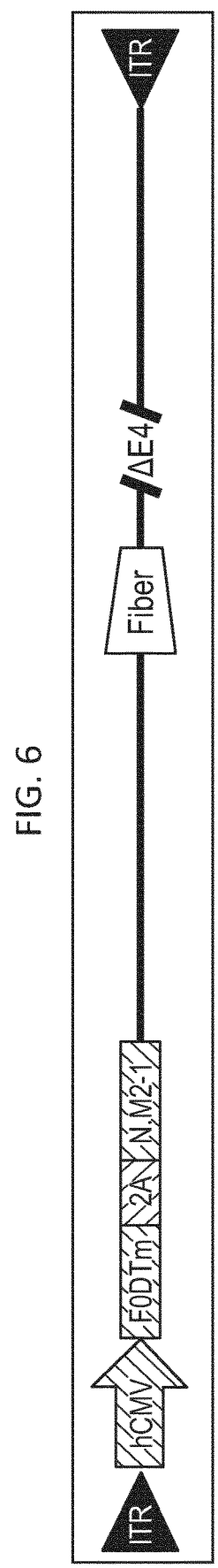

FIG. 6: Another simian adenoviral construct of with a single expression cassette. Inverted terminal repeats (ITR) flank the 3' and 5' ends; human CMV (hCMV) is the cytomegalovirus promoter; FΔTM (FODTM) and N.M2-1 are RSV antigens; 2A is a self-cleaving linking sequence; ΔE4 denotes that the early gene 4 is deleted; fiber denotes the adenoviral gene encoding the fiber protein. In the vector of FIG. 6, the transgene expression cassette is inserted in place of the E1 region of the adenoviral genome.

Figure 7:
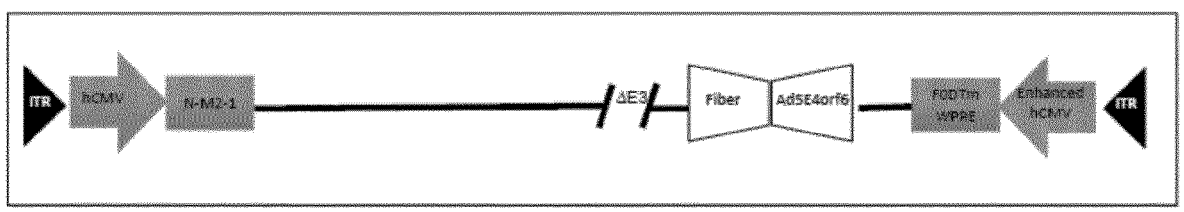

FIG. 7: A simian adenoviral construct according to the invention with a dual expression cassette. Inverted terminal repeats (ITR) flank the 3' and 5' ends; human CMV (hCMV) is the cytomegalovirus promoter; Enchanced hCMV is the enhanced cytomegalovirus promoter; N-M2-1 and FΔTM (FODTM) are the RSV antigens; WPRE is the Woodchuck Hepatitis Postranscriptional Regulatory Element; ΔE3 denotes that the early gene 3 is deleted; fiber denotes the adenoviral gene encoding the fiber protein; and Ad5E4orf6 in a substitute in the early gene 4 (E4) region.

The vector of FIG. 7 was constructed by inserting a first transgene expression cassette in place of the E1 region of the adenoviral genome, and a second transgene expression cassette in the HE2 region, i.e., downstream of the right ITR.

Figure 8:
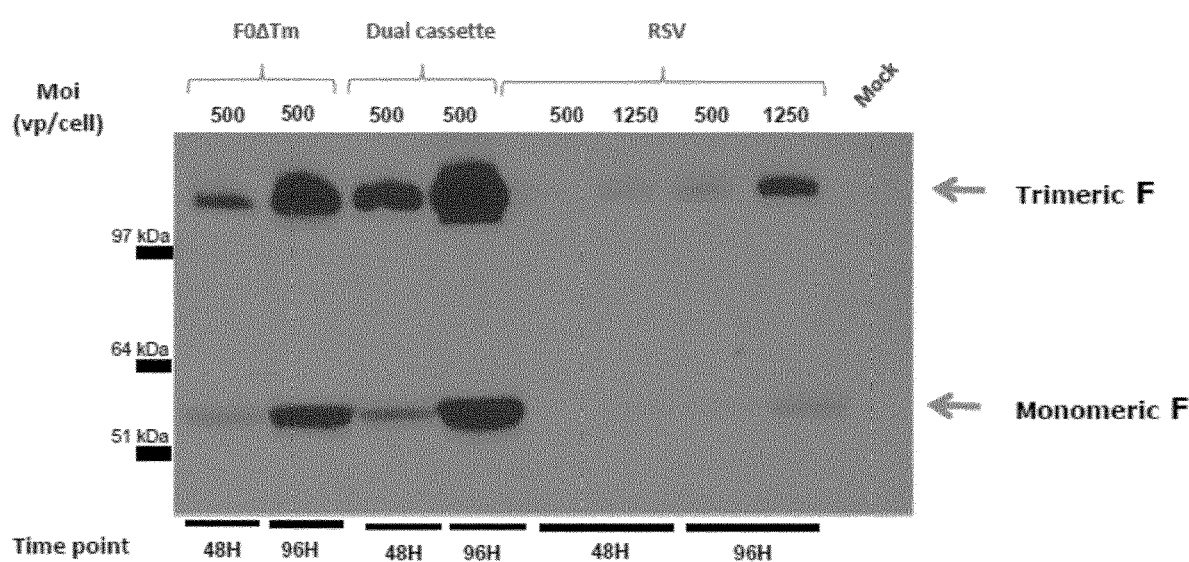

FIG. 8: Comparison of the expression levels of vectors expressing F0ΔTM transgene in a MRC5 cell line, demonstrated by western blot at 48 hours and 96 hours post-infection under non-reducing conditions. Cells were infected at multiplicities of infection of 500 and 1250.

Figure 9:
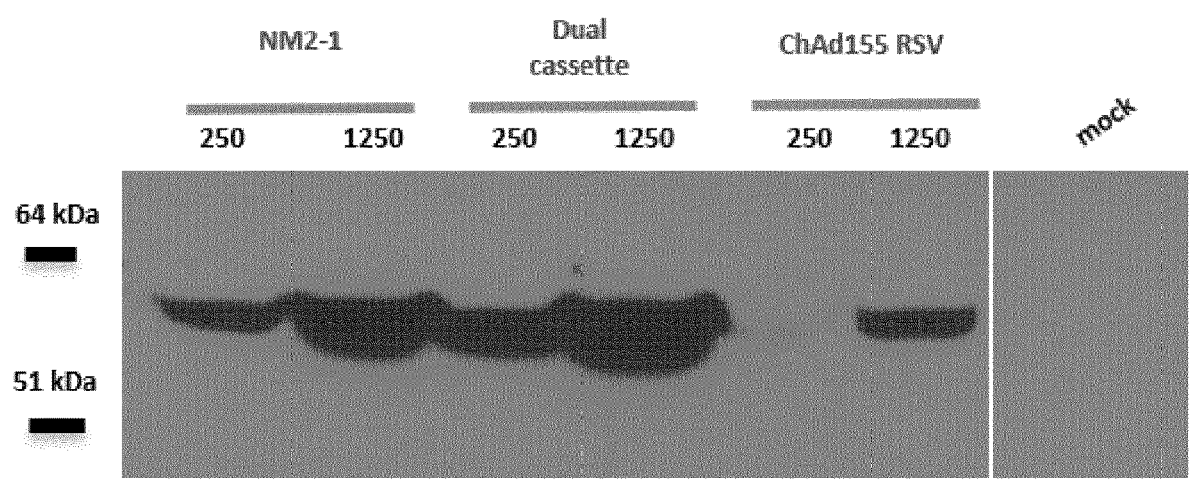

FIG. 9: Comparison of the expression levels of vectors expressing NM2-1 transgene in a MRC5 cell line, demonstrated by western blot at 48 hours post-infection under reducing conditions. Cells were infected at multiplicities of infection of 250 and 1250.

Figure 10:
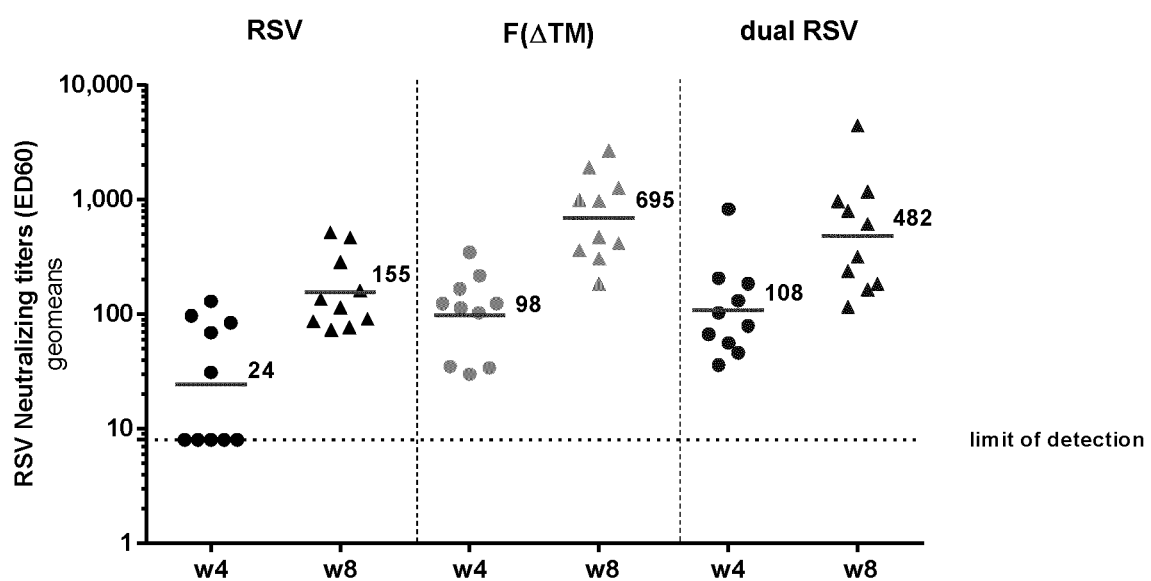

FIG. 10: Comparison of the immunogencity from ChAd155 vectors expressing the RSV antigen FΔTm. The data was collected at 4 weeks and 8 weeks after vaccination with a dose of $5 \times 10^8$ virus particles.

Figure 11:
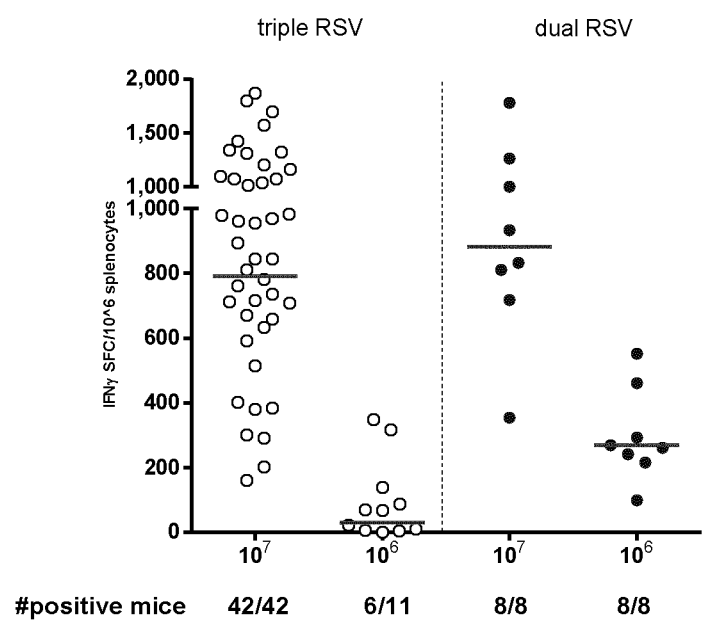

FIG. 11: Comparison of the immunogencity from ChAd155 vectors expressing the M2 RSV antigen. The data was collected at 3 weeks after vaccination with a dose of either $10^7$ or $10^6$ virus particles.

Figure 12A:
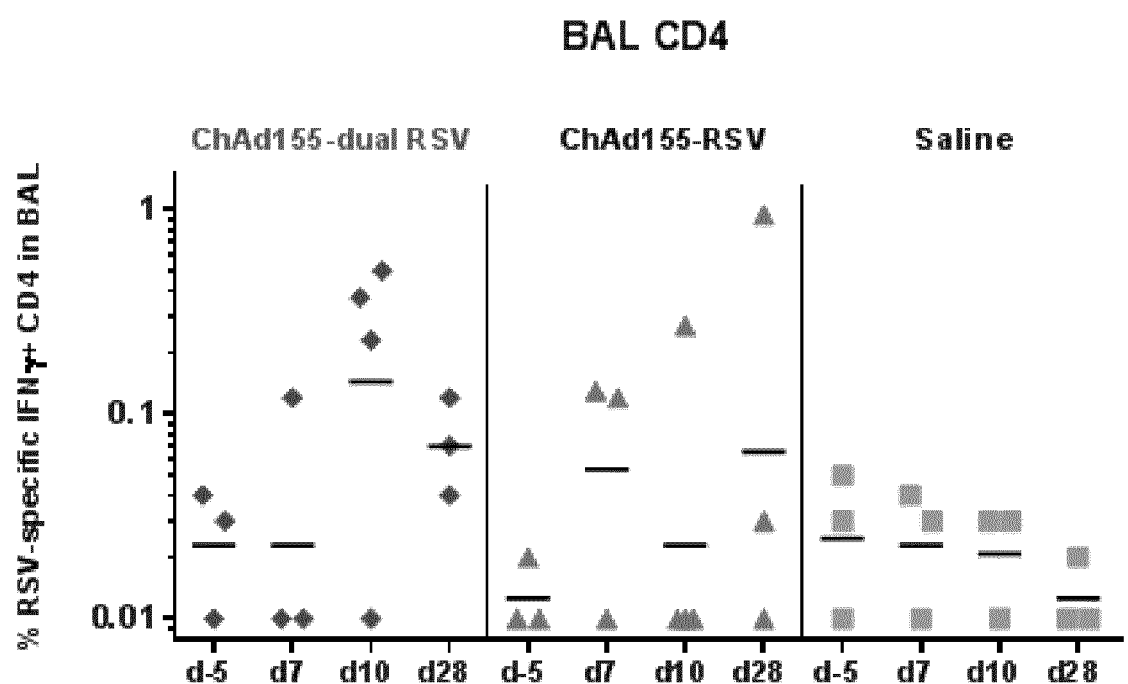
Figure 12B:
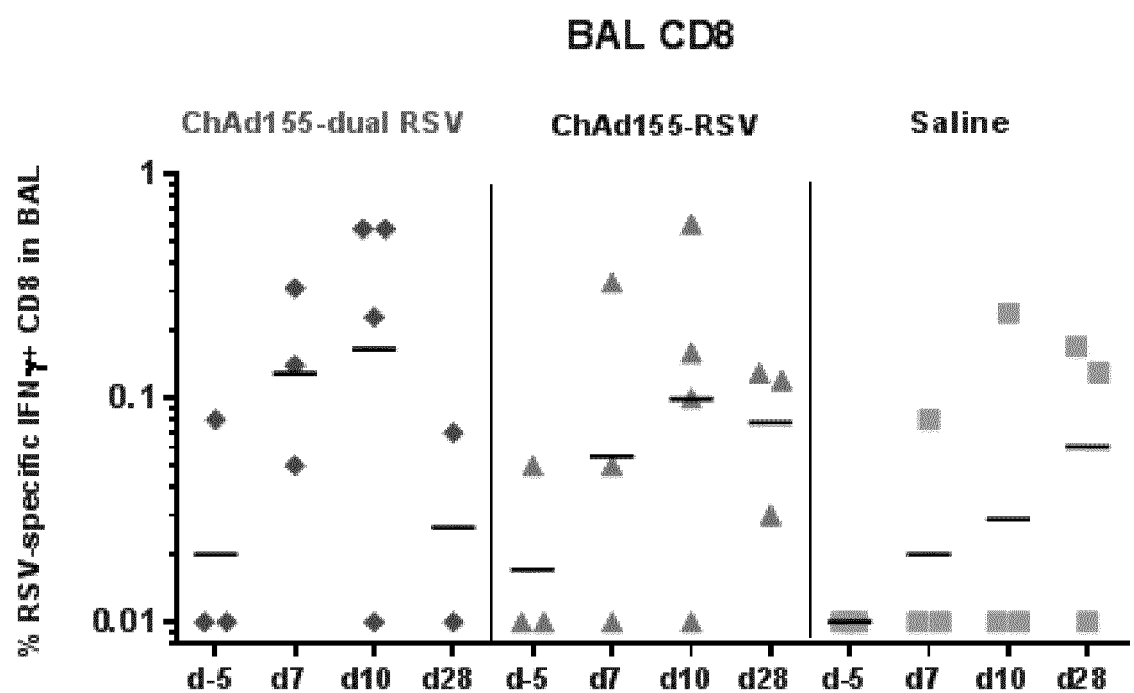

FIG. 12A and 12B: Illustrate the results from the experiment of Example 9 to investigate the lung T cell responses from ChAd155 vectors. FIG. 12A shows the CD4+ response, and FIG. 12B shows the CD8+ response.

Figure 13A:
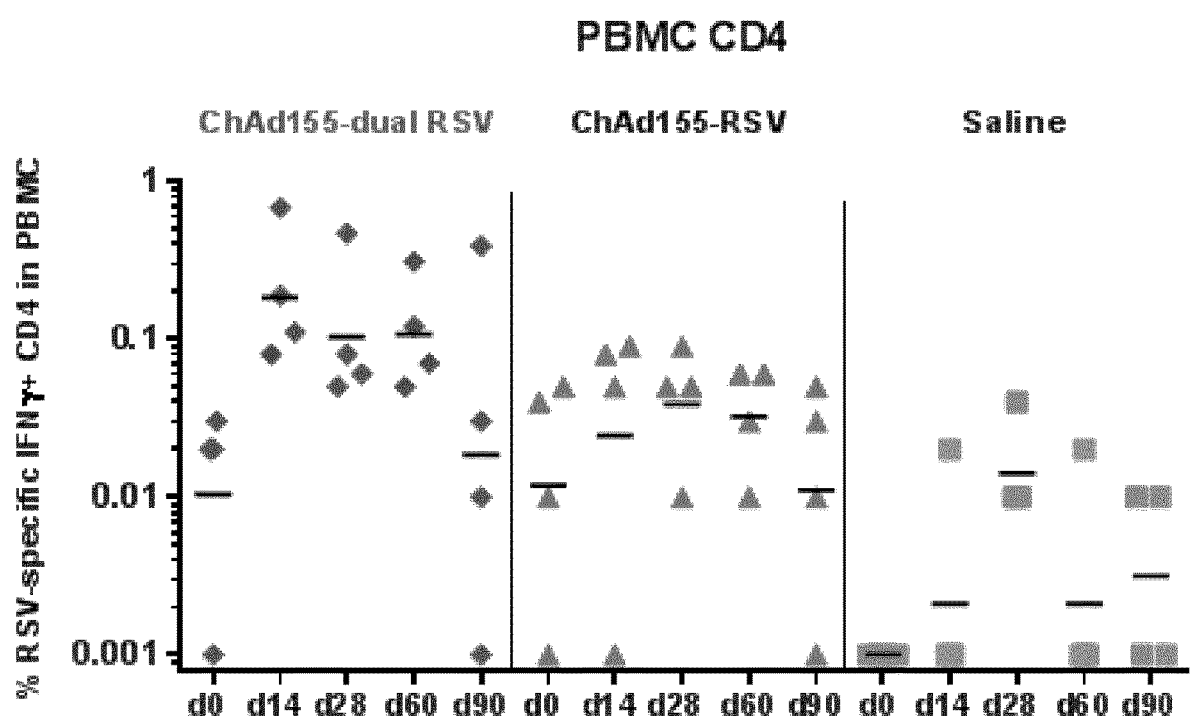
Figure 13B:
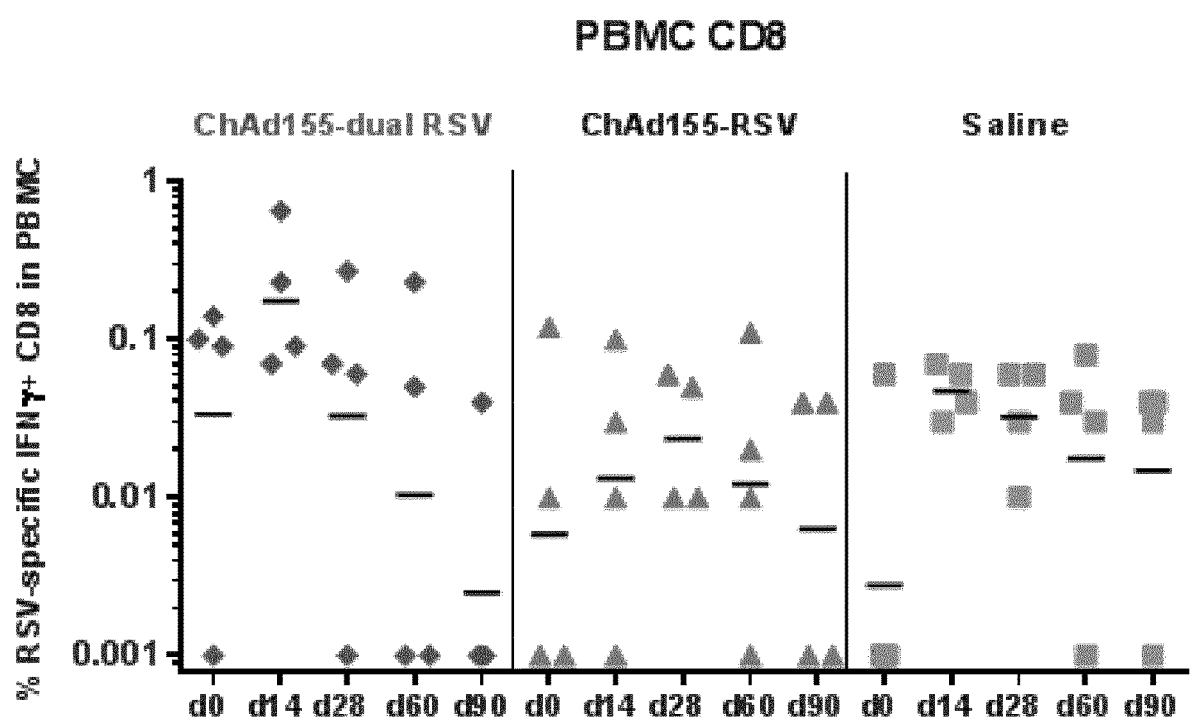

FIGS. 13A and 13B: Show the results from the experiment of Example 9 to investigate the peripheral T cell responses from ChAd155 vectors. FIG. 13A shows the PBMC CD4+ response, and FIG. 13B shows the PBMC CD8+response.

Figure 14A:
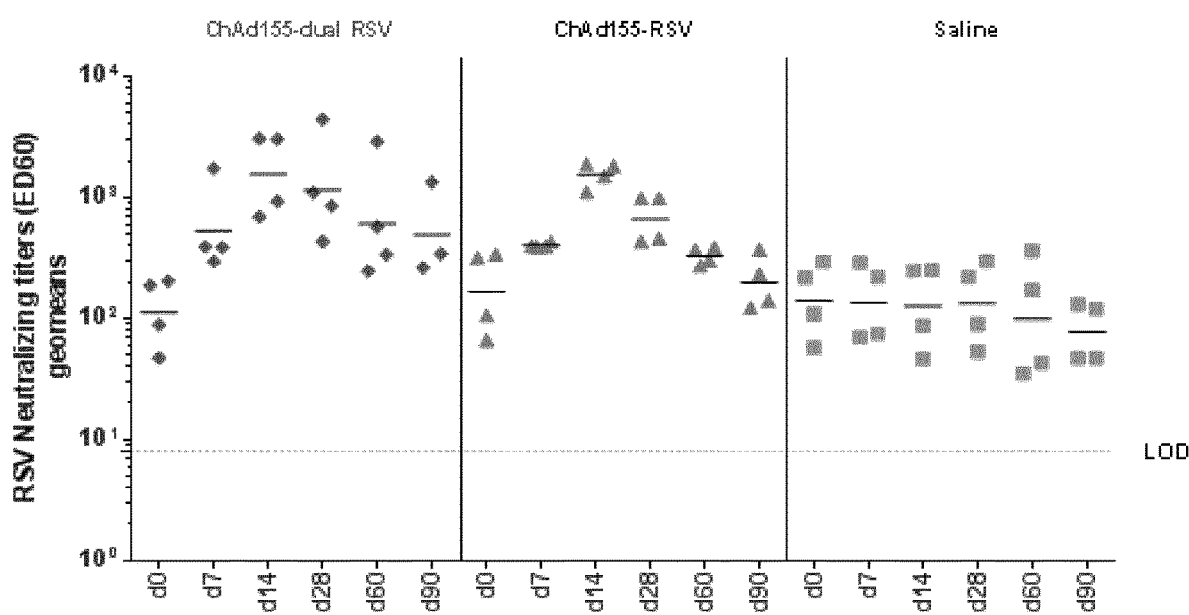
Figure 14B:
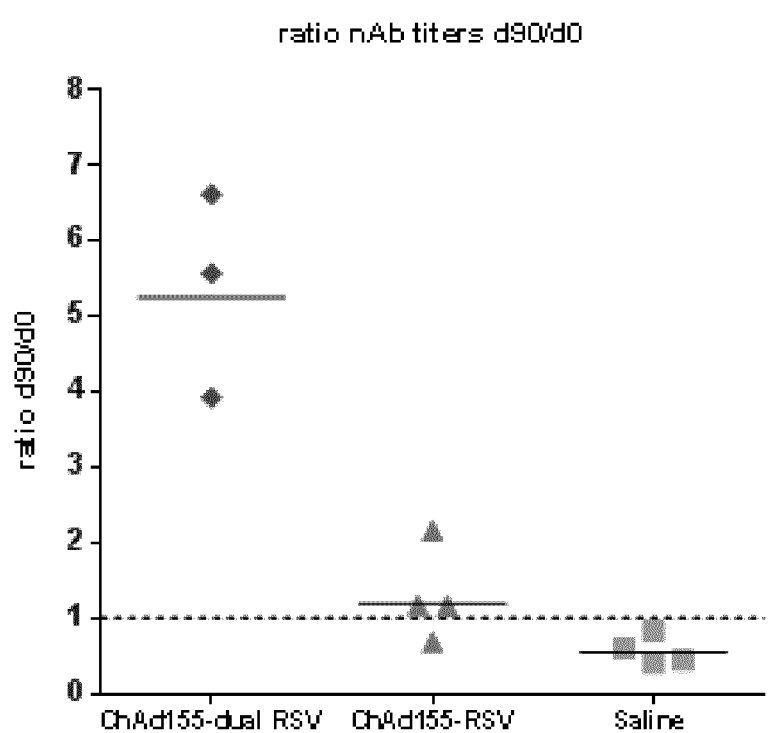

FIG. 14A and 14B: Also show results from Example 9. FIG. 14A shows the RSV neutralising Ab titres, and FIG. 14B illustrates the ratio of the nAb from day D90 to D0.

Figure 15A:
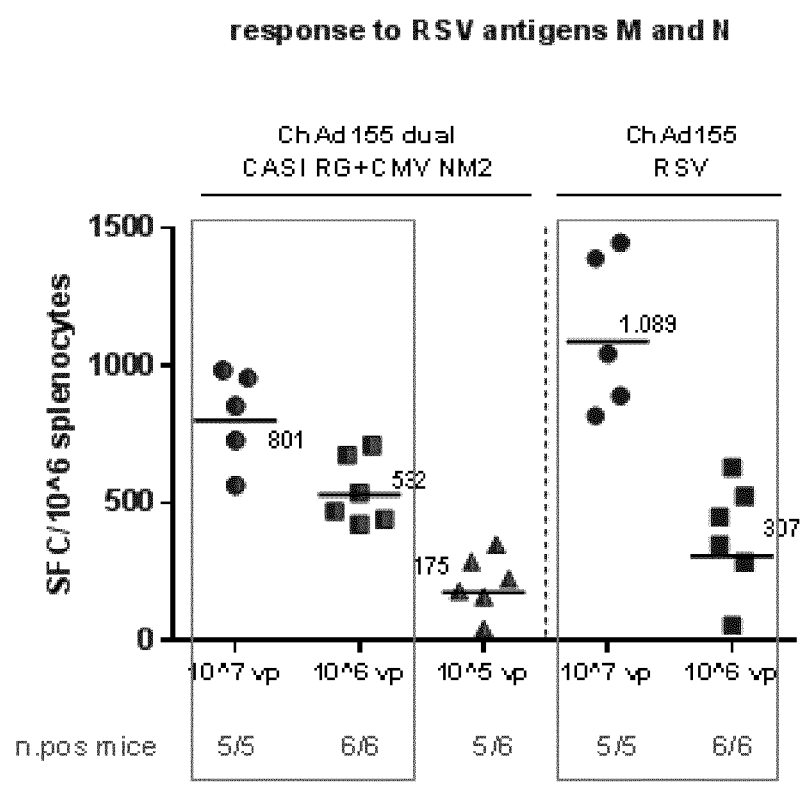

FIG. 15A. 15B and 15C: Show the results of the immunogencity experiment of Example 10.

Figure 16A:
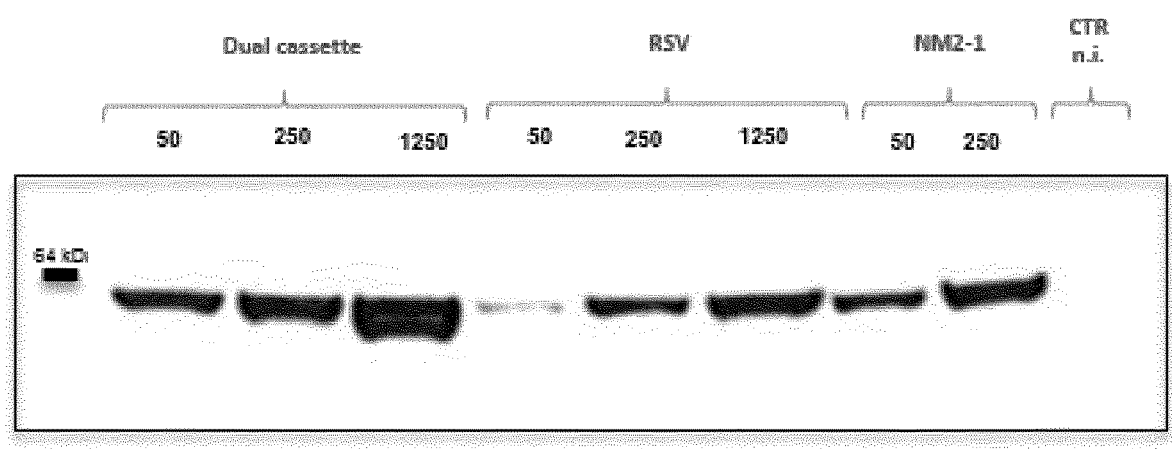
Figure 16B:
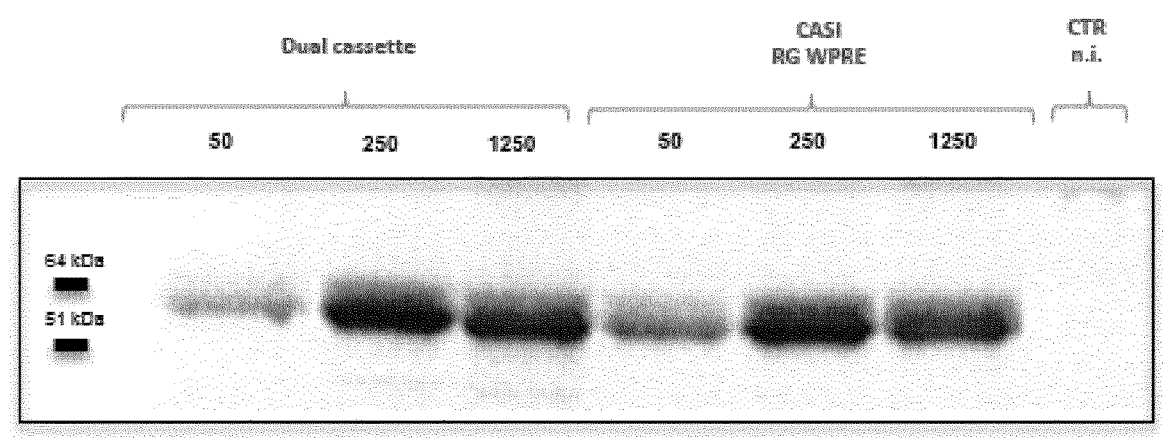

FIG. 16A and FIG. 16B: Show the results of with the expression of ChAd155 dual encoding rabies G and RSV NM2 proteins in HeLa cells in Example 11.

ANNOTATION OF THE SEQUENCES

SEQ ID NO: 1—Polynucleotide sequence encoding wild type ChAd155

SEQ ID NO: 2—Polynucleotide sequence encoding wild type ChAd83

SEQ ID NO: 3—Polynucleotide sequence encoding the CASI promoter

SEQ ID NO: 4—Polynucleotide sequence encoding ChAd155/RSV

SEQ ID NO: 5—RSV F0ΔTM-N-M2-1 amino acid sequence

SEQ ID NO: 6—Polynucleotide sequence encoding the enhanced hCMV promoter

SEQ ID NO: 7—Polynucleotide sequence encoding the hCMV NM2 bghpolyA cassette

SEQ ID NO: 8—NM2 amino acid (protein) sequence

SEQ ID NO: 9—Polynucleotide sequence encoding the hCMV F0 WPRE bghpolyA cassette SEQ ID NO: 10—F0 amino acid (protein) sequence SEQ ID NO: 11—Amino acid sequence of a flexible linker SEQ ID NO: 12—Amino acid sequence of a flexible linker

DETAILED DESCRIPTION OF THE INVENTION

Adenoviruses

Adenoviruses are nonenveloped icosahedral viruses with a linear double stranded DNA genome of approximately 36 kb. Adenoviruses can transduce numerous cell types of several mammalian species, including both dividing and nondividing cells, without integrating into the genome of the host cell. They have been widely used for gene transfer applications due to their proven safety, ability to achieve highly efficient gene transfer in a variety of target tissues, and large transgene capacity. Human adenoviral vectors are currently used in gene therapy and vaccines but have the drawback of a high worldwide prevalence of pre-existing immunity, following previous exposure to common human adenoviruses.

Adenoviruses have a characteristic morphology with an icosahedral capsid comprising three major proteins, hexon (II), penton base (III) and a knobbed fiber (IV), along with a number of other minor proteins, VI, VIII, IX, IIIa and IVa2. The hexon accounts for the majority of the structural components of the capsid, which consists of 240 trimeric hexon capsomeres and 12 penton bases. The hexon has three conserved double barrels and the top has three towers, each tower containing a loop from each subunit that forms most of the capsid. The base of the hexon is highly conserved between adenoviral serotypes, while the surface loops are variable. The penton is another adenoviral capsid protein; it forms a pentameric base to which the fiber attaches. The trimeric fiber protein protrudes from the penton base at each of the 12 vertices of the capsid and is a knobbed rod-like structure. The primary role of the fiber protein is to tether the viral capsid to the cell surface via the interaction of the knob region with a cellular receptor. Variations in the flexible shaft, as well as knob regions of fiber, are characteristic of the different adenovral serotypes.

The adenoviral genome has been well characterized. The linear, double-stranded DNA is associated with the highly basic protein VII and a small peptide pX (also termed mu). Another protein, V, is packaged with this DNA-protein complex and provides a structural link to the capsid via protein VI. There is general conservation in the overall organization of the adenoviral genome with respect to specific open reading frames being similarly positioned, e.g. the location of the E1A, E1B, E2A, E2B, E3, E4, L1, L2, L3, L4 and L5 genes of each virus. Each extremity of the adenoviral genome comprises a sequence known as an inverted terminal repeat (ITR), which is necessary for viral replication. The 5' end of the adenoviral genome contains the 5' cis-elements necessary for packaging and replication; i.e., the 5' ITR sequences (which can function as origins of replication) and the native 5' packaging enhancer domains, which contain sequences necessary for packaging linear adenoviral genomes and enhancer elements for the E1 promoter. The 3' end of the adenoviral genome includes 3' cis-elements, including the ITRs, necessary for packaging and encapsidation. The virus also comprises a virus-encoded protease, which is necessary for processing some of the structural proteins required to produce infectious virions.

The structure of the adenoviral genome is described on the basis of the order in which the viral genes are expressed following host cell transduction. More specifically, the viral genes are referred to as early (E) or late (L) genes according to whether transcription occurs prior to or after onset of DNA replication. In the early phase of transduction, the E1A, E1B, E2A, E2B, E3 and E4 genes of adenovirus are expressed to prepare the host cell for viral replication. The E1 gene is considered a master switch, it acts as a transcription activator and is involved in both early and late gene transcription. E2 is involved in DNA replication; E3 is involved in immune modulation and E4 regulates viral mRNA metabolism. During the late phase of infection, expression of the late genes L1-L5, which encode the structural components of the viral particles, is activated. Late genes are transcribed from the Major Late Promoter (MLP) with alternative splicing.

HE1 and HE2 sites were identified as potential insertion sites for a transgene since the insertion in these specific points does not interrupt the coding sequences or important regulatory sequences of a chimp adenovirus, such as a Type C or E chimp adenovirus, for example, ChAd155 and ChAd83. The HE1 and HE2 sites can be identified by sequence alignment in any chimp adenovirus. Therefore, cloning of expression cassettes in the HE1 and HE2 sites of the ChAd genomes doesn't impact the virus replication cycle.

Adenoviral Replication

Historically, adenovirus vaccine development has focused on defective, non-replicating vectors. They are rendered replication defective by deletion of the E1 region genes, which are essential for replication. Typically, non-essential E3 region genes are also deleted to make room for exogenous transgenes. An expression cassette comprising the transgene under the control of an exogenous promoter is then inserted. These replication-defective viruses are then produced in E1-complementing cells.

The term "replication-defective " or "replication-incompetent" adenovirus refers to an adenovirus that is incapable of replication because it has been engineered to comprise at least a functional deletion (or "loss-of-function" mutation), i.e. a deletion or mutation which impairs the function of a gene without removing it entirely, e.g. introduction of artificial stop codons, deletion or mutation of active sites or interaction domains, mutation or deletion of a regulatory sequence of a gene etc, or a complete removal of a gene encoding a gene product that is essential for viral replication, such as one or more of the adenoviral genes selected from E1A, E1B, E2A, E2B, E3 and E4 (such as E3 ORF1, E3

ORF2, E3 ORF3, E3 ORF4, E3 ORF5, E3 ORF6, E3 ORF7, E3 ORF8, E3 ORF9, E4 ORF7, E4 ORF6, E4 ORF4, E4 ORF3, E4 ORF2 and/or E4 ORF1). Suitably, E1 and optionally E3 and/or E4 are deleted. If deleted, the aforementioned deleted gene region will suitably not be considered in the alignment when determining percent identity with respect to another sequence.

Vectors of the Invention

Viral vectors based on non-human simian adenovirus represent an alternative to the use of human derived vectors for gene therapy and genetic vaccines. Certain adenoviruses isolated from non-human simians are closely related to adenoviruses isolated from humans, as demonstrated by their efficient propagation in cells of human origin. As humans develop little or no immunity to simian adenoviruses, they promise to provide an improved alternative to human adenoviral uses.

"Low seroprevalence" may mean having a reduced pre-existing neutralizing antibody level as compared to human adenovirus 5 (Ad5). Similarly or alternatively, "low seroprevalence" may mean less than about 30% seroprevalence, less than about 20% seroprevalence, less than about 15% seroprevalence, less than about 10% seroprevalence, less than about 5% seroprevalence, less than about 4% seroprevalence, less than about 3% seroprevalence, less than about 2% seroprevalence, less than about 1% seroprevalence or no detectable seroprevalence. Seroprevalence can be measured as the percentage of individuals having a clinically relevant neutralizing titer (defined as a 50% neutralisation titer >200) using methods as described in Hum. Gene Ther. (2004) 15:293.

In one embodiment, the adenoviral vector of the present invention is derived from a nonhuman simian adenovirus, also referred to as a "simian adenovirus." Numerous adenoviruses have been isolated from nonhuman simians such as chimpanzees, bonobos, rhesus macaques, orangutans and gorillas. Vectors derived from these adenoviruses can induce strong immune responses to transgenes encoded by these vectors. Certain advantages of vectors based on nonhuman simian adenoviruses include a relative lack of cross-neutralizing antibodies to these adenoviruses in the human target population, thus their use overcomes the pre-existing immunity to human adenoviruses. For example, some simian adenoviruses have no cross reactivity with preexisting human neutralizing antibodies and cross-reaction of certain chimpanzee adenoviruses with pre-existing human neutralizing antibodies is only present in 2% of the target population, compared with 35% in the case of certain candidate human adenovirus vectors (Sci. Transl. Med. (2012) 4:1).

Adenoviral vectors of the invention are derived from a simian adenovirus, e.g., from chimpanzees (*Pan troglodytes*), bonobos (*Pan paniscus*), gorillas (*Gorilla gorilla*) and orangutans (*Pongo abelii* and *Pongo pygnaeus*). They include adenoviruses from Group B, Group C, Group D, Group E and Group G. Chimpanzee adenoviruses include, but are not limited to AdY25, ChAd3, ChAd19, ChAd25.2, ChAd26, ChAd27, ChAd29, ChAd30, ChAd31, ChAd32, ChAd33, ChAd34, ChAd35, ChAd37, ChAd38, ChAd39, ChAd40, ChAd63, ChAd83, ChAd155, ChAd15, SadV41 and ChAd157 ChAd3, ChAd19, ChAd25.2, ChAd26, ChAd27, ChAd29, ChAd30, ChAd31, ChAd32, ChAd33, ChAd34, ChAd35, ChAd37, ChAd38, ChAd39, ChAd40, ChAd63, ChAd83, ChAd155, ChAd15, SadV41, sAd4310A, sAd4312, SAdV31, SAdV-A1337, ChAdOx1, ChAdOx2 and ChAd157. Alternatively, adenoviral vectors may be derived from nonhuman simian adenoviruses isolated from bonobos, such as PanAd1, PanAd2, PanAd3, Pan 5, Pan 6, Pan 7 (also referred to as C7) and Pan 9. Vectors may include, in whole or in part, a nucleotide encoding the fiber, penton or hexon of a non-human adenovirus.

In an embodiment of the adenoviral vectors of the invention, the adenoviral vector has a seroprevalence of less than 30%, less than 20%, less than 10% or less than 5% in human subjects, preferably no seroprevalence in human subjects and more preferably no seroprevalence in human subjects that have not previously been in contact with a chimpanzee adenovirus.

In embodiments of the adenoviral vectors of the invention, the adenoviral DNA is capable of entering a mammalian target cell, i.e. it is infectious. An infectious recombinant adenoviral vector of the invention can be used as a prophylactic or therapeutic vaccine and for gene therapy. Thus, in an embodiment, the recombinant adenoviral vector comprises an endogenous molecule for delivery into a target cell. The target cell is a mammalian cell, e.g. a bovine cell, a canine cell, a caprine cell, a cervine cell, a chimpanzee cell, a chiroptera cell, an equine cell, a feline cell, a human cell, a lupine cell, an ovine cell, a porcine cell, a rodent cell, an ursine cell or a vulpine cell. Theendogenous molecule for delivery into a target cell is an expression cassette.

In an embodiment of the invention, the vector comprises a left ITR region, a deleted E1 region, then a deleted E3 region, and, optionally, additional enhancer elements; these are followed by a fiber region, an E4 region and a right ITR. Translation occurs in the rightward and leftward directions. In this embodiment, the first expression cassette is inserted in the deleted E1 region, and the second expression cassette is insertion in the deleted E3 region. In a further embodiment, the promoters of the two expression cassettes are CMV promoters. In a yet further embodiment, the enhancer element is the Hepatitis B Postranslational Regulatory Element (HPRE) or the Woodchuck Hepatitis Postranslational Regulatory Element (WPRE).

In one embodiment of the invention, the vector comprises left and right ITR regions; a deleted E1 region; at least a partially deleted E3 region; a fiber region; an E4 region; two expression cassettes, each comprising: a promoter and at least one an antigen of interest and, optionally, one or more enhancer elements. The first expression cassette is inserted in the deleted E1 region, and the second expression cassette is inserted at the HE1 site, i.e., between the stop codons of the fiber gene and an E4 region ("the HE1 site"). The ChAd155 HE1 insertion site is between bp 34611 and 34612 of the wild type ChAd155 sequence. The ChAd83 HE1 insertion site is between bp 33535 and 33536 of the wild type ChAd83 sequence. Translation occurs in the rightward and leftward directions. In a further embodiment, the promoters are CMV promoters. In a preferred embodiment, one promoter is a CMV promoter and the other is a eCMV promoter. In a yet further embodiment, the enhancer element is HPRE or WPRE.

In a further embodiment, the vector comprises left and right ITR regions; a deleted E1 region; at least a partially deleted E3 region; a fiber region; an E4 region; two expression cassettes, each comprising: a promoter, at least one antigen of interest and, optionally, one or more enhancer elements. The first expression cassette is inserted in the deleted E1 region, and the second expression cassette is inserted at the HE2 site, i.e., between the end of the left ITR and the cap site of the E4 mRNA ("the HE2 site"). The ChAd155 HE2 insertion site is between bp 37662 and 37663 of the wild type ChAd155 sequence. The ChAd83 HE2 insertion site is between bp 36387 and 36388 of the wild type ChAd83 sequence. Translation occurs in the rightward and leftward directions. In a further embodiment, the promoters are CMV promoters. In a preferred embodiment, one promoter is a CMV promoter and the other is a eCMV promoter. In a yet further embodiment, the enhancer element is HPRE or WPRE (the enhancer element increases expression of the transgene).

The HE1 and HE2 sites were identified as insertion sites for a transgene, as the insertion in these specific points does not interrupt the coding sequences or regulatory sequences of ChAd155 and ChAd83. Therefore, inserting expression cassettes in the HE1 or HE2 sites of the ChAd genome does not affect the viral replication cycle.

In an embodiment of the invention, the vector is a functional or an immunogenic derivative of an adenoviral vector. By "derivative of an adenoviral vector" is meant a modified version of the vector, e.g., one or more nucleotides of the vector are deleted, inserted, modified or substituted.

Regulatory Elements

Regulatory elements, i.e., expression control sequences, include appropriate transcription initiation, termination, promoter and enhancer sequences; efficient RNA processing signals such as splicing and polyadenylation (poly A) signals including rabbit beta-globin polyA; tetracycline regulatable systems, microRNAs, posttranscriptional regulatory elements (e.g., WPRE, posttranscriptional regulatory element of woodchuck hepatitis virus); sequences that stabilize cytoplasmic mRNA; sequences that enhance translation efficiency (e.g., Kozak consensus sequence); sequences that enhance protein stability; and when desired, sequences that enhance secretion of an encoded product.

A "promoter" is a nucleotide sequence that permits the binding of RNA polymerase and directs the transcription of a gene. Typically, a promoter is located in a non-coding region of a gene, proximal to the transcriptional start site. Sequence elements within promoters that function in the initiation of transcription are often characterized by consensus nucleotide sequences. Examples of promoters include, but are not limited to, promoters from bacteria, yeast, plants, viruses, and mammals, including simians and humans. A great number of expression control sequences, including promoters which are internal, native, constitutive, inducible and/or tissue-specific, are known in the art and may be utilized.

Promoters of the invention will typically be heterologous promoters. Promoters of the invention can be constitutive.

Examples of promoters include, but are not limited to, promoters from bacteria, yeast, plants, viruses, and mammals (including humans).

Examples of promoters include, without limitation, the TBG promoter, the retroviral Rous sarcoma virus LTR promoter (optionally with the enhancer), the cytomegalovirus (CMV) promoter (optionally with the CMV enhancer, see, e.g., Boshart et al, Cell, 41:521-530 (1985)), the CASI promoter, the SV40 promoter, the dihydrofolate reductase promoter, the β-actin promoter, the phosphoglycerol kinase (PGK) promoter, and the EF1a promoter (Invitrogen).

Suitable promoters include the cytomegalovirus (CMV) promoter and the CASI promoter. The CMV promoter is strong and ubiquitously active. It has the ability to drive high levels of transgene expression in many tissue types and is well known in the art. The CMV promoter can be used in vectors of the invention, either with or without a CMV enhancer.

The CASI promoter is a synthetic promoter described as a combination of the CMV enhancer, the chicken beta-actin promoter, and a splice donor and splice acceptor flanking the ubiquitin (UBC) enhancer (U.S. Pat. No. 8,865,881).

In some embodiments, the CASI promoter can include a nucleic acid sequence having at least about 90%, at least about 95%, at least about 96%, at least about 97%, at least about 98%, at least about 99%, or more, sequence identity to SEQ ID NO: 3. In some embodiments, the promoter comprises or consists of a nucleic acid sequence of SEQ ID NO: 3.

In some embodiments, the enhanced hCMV promoter can include a nucleic acid sequence having at least about 90%, at least about 95%, at least about 96%, at least about 97%, at least about 98%, at least about 99%, or more, sequence identity to SEQ ID NO: 6. In some embodiments, the promoter comprises or consists of a nucleic acid sequence of SEQ ID NO: 6.

Optionally, vectors carrying transgenes encoding therapeutically useful or immunogenic products may also include selectable markers or reporter genes. The reporter gene may be chosen from those known in the art. Suitable reporter genes include, but are not limited to enhanced green fluorescent protein, red fluorescent protein, luciferase and secreted embryonic alkaline phosphatase (seAP), which may include sequences encoding geneticin, hygromicin or purimycin resistance, among others. Such selectable reporters or marker genes (which may or may not be located outside the viral genome to be packaged into a viral particle) can be used to signal the presence of the plasmids in bacterial cells, such as ampicillin resistance. Other components of the vector may include an origin of replication.

A "posttranscriptional regulatory element," as used herein, is a DNA sequence that, when transcribed, enhances the expression of the transgene(s) or fragments thereof that are delivered by viral vectors of the invention. Postranscriptional regulatory elements include, but are not limited to the Hepatitis B Virus Postranscriptional Regulatory Element (HPRE) and the Woodchuck Hepatitis Postranscriptional Regulatory Element (WPRE). The WPRE is a tripartite cis-acting element that has been demonstrated to enhance transgene expression driven by certain, but not all promoters.

In embodiments of the invention, a ChAd155 vector may comprise one or more of a promoter, an enhancer, and a reporter gene. For example, vectors of the invention may comprise ChAd155-enhanced hCMV -SeAP, ChAd155-CASI-seAP and ChAd155-hCMV-seAP, optionally with a tetracycline on/off transcriptional control and ChAd155-CMV-hFerL-chEF1-seAP with a tetracycline on/off transcriptional control.

In embodiments of the invention, a ChAd83 vector may comprise one or more of a promoter, an enhancer, and a reporter gene. For example, vectors of the invention may comprise ChAd155-enhanced hCMV-SeAP, ChAd83-enhanced hCMV-SeAP, ChAd155-CASI-seAP and ChAd83-hCMV-seAP, optionally with a tetracycline on/off transcriptional control and ChAd83-CMV-hFerL-chEF1-seAP with a tetracycline on/off transcriptional control.

Vectors of the invention are generated using techniques provided herein, in conjunction with techniques known to those of skill in the art. Such techniques include conventional cloning techniques of cDNA such as those described in texts, use of overlapping oligonucleotide sequences of the adenovirus genomes, polymerase chain reaction, and any suitable method which provides the desired nucleotide sequence.

Transgenes

A "transgene" is a nucleic acid sequence, heterologous to the vector sequences flanking the transgene, which encodes a polypeptide of interest. The nucleic acid coding sequence is operatively linked to regulatory components in a manner which permits transgene transcription, translation, and/or expression in a host cell. In embodiments of the invention, the vectors express transgenes at a therapeutic or a prophylactic level. A "functional derivative" of a transgenic polypeptide is a modified version of a polypeptide, e.g., wherein one or more amino acids are deleted, inserted, modified or substituted.

The transgene may be used for prophylaxis or treatment, e.g., as a vaccine for inducing an immune response, to correct genetic deficiencies by correcting or replacing a defective or missing gene, or as a cancer therapeutic. As used herein, induction of an immune response refers to the ability of a protein to induce a T cell and/or a humoral antibody immune response to the protein.

The immune response elicited by the transgene may be an antigen specific B cell response, which produces neutralizing antibodies. The elicited immune response may be an antigen specific T cell response, which may be a systemic and/or a local response. The antigen specific T cell response may comprise a CD4+ T cell response, such as a response involving CD4+ T cells expressing cytokines, e.g. interferon gamma (IFN gamma), tumor necrosis factor alpha (TNF alpha) and/or interleukin 2 (IL2). Alternatively, or additionally, the antigen specific T cell response comprises a CD8+ T cell response, such as a response involving CD8+ T cells expressing cytokines, e.g., IFN gamma, TNF alpha and/or IL2.

The composition of the transgene sequence will depend upon the use to which the resulting vector will be put. In an embodiment, the transgene is a sequence encoding a product which is useful in biology and medicine, such as a prophylactic transgene, a therapeutic transgene or an immunogenic transgene, e.g., protein or RNA. Protein transgenes include antigens. Antigenic transgenes of the invention induce an immunogenic response to a disease causing organism.

Transgenes of the invention include respiratory syncytial virus (RSV) antigens or fragments thereof.

As a result of the redundancy in the genetic code, a polypeptide can be encoded by a variety of different nucleic acid sequences. Coding is biased to use some synonymous codons, i.e., codons that encode the same amino acid, more than others. By "codon optimized," it is meant that modifications in the codon composition of a recombinant nucleic acid are made without altering the amino acid sequence. Codon optimization has been used to improve mRNA expression in different organisms by using organism-specific codon-usage frequencies.

In addition to, and independently from, codon bias, some synonymous codon pairs are used more frequently than others. This codon pair bias means that some codon pairs are overrepresented and others are underrepresented. Codon pair deoptimization has been used to reduce viral virulence. For example, it has been reported that polioviruses modified to contain underrepresented codon pairs demonstrated decreased translation efficiency and were attenuated compared to wild type poliovirus (Science (2008) 320:1784). Engineering a synthetic attenuated virus by codon pair deoptimization can produce viruses that encode the same amino acid sequences as wild type but use different pairwise arrangements of synonymous codons. Viruses attenuated by codon pair deoptimization generated up to 1000-fold fewer plaques compared to wild type, produced fewer viral particles and required about 100 times as many viral particles to form a plaque.

In contrast, polioviruses modified to contain codon pairs that are overrepresented in the human genome acted in a manner similar to wild type RNA and generated plaques identical in size to wild type RNA (Coleman et al. (2008) Science 320:1784). This occurred despite the fact that the virus with overrepresented codon pairs contained a similar number of mutations as the virus with underrepresented codon pairs and demonstrated enhanced translation compared to wild type. This observation suggests that codon pair optimized constructs would be expected to act in a manner similar to their non-codon pair optimized counterparts and would not be expected to provide a functional advantage. Without wishing to be constrained by theory, this may be because natural evolution has optimized codon pairing.

A construct of the invention may comprise a codon optimized nucleic acid sequence. Alternatively or additionally, a vector of the invention comprises a codon optimized sequence of a transgene or an immunogenic derivative or fragment thereof. A construct of the invention may comprise a codon pair optimized nucleic acid sequence. Alternatively or additionally, a vector of the invention comprises or consists of a codon pair optimized sequence of a transgene or an immunogenic derivative or fragment thereof.

Respiratory Syncytial Virus (RSV) Transgenes

In one embodiment, the present invention provides the use of a recombinant simian-derived adenoviral vector comprising two expression cassettes, wherein each expression cassette comprises an immunogenic transgene derived from human respiratory syncytial virus (RSV), in the treatment or prophylaxis of RSV infection. In one embodiment, the recombinant simian-derived adenoviral vector of the present invention comprises an RSV F antigen in one of the expression cassettes, and another RSV viral antigen in the other expression cassette. Suitable antigens are discussed further below. In one embodiment, the recombinant simian-derived adenoviral vector comprises RSV M and N antigens in the second expression cassette. In such embodiments, the vector preferably encodes an RSV F0ΔTM antigen (fusion (F) protein deleted of the transmembrane and cytoplasmic regions), and RSV M2-1 (transcription anti-termination) and N (nucleocapsid) antigens.

Infection with RSV does not confer full protective immunity. Infection in infancy is followed by symptomatic RSV re-infections which continue throughout adulthood. These re-infections generally go undiagnosed because they usually present as common acute upper respiratory tract infections. In more vulnerable persons (e.g., immunocompromised adults or elderly), re infections can however also lead to severe disease. Both arms of the immune system (humoral and cellular immunity) are involved in protection from severe disease [Guvenel A K, Chiu C and Openshaw P J. Current concepts and progress in RSV vaccine development. *Expert Rev Vaccines.* 2014; 13(3): 333-44.].

The humoral immune response is capable of neutralizing the virus and inhibiting viral replication, thereby playing a major role in protection against lower respiratory RSV infection and severe disease [Piedra P A, Jewell A M, Cron S G, et al., Correlates of immunity to respiratory syncytial virus (RSV) associated-hospitalization: establishment of minimum protective threshold levels of serum neutralizing antibodies. Vaccine. 2003; 21(24): 3479-82.]. Passive immunization, in the form of Immunoglobulin G (IgG) RSV-neutralizing monoclonal antibodies (Synagis) given prophylactically, has been shown to prevent RSV disease to some extent in premature infants and newborns with bronchopulmonary dysplasia or underlying cardiopulmonary disease [Cardenas S, Auais A and Piedimonte G. Palivizumab in the prophylaxis of respiratory syncytial virus infection. Expert Rev Anti Infect Ther. 2005; 3(5): 719-26.].

T cells are also involved in the control of RSV disease. Lethal RSV infections have been described in patients with low CD8 T cells counts, as in the case of severe combined immunodeficiency, bone marrow and lung transplant recipients [Hertz, 1989]. The histopathology of fatal cases of RSV infection of newborns shows that there is a relative paucity of CD8 T cells in the lung infiltrate [Welliver T P, Garofalo R P, Hosakote Y, et al., Severe human lower respiratory tract illness caused by respiratory syncytial virus and influenza virus is characterized by the absence of pulmonary cytotoxic lymphocyte responses. J Infect Dis. 2007. 195(8): 1126-36.]. Moreover, the presence of CD8 T cells producing Interferon-gamma (IFN-y) has been associated with diminished Th2 responses and reduced eosinophilia in animal models of RSV [Castilow E M and Varga S M. Overcoming T cell-mediated immunopathology to achieve safe RSV vaccination. Future Virol. 2008; 3(5): 445-454.; Stevens W W, Sun J, Castillo J P, et al., Pulmonary eosinophilia is attenuated by early responding CD8(+) memory T cells in a murine model of RSV vaccine-enhanced disease. Viral Immunol. 2009; 22(4): 243-51.].

Suitable antigens of RSV which are useful as immunogens to immunize a human or non-human animal can be selected from: the fusion protein (F), the attachment protein (G), the matrix protein (M2) and the nucleoprotein (N). The term "F protein" or "fusion protein" or "F protein polypeptide" or "fusion protein polypeptide" refers to a polypeptide or protein having all or part of an amino acid sequence of an RSV Fusion protein polypeptide. Similarly, the term "G protein" or "G protein polypeptide" refers to a polypeptide or protein having all or part of an amino acid sequence of an RSV Attachment protein polypeptide. The term "M protein" or "matrix protein" or "M protein polypeptide" refers to a polypeptide or protein having all or part of an amino acid sequence of an RSV Matrix protein and may include either or both of the M2-1 (which may be written herein as M2.1) and M2-2 gene products. Likewise, the term "N protein" or "Nucleocapsid protein" or "N protein polypeptide" refers to a polypeptide or protein having all or part of an amino acid sequence of an RSV Nucleoprotein.

Two groups of human RSV strains have been described, the A and B groups, based mainly on differences in the antigenicity of the G glycoprotein. Numerous strains of RSV have been isolated to date, any of which are suitable in the context of the antigens of the immunogenic combinations disclosed herein. Exemplary strains indicated by GenBank and/or EMBL Accession number can be found in US published application number 2010/0203071 (WO2008114149), which is incorporated herein by reference for the purpose of disclosing the nucleic acid and polypeptide sequences of RSV F and G proteins suitable for use in present invention. In an embodiment, the RSV F protein can be an ectodomain of an RSV F Protein (F0ΔTM).

Exemplary M and N protein nucleic acids and protein sequences can be found, e.g., in US published application number 2014/0141042 (WO2012/089833), which are incorporated herein for purpose of disclosing the nucleic acid and polypeptide sequences of RSV M and N proteins suitable for use in present invention.

Suitably, for use with in present invention, transgene nucleic acids encode an RSV F antigen and RSV, M and N antigens. More specifically, the nucleic acids encode an RSV F0ΔTM antigen (fusion (F) protein deleted of the transmembrane and cytoplasmic regions), and RSV M2-1 (transcription anti-termination) and N (nucleocapsid) antigens.

Fusion (F) Protein Deleted of the Transmembrane and Cytoplasmic Regions (F0ΔTM)

The RSV F protein is a major surface antigen and mediates viral fusion to target cells. The F protein is an antigen which is highly conserved among RSV subgroups and strains. The F protein is a target for neutralizing antibodies, including the prophylactic RSV-neutralizing monoclonal antibody Synagis. Deletion of the transmembrane region and cytoplasmic tail permits secretion of the F0ΔTM protein. Neutralizing antibodies including Synagis, that recognize this soluble form of the F protein, inhibit RSV infectivity in vitro [Magro M, Andreu D, Gómez-Puertas P, et al., Neutralization of human respiratory syncytial virus infectivity by antibodies and low-molecular-weight compounds targeted against the fusion glycoprotein. J Virol. 2010; 84(16): 7970-82.].

Nucleocapsid (N) Protein

The N protein is an internal (non-exposed) antigen, highly conserved between RSV strains and known to be a source of many T cell epitopes. The N protein is essential for the replication and transcription of the RSV genome. The primary function of the N protein is to encapsulate the virus genome for the purposes of RNA transcription, replication and packaging and protects it from ribonucleases.

Transcription Anti-Termination (M2-1) Protein

The M2-1 protein is a transcription anti-termination factor that is important for the efficient synthesis of full-length messenger RNAs (mRNAs) as well as for the synthesis of polycistronic readthrough mRNAs, which are characteristic of non-segmented negative-strand RNA viruses. M2-1 is an internal (non-exposed) antigen, which is highly conserved between RSV strains and known to be a source of many T cell epitopes.

N-M2-1 Fusion Protein

A polynucleotide encoding a linker is positioned between the polynucleotide encoding an RSV N antigen, or fragment thereof, and the polynucleotide encoding an RSV M2.1 antigen, or fragment thereof. Thus, in certain preferred examples, an expression cassette contains a transgene which encodes a fused RSV viral protein N-linker-M2.1 It is preferred that the linker is a flexible linker, preferably a flexible linker comprising an amino acid sequence according to SEQ ID NO: 11 (Gly-Gly-Gly-Ser-Gly-Gly-Gly) or SEQ ID NO: 12 (Gly-Gly-Gly-Gly-Ser-Gly-Gly-Gly-Gly).

Delivery of Adenoviral Vectors

In some embodiments, the recombinant adenoviral vector of the invention is administered to a subject by epicutaneous administration, intradermal administration, intramuscular injection, intraperitoneal injection, intravenous injection, nasal administration, oral administration, rectal administration, subcutaneous injection, transdermal administration or intravaginal administration.

In an embodiment of the invention, the vectors can be administered intramuscularly (IM), i.e., injection directly into muscle. Muscles are well vascularized and the uptake is typically rapid.

Adjuvants

Approaches to establishing strong and lasting immunity to specific pathogens include addition of adjuvants to vaccines. By "adjuvant" is meant an agent that augments, stimulates, activates, potentiates or modulates the immune response to an active ingredient of the composition. The adjuvant effect may occur at the cellular or humoral level, or both. Adjuvants stimulate the response of the immune system to the actual antigen but have no immunological effect themselves. Alternatively or additionally, adjuvented compositions of the invention may comprise one or more immunostimulants. By "immunostimulant" it is meant an agent that induces a general, temporary increase in a subject's immune response, whether administered with the antigen or separately.

A composition of the invention may be administered with or without an adjuvant. Alternatively, or additionally, the composition may comprise, or be administered in conjunction with, one or more adjuvants (e.g. vaccine adjuvants), in particular the composition comprises an immunologically effective amount of a vector of the invention encoding a transgene.

Methods of Use/Uses

Methods are provided for inducing an immune response against a disease caused by a pathogen in a subject in need thereof comprising a step of administering an immunologically effective amount of a construct or composition as disclosed herein. In some embodiments are provided the use of the constructs or compositions disclosed herein for inducing an immune response to a transgenic antigen in a subject in need thereof. Vectors of the invention may be applied for the prophylaxis, treatment or amelioration of diseases due to infection.

Embodiments of the invention provide the use of adenoviral vectors or compositions disclosed herein for inducing an immune response in a subject to a transgenic antigen derived from respiratory syncytial virus (RSV). Vectors of the invention may be applied for the prophylaxis, treatment or amelioration of disease due to infection with RSV.

Methods of the invention include the use of a vector of the invention in medicine. They include the use of a vector of the invention for the treatment of a disease caused by a pathogen. A vector of the invention can be used in the manufacture of a medicament for treating a disease caused by a pathogen.

Methods of the invention include the use of a vector of the invention for the treatment or prevention of a disease caused by respiratory syncytial virus (RSV). An adenoviral vector of the invention can be used as a medicament in the treatment of respiratory syncytial virus (RSV). A vector of the invention can be used in the manufacture of a medicament for the prevention or treatment of a disease caused by respiratory syncytial virus (RSV).

Effective immunization with adenoviral vectors depends on the intrinsic immnomodulatory capability of the adenoviral vector backbone. Immunologically less potent adenoviruses induce less antigen expression. Effective immunization also depends on the ability of the promoter to drive strong and sustained transgene expression. For example, adenoviral vectors driven by the cytomegalovirus immediate-early (CMV-IE) promoter do not sustain long-term transgene expression because they induce cytokines that dampen expression.

By "subject" is intended a vertebrate, such as a mammal e.g. a human or a veterinary mammal. In some embodiments the subject is human.

General

Vectors of the invention are generated using techniques and sequences provided herein, in conjunction with techniques known to those of skill in the art. Such techniques include conventional cloning techniques of cDNA such as those described in texts, use of overlapping oligonucleotide sequences of the adenovirus genomes, polymerase chain reaction, and any suitable method which provides the desired nucleotide sequence.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word or is intended to include "and" unless the context clearly indicates otherwise. The term "plurality" refers to two or more. Additionally, numerical limitations given with respect to concentrations or levels of a substance, such as solution component concentrations or ratios thereof, and reaction conditions such as temperatures, pressures and cycle times are intended to be approximate. The term "about" used herein is intended to mean the amount ±10%.

The present invention will now be further described by means of the following non-limiting examples.

EXAMPLES

Example 1: Construction of Chimpanzee Adenoviruses with a Single Expression Cassette Wild type chimpanzee adenoviruses type 155 (ChAd155) (WO 2016/198621) and type 83 (ChAd83) (WO 2010/086189) were isolated from healthy chimpanzees using standard procedures and were constructed as described in Sci Transl Med (2012) 4:1 and WO 2010/086189.

In Example 1, the ChAd155 and ChAd 83 vectors were each constructed by inserting a single transgene expression cassette. The expression cassette components used either the classical human CMV promoter or the CASI promoter, rabies glycoprotein as a model antigen and, optionally, a WPRE enhancer. Three different insertion sites were tested for the transgene cassette:
(i) replacing the E3 region with the transgene cassette,
(ii) inserting the transgene cassette between the fiber and the E4 region (site HE1), and
(iii) inserting the transgene cassette downstream of the right ITR (site HE2).

This numbering of these insertion sites corresponds to the illustrations of FIG.1 where:
(i) the top panel illustrates the RC1 vector, in which a transgene cassette replaced the E3 region,
(ii) the middle panel illustrates the RC3 vector, in which a transgene cassette is inserted between the stop codons of the fiber gene and the E4 region (site HE1), and
(iii) the bottom panel illustrates the RC2 vector, in which a transgene cassette is inserted downstream of the right ITR (site HE2).

In the vectors shown in Example 1, the E1 region remains intact in all configurations.

The transgene was inserted by homologous recombination techniques in the following positions of the SEQ ID NO: 1 and of the SEQ ID NO: 2:

HE1 ChAd155: insertion site between bp 34611 and 34612 of SEQ ID NO: 1; HE2 ChAd155: insertion site between bp 37662 and 37663 of SEQ ID NO: 1; HE1 ChAd83: insertion site between bp 33535 and 33536 of SEQ ID NO: 2; HE2 ChAd83: insertion site between bp 36387 and 36388 of SEQ ID NO: 2.

When the transgene cassette was inserted in site HE1, ChAd155 failed to replicate. However, insertion of a transgene cassette into the HE1 site of ChAd83 produced a viable vector.

Example 2: Virus Production, Vector Titer and Expression of Vectors of Example 1

To identify an animal model in which to evaluate vector replication, a type C adenovirus ChAd155 RC2 and a type E adenovirus ChAd83 RC2 vectors of Example 1 were assessed for their ability to replicate, measured by vector titer and genome copy number, in cells of various animal origins. The results are shown in Table 1.

TABLE 1

Replication and Expression of RC2 ChAd155 and RC2 ChAd83 of Example 1

| Cell line: | | Vector | Genome | Expression | |
|---|---|---|---|---|---|
| Species | Vector | Titer | Copy | Day 2 | Day 7 |
| MRC5: Human | ChAd155 | +++ | +++ | ++ | ++++ |
| | ChAd83 | +++++ | +++++ | +++ | +++++ |
| PK15: Swine | ChAd155 | +++++ | +++++ | NA | NA |
| | ChAd83 | +++ | ++++ | NA | NA |
| NMuLi: Mouse | ChAd155 | ++ | +++ | +++ | +++ |
| | ChAd83 | ND | + | ++ | ++ |
| Vero: Non-human primate | ChAd155 | ++ | ++++ | +++ | +++ |
| | ChAd83 | ND | + | + | + |

ND = not detected;
NA = not available

As shown in Table 1, human MRC5 cells and swine PK15 cells produced high vector titers and high genome copy numbers of both ChAd155 and ChAd83. Murine NMuLi and non-human primate Vero cells also produced RC ChAd155 but to a lesser extent than the human or swine cells. RC ChAd83 failed to grow well in murine NMuLi cells and, surprisingly, in non-human primate Vero cells.

Human MRC5, mouse NMuLi and non-human primate Vero cells supported the expression of RC ChAd155 through day 7. Human MRC5 cells supported the expression of RC ChAd83 through day 7, as did mouse NMuLi and non-human primate Vero cells, but to a lesser extent than the human cells.

Virus Production

FIG. 2 shows the amount of virus produced by human primary MRC5 cells infected with either ChAd155 or ChAd83, each comprising either the RC1 or RC2 vector construction of Example 1. The cells were harvested seven days post-infection and the vector titer was evaluated in cell lysates obtained following three freeze-thaw cycles. Vector titers were measured by quantitative PCR (QPCR) analysis with primers designed for the respective promoter regions. The multiplicity of infection (moi) was 1250 virus particles per cell. The virus production is indicated in the number of virus particles per cell (vp/cell) above the bars.

Human MRC5 cells supported production of ChAd155 comprising either RC1 ($2.17 \times 10^3$ vp/cell) or RC2 ($4.40 \times 10^3$ vp/cell) and also supported production of ChAd83 comprising either RC1 ($1.18 \times 10^4$ vp/cell) or RC2 ($1.06 \times 10^5$ vp/cell). As shown in FIG. 2, ChAd83 was produced at a higher level than ChAd155; the ChAd83 vector comprising RC2 was the most robust of the four viral/vector combinations.

FIG. 2B shows the amount of virus produced by human primary MRC5 cells infected with ChAd83 comprising the RC1, RC2 or RC3 vector construction of Example 1. The cells were harvested two and seven days post-infection. As with FIG. 2A, vector titers were measured by quantitative PCR (QPCR) analysis with primers designed for the respective promoter regions. The multiplicity of infection (moi) was 250 or 1250 virus particles per cell. The virus production is indicated in the number of virus particles per cell (vp/cell) above the bars.

Human MRC5 cells supported production of ChAd83 comprising RC1, RC2 or RC3. As shown in FIG. 2B, there was higher virus production for the RC2 and RC3 ChAd83 vectors than for the RC1 vector. There was also higher virus production for the ChAd83 RC2 HE2 vector than the RC3 HE1 vector.

Vector Genome Copy Number

After infection, the vector is replicated in the cell and the vector genome copy number can be measured by QPCR. Vector DNA replication can occur even in cells not fully permissive for viral replication and propagation. QPCR of vector DNA provides a measure of vector replication within the infected cell, independently of the ability of the virus to complete the replication cycle and be released as mature viral progeny. Vector replication can thus be quantified in animal species, tissue types and cell types which are not permissive for ChAd virus replication or propagation.

Vector genome copy number was measured in parallel with vector titer and the results shown in FIG. 3A and FIG. 3B.

As with the virus production shown in FIG. 2A, Human MRC5 cells were infected with either ChAd155 or ChAd83, each comprising either the RC1 or RC2 vector construction of Example 1. The cells were harvested seven days post-infection, the total DNA extracted, the viral genome quantified by QPCR and the results expressed as vector genome copy per cell. The multiplicity of infection (moi) was 250 virus particles per cell and the numbers of virus particles per cell are indicated above the bars denoting viral genome copies per cell. The copy number is directly proportional to the level of transgene expression.

As shown in FIG. 3A, the amount of viral DNA replication of RC1 ($6.21 \times 10^3$ vp/cell) and RC2 ($6.71 \times 10^3$ vp/cell) by ChAd155 was similar. ChAd83 produced more RC1 ($2.76 \times 10^4$ vp/cell) and RC2 ($9.19 \times 10^4$ vp/cell) viral DNA than ChAd155. The highest level of viral DNA replication was observed by ChAd83 RC2.

As with the virus production shown in FIG. 2B, Human MRC5 cells were infected with ChAd83, comprising the RC1, RC2 or RC3 vector construction of Example 1. The cells were harvested at two and seven days post-infection, the total DNA extracted, the viral genome quantified by QPCR and the results expressed as vector genome copy per cell. The multiplicity of infection (moi) was 250 or 1250 virus particles per cell and the numbers of virus particles per cell are indicated above the bars denoting viral genome copies per cell. The copy number is directly proportional to the level of transgene expression.

As shown in FIG. 3B, the amount of viral DNA replication was higher for the RC2 and RC3 ChAd83 vectors than for the RC1 vector. There was comparable viral DNA replication between the RC2 and RC3 ChAd83 vectors.

Example 3: Adenoviral Genome Copy Number of Vectors of Example 1

The efficiency of the replication competent adenoviral vectors with the constructs of Example 1, expressed as vector copies per cell, was evaluated in cell cultures derived from both mice and non-human primates. FIG. 4(a) shows the genome copy number of replication competent vectors grown in murine hepatic NMuLi cells grown in monolayers and infected with ChAd155 RC1, ChAd155 RC2, ChAd83 RC1 or ChAd83 RC2 at a multiplicity of infection of 250 virus particles per cell. Total DNA was extracted at five days post-infection and the vector replication was measured by QPCR using primers annealing to the vector's promoter region.

The results, expressed as vector copies per cell, are shown in FIG. 4(a). ChAd155 amplified both the RC1 and RC2 vector with high efficiency in NMuLi cells. ChAd155 replicated the RC1 ($1.73 \times 10^4$) and RC2 ($1.92 \times 10^4$) vectors to approximately the same degree. ChAd83 was less efficient than ChAd155 in replicating the RC1 and RC2 vectors. ChAd83 replicated the vector DNA only in small amounts in the murine cells. RC1 vector replicated at a level of $5.47 \times 10^2$ copies per cell and the RC2 vector at a level of $6.74 \times 10^2$ copies per cell.

Non-human primate Vero cells were also grown in monolayers and infected with ChAd155 RC1, ChAd155 RC2, ChAd83 RC1 or ChAd83 RC2 (FIG. 4(b)). Two different multiplicities of infection were used: 50 and 250 virus particles per cell. Total DNA was extracted at five days post-infection and the vector replication was measured by QPCR using primers annealing to the vector's promoter region.

The results, expressed as vector copies per cell, are shown in FIG. 4(b). The Vero primate cell line was permissive for ChAd155 RC1 ($3.71 \times 10^3$ copies per cell at an moi of 50 and $4.93 \times 10^4$ copies per cell at an moi of 250) and ChAd155 RC2 ($8.15 \times 10^3$ copies per cell at an moi of 50 and $7.05 \times 10^4$ copies per cell at an moi of 250). The Vero primate cell line was poorly, if at all, permissive for ChAd83 RC1 or ChAd83 RC2. No ChAd83 RC1 or ChAd83 RC2 vectors were detected to be expressed from Vero cells at an moi of 50. At an moi of 250, ChAd83 replicated the RC1 vector at a level of $1.13 \times 10^2$ copies per cell and the RC2 vector at a level of $1.29 \times 10^3$ copies per cell.

Example 4: Transgene Expression from Murine and Non-human Primate Cells of Vectors of Example 1

Western blot analysis was performed to compare the level of transgene expression by ChAd155 RC1 and ChAd155 RC2 in murine NMuLi cells (FIG. 5(a)). The cells were infected with ChAd155 RC1 or ChAd155 RC2 at a multiplicity of infection of 50, 250 or 1250 viral particles per cell. The cells were harvested at two and five days post infection, extracts prepared using standard methods and an equivalent amount of total cell extract loaded onto SDS-PAGE gels. Following electrophoretic separation, the proteins were transferred onto nitrocellulose membranes, which were then probed with a commercially available monoclonal antibody to the rabies glycoprotein transgene.

FIG. 5(a) demonstrates that both ChAd155 RC1 and ChAd155 RC2 express a transgene in murine NMuLi cells. Expression was observed at both two and five days post infection, indicated by the band of about 51 kDa, which corresponds to the expected molecular weight of the rabies glycoprotein (RG). The ChAd155 RC2 vector produced a higher level of transgene expression than the ChAd155 RC1 vector at both two and five days post-infection. Western blot analysis was then performed to compare the level of transgene expression by ChAd155 RC1, ChAd155 RC2, ChAd83 RC1 and ChAd83 RC2 in murine NMuLi cells (FIG. 5(b)). The cells were infected with ChAd155 RC1, ChAd155 RC2, ChAd83 RC1 or ChAd83 RC2 at a multiplicity of infection of 50, 250 or 1250 viral particles per cell (250 and 1250 for ChAd83 RC1). The cells were processed for western blot. The cells were harvested at two and seven days post infection, extracts prepared using standard methods and an equivalent amount of extract loaded onto SDS-PAGE gels. Following electrophoretic separation, the proteins were transferred onto nitrocellulose membranes, which were then probed with a commercially available monoclonal antibody to the rabies glycoprotein transgene.

FIG. 5(b) demonstrates that ChAd155 RC1, ChAd155 RC2, ChAd83 RC1 and ChAd83 RC2 express a transgene in murine NMuLi cells. Expression was observed at both two and five days post infection, indicated by the band of about 51 kDa, which corresponds to the expected molecular weight of the rabies glycoprotein (RG). ChAd155 demonstrated more efficient expression of the transgene than ChAd83. At two days post-infection, robust transgene expression by ChAd155 RC2 was observed even at the low multiplicity of 50 vp/cell, whereas robust transgene expression by ChAd155 RC1 was first observed at higher mois. Also, RC2 demonstrated more efficient transgene expression than RC1 in both ChAd155 and ChAd83 viral serotypes. RC2 was more robustly expressed than RC1 in each of the direct comparisons.

Western blot analysis was performed to compare the level of transgene expression by ChAd83 RC1, RC2 and RC3 in MRC5 cells (FIG. 5(a)). The cells were infected with ChAd83 RC1, RC2 or RC3 at a multiplicity of infection of 250 or 1250 viral particles per cell. The cells were harvested at two and seven days post infection, extracts prepared using standard methods and an equivalent amount of total cell extract loaded onto SDS-PAGE gels. Following electrophoretic separation, the proteins were transferred onto nitrocellulose membranes, which were then probed with a commercially available monoclonal antibody to the rabies glycoprotein transgene.

FIG. 5(c) demonstrates that all of ChAd83 RC1, RC2 and RC3 express a transgene in MRC5 cells. Expression was observed at both two and seven days post infection, indicated by the band of about 51 kDa, which corresponds to the expected molecular weight of the rabies glycoprotein (RG). The ChAd83 RC2 vector produced a higher level of transgene expression than the ChAd83 RC1 and RC3 vectors at both two and seven days post-infection. There was no rabies glycoprotein detection for the RC1 and RC3 vectors at 7days.

Example 5: Construction of Alternative Chimpanzee Adenoviruses with a Single Expression Cassette As in Example 1, wild type chimpanzee adenoviruses type 155 (ChAd155) (WO 2016/198621) isolated from healthy chimpanzees using standard procedures were constructed as replication defective viruses as described in Sci Transl Med (2012) 4:1 and WO 2010/086189.

In Example 5, the ChAd155 is constructed by inserting a single transgene expression cassette. This expression cassette comprises the classical human CMV (hCMV) promoter, F0ΔTM, N and M2-1 RSV antigens and, optionally, a WPRE enhancer. This vector is shown in FIG. 6. The expression cassette is inserted into the E1 region of the adeno virus (after the E1 region has been deleted).

The ChAd155 shown in FIG. 6 comprises a transgene encoding all of the RSV F0ΔTM, M2-1 and N antigens, wherein a self-cleavage site ("2A") is included between the RSV F0ΔTM antigen and the composite RSV N.M2-1 antigen, in which a flexible linker is included between the RSV M2-1 and N antigens.

The ChAd155 RSV vector of Example 5 compises the polynucleotide of SEQ ID NO: 4 and encodes the polypeptide of SEQ ID NO: 5.

Example 6: Construction of a Chimpanzee Adenoviruses with a Dual Expression Cassette Again, wild type chimpanzee adenoviruses type 155 (ChAd155) (WO 2016/198621) isolated from healthy chimpanzees using standard procedures were constructed as replication defective viruses as described in Sci Transl Med (2012) 4:1 and WO 2010/086189.

The ChAd155 of Example 6 is constructed by inserting two transgene expression cassettes into two different locations in the adenovirus:
(1) The first expression cassette components comprise the classical human CMV (hCMV) promoter and N.M2-1 RSV composite antigen. This first expression cassette is inserted into the E1 region of the adenovirus (after the E1 region has been deleted).
(2) The second expression cassette comprises an enhanced classical human CMV (enhanced hCMV) promoter, the F0ΔTM RSV antigen and a WPRE enhancer. This first expression cassette is inserted into the HE2 region of the adenovirus (after the HE2 region has been deleted).

This vector comprising a dual expression cassette is shown in FIG. 7.

In the construct of FIG. 7, Ad5E4orf6 has been substituted into the early gene 4 (E4) region. The substitution is necessary to increase the productivity in HEK 293 cells.

Example 7: Transgene expression from the Dual Expression Cassette of Example 6

Western blot analysis was performed to compare the level of transgene expression in the ChAd155 vector of Example 6 (labelled "Dual" or "Dual cassette" in the figures) in MRC5 cells with:
(i) a vector comprising a single F expression cassette (ChAd155-F0ΔTM, labelled "F0ΔTm"),
(ii) a vector comprising a single NM2 expression cassette (ChAd155-NM2, labelled "NM2-1"), and
(iii) the vector of Example 5 comprising a single expression cassette containing the F and N.M2-1 RSV antigens (ChAd155-F0ΔTM.NM2, also labelled "RSV")

The western blot analysis is shown in FIG. 8 and FIG. 9.

As shown in FIG. 8, the cells were infected with ChAd155-F0ΔTM, ChAd155-F0ΔTM.NM2 ("RSV") or the ChAd155 dual cassette of Example 6 at a multiplicity of infection of 500 viral particles per cell. In addition, cells were infected with ChAd155-F0ΔTM.NM2 ("RSV") at a multiplicity of infection of 500 or 1250 viral particles per cell. The cells were harvested at 48 hours and 96 hours post infection, extracts prepared using standard methods and an equivalent amount of total cell extract loaded onto SDS-PAGE gels.

FIG. 8 shows that the ChAd155 dual cassette provides an expression level of the F antigen which is comparable to ChAd155F0ΔTM and higher than ChAd155-FΔTM.NM2 in MRC5 cells.

As shown in FIG. 9, the cells were infected with ChAd155-NM2, ChAd155-F0ΔTM.NM2 ("RSV") or the ChAd155 dual cassette of Example 6 at a multiplicity of infection of 250 and 1250 viral particles per cell. The cells were harvested at 48 hours post infection, extracts prepared using standard methods and an equivalent amount of total cell extract loaded onto SDS-PAGE gels.

In FIG. 9, the ChAd155 dual cassette provides NM2-1 expression level at least comparable to the ChAd155-NM2 single vector and higher than ChAd155-FΔTM.NM2 ("RSV") in MRC5 cells.

Example 8: Immunogencity of the Dual Expression Cassette of Example 6

The immunogenicity of the dual expression cassette of Example 6 was evaluated in CD1 outbred mice (10 per group). The experiment was performed by injecting $5 \times 10^8$ viral particles intramuscularly into the mice. The B-cell response was measured at 4 and 8 weeks after the immunization by measuring the RSV neutralising titres. Each dot represents the response in a single mouse, and the line corresponds to the mean for each dose group. The results of this analysis are shown in FIG. 10.

FIG. 10 shows that the ChAd155 dual cassette provides a B-cell response comparable to ChAd155F0ΔTM and higher than that produced by ChAd155-F0ΔTM.NM2 ("RSV").

The immunogenicity of the dual expression cassette of Example 6 was also evaluated in BALB/c inbred mice (48, 11 or 8 per group). The experiment was performed by injecting $10^7$ or $10^6$ viral particles intramuscularly. The T-cell response was measured 3 weeks after the immunization by ex vivo IFN-gamma enzyme-linked immunospot (ELISpot) using a M2 peptide T cell epitope mapped in BALB/c mice. The results are shown in FIG. 11, expressed as IFN-gamma Spot Forming Cells (SFC) per million splenocytes. Each dot represents the response in a single mouse, and the line corresponds to the mean for each dose group. Injected dose in number of virus particles are shown on the x axis. The results are shown in FIG. 11.

FIG. 11 shows that the ChAd155 dual cassette provides a T-cell response higher than that produced by the single cassette ChAd155-F0ΔTM.NM2 ("triple RSV", the results for which are obtained from historical data). This difference in response is greater for the $10^6$ vp dose.

FIG. 11 refers to "#positive mice", i.e. the number of mice which responded to the vaccine.

Example 9: Immunogencity of the Dual Expression Cassette of Example 6 in Cows The study design is detailed in Table 2 below:

| Group | No. Cows | Vaccine | Route | Dose | Immunization | End of Study |
|---|---|---|---|---|---|---|
| Gp1 | 4 | ChAd155 single RSV | Intramuscular (IM) | $1 \times 10^{11}$ | D0 | D90 |
| Gp2 | 4 | ChAd155 dual RSV | Intramuscular (IM) | $1 \times 10^{11}$ | D0 | D90 |
| Gp3 | 4 | Saline | Intramuscular (IM) | N/A | D0 | D90 |

The "ChAd155 single RSV" is the ChAd155 of Example 5, and the "ChAd155 dual RSV" is the ChAd155 of Example 6.

A total of 12 adult cows were enrolled in the study. The cows ranged in age from 2.7 years to 7.8 years and had a mean range of 4.8 years.

Before they were enrolled in the study, the cows were pre-screened for bovine RSV (BRSV) antibodies by ELISA. This allowed study groups to be established that had a similar distribution and mean BRSV Ab titer (so as to not bias any of the groups).

Samples were collected from the cows before vaccination (D-5 or D0) and after vaccination (D7, 10, 14, 28, 60, 90). In this study, the cows were vaccinated with 1×10^11 viral particles of one of the two vaccines or with saline on day zero (DO).

A Bronchoalveolar lavage (BAL) was performed at day −5, 7, 10 or 28 after vaccination to isolate T cells in the lungs of the cow. Then IFN-gamma cytokine production of the CD4+ and CD8+ T cells upon stimulation with RSV antigens (in the form of peptide pools) encoded in the vaccines was detected using intracellular cytokine staining (ICS) (i.e. IFNγ ICS was used to detect the lung T cell responses in the animals). The results of this experiment are shown in FIGS. 12A and 12B. It can be concluded from this experiment that the ChAd155-dual RSV induces consistent RSV-specific CD4+ and CD8+ responses in Bronchoalveolar lavage (BAL).

Blood samples were also taken from the cows on day 0, 14, 28, 60 and 90 after vaccination in order for IFN-gamma cytokine production of the RSV-specific CD4+ and CD8+ responses of the peripheral blood mononuclear cells (PBMC) to be detected using intracellular cytokine staining (ICS) (i.e. IFNγ ICS was used to detect the peripheral T cell responses). The results of this experiment are shown in FIGS. 13A and 13B. Based on these results, it can be concluded that the ChAd155-dual RSV consistently expand the pre-existing RSV-specific CD4+ and CD8+ responses in PBMC.

The blood samples were also used to detect neutralising antibodies (nAbs) for RSV in the serum (i.e. the peripheral humoral response was detected). The results of this experiment are shown in FIGS. 14A and 14B. These results show that the ChAd155-dual RSV boosts RSV nAbs in serum which are maintained at levels higher than baseline 3 months after vaccination.

Example 10: Immunogenicity of ChAd155 Dual Encoding Rrabies G and RSV NM2 Proteins Three different ChAd155 vectors used constructed in this experiment:
ChAd155 encoding both rabies G (RG) and RSV NM2 proteins (called "ChAd155 dual" in this example, and ChAd155 dual hCMV NM 2-1—CASI RG WPRE);
ChAd155 encoding just the rabies G (RG) protein (called "ChAd155 RG" in this example, and ChAd155(ΔE4) CASI RG WPRE); and
The ChAd155 vector shown in FIG. 6, i.e. the vector with transgene encoding all of the RSV F0ΔTM, M2-1 and N antigens(called "ChAd155 RSV").

Three different doses of the ChAd155 dual adenovirus were administered to mice: a highest dose of $10^7$ viral particles, and a middle dose of $10^6$ viral particles, and a lowest dose of $10^5$ viral particles.

Two different doses of the ChAd155 RG and RSV vectors were administered to mice. For the ChAd155 RSV, this was a higher dose of $10^7$ vaccine particles, and a lower dose of $10^6$ vaccine particles. For the ChAd155 RG, this was a higher dose of $10^6$ vaccine particles, and a lower dose of $10^5$ vaccine particles. Mice were sacrificed 3 weeks later and splenocytes tested by IFNγ ELISpot for T cell response to the vaccine encoded antigens.

Figure 15B:
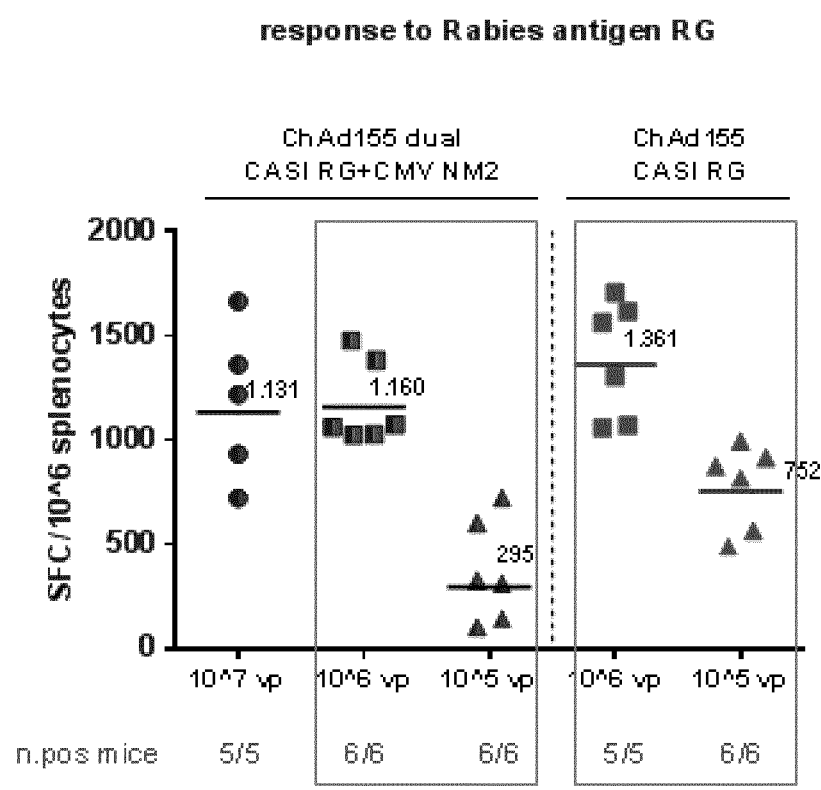
Figure 15C:
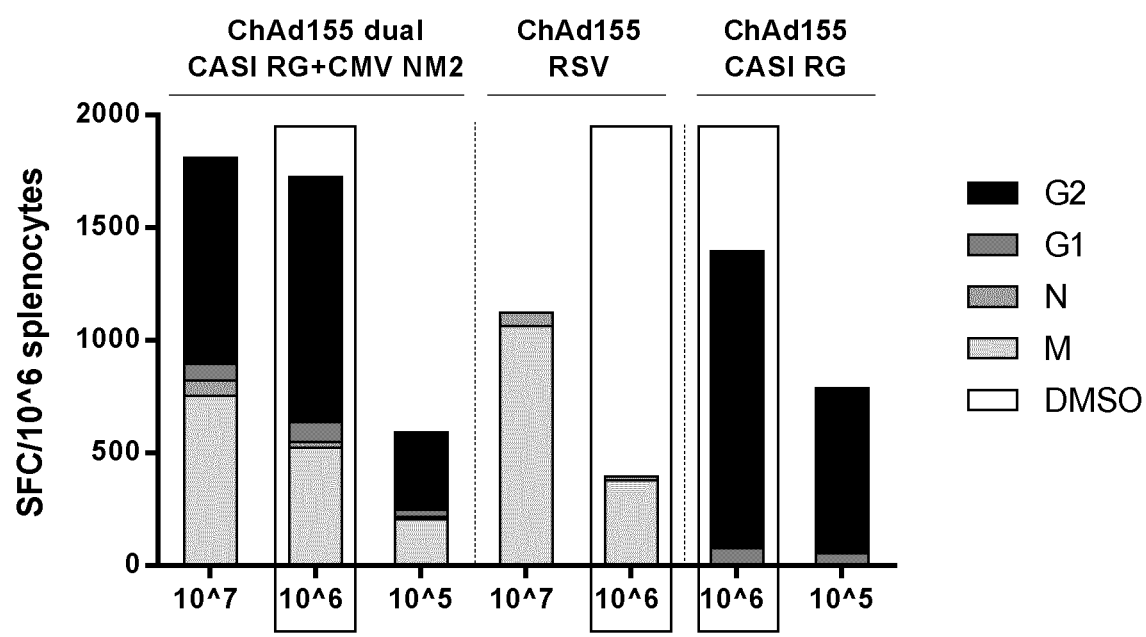

The results of this experiment are shown in FIGS. 15A, 15B and 15C. As can be seen from FIG. 15A, 15B and 15C, the ChAd155 dual RG-NM2 vector shows overall comparable immune responses to the vectors encoding each of the RG and NM2 antigens alone.

FIG. 15C compares the cumulative response to all encoded antigens at the common $10^6$ vp dosage used for all three different vectors. The rabies G protein is listed twice (G1 and G2) as two pools of overlapping peptides were used to cover the whole sequence of the protein Therefore, placing the two antigens in the same vector still produces a comparable immune response while allowing antigens for different pathogens to be provided in the same vector.

Example 11: Expression of ChAd155 Dual Encoding Rabies G and RSV NM2 Proteins in HeLa Cells In the experiments of Example 11, HeLa cells were infected with the purified "ChAd155 dual", "ChAd155 RG" and "ChAd155 RSV" used in Example 10.

Multiplicities of infection (MOI) of 50, 250 and 1250 were used in this experiment.

In order to obtain the Western Blot shown in FIG. 16A (obtained under reducing conditions), the cell lysate was harvested 48 hours post-infection. The estimated size of the NM2-1 is 65 kDa. FIG. 16A shows a comparable expression level for ChAd155 dual cassette and ChAd155 NM2-1. In addition, the NM2-1 expression level was higher for the ChAd155 dual cassette than the ChAd155 RSV vector.

To obtain the Western Blot shown in FIG. 16B, the supernatent was harvested 48 hours post-infection. The estimated size of the rabies glycoprotein is 57.6 kDa. FIG. 16B shows a comparable expression level for the ChAd155 dual and ChAd155 RG adenoviruses.

In addition, infectivity data was also collected using the four different vectors. The infectivity of purified virus was evaluated in adherent Procell 92 cells by Hexon Immunostaining. The results are given in Table 3 below (vp=virus particle, ifu=infectious unit, and R is the ratio between these two numbers). The infectivity results indicate that all of the vectors have similar infectivity. In addition, as all of the R values were below 300, the infectivity of all vectors was deemed to be within the range of acceptability.

TABLE 3

|  | Vp/ml | Ifu/ml | R (vp/ifu) |
| --- | --- | --- | --- |
| ChAd155 hCMV NM 2-1-CASI RG WPRE | 5.51E+11 | 4.53E+09 | 122 |
| ChAd155(ΔE4)hCMV-RSV | 1.12E+11 | 1.05E+09 | 107 |
| ChAd155(ΔE4)hCMV NM2-1 | 5.68E+11 | 4.26E+09 | 133 |
| ChAd155(ΔE4)CASI RG WPRE | 3.48E+11 | 3.35E+09 | 104 |

DESCRIPTION OF THE SEQUENCES

SEQ ID NO: 1 Polynucleotide sequence encoding wild type ChAd155
CATCATCAATAATATACCTTATTTTGGATTGAAGCCAATATGATAATGAGATGGGCGGCGCGGGGCGGGAG
GCGGGTCCGGGGGCGGGCCGGCGGGCGGGCCGGTGTGGCGGAAGTGGACTTTGTAAGTGTGGCGGATGTGACTTGCT
AGTGCCGGGCGCGGTAAAAGTGACGTTTTCCGTGCGCGACAACGCCCACGGGAAGTGACATTTTTCCCGCGGTTTTT

| DESCRIPTION OF THE SEQUENCES |
|---|
| ACCGGATGTTGTAGTGAATTTGGGCGTAACCAAGTAAGATTTGGCCATTTTCGCGGGAAAACTGAAACGGGGAAGTG |
| AAATCTGATTAATTTCGCGTTAGTCATACCGCGTAATATTTGTCGAGGGCCGAGGGACTTTGGCCGATTACGTGGAG |
| GACTCGCCCAGGTGTTTTTTGAGGTGAATTTCCGCGTTCCGGGTCAAAGTCTCCGTTTTATTATTATAGTCAGCTGA |
| CGCGGAGTGTATTTATACCCTCTGATCTCGTCAAGTGGCCACTCTTGAGTGCCAGCGAGTAGAGTTTTCTCCTCTGC |
| CGCTCTCCGCTCCGCTCCGCTCGGCTCTGACACCGGGGAAAAAATGAGACATTTCACCTACGATGGCGGTGTGCTCA |
| CCGGCCAGCTGGCTGCTGAAGTCCTGGACACCCTGATCGAGGAGGTATTGGCCGATAATTATCCTCCCTCGACTCCT |
| TTTGAGGCCACCTACACTTCACGAACTCTACGATCTGGATGTGGTGGGGCCCAGCGATCCGAACGAGCAGGCGGTTTC |
| CAGTTTTTTTCCAGAGTCCATGTTGTTGGCCAGCCAGGAGGGGGTCGAACTTGAGACCCCTCCTCCGATCGTGGATT |
| CCCCCGATCCGCCGCAGCTGACTAGGCAGCCCGAGCGCTGTGCGGGACCTGAGACTATGCCCCAGCTGCTACCTGAG |
| GTGATCGATCTCACCTGTAATGAGTCTGGTTTTCCACCCAGCGAGGATGAGGACGAAGAGGGTGAGCAGTTTGTGTT |
| AGATTCTGTGGAACAACCCGGGCGAGGATGCAGGTCTTGTCAATATCACCGGAAAAACACAGGAGACTCCCAGATTA |
| TGTGTTCTCTGTGTTATATGAAGATGACCTGTATGTTTATTTACAGTAAGTTTATCATCTGTGGGCAGGTGGGCTAT |
| AGTGTGGGTGGTGGTCTTTGGGGGGTTTTTAATATATGTCAGGGGTTATGCTGAAGACTTTTTTATTGTGATTTTT |
| AAAGGTCCAGTGTCTGAGCCCGAGCAAGAACCTGAACCGGAGCCTGAGCCTTCTCGCCCCAGGAGAAAGCCTGTAAT |
| CTTAACTAGACCCAGCGCACCGGTAGCGAGAGGCCTCAGCAGCGCGGAGACCACCGACTCCGGTGCTTCCTCATCAC |
| CCCCGGAGATTCACCCCCTGGTGCCCCTGTGTCCCGTTAAGCCCGTTGCCGTGAGAGTCAGTGGGCGGCGGTCTGCT |
| GTGGAGTGCATTGAGGACTTGCTTTTTGATTCACAGGAACCTTTGGACTTGAGCTTGAAACGCCCCAGGCATTAAAC |
| CTGGTCACCTGGACTGAATGAGTTGACGCCTATGTTTGCTTTTGAATGACTTAATGTGTATAGATAATAAAGAGTGA |
| GATAATGTTTTAATTGCATGGTGTGTTTAACTTGGGCGGAGTCTGCTGGGTATATAAGCTTCCCTGGGCTAAACTTG |
| GTTACACTTGACCTCATGGAGGCCTGGGAGTGTTTGGAGAACTTTGCCGGAGTTCGTGCCTTGCTGGACGAGAGCTC |
| TAACAATACCTCTTGGTGGTGAGGTATTTGTGGGGCTCTCCCCAGGGCAAGTTAGTTTGTAGAATCAAGGAGGATT |
| ACAAGTGGGAATTTGAAGAGCTTTTGAAATCCTGTGGTGAGCTATTGGATTCTTTGAATCTAGGCCACCAGGCTCTC |
| TTCCAGGAGAAGGTCATCAGGACTTTGGATTTTTCCACACCGGGGCGCATTGCAGCCGCGGTTGCTTTTCTAGCTTT |
| TTTGAAGGATAGATGGAGCGAAGAGACCCACTTGAGTTCGGGCTACGTCCTGGATTTTCTGGCCATGCAACTGTGGA |
| GAGCATGGATCAGACACAAGAACAGGCTGCAACTGTTGTCTTCCGTCCGCCCGTTGCTGATTCCGGCGGAGGAGCAA |
| CAGGCCGGGTCAGAGGACCGGGCCCGTCGGGATCCGGAGGAGAGGGCACCGAGGCCGGGCGAGAGGAGCGCGCTGAA |
| CCTGGGAACCGGGCTGAGCGGCCATCCACATCGGGAGTGAATGTCGGGCAGGTGGTGGATCTTTTTCCAGAACTGCG |
| GCGGATTTTGACTATTAGGGAGGATGGGCAATTTGTTAAGGGTCTTAAGAGGGAGAGGGGGGCTTCTGAGCATAACG |
| AGGAGGCCAGTAATTTAGCTTTTAGCTTGATGACCAGACACCGTCCAGAGTGCATCACTTTTCAGCAGATTAAGGAC |
| AATTGTGCCAATGAGTTGGATCTGTTGGGTCAGAAGTATAGCATAGAGCAGCTGACCACTTACTGGCTGCAGCCGGG |
| TGATGATCTGGAGGAAGCTATTAGGGTGTATGCTAAGGTGGCCCTGCGGCCCGATTGCAAGTACAAGCTCAAGGGGC |
| TGGTGAATATCAGGAATTGTTGCTACATTTCTGGCAACGGGGCGGAGGTGGAGATAGAGACCGAAGACAGGGTGGCT |
| TTCAGATGCAGCATGATGAATATGTGGCCGGGGGTGCTGGGCATGGCGGGGTGGTGATTATGAATGTGAGGTTCAC |
| GGGGCCCAACTTTAACGGCACGGTGTTTTTGGGGAACACCAACCTGGTCCTGCACGGGGTGAGCTTCTATGGGTTTA |
| ACAACACCTGTGTGGAGGCCTGGACCGATGTGAAGGTCCGCGGTTGCGCCTTTTATGGATGTTGGAAGGCCATAGTG |
| AGCCGCCCTAAGAGCAGGAGTTCCATTAAGAAATGCTTGTTTGAGAGGTGCACCTTGGGGATCCTGGCCGAGGGCAA |
| CTGCAGGGTGCGCCACAATGTGGCCTCCGAGTGCGGTTGCTTCATGCTAGTCAAGAGCGTGGCGGTAATCAAGCATA |
| ATATGGTGTGCGGCAACAGCGAGGACAAGGCCTCACAGATGCTGACCTGCACGGATGGCAACTGCCACTTGCTGAAG |
| ACCATCCATGTAACCAGCCACAGCCGGAAGGCCTGGCCCGTGTTCGAGCACAACTTGCTGACCCGCTGCTCCTTGCA |
| TCTGGGCAACAGGCGGGGGGTGTTCCTGCCCTATCAATGCAACTTTAGTCACACCAAGATCTTGCTAGAGCCCGAGA |
| GCATGTCCAAGGTGAACTTGAACGGGGTGTTTGACATGACCATGAAGATCTGGAAGGTGCTGAGGTACGACGAGACC |
| AGGTCCCGGTGCAGACCCTGCGAGTGCGGGGGCAAGCATATGAGGAACCAGCCCGTGATGCTGGATGTGACCGAGGA |
| GCTGAGGACAGACCACTTGGTTCTGGCCTGCACCAGGGCCGAGTTTGGTTCTAGCGATGAAGACACAGATTGAGGTG |
| GGTGAGTGGGCGTGGCCTGGGGTGGTCATGAAAATATATAAGTTGGGGGTCTTAGGGTCTCTTTATTTGTGTTGCAG |
| AGACCGCCGGAGCCATGAGCGGGAGCAGCAGCAGCAGCAGCAGTAGCAGCAGCGCCTTGGATGGCAGCATCGTGAGCCT |
| TATTTGACGACGCGGATGCCCCACTGGGCCGGGGTGCGTCAGAATGTGATGGGCTCCAGCATCGACGGCCGACCCGT |
| CCTGCCCGCAAATTCCGCCACGCTGACCTATGCGACCGTCGCGGGGACGCCGTTGGACGCCACCGCCGCCGCCGCCG |
| CCACCGCAGCCGCCTCGGCCGTGCGCAGCCTGGCCACGGACTTTGCATTCCTGGGACCACTGGCGACAGGGGCTACT |
| TCTCGGGCCGCTGCTGCCGCCGTTCGCGATGACAAGCTGACCGCCCTGCTGGCGCAGTTGGATGCGCTTACTCGGGA |
| ACTGGGTGACCTTTCTCAGCAGGTCATGGCCCTGCGCCAGCAGGTCTCCTCCCTGCAAGCTGGCGGGAATGCTTCTC |
| CCACAAATGCCGTTTAAGATAAATAAAACCAGACTCTGTTTGGATTAAAGAAAAGTAGCAAGTGCATTGCTCTCTTT |
| ATTTCATAATTTTCCGCGCGCGATAGGCCCTAGACCAGCGTTCTCGGTCGTTGAGGGTGCGGTGTATCTTCTCCAGG |
| ACGTGGTAGAGGTGGCTCTGGACGTTGAGATACATGGCATGAGTCCCGGGGAGGTGGAGGTAGCACCACTGCAG |
| AGCTTCATGCTCCGGGGTGGTGTTGTAGATGATCCAGTCGTAGCAGGAGCGCTGGGCATGGTGCCTAAAAATGTCCT |
| TCAGCAGCAGGCCGATGGCCAGGGGGAGGCCCTTGGTGTAAGTGTTTACAAAACGGTTAAGTTGGGAAGGGTGCATT |
| CGGGGAGAGATGATGTGCATCTTGGACTGTATTTTTAGATTGGCGATGTTTCCGCCCAGATCCCTTCTGGGATTCAT |
| GTTGTGCAGGACCACCAGTACAGTGTATCCGGTGCACTTGGGGAATTTGTCATGCAGTTAGAGGGAAAAGCGTGGA |
| AGAACTTGGAGACGCCCTTGTGGCCTCCCAGATTTTCCATGCATTCGTCCATGATGATGGCAATGGGCCCGCGGGGA |
| GCAGCTTGGGCAAAGATATTTCTGGGTCGCTGACGTCGTAGTTGTGTTCCAGGGTGAGGTCGTCATAGGCCATTTT |
| TACAAAGCGCGGGCGGAGGGTGCCCGACTGGGGGATGATGGTCCCCTCTGGCCCTGGGGCGTAGTTGCCCTCGCAGA |
| TCTGCATTTCCCAGGCCTTAATCTCGAGGGGGGAATCATATCACTCCCGGTCGACGATGAAGAAAACGGTTTCCGGA |
| GCCGGGAGATTAACTGGGATGAGAGCAGGTTTCTAAGCAGCTGTGATTTTCCACAACCGGTGGGCCCATAAATAAC |
| ACCTATAACCGGTTGCAGCTGGTAGTTTAGAGAGCTGCAGCTGCCGTCGTCCCGAGGAGGGGGGCCACCTCGTTGA |
| GCATGTCCCTGACGCGCATGTTCTCCCCGACCAGATCCGCCAGAAGGCGCTCGCCGCCCAGGACAGCAGCTCTTGC |
| AAGGAAGCAAAGTTTTTCAGCGGCTTGAGGCCGTCCGCCGTGGGCATGTTTTCAGGGTCTGGCTCAGCAGCTCCAG |
| GCGGTCCCAGAGCTCGGTGACGTGCTCTACGGCATCTCTATCCAGCATATCTCCTCGTTTCGCGGGTTGGGGCGACT |
| TTCGCTGTAGGGCACCAAGCGGTGGTCGTCCAGCGGGGCCAGATCATGTCCTTCCATGGGCAGGGTCCTCGTCA |
| GGGTGGTCTGGGTCACGGTGAAGGGGTGCGCTCCGGGCTGAGCGCTTGCCAAGGTGCGCTTGAGGCTGGTTCTGCTG |
| GTGCTGAAGCGCTGCCGGTCTTCGCCCTGCGCGTCGGCCAGGTAGCATTTGACCATGGTGTCATAGTCCAGCCCCTC |
| CGCGGCGTGTCCCTTGGCGCGCAGCTTGCCCTTGGAGGTGGCGCCGCACGAGGGGCAGAGCAGGCTCTTGAGCGCGT |
| AGAGCTTGGGGCGAGGAAGACCGATTCGGGGAGGTAGGCGTCCGCGCCAGACCCCACAGCCTCTCGCACTCC |
| ACCAGCCAGGTGAGCTCGGGCGCGCGGGTCAAAAACCAGGTTTCCCCATGCTTTTTGATGCGTTTCTTACCTCG |
| GGTCTCCATGAGGTGGTGTCCCCGCTCGGTGACGAAGAGGCTGTCCGTGTCTCCGTAGACCGACTTGAGGGGTCTTT |
| TCTCCAGGGGGGTCCCTCGGTCTTCCTCGTAGAGGAACTCGGACCACTCTGAGACGAAGGCCCGCGTCCAGGCAGG |
| ACGAAGGAGGCTATGTGGGAGGGGTAGCGGTCGTTGTCCACTAGGGGTCCACCTTCTCCAAGGTGTGAAGACACAT |
| GTCGCCTTCCTCGGCGTCCAGGAAGGTGATTGGCTTGTAGGTGTAGGCCACGTGACCGGGGTTCCTGACGGGGGG |
| TATAAAAGGGGGTGGGGCGCGCTCGTCGTCACTCTCTTCCGCATCGCTGTCTGCGAGGGCCAGCTGCTGGGGTGAG |

| DESCRIPTION OF THE SEQUENCES |
|---|
| TATTCCCTCTCGAAGGCGGGCATGACCTCCGCGCTGAGGTTGTCAGTTTCCAAAAACGAGGAGGATTTGATGTTCAC |
| CTGTCCCGAGGTGATACCTTTGAGGGTACCCGCGTCCATCGGTCAGAAAACACGATCTTTTTATTGTCCAGCTTGG |
| TGGCGAACGACCCGTAGAGGGCGTTGGAGAGCAGCTTGGCGATGGAGCGCAGGGTCTGGTTCTTGTCCCTGTCGGCG |
| CGCTCCTTGGCCGCGATGTTGAGCTGCACGTACTCGCGCGCGACGCAGCGCCACTCGGGGAAGACGGTGGTGCGCTC |
| GTCGGGCACCAGGCGCACGCGCCAGCCGCGGTTGTGCAGGGTGACCAGGTCCACGCTGGTGGCGACCTCGCCGCGCA |
| GGCGCTCGTTGGTCCAGCAGAGACGGCCGCCCTTGCGCGAGCAGAAGGGGGGCAGGGGGTCGAGCTGGGTCTCGTCC |
| GGGGGGTCCGCGTCCACGGTGAAAACCCCGGGGCGCAGGCGCGCGTCGAAGTAGTCTATCTTGCAACCTTGCATGTC |
| CAGCGCCTGCTGCCAGTCGCGGGCGGCGAGCGCGCGCTCGTAGGGGTTGAGCGGCGGGCCCCAGGGCATGGGGTGGG |
| TGAGTGCGGAGGCGTACATGCCGCAGATGTCATAGACGTAGAGGGGCTCCCGCAGGACCCCGATGTAGGTGGGGTAG |
| CAGCGGCCGCCGCGGATGCTGGCGCGCACGTAGTCATACAGCTCGTGCGAGGGGGCGAGGAGGTCGGGGCCCAGGTT |
| GGTGCGGGCGGGGCGCTCCGCGCGGAAGACGATCTGCCTGAAGATGGCATGCGAGTTGGAAGAGATGGTGGGGCGCT |
| GGAAGACGTTGAAGCTGGCGTCCTGCAGGCCGACGGCGTCGCGCACGAAGGAGGCGTAGGAGTCGCGCAGCTTGTGT |
| ACCAGCTCGGCGGTGACCTGCACGTCGAGCGCGCAGTAGTCGAGGGTCTCGCGGATGATGTCATATTTAGCCTGCCC |
| CTTCTTTTTCCACAGCTCGCGGTTGAGGACAAACTCTTCGCGGTCTTTCCAGTACTCTTGGATCGGGAAACCGTCCG |
| GTTCCGAACGGTAAGAGCCTAGCATGTAGAACTGGTTGACGGCCTGGTAGGCGCAGCAGCCCTTCTCCACGGGGAGG |
| GCGTAGGCCTGCGCGGCCTTGCGGAGCGAGGTGTGGGTCAGGGCGAAGGTGTCCCTGACCATGACTTTGAGGTACTG |
| GTGCTTGAAGTCGGAGTCGTCGCAGCCGCCCCGCTCCCAGAGCGAGAAGTCGGTGCGCTTCTTGGAGCGGGGGTTGG |
| GCAGAGCGAAGGTGACATCGTTGAAGAGGATTTTGCCCGCGCGGGGCATGAAGTTGCGGGTGATGCGGAAGGGCCCC |
| GGCACTTCAGAGCGGTTGTTGATGACCTGGGCGGCGAGCACGATCTCGTCGAAGCCGTTGATGTTGTGGCCCACGAT |
| GTAGAGTTCCAGGAAGCGGGGCCGGCCCTTTACGGTGGGCAGCTTCTTTAGCTCTTCGTAGGTGAGCTCCTCGGGCG |
| AGGCGAGGCCGTGCTCGGCCAGGGCCCAGTCCGCGAGGTGCGGGTTGTCTCTGAGGAAGGACTTCCAGAGGTCGCGG |
| GCCAGGAGGGTCTGCAGGCGGTCTCTGAAGGTCCTGAACTGGCGGCCCACGGCCATTTTTTCGGGGGTGATGCAGTA |
| GAAGGTGAGGGGGTCTTGCTGCCAGCGGTCCCAGTCGAGCTGCAGGGCGAGGTCGCGCGCGGCGGTGACCAGGCGCT |
| CGTCGCCCCCGAATTTCATGACCAGCATGAAGGGCACGAGCTGCTTTCCGAAGGCCCCCATCCAAGTGTAGGTCTCT |
| ACATCGTAGGTGACAAAGAGGCGCTCCGTGCGAGGATGCGAGCCGATCGGGAAGAACTGGATCTCCCGCCACCAGTT |
| GGAGGAGTGGCTGTTGATGTGGTGGAAGTAGAAGTCCCGTCGCCGGGCCGAACACTCGTGCTGGCTTTTGTAAAAGC |
| GAGCGCAGTACTGGCAGCGCTGCACGGGCTGTACCTCATGCACGAGATGCACCTTTCGCCCGCGCACGAGGAAGCCG |
| AGGGGAAATCTGAGCCCCCCGCCTGGCTCGCGGCATGGCTGGTTCTCTTCTACTTTGGATGCGTGTCCGTCTCCGTC |
| TGGCTCCTCGAGGGGTGTTACGGTGGAGCGGACCACCACGCCGCGCGAGCCGCAGGTCCAGATATCGGCGCGCGGCG |
| GTCGGAGTTTGATGACGACATCGCGCAGCTGGGAGCTGTCCATGGTCTGGAGCTCCCGCGGCGGCGGCAGGTCAGCC |
| GGGAGTTCTTGCAGGTTCACCTCGCAGAGTCGGGCCAGGGCGCGGGGCAGGTCTAGGTGGTACCTGATCTCTAGGGG |
| CGTGTTGGTGGCGGCGTCGATGGCTTGCAGGAGCCCGCAGCCCCGGGGCGGCGACGACGGTGCCCCGCGGGGGTGGTGG |
| TGGTGGTGGCGGTGCAGCTCAGAAGCGGTGCCGCGGGCGGGCCCCCGGAGGTAGGGGGGGCTCCGGTCCCGCGGGCA |
| GGGGCGGCAGCGGCACGTCGGCGTGGAGCGCGGGCAGGAGTTGGTGCTGTGCCCGGAGGTTGCTGGCGAAGGCGACG |
| ACGCGGCGGTTGATCTCCTGGATCTGGCGCCTCTGCGTGAAGACGACGGGCCCGGTGAGCTTGAACCTGAAAGAGAG |
| TTCGACAGAATCAATCTCGGTGTCATTGACCGCGGCCTGGCGCAGGATCTCCTGCACGTCTCCCGAGTTGTCTTGGT |
| AGGCGATCTCGGCCATGAACTGCTCGATCTCTTCCTCCTGGAGGTCTCCGCGTCCGGCGCGTTCCACGGTGGCCGCC |
| AGGTCGTTGGAGATGCGCCCCATGAGCTGCGAGAAGGCGTTGAGTCCGCCCTCGTTCCAGACTCGGCTGTAGACCAC |
| GCCCCCCTGGTCATCGCGGGCGCGCATGACCACCTGCGCGAGGTTGAGCTCCACGTGCCGCGCGAAGACGGCGTAGT |
| TGCGCAGACGCTGGAAGAGGTAGTTGAGGGTGGTGGCGGTGTGCTCGGCCACGAAGAAGTTCATGACCCAGCGGCGC |
| AACGTGGATTCGTTGATGTCCCCCAAGGCCTCCAGCCGTTCCATGGCCTCGTAGAAGTCCACGGCGAAGTTGAAAAA |
| CTGGGAGTTGCGCGCCGACACGGTCAACTCCTCCTCCAGAAGACGGATGAGCTCGGCGACGGTGTCGCGCACCTCGC |
| GCTCGAAGGCTATGGGGATCTCTTCCTCCGCTAGCATCACCACCTCCTCCTCTTCCTCCTCTTCTGGCACTTCCATG |
| ATGGCTTCCTCCTCTTCGGGGGGTGGCGGCGGCGGCGGTGGGGGAGGGGGCGCTCTGCGCCGGCGGCGGCGCACCGG |
| GAGGCGGTCCACGAAGCGCGCGATCATCTCCCCGCGGCGGCGGCCATGGTCTCGGTGACGGCGCGGCCGTTCTCCC |
| GGGGGCGCAGTTGGAAGACGCCGCCGGACATCTGGTGCTGGGGCGGGTGGCCGTGAGGCAGCGAGACGGCGCTGACG |
| ATGCATCTCAACAATTGCTGCGTAGGTACGCCGCCGAGGGACCTGAGGGAGTCCATATCCACCGGATCCGAAAACCT |
| TTCGAGGAAGGCGTCTAACCAGTCGCAGTCGCAAGGTAGGCTGAGCACCGTGGCGGGCGGCGGGGGGTGGGGGGAGT |
| GTCTGGCGGAGGTGCTGCTGATGATGTAATTGAAGTAGGCGGACTTGACACGGCGGATGCTGACAGGAGCACCATG |
| TCCTTGGGTCCGGCCTGCTGGATGCGGAGGCGGTCGGCTATGCCCCAGGCTTCGTTCTGGCATCGGCGCAGGTCCTT |
| GTAGTAGTCTTGCATGAGCCTTTCCACCGGCACCTCTTCTCCTTCCTCTTCTGCTTCTTCCATGTCTGCTTCGGCCC |
| TGGGGCGGCGCCGCGCCCCCTGCCCCCATGCGCGTGACCCCGAACCCCCTGAGCGGTTGGAGCAGGGCCAGGTCG |
| GCGACGACGCGCTTCGGCCAGGATGGCCTGCTGCACCTGCGTGAGGGTGGTTGGAAGTCATCCAAGTCCACGAAGCG |
| GTGGTAGGCGCCCGTGTTGATGGTGTAGGTGCAGTTGGCCATGACGGACCAGTTGACGGTCTGGTGGCCCGGTTGCG |
| ACATCTCGGTGTACCTGAGTCGCGAGTAGGCGCGGGAGTCGAAGACGTAGTCGTTGCAAGTCCGCACCAGGTACTGG |
| TAGCCCACCAGGAAGTGCGGCGGCGGCTGGCGGTAGAGGGGCCAGCGCAGGGTGGCGGGGGCTCCGGGGGCCAGGTC |
| TTCCAGCATGAGGCGGTGGTAGGCGTAGATGTACCTGGACATCCAGGTGATACCCGCGGCCGGCGGTGGTGGAGGCGCGCG |
| GGAAGTCGCGCACCCGGTTCCAGATGTTGCGCAGGGGCAGAAAGTGCTCCATGGTAGGCGTGCTCTGTCCAGTCAGA |
| CGCGCGCAGTCGTTGATACTCTAGACCAGGGAAAACGAAAGCCGGTCAGCGGGCACTCTTCCGTGGTCTGGTGAATA |
| GATCGCAAGGGTATCATGGCGGAGGGCCTCGGTTCGAGCCCGGGTCCGGGCCGGACGGTCCGCCATGATCCACGCG |
| GTTACCGCCCGCGTGTCGAACCCAGGTGTGCGACGTCAGACAACGGTGGAGTGTTCCTTTTGGCGTTTTTCTGGCCG |
| GGCGCCGGCCGCGTAAGAGACTAAGCCGCGAAAGCGAAAGCAGTAAGTGGCTCGCTCCCCGTAGCCGGAGGGATC |
| CTTGCTAAGGGTTGCGTTGCGGCGAACCCCGGTTCGAATCCCGTACTCGGGCCGGCCGGACCCGCGGCTAAGGTGTT |
| GGATTGGCCTCCCCCTCGTATAAAGACCCCGCTTGCGGATTGACTCCGGACACGGGACGAGCCCCTTTTATTTTTG |
| CTTTCCCCAGATGCATCCGGTGCTGCGGCAGATGCGCCCCCCGCCCCAGCAGCAGCAACAACACCAGCAAGAGCGGC |
| AGCAACAGCAGCGGGAGTCATGCAGGGCCCCCTCACCCACCCTCGGCGGGCCACCTCGGCGTCCGCGGCCGTG |
| TCTGGCGCCTGCGGCGGCGGCGGGGGGCCGGCTGACGACCCCGAGGAGCCCCCGCGGCGCAGGGCCAGACACTACCT |
| GGACCTGGAGGAGGGCGAGGGCCTGGCGCGGCTGGGGGCGCCGTCTCCCGAGCGCCACCCGCGGGTGCAGCTGAAGC |
| GCGACTCGCGCGAGGCGTACGTGCCTCGGCAGAACCTGTTCAGGGACCGCGCGGGCGAGGAGCCCGAGGAGATGCGG |
| GACAGGAGGTTCAGCGCAGGGCGGGAGCTGCGGCAGGGGCTGAACCGCGAGCGGCTGCTGCGCGAGGAGGACTTTGA |
| GCCCGACGCGCGGACGGGATCAGCCCCGCGCGCGCACGTGGCGCGCGACCTGGTGACGGCGTACGAGCAGA |
| CGGTGAACCAGGAGATCAACTTCCAAAAGAGTTTCAACAACCACGTGCGCACGCTGGTGGCGCGCGAGGAGGTGACC |
| ATCGGGCTGATGCACCTGTGGGACTTTGTAAGCGCGCTGGTGCAGAACCCCAACAGCAAGCCTCTGACGGCGCAGCT |
| GTTCCTGATAGTGCAGCACAGCAGGGACAACGAGGCGTTTAGGGACGCGCTGCTGAACATCACCGAGCCCGAGGGTC |
| GGTGGCTGCTGGACCCTGATTAACATCCTGCAGAGCATAGTGGTGCAGGAGCGCAGCCTGAGCCTGGCCGACAAGGTG |
| GCGGCCATCAACTACTCGATGCTGAGCCTGGGCAAGTTTTACGCGCGCAAGATCTACCAGACGCGTACGTGCCCAT |
| AGACAAGGAGGGTGAAGATCGACGGTTTTTACATGCGCATGGCGCTGAAGGTGCTCACCCTGAGCGACGACCTGGGCG |

| DESCRIPTION OF THE SEQUENCES |
|---|
| TGTACCGCAACGAGCGCATCCACAAGGCCGTGAGCGTGAGCCGGCGGCGCGAGCTGAGCGACCGCGAGCTGATGCAC |
| AGCCTGCAGCGGGCGCTGGCGGGCGCCGGCAGCGGCGACAGGGAGGCGGAGTCCTACTTCGATGCGGGGCGGACCT |
| GCGCTGGGCGCCCAGCCGGCGGGCCCTGGAGGCCGCGGGGGTCCGCGAGGACTATGACGAGGACGGCGAGGAGGATG |
| AGGAGTACGAGCTAGAGGAGGGCGAGTACCTGGACTAAACCGCGGGTGGTGTTTCCGGTAGATGCAAGACCCGAACG |
| TGGTGGACCCGGCGCTGCGGGCGGCTCTGCAGAGCCAGCCGTCCGGCCTTAACTCCTCAGACGACTGGCGACAGGTC |
| ATGGACCGCATCATGTCGCTGACGGCGCGTAACCCGGACGCGTTCCGGCAGCAGCCGCAGGCCAACAGGCTCTCCGC |
| CATCCTGGAGGCGGTGGTGCCTGCGCGCTCGAACCCCACGCACGAGAAGGTGCTGGCCATAGTGAACGCGCTGGCCG |
| AGAACAGGGCCATCCGCCCGGACGAGGCCGGGCTGGTGTACGACGCGCTGCTGCAGCGCGTGGCCCGCTACAACAGC |
| GGCAACGTGCAGACCAACCTGGACCGGCTGGTGGGGGACGTGCGCGAGGCGGTGGCGCAGCGCGAGCGCGCGGATCG |
| GCAGGGCAACCTGGCTCCATGGTGGCGCTGAATGCCTTCCTGAGCACGCAGCCGGCCAACGTGCCGCGGGGGCAGG |
| AAGACTACACCAACTTTGTGAGCGCGCTGCGGCTGATGGTGACCGAGACCCCCAGAGCGAGGTGTACCAGTCGGGC |
| CCGGACTACTTCTTCCAGACCAGCAGACAGGGCCTGCAGACGGTGAACCTGAGCCAGGCTTTCAAGAACCTGCGGG |
| GCTGTGGGGCGTGAAGGCGCCCACCGGCGACCGGGCGACGGTGTCCAGCCTGCTGACGCCCAACTCGCGCCTGCTGC |
| TGCTGCTGATCGCGCCGTTCACGGACAGCGGCAGCGTGTCCCGGGACACCTACCTGGGGCACCTGCTGACCCTGTAC |
| CGCGAGGCCATCGGGCAGGCGCAGGTGGACGAGCACACCTTCCAGGAGATCACCAGCGTGAGCCGCGCGCTGGGGCA |
| GGAGGACACGAGCAGCCTGGAGGCGACTCTGAACTACCTGCTGACCAACCGGCGGCAGAAGATTCCCTCGCTGCACA |
| GCCTGACCTCCGAGGAGGAGCGCATCTTGCGCTACGTGCAGCAGAGCGTGAGCCTGAACCTGATGCGCGACGGGGTG |
| ACGCCCAGCGTGGCGCTGGACATGACCGCGCGCAACATGGAACCGGGCATGTACGCCGCGCACCGGCCTTACATCAA |
| CCGCCTGATGGACTACCTGCATCGCGCGGCGGCCGTGAACCCCGAGTACTTTACCAACGCCATCCTGAACCCGCACT |
| GGCTCCCGCCGCCCGGGTTCTACAGCGGGGGCTTCGAGGTCCCGGAGCAACGATGGCTTCCTGTGGGACGACATG |
| GACGACAGCGTGTTCTCCCCGCGGCCGCAGGCGCTGGCGGAAGCGTCCCTGCTGCGTCCCAAGAAGGAGGAGGAGGA |
| GGAGGCGAGTCGCCGCCGCGGCAGCAGCGGCGTGGCCTTCTCTGTCCGAGCTGGGGGCGGCAGCCGCCGCGCGCCCCG |
| GGTCCCTGGGCGGCAGCCCCTTTCCGAGCCTGGTGGGGTCTCTGCACAGCGAGCGCACCACCCGCCCTCGGCTGCTG |
| GGCGAGGACGAGTACCTGAATAACTCCCTGCTGCAGCCGGTGCGGGACGAGGAAAAACCTGCCTCCCGCCTTCCCAACAA |
| CGGGATAGAGAGCCTGGTGGACAAGATGAGCAGATGGAAGACCTATGCGCAGGAGCACAGGGACGCGCCTGCGCTCC |
| GGCCGCCCACGCGGCGCCAGCGCCACGACCGGCAGCGGGGGCTGGTGTGGGATGACGAGGACTCCGCGGACGATAGC |
| AGCGTGCTGGACCTGGGAGGGAGCGGCAACCCGTTCGCGCACCTGCGCCCCGCCTGGGGAGGATGTTTTAAAAAAA |
| AAAAAAAAAAGCAAGAAGCATGATGCAAAATTAAATAAAACTCACCAAGGCCATGGCGACCGAGCGTTGGTTTCTT |
| GTGTTCCCTTCAGTATGCGGCGCGCGGCGATGTACCAGGAGGGACCTCCTCCCTCTTACGAGAGCGTGGTGGGCGCG |
| GCGGCGGCGGCGCCCTCTTCTCCCTTTGCGTCGCAGCTGCTGGAGCCGCCGTACGTGCCTCCGCGCTACCTGCGGCC |
| TACGGGGGGGAGAAACAGCATCCGTTACTCGGAGCTGGCGCCCCTGTTCGACACCACCCGGGTGTACCTGGTGGACA |
| ACAAGTCGGCGGACGTGGCCTCCCTGAACTACCAGAACGACCACCAGCAATTTTTTGACCACGGTCATCCAGAACAAT |
| GACTACAGCCCGAGCGAGGCCAGCACCCAGACCATCAATCTGGATGACCGGTCGCACTGGGGCGGCGACCTGAAAAC |
| CATCCTGCACACCAACATGCCCAACGTGAACGAGTTCATGTTCACCAATAAGTTCAAGGCGCGGGTGATGGTGTCGC |
| GCTCGCACACCAAGGAAGACCGGGTGGAGCTGAAGTACGAGTGGGTGGAGTTCGAGCTGCCAGAGGGCAACTACTCC |
| GAGACCATGACCATTGACCTGATGAACAACGCGATCGTGGAGCACTATCTGAAAGTGGGCAGGCAGAACGGGGTCCT |
| GGAGAGCGACATCGGGGTCAAGTTCGACACCAGGAACTTCCGCCTGGGGCTGGACCCCGTGACCGGGCTGGTTATGC |
| CCGGGGTGTACACCAACGAGGCCTTCCATCCCGACATCATCCTGCTGCCCGGCTGCGGGGTGGACTTCACTTACAGC |
| CGCCTGAGCAACCTCCTGGGCATCCGCAAGCGGCAGCCCTTCCAGGAGGGCTTCAGGATCACCTACGAGGACCTGGA |
| GGGGGGCAACATCCCCGCGCTCCTCGATGTGGAGGCCTACCAGGATAGCTTGAAGGAAAATGAGGCGGGACAGGAGG |
| ATACGCCCCCGCCGCCTCCGCCGCCGCCGAGCAGGGCGAGGATGCTGCTGACACCGCGGCGACCGGAGCGGGGCAGAG |
| GCCGACCCCGCTATGGTGGTGGAGGCTCCCGAGCAGGAGGAGGACATGAATGACAGTGCGGTGCGCGGAGACACCTT |
| CGTCACCCGGGGGAGGAAAAGCAAGCGGAGGCCGAGGCCGCGGCCGAGGAAAAGCAACTGGCGGCAGCAGCGGCGG |
| CGGCGGCGTTGGCCGCGGCGGAGGCTGAGTCTGAGGGGACCAAGCCCGCCAAGGAGCCCGTGATTAAGCCCCTGACC |
| GAAGATAGCAAGAAGCGCAGTTACAACCTGCTCAAGGACAGCACCAACAACGCGTACCGCAGCTGGTACCTGGCCTA |
| CAACTACGGCGACCCGTCGACGGGGGTGCGCTCCTGGACCCTGCTGTGCACGCCGGACGTGACCTGCGGCTCGGAGC |
| AGGTGTACTGGTCGCTGCCCGACATGATGCAAGACCCCGTGACCTTCCGCTCCACGCGGCAGGTCAGCAACTTCCCG |
| GTGGTGGGCGCCGAGCTGCTGCCCGTGCACTCCAAGAGCTTCTACAACGACCAGGCCGTCTACTCCCAGCTCATCCG |
| CCAGTTCACCTCTCTGACCCACGTGTTCAATCGCTTTCCTGAGAACCAGATTCTGGCGCGACCGGAGCGTTCGCCCCCACCA |
| TCACCACCGTCAGTGAAAACGTTCCTGCTCTCACAGATCACGGGACGCTACCGCTGCGCAACAGCATCGGAGGAGTC |
| CAGCGAGTGACCGTTACTGACGCCAGACGCCGCACCTGCCCCTACGTTTACAAGGCCTTGGGCATAGTCTCGCCGCG |
| CGTCCTTTCCAGCCGCACTTTTTGAGCAACACCACCATCATGTCCATCCTGATCTCACCCAGCAATAACTCCGGCTG |
| GGGACTGCTGCGCGCGCCCAGCAAGATGTTCGGAGGGGCGAGGAAGCGTTCCGAGCAGCACCCCGTGCGCGTGCGCG |
| GCACTTCCGCGCCCCTGGGGAGCGCACAAACGCGGCCGCGCGGGGCGCACCACCGTGGACGACGCCATCGACTCG |
| GTGGTGGAGCAGGCGCGCAACTACAGGCCCGCGGTCTCTACCGTGGACGCGGCCATCCAGACCGTGGTGCGGGGCGC |
| GCGGCGGTACGCCAAGCTGAAGAGCCGCCGGAAGCGCGTGGCCCGCCGCCACCGCCGCCGACCCGGGGCCGCCGCCA |
| AACGCGCCGCCGCGGCCCTGCTTCGCCGGGCCAAGCGCACGGGCCGCCGCCATGAGGGCCGCGCCGCGCCGCCGCTTG |
| GCCGCCGGCATCACCGCCGCCACCATGGCCCCCCGTACCCGAAGACGCGCGGCCGCCGCCGCCGCCGCCGCCATCAG |
| TGACATGGCCAGCAGGCGCCGGGCAACGTGTACTGGGTGCGCGACTCGGTGACCGGCACGCGCGTGCCCGTGCGCT |
| TCCGCCCCCCGCGGACTTGAGATGATGTGAAAAAACAACACTGAGTCTCCTGCTGTTGTGTGTATCCCAGCGGCGGC |
| GGCGCGCGCAGCGTCATGTCCAAGCGCAAAATCAAAGAAGAGATGCTCCAGGTCGTCGCGGAGATCTATGGGCC |
| CCCGAAGAAGGAAGAGCAGGATTCGAAGCCCCGCAAGATAAAGCGGGTCAAAAAGAAAAAGAAAGATGATGACGATG |
| CCGATGGGGAGGTGGAGTTCCTGCGCGCCACGGCGCCCAGGCGCCGGTGCAGTGGAAGGGCCGGCGCGTAAAGCGC |
| GTCCTGCGCCCCGGCACCGCGGTGGTCTTCACGCCCGGCGAGCGCTCCACCCGGACTTTCAAGCGCGTCTATGACGA |
| GGTGTACGGCGACGAAGACCTGCTGGAGCAGGCCAACGAGCGCTTCGGAGAGTTTGCTTACGGGAAGCGTCAGCGGG |
| CGCTGGGGAAGGAGGACCTGCTGGCGCTGCCGCTGGACCAGGGCAACCCCACCCCCAGTCTGAAGCCCGTGACCCTG |
| CAGCAGGTGCTGCCGAGCAGCGCACCCTCCGAGGCGAAGCGGGGTCTGAAGCGCGAGGGCGGCGACCTGGCGCCCAC |
| CGTGCAGCTCATGGTGCCCAAGCGGCAGAGGCTGGAGGATGTGCTGGAGAAAATGAAAGTAGACCCCGGTCTGCAGC |
| CGGACATCAGGGTCCGCCCCATCAAGCAGGTGGCGCGGGCCTCGGCGTGCAGACCGTGGACGTGGTCATCCCCACC |
| GGCAACTCCCCGCCGCCGCCACCACTACCGCTGCCTCCACGGACATGGAGACACAGACCGATCCCGCCGCAGCCGC |
| AGCCGCAGCCGCCGCGCGACCTCCTCGGCGGAGGTGCAGACGGACCCTGGCTGCGCCGGCGATGTCAGCTCCCC |
| GCGCGCGTCGCGGCGCAGGAAGTACGCGCCGCCAACGCGCTCCTGCCCGAGTACCCCTTGCATCCTTCCATCGCG |
| CCCACCCCGGCTACCGAGGCTATACCTACCGCCCGCGAAGAGCCAAGGGTTCCACCCGCCGTCCCCGCCGACGCGC |
| CGCCGCCACCACCCGCCGCCGCCGCCGCAGACGCCAGCCCGCACTGGCTCCAGTCTCCGTGAGGAAAGTGGCGCGCG |
| ACGGACACACCCTGGTGCTGCCCAGGGCGCGCTACCACCCCAGCATCGTTTAAAAGCCTGTTGTGGTTCTTGCAGAT |
| ATGGCCCTCACTTGCCGCCTCCGTTTCCCGGTGCCGGGATACCGAGGAGGAAGATCGCGCCGCAGGAGGGGTCTGGC |
| CGGCCGCGGCCTGAGCGGAGGCAGCCGCCGCGCGCACCGGCGGCGACGCGCCACCAGCCGACGCATGCGCGGCGGGG |

| DESCRIPTION OF THE SEQUENCES |
|---|
| TGCTGCCCCTGTTAATCCCCCTGATCGCCGCGGCGATCGGCGCCGTGCCCGGGATCGCCTCCGTGGCCTTGCAAGCG |
| TCCCAGAGGCATTGACAGACTTGCAAACTTGCAAATATGGAAAAAAAAACCCCAATAAAAAAGTCTAGACTCTCACG |
| CTCGCTTGGTCCTGTGACTATTTTGTAGAATGGAAGACATCAACTTTGCGTCGCTGGCCCCGCGTCACGGCTCGCGC |
| CCGTTCCTGGGACACTGGAACGATATCGGCACCAGCAACATGAGCGGTGGCGCCTTCAGTTGGGGCTCTCTGTGGAG |
| CGGCATTAAAAGTATCGGGTCTGCCGTTAAAAATTACGGCTCCCGGGCCTGGAACAGCAGCACGGGCCAGATGTTGA |
| GAGACAAGTTGAAAGAGCAGAACTTCCAGCAGAAGGTGGTGGAGGGCCTGGCCTCCGGCATCAACGGGGTGGTGGAC |
| CTGGCCAACCAGGCCGTGCAGAATAAGATCAACAGCAGACTGGACCCCCGGCCGCCGGTGGAGGAGGTGCCGCCGGC |
| GCTGGAGACGGTGTCCCCGATGGGCGTGGCGAGAAGCGCCCGCGGCCCGATAGGGAAGAGACCACTCTGGTCACGC |
| AGACCGATGAGCCGCCCCCGTATGAGGAGGCCCTGAAGCAAGGTCTGCCCACCACGCGGCCCATCGCGCCCATGGCC |
| ACCGGGGTGGTGGGCCGCCACACCCCCGCCACGCTGGACTTGCCTCCGCCCGCCGATGTGCCGCAGCAGCAGAAGGC |
| GGCACAGCCGGGCCCGCCCGCGACCGCCTCCCGTTCCTCCGCCGGTCCTCTGCGCCGCGCGGCCAGCGGCCCCCGCG |
| GGGGGGTCGCGAGGCACGGCAACTGGCAGAGCACGCTGAACAGCATCGTGGGTCTGGGGGTGCGGTCCGTGAAGCGC |
| CGCCGATGCTACTGAATAGCTTAGCTAACGTGTTGTATGTGTGTATGCGCCCTATGTCGCCGCCAGAGGAGCTGCTG |
| AGTCGCCGCCGTTCGCGCGCCCACCACCACCGCCACTCCGCCCCTCAAGATGGCGACCCCATCGATGATGCCGCAGT |
| GGTCGTACATGCACATCTCGGGCCAGGACGCCTCGGAGTACCTGGGCCCCGGGCTGGTGCAGTTCGCCCGCGCCACC |
| GAGAGCTACTTCAGCCTGAGTAACAAGTTTAGGAACCCCACGGTGGCGCCCACGCACGATGTGACCACCGACCGGTC |
| TCAGCGCCTGACGCTGCGGTTCATTCCCGTGGACCGCGAGGACACCGCGTACTCGTACAAGGCGCGGTTCACCCTGG |
| CCGTGGGCGACAACCGCGTGCTGGACATGGCCTCCACCTACTTTGACATCCGCGGGGTGCTGGACCGGGGTCCCACT |
| TTCAAGCCCTACTCTGGCACCGCCTACAACTCCCTGGCCCCCAAGGGCGCTCCCAACTCCTGCGAGTGGGAGCAAGA |
| GGAAACTCAGGCAGTTGAAGAAGCAGCAGAAGAGGAAGAAGATGCTGACGGTCAAGCTGAGGAAGAGCAAGCAG |
| CTACCAAAAAGACTCATGTATATGCTCAGGCTCCCCTTTCTGGCGAAAAAATTAGTAAAGATGGTCTGCAAATAGGA |
| ACGGACGCTACAGCTACAGAACAAAAACCTATTTATGCAGACCCTACATTCCAGCCCGAACCCCAAATCGGGGAGTC |
| CCAGTGGAATGAGGCAGATGCTACAGTCGCCGGCGGTAGAGTGCTAAAGAAATCTACTCCCATGAAACCATGCTATG |
| GTTCCTATGCAAGCACCCACAAATGCTAATGGAGGTCAGGGTGTACTAACGGCAAATGCCCAGGGACGCTAGAATCT |
| CAGGTTGAAATGCAATTCTTTTCAACTTCTGAAAACGCCCGTAACGAGGCTAACAACATTCAGCCCAAATTGGTGCT |
| GTATAGTGAGGATGTGCACATGGAGACCCCGGATACGCACCTTTCTTACAAGCCCGCAAAAAGCGATGACAATTCAA |
| AAATCATGCTGGGTCAGCAGTCCATGCCCAACAGACCTAATTACATCGGCTTCAGAGACAACTTTATCGGCCTCATG |
| TATTACAATAGCACTGGCAACATGGGAGTGCTTGCAGGTCAGGGTCTCAGTTGAATGCAGTGGTGGACTTGCAAGA |
| CAGAAACACAGAACTGTCCTACCAGCTCTTGCTTGATTCCATGGGTGACAGAACCAGATACTTTTCCATGTGGAATC |
| AGGCAGTGGACAGTTATGACCCAGATGTTAGAATTATTGAAAATCATGGAACTGAAGACGAGCTCCCCAACTATTGT |
| TTCCCTCTGGGTGGCATAGGGGTAACTGACACTTACCAGGCTGTTAAAACCAACAATGGCAATAACGGGGGCCAGGT |
| GACTTGGACAAAAGATGAAACTTTTGCAGATCGCAATGAAATAGGGGTGGAGAACAATTTCGCTATGGAGATCAACC |
| TCAGTGCCAACCTGTGGAGAAACTTCCTGTACTCCAACGTGGCGCTGTACCTACCAGACAAGCTTAAGTACAACCCC |
| TCCAATGTGGACATCTCTGACAACCCCAACACCTACGATTACATGAACAAGCGAGTGGTGGCCCGGGGCTGGTGGA |
| CTGCTACATCAACCTGGGCGCGCGCTGGTCGCTGGACTACATGGACAACGTCAACCCCTTCAACCACCACCGCAATG |
| CGGGCCTGCGCTACCGCTCCATGCTCCTGGGCAACGGGCGCTACGTGCCCTTCCACATCCAGGTGCCCCAGAAGTTC |
| TTTGCCATCAAGAACCTCCTCCTCCTGCCGGGCTCCTACACCTACGAGTGGAACTTCAGGAAGGATGTCAACATGGT |
| CCTCCAGAGCTCTCTGGGTAACGATCTCAGGGTGGACGGGGCCAGCATCAAGTTCGAGAGCATCTGCCTCTACGCCA |
| CCTTCTTCCCCATGGCCCACAACACGGCCTCCACGCTCGAGGCCATGCTCAGGAACGACACCAACGACCAGTCCTTC |
| AATGACTACCTCTCCGCCGCCAACATGCTCTACCCCATACCCGCCAACGCCACCAACGTCCCCATCTCCATCCCCTC |
| GCGCAACTGGGCGGCCTTCCGCGGCTGGGCCTTCACCCGCCTCAAGACCAAGGAGACCCCCTCCCTGGGCTCGGGAT |
| TCGACCCCTACTACACCTACTCGGGCTCCATTCCCTACCTGGACGGCACCTTCTACCTCAACCACACTTTCAAGAAG |
| GTCTCGGTCACCTTCGACTCCTCGGTCAGCTGGCCGGGCAACGACCGTCTGCTCACCCCCAACGAGTTCGAGATCAA |
| GCGCTCGGTCGACGGGGAGGGCTACAACGTGGCCCAGTGCAACATGACCAAGGACTGGTTCCTGGTCCAGATGCTGG |
| CCAACTACAACATCGGCTACCAGGGCTTCTACATCCCAGAGAGCTACAAGGACAGGATGTACTCCTTCTTCAGGAAC |
| TTCCAGCCCATGAGCCGGCAGGTGGTGGACCAGACCAAGTACAAGGACTACCAGGAGGTGGGCATCATCCACCAGCA |
| CAACAACTCGGGCTTCGTGGGCTACCTCGCCCCCACCATGCGCGAGGGACAGGCCTACCCCGCCAACTTCCCCTATC |
| CGCTCATAGGCAAGACCGCGGTCGACAGCATCACCCAGAAAAGTTCCTCTGCGACCGCACCCTCTGGCGCATCCCC |
| TTCTCCAGCAACTTCATGTCCATGGGTGCGCTCTCGGACCTGGGCCAGAACTTGCTCTACGCCAACTCCGCCCACGC |
| CCTCGACATGACCTTCGAGGTCGACCCCATGGACGAGCCCACCCTTCTCTATGTTCTGTTCGAAGTCTTTGACGTGG |
| TCCGGGTCCACCAGCCGCACCGCGGCGTCATCGAGACCGTGTACCTGCGTACGCCCTTCTCGGCCGGCAACGCCACC |
| ACCTAAAGAAGCAAGCCGCAGTCATCGCCGCCTGCATGCCGTCGGGTTCCACCGAGCAAGAGCTCAGGGCCATCGTC |
| AGAGACCTGGGATGCGGGCCCTATTTTTGGGCACCTTCGACAAGCGCTTCCCTGGCTTTGTCTCCCCACACAAGCT |
| GGCCTGCGCCATCGTCAACACGGCCGGCCGCGAGACCGGGGGCGTGCACTGGCTGGCCTTCGCCTGGAACCCGCGCT |
| CCAAAACATGCTTCCTCTTTGACCCCTTCGGCTTTTCGGACCAGCGGCTCAAGCAAATCTACGAGTTCGAGTACGAG |
| GGCTTGCTGCGTCGCAGCGCCATCGCCTCCTCGCCCGACCGCTGCGTCACCCTCGAAAAGTCCACCCAGACCGTGCA |
| GGGGCCCGACTCGGCCGCCTGCGGTCTCTTCTGCTGCATGTTTCTGCACGCCTTTGTGACTGGCCTCAGAGTCCCA |
| TGGACCGCAACCCCACCATGAACTTGCTGACGGGGGTGCCCAACTCCATGCTCCAGAGCCCCCAGGTCGAGCCCACC |
| CTGCCGCAACCAGGAGCAGCTCTACAGCTTCCTGGAGCGCCACTCGCCTTACTTCCGCCGCCACAGCGCACAGAT |
| CAGGAGGGCCACCTCCTTCTGCCACTTGCAAGAGATGCAAGAAGGGTAATAACGATGTACACACTTTTTTTCTCAAT |
| AAATGGCATCTTTTTATTTATACAAGCTCTCTGGGGTATTCATTTCCCACCACCACCCGCCGTTGTCGCCATCTGGC |
| TCTATTTAGAAATCGAAAGGGGTTCTGCCGGGAGTCGCCGTGCGCCACGGGCAGGGACACGTTCGTAGTACTGGTAGCG |
| GGTGCCCCACTTGAACTCGGGCACCACCAGGCGAGGCAGCTCGGGGAAGTTTTCGCTCCACAGGCTGCGGGTCAGCA |
| CCAGCGCGTTCATCAGGTCGGGCGCCGAGATCTTGAAGTCGCAGTTGGGGCCGCCGCCCTGCGCGCGCGAGTTGCGG |
| TACACCGGGTTGCAGCACTGGAACACCAACAGCGCCGGGTGCTTCACGCTGGCCAGCACGCTGCGGTCGGAGATCAG |
| CTCGGCGTCCAGGTCCTCCGCGTTGCTCAGCGCGAACGGGGTCATCTTGGGCACTTGCCGCCCCAGGAAGGGCGCGT |
| GCCCGGTTTCGAGTTGCAGTCGCAGCGCAGCGGGATCAGCAGGTGCCCGTGCCCGGACTCGGCGTTGGGGTACAGC |
| GCGCGCATGAAGGCCTGCATCTGGCGAAGGCCATCTGGGCCTTGGCGCCCTCCGAGAAGAACATGCCGCAGGACTT |
| GCCCGAGAACTGGTTTGCGGGGCAGCTGGCGTCGTGCAGGCAGCAGCGCGCGTCGGTGTTGGCGATCTGCACCACGT |
| TGCGCCCCCACCGGTTCTTCACGATCTTGGCCTTGGACGATTGCTCCTTCAGCGCGCGCTGCCCGTTCTCGCTGGTC |
| ACATCCATCTCGATCACATGTTCCTTGTTCACCATGCTGCTGCCGTGCAGAACATTCAGCTCGCCCTCCGTCTCGGT |
| GCAGCGGTGCTGCCACAGCGCGCAGCCCGTGGGCTCGAAAGACTTGTAGGTCACCTCCGCGAAGGACTGCAGGTACC |
| CCTGCAAAAGCGGCCCATCATGGTCACGAAGGTCTTGTTGCTGCTGAAGGTCAGCTGCAGCCCGCGGTGCTCCTCG |
| TTCAGCCAGGTCTTGCACACGCCGCCAGCGCCTCCACCTGGTCGGGCAGCATCTTGAAGTTCACCTTCAGCTCATT |
| CTCCACGTGGTACTTGTCCATCAGCGTGCGCGCCGCCTCCATGCCCTTCTCCCAGGCCGACACCAGCGGCAGGCTCA |
| CGGGGTTCTTCACCATCACCGTGGCCGCCGCCTCCGCCGCGCTTTCGCTTTCCGCCCCGCTGTTCTCTTCCTCTTCC |
| TCCTCTTCCTCGCCGCCGCCCACTCGCAGCCCCCGCACCACGGGGTCGTCTTCCTGCAGGCGCTGCACCTTGCGCTT |

-continued

| DESCRIPTION OF THE SEQUENCES |
|---|
| GCCGTTGCGCCCCTGCTTGATGCGCACGGGCGGGTTGCTGAAGCCCACCATCACCAGCGCGGCCTCTTCTTGCTCGT |
| CCTCGCTGTCCAGAATGACCTCCGGGGAGGGGGGGTTGGTCATCCTCAGTACCGAGGCACGCTTCTTTTTCTTCCTG |
| GGGGCGTTCGCCAGCTCCGCGGCTGCGGCCGCTGCCGAGGTCGAAGGCCGAGGGCTGGGCGTGCGCGGCACCAGCGC |
| GTCCTGCGAGCCGTCCTCGTCCTCCTCGGACTCGAGACGGAGGCGGGCCCGCTTCTTCGGGGGCGCGCGGGGCGGCG |
| GAGGCGGCGGCGGCGACGGAGACGGGGACGAGACATCGTCCAGGGTGGGTGGACGGCGGGCGCGCCGCGTCCGCGC |
| TCGGGGGTGGTCTCGCGCTGGTCCTCTTCCCGACTGGCCATCTCCCACTGCTCCTTCTCCTATAGGCAGAAAGAGAT |
| CATGGAGTCTCTCATGCGAGTCGAGAAGGAGGAGGACAGCCTAACCGCCCCCTCTGAGCCCTCCACCACCGCCGCCA |
| CCACCGCCAATGCCGCCGCGGACGACGCGCCCACCGAGACCACCGCCAGTACCACCCTCCCCAGCGACGCACCCCCG |
| CTCGAGAATGAAGTGCTGATCGAGCAGGACCCGGGTTTTGTGAGCGGAGAGGAGGATGAGGTGGATGAGAAGGAGAA |
| GGAGGAGGTCGCCGCCTCAGTGCCAAAAGAGGATAAAAAGCAAGACCAGGACGACGCAGATAAGGATGAGACAGCAG |
| TCGGGCGGGGGAACGGAAGCCATGATGCTGATGACGGCTACCTAGACGTGGGAGACGACGTGCTGCTTAAGCACCTG |
| CACCGCCAGTGCGTCATCGTCTGCGACGCGCTGCAGGAGCGCTGCGAAGTGCCCCTGGACGTGGCGGAGGTCAGCCG |
| CGCCTACGAGCGGCACCTCTTCGCGCCGCACGTGCCCCCAAGCGCGGGAGAACGGCACCTGCGAGCCCAACCCGC |
| GTCTCAACTTCTACCCGGTCTTCGCGGTACCCGAGGTGCTGGCCACCTACCATCTTTTTCCAAAACTGCAAGATC |
| CCCCTCTCCTGCCGCGCCAACCGCACCCGCGCCGACAAAACCCTGACCCTGCCGCAGGGCGCCCACATACCTGATAT |
| CGCCTCTCTGGAGGAAGTGCCCAAGATCTTCGAGGGTCTCGGTCGCGACGAGAAACGGGCGGCGAACGCTCTGCACG |
| GAGACAGCGAAAACGAGAGTCACTCGGGGGTGCTGGTGGAGCTCGAGGGCGACAACGCGCGCCTGGCCGTACTCAAG |
| CGCAGCATAGAGGTCACCCACTTTGCCTACCCGGCGCTCAACCTGCCCCCCAAGGTCATGAGTGTGGTCATGGGCGA |
| GCTCATCATGCGCCGCGCCCAGCCCCTGGCCGCGGATGCAAACTTGCAAGAGTCCTCCGAGGAAGGCCTGCCCGCGG |
| TCAGCGACGAGCAGCTGGCGCGCTGGCTGGAGACCCGCAGACCCCGCGCAGCTGGAGGAGCGGCGCAAGCTCATGATG |
| GCCGCGGTGCTGGTCACCGTGGAGCTCGAGTGTCTGCAGCGCTTCTTCGCGGACCCCGAGATGCAGCGCAAGCTCGA |
| GGGAGACCCTGCACTACACCTTCCGCCAGGGCTACGTGCGCCAGGCCTGCAAGATCTCCAACGTGGAGCTCTGCAACC |
| TGGTCTCCTACCTGGGCATCCTGCACGAGAACCGCCTCGGGCAGAACGTCCTGCACTCCACCCTCAAAGGGGAGGCG |
| CGCCGCGACTACATCCGCGACTGCGCCTACCTCTTCCTCTGCTACACCTGGCAGACGGCCATGGGGGGGTCTGGCAGCA |
| GTGCCTGGAGGAGCGCAACCTCAAGGAGCTGGAAAAGCTCCTCAAGCGCACCCTCAGGGACCCTCTGGACGGGCTTCA |
| ACGAGCGCTCGGTGGCCGCCGCGCTGGCGGACATCATCTTTCCCGAGCGCCTGCTCAAGACCCTGCAGCAGGGCCTG |
| CCCGACTTCACCAGCCAGAGCATGCTGCAGAACTTCAGGACTTTCATCCTGGAGCGCTCGGGCATCCTGCCGGCCAC |
| TTGCTGCGCGCTGCCCAGCGACTTCGTGCCCATCAAGTACAGGGAGTGCCCGCCGCCGCTCTGGGGCCACTGCTACC |
| TCTTCCAGCTGGCCAACTACCTCGCCTACCACTCGGACCTCATGGAAGACGTGAGCGGCGAGGGCCTGCTCGAGTGC |
| CACTGCCGCTGCAACCTCTGCACGCCCCACCGCTCTCTAGTCTGCAACCCGCAGCTGCTCAGCGAGAGTCAGATTAT |
| CGGTACCTTCGAGCTGCAGGGTCCCTCGCCTGACGAGAAGTCCGCGGCTCCAGGGCTGAAACTCACTCCGGGGCTGT |
| GGACTTCCGCCTACCTACGCAAATTTGTACCTGAGGACTACCACGCCCACGAGATCAGGTTCTACGAAGACCAATCC |
| CGCCCGCCCAAGGCGGAGCTCACCGCCTGCGTCATCACCCAGGGGCACATCCTGGGCCAATTGCAAGCCATCAACAA |
| AGCCCGCCGAGAGTTCTTGCTGAAAAAGGGTCGGGGGGTGTACCTGGACCCCCAGTCCGGCGAGGAGCTAAACCCGC |
| TACCCCCGCCGCCGCCCCAGCAGCGGGACCTTGCTTCCCAGGATGGCACCCAGAAAGAAGCAGCAGCCGCCGCCGCC |
| GCCGCAGCCATACATGCTTCTGGAGGAAGAGGAGGAGGACTGGGACAGTCAGGCAGGAGGGTTTCGGACGAGGAGC |
| AGGAGGAGATGATGGAAGACTGGGAGGAGGACAGCAGCCTAGACGAGGAAGCTTCAGAGGCGAAGAGGTGGCAGAC |
| GCAACACCATCGCCCTCGGTCGCAGCCCCCTCGCCGGGGCCCCTGAAATCCTCCGAACCCAGCACCAGCGCTATAAC |
| CTCCGCTCCTCCGGCGCCGGCGCCACCCGCCCGCAGACCCAACCGTAGATGGGACACCACAGGAACCGGGGTCGGTA |
| AGTCCAAGTGCCCGCCGCCGCCACCGCAGCAGCAGCAGCAGCAGCAGCGCCAGGGCTACCGCTCGTGGCGCGGGCACAAG |
| AACGCCATAGTCGCCTGCTTGCAAGACTGCGGGGGCAACATCTCTTTCGCCCGCCGCTTCCTGCTATTCCACCACG |
| GGTCGCCTTTCCCCGCAATGTCCTGCATTACTACCGTCATCTCTACAGCCCCTACTGCAGCGGCGACCCAGAGGCGG |
| CAGCGGCAGCCACAGCGGCGACCACCACCTAGGAAGATATCCTCCGCGGGCAAGACAGCGGCAGCAGCGGCCAGGAG |
| ACCCGCGGCAGCAGCGGCGGGAGCGGTGGGCGCACTGCGCCTCTCGCCCAACGAACCCCTCTCGACCCGGGAGCTCA |
| GACACAGGATCTTCCCCACTTTGTATGCCATCTTCCAACAGACAGAGGCCAGGAGCAGGAGCTGAAAATAAAAAAC |
| AGATCTCTGCGCTCCCTCACCCGCAGCTGTCTGTATCACAAAAGCGAAGATCAGCTCTTCGGCGCACGCTGGAGGACGC |
| GGAGGCACTCTTCAGCAAATACTGCGCGCTCACTCTTAAAGACTAGCTCCGCGCCCTTCTCGAATTTAGGCGGGAGA |
| AAACTACGTCATCGCCGGCCGCCGCCCAGCCCGCCCAGCCGAGATGAGCAAAGAGATTCCCACGCCATACATGTGGA |
| GCTACCAGCCGCAGATGGGACTCGCGGCGGGAGCGGCCCAGGACTACTCCACCCGCATGAACTACATGAGCGCGGGA |
| CCCCACATGATCTCACAGGTCAACGGGATCCGCGCCCAGCGAAACCAAATACTGCTGGAACAGGCGGCCATCACCGC |
| CACGCCCCGCCATAATCTCAACCCCCGAAATTGGCCCGCCGCCTCGTGTACCAGGAAACCCCTCCGCCACCACCG |
| TACTACTTCCGCGTGACGCCCAGGCCGAAGTCCAGATGACTAACTCAGGGGCGCAGCTCGCGGGCGGCTTTCGTCAC |
| GGGGCGCGGCCGCTCCGACCAGGTATAAGACACCTGATGATCAGAGGCCGAGGTATCCAGCTCAACGACGAGTCGGT |
| GAGCTCTTCGCTCGGTCTCCGTCCGGACGGAACTTTCCAGCTCGCCGGATCCGGCCGCTCTTCGTTCACGCCCCGCC |
| AGGCGTACCTGACTCTGCAGACCTCGTCCTGGGAGCCCCGCTCCGGCGGCATCGGAACCCTCCAGTTCGTGGAGGAG |
| TTCGTGCCCTCGGTCTACTTCAACCCCTTCTCGGGACCTCCCGGACGCTACCCCGACCAGTTCATTCCGAACTTTGA |
| CGCGGTGAAGGACTCGGCGGACGGCTACGACTGAATGTCAGGTGTCAGGACAGAGCAGCTTCGCCTGAGACACCTCG |
| AGCACTGCCGCCGCCACAAGTGCTTCGCCCGCGGTTCTGGTGAGTTCTGCTACTTTCAGCTACCCGAGGAGCATACC |
| GAGGGGCCGGCGCACGGCGTCCGCCTGACCACCCAGGGCGAGGTTACCTGTTCCCTCATCCGGGAGTTTACCCTCCG |
| TCCCCTGCTAGTGGAGCGGGAGCGGGGTCCCTGTGTCCTAACTATCGCCTGCAACTGCCCTAACCCTGGATTACATC |
| AAGATCTTTGCTGTCATCTCTGTGCTGAGTTTAATAAACGCTGAGATCAGAATCTACTGGGGCTCCTGTCGCCATCC |
| TGTGAACGCCACCGTCTTCACCCACCCCGACCAGGCCCAGGCGAACCTCACCTGCGGTCTGCATCGGAGGGCCAAGA |
| AGTACCTCACCTGGTACTTCAACGGCACCCCCTTTGTGGTTTACAACAGCTTCGACGGGACGGAGTCTCCCTGAAA |
| GACCAGCTCTCCGGTCTCAGCTACTCCATCCACAAGAACACCACCCTCCAACTCTTCCCTCCCTACCTGCCGGGAAC |
| CTACGAGTGCGTCACCGGCCGCTGCACCCACCTCACCCGCCTGATCGTAAACCAGAGCTTTCCGGGAACAGATAACT |
| CCCTCTTCCCCAGAACAGGAGGTGAGCTCAGGAAACTCCCCGGGAACTTCCCGGGGACTACCTTCGACCCTTGTG |
| GGGTTAGGATTTTTTATTACCGGGTTGCTGGCTCTTTTAATCAAAGTTTCCTTGAGATTTGTTCTTTCCTTCTACGT |
| GTATGAACACCTCAACCTCCAATAACTCTACCCTTTCTTCGGAATCAGGTGACTTCTCTGAAATCGGGCTTGGTGTG |
| CTGCTTACTCTGTTGATTTTTTTCCTTATCATACTCAGCCTTCTGTGCCTCAGGCTCGCCGCCTGCTGCGCACACAT |
| CTATATCTACTGCTGGTTGCTCAAGTGCAGGGTCGCCACCCAAGATGAACAGGTACATGGTCCTATCGATCCTAGG |
| CCTGCTGGCCCTGGCGGCCTGCAGCGCCGCCAAAAAAGAGATTACCTTTGAGGAGCCCGCTTGCAATGTAACTTTCA |
| AGCCCGAGGGTGACCAATGCACCACCCTCGTCAAATGCGTTACCAATCATGAGAGGCTGCGCATCGACTACAAAAAC |
| AAAACTGGCCAGTTTGCGGTCTATAGTGTGTTTACGCCCGGAGACCCCTCTAACTACTCTGTCACCGTCTTCCAGGG |
| CGGACAGTCTAAGATATTCAATTACACTTTCCCTTTTTATGAGTTATGCGATGCGGTCATGTACATGTCAAAACAGT |
| ACAACCTGTGGCCTCCCTCTCCCCAGGCGTGTGTGGAAAATACTGGGTCTTACTGCTGTATGGCTTTCGCAATCACT |
| ACGCTCGCTCTAATCTGCACGGTGCTATACATAAAATTCAGGCAGAGGCGAATCTTTATCGATGAAAAGAAATGCC |
| TTGATCGCTAACACCGGCTTTCTATCTGCAGAATGAATGCAATCACCTCCCTACTAATCACCACCACCCTCCTTGCG |

| DESCRIPTION OF THE SEQUENCES |
|---|
| ATTGCCCATGGGTTGACACGAATCGAAGTGCCAGTGGGGTCCAATGTCACCATGGTGGGCCCCGCCGGCAATTCCAC |
| CCTCATGTGGGAAAAATTTGTCCGCAATCAATGGGTTCATTTCTGCTCTAACCGAATCAGTATCAAGCCCAGAGCCA |
| TCTGCGATGGGCAAAATCTAACTCTGATCAATGTGCAAATGATGGATGCTGGGTACTATTACGGGCAGCGGGGAGAA |
| ATCATTAATTACTGGCGACCCCACAAGGACTACATGCTGCATGTAGTCGAGGCACTTCCCACTACCACCCCCACTAC |
| CACCTCTCCCACCACCACCACCACTACTACTACTACTACTACTACTACTACTACCACTACCGCTGCCCGCCATA |
| CCCGCAAAAGCACCATGATTAGCACAAAGCCCCCTCGTGCTCACTCCCACGCCGGCGGGCCCATCGGTGCGACCTCA |
| GAAACCACCGAGCTTTGCTTCTGCCAATGCACTAACGCCAGCGCTCATGAACTGTTCGACCTGGAGAATGAGGATGT |
| CCAGCAGAGCTCCGCTTGCCTGACCCAGGAGGCTGTGGAGCCCGTTGCCCTGAAGCAGATCGGTGATTCAATAATTG |
| ACTCTTCTTCTTTTGCCACTCCCGAATACCCTCCCGATTCTACTTTCCACATCACGGGTACCAAAGACCCTAACCTC |
| TCTTTCTACCTGATGCTGCTGCTCTGTATCTCTGTGGTCTCTTCCGCGCTGATGTTACTGGGGATGTTCTGCTGCCT |
| GATCTGCCGCAGAAAGAGAAAAGCTCGCTCTCAGGGCCAACCACTGATGCCCTTCCCCTACCCCCCGGATTTTGCAG |
| ATAACAAGATATGAGCTCGCTGCTGACACTAACCGCTTTACTAGCCTGCGCTCTAACCCTTGTCGCTTGCGACTCGA |
| GATTCCACAATGTCACAGCTGTGGCAGGAGAAAATGTTACTTTCAACTCCACGGCCGATACCCAGTGGTCGTGGAGT |
| GGCTCAGGTAGCTACTTAACTATCTGCAATAGCTCCACTTCCCCCGGCATATCCCCAACCAAGTACCAATGCAATGC |
| CAGCCTGTTCACCCTCATCAACGCTTCCACCCTGGACAATGGACTCTATGTAGGCTATGTACCCTTTGGTGGGCAAG |
| GAAAGACCCACGCTTACAACCTGGAAGTTCGCCAGCCCAGAACCACTACCCAAGCTTCTCCCACCACCACCACCACC |
| ACCACCATCACCAGCAGCAGCAGCAGCAGCAGCCACAGCAGCAGCAGCAGATTATTGACTTTGGTTTTGGCCAGCTC |
| ATCTGCCGCTACCCAGGCCATCTACAGCTCTGTGCCCGAAACCACTCAGATCCACCGCCCAGAAACGACCACCGCCA |
| CCACCCTACACACCTCCAGCGATCAGATGCCGACCAACATCACCCCCTTGGCTCTTCAAATGGGACTTACAAGCCCC |
| ACTCCAAAACCAGTGGATGCGGCCGAGGTCTCCGCCCTCGTCAATGACTGGGCGGGGCTGGGAATGTGGTGGTTCGC |
| CATAGGCATGATGGCGCTCTGCCTGCTTCTGCTCTGGCTCATCTGCTGCCTCCACCGCAGGCGAGCCAGACCCCCCA |
| TCTATAGACCCATCATTGTCCTGAACCCCGATAATGATGGGATCCATAGATTGGATGGCCTGAAAAACCTACTTTTT |
| TCTTTTACAGTATGATAAATTGAGACATGCCTCGCATTTTCTTGTACATGTTCCTTCTCCCACCTTTTCTGGGGTGT |
| TCTACGCTGGCCGCTGTGTCTCACCTGGAGGTAGACTGCCTCTCACCCTTCACTGTCTACCTGCTTTACGGATTGGT |
| CACCCTCACTCTCATCTGCAGCCTAATCACAGTAATCATCGCCTTCATCCAGTGCATTGATTACATCTGTGTGCGCC |
| TCGCATACTTCAGACACCACCCGCAGTACCGAGACAGGAACATTGCCCAACTTCTAAGACTGCTCTAATCATGCATA |
| AGACTGTGATCTGCCTTCTGATCCTCTGCATCCTGCCCACCCTCACCTCCTGCCAGTACACCACAAAATCTCCGCGC |
| AAAAGACATGCCTCCTGCCGCTTCACCCAACTGTGGAATATACCCAAATGCTACAACGAAAAGAGCGAGCTCTCCGA |
| AGCTTGGCTGTATGGGGTCATCTGTGTCTTAGTTTTCTGCAGCACTGTCTTTGCCCTCATAATCTACCCCTACTTTG |
| ATTTGGGATGGAACGCGATCGATGCCATGAATTACCCCACCTTTCCCGCACCCGAGATAATTCCACTGCGACAAGTT |
| GTACCCGTTGTCGTTAATCAACGCCCCCATCCCCTACGCCCACTGAAATCAGCTACTTTAACCTAACAGGCGGAGA |
| TGACTGACGCCCTAGATCTAGAAATGGACGGCATCAGTACCGAGCAGCGTCTCCTAGAGAGGCGCAGGCAGGCGGCT |
| GAGCAAGAGCGCCTCAATCAGGAGCTCCGAGATCTCGTTAACCTGCACCAGTGCAAAAGAGGCATCTTTTGTCTGGT |
| AAAGCAGGCCAAAGTCACCTACGAGAAGACCGGCAACAGCCACCGCCTCAGTTACAAATTGCCCACCCAGCGCCAGA |
| AGCTGGTGCTCATGGTGGGTGAGAATCCCATCACCGTCACCCAGCACTCGGTAGAGACCGAGGGGTGTCTGCACTCC |
| CCCTGTCGGGGTCCAGAAGACCTCTGCACCCTGGTAAAGACCCTGTGCGGTCTCAGAGATTTAGTCCCCTTTAACTA |
| ATCAAACACTGGAATCAATAAAAAGAATCACTTACTTAAAATCAGACAGCAGGTCTCTGTCCAGTTTATTCAGCAGC |
| ACCTCCTTCCCCTCCTCCCAACTCTGGTACTCCAAACGCCTTCTGGCGGCAAACTTCCTCCACACCCTGAAGGGAAT |
| GTCAGATTCTTGCTCCTGTCCCTCCGCACCCACTATCTTCATGTTGTTGCAGATGAAGCGCACCAAAACGTCTGACG |
| AGAGCTTCAACCCCGTGTACCCCTATGACACGGAAAGCGGCCCTCCCTCCGTCCCTTTCCTCACCCCTCCCTTCGTG |
| TCTCCCGATGGATTCCAAGAAAGTCCCCCCGGGGTCCTGTCTCTGAACCTGGCCGAGCCCCTGGTCACTTCCCACGG |
| CATGCTCGCCCTGAAAATGGGAAGTGGCCTCTCCCTGGACGACGCTGGCAACCTCACCTCTCAAGATATCACCACCG |
| CTAGCCCTCCCCTCAAAAAAACCAAGACCAACCTCAGCCTAGAAACCTCATCCCCCCTAACTGTGAGCACCTCAGGC |
| GCCCTCACCGTAGCAGCCGCCGCTCCCCTGGCGGTGGCCGGCACCTCCCTCACCATGCAATCAGAGGCCCCCCTGAC |
| AGTACAGGATGCAAAACTCACCCTGGCCACCAAAGGCCCCCTGACCGTGCTGAAGGCAAACTGGCCTTGCAAACAT |
| CGGCCCCGCTGACGGCCGCTGACAGCAGCACCCTCACAGTCAGTGCCACACCACCCCTTAGCACAAGCAATGGCAGC |
| TTGGGTATTGACATGCAAGCCCCCATTTACACCACCAATGGAAAACTAGGACTTAACTTTGGCGCTCCCCTGCATGT |
| GGTAGACAGCCTAAATGCACTGACTGTAGTTACTGGCCAAGGTCTTACGATAAACGGAACAGCCCTACAAACTAGAG |
| TCTCAGGTGCCCTCAACTATGACACATCAGGAAACCTAGAATTGAGAGCTGCAGGGCCTATGCAGTTGATGCAAAT |
| GGTCAACTTATCCTTGATGTAGCTTACCCATTTGATGCACAAAACAATCTCAGCCTTAGGCTTGGACAGGGACCCCT |
| GTTTGTTAACTCTGCCCACAACTTGGATGTTAACTACAACAGAGGCCTCTACCTGTTCACATCTGGAAATACCAAA |
| AGCTAGAAGTTAATATCAAAACAGCCAAGGGTCTCATTTATGATGACACTGCTATAGCAATCAATGCGGGTGATGGG |
| CTACAGTTTGACTCAGGCTCAGATACAAATCCATTAAAAACTAAACTTGGATTGGATTATGACTCCAGCAG |
| AGCCATAATTGCTAAACTGGGAACTGGCCTAAGCTTTGACAACACAGGTGCCATCACAGTAGGCAACAAAAATGATG |
| ACAAGCTTACCTTGTGGACCACACCAGACCCATCCCCTAACTGTAGAATCTATTCAGAGAAAGATGCTAAATTCACA |
| CTTGTTTTGACTAAATGCGGCAGTCAGGTGTTGGCCAGCGTTTCTGTTTTATCTGTAAAAGGTAGCCTTGCGCCCAT |
| CAGTGGCACAGTAACTAGTGCTCAGATTGTCCTCAGATTTGATGAAGGTGCTTCTAACAAGCAATTCTTCCCTTG |
| ACCCTCAATACTGGAACTACAGAAAAGGTGACCTTACAGAGGGCACTGCATATACCAACGCAGTGGGATTTATGCCC |
| AACCTCACAGCATACCCAAAAACACAGAGCCAAACTGCTAAAAGCAACATTGTAAGTCAGGTTTACTTGAATGGGGA |
| CAAATCCAAACCCATGACCCTCACCATTACCCTCAATGGAACTAATGAAACAGGAGATGCCACAGTAAGCACTTACT |
| CCATGTCATTCTCATGGAACTGGAATGGAAGTAATTACATTAATGAAACAACCTCCTCCACCTTCTCC |
| TACATCGCCCAAGAATAAAAAGCATGACGCTGTTGATTTGATTCAATGTGTTTCTGTTTTATTTTCAAGCACAACAA |
| AATCATTCAAGTCATTCTTCCATCTTAGCTTAATAGACACAGTAGCTTAATAGACCCAGTAGTGCAAAGCCCCATTC |
| TAGCTTATAGATCAGACAGTGATAATTAACCACCACCACCACCATACCTTTTGATTCAGGAAATCATGATCATCACA |
| GGATCCTAGTCTTCAGGCCGCCCCTCCCTCCCAAGCACAGAATACACAGTCCTCTCCCCCGACTGGCTTTAAAT |
| AACACCATCTGGTTGGTCACAGACATGTTCTTAGGGGTTATATCCACACGGTCTCTGCCGCGCCAGGCGCTCGTC |
| GGTGATGTTGATAAACTCTCCCGGCAGCTCGCTCAAGTTCACGTCGCTGTCCAGCGGCTGAACCTCCGCTGACGG |
| ATAACTGTGCGACCGGCTGCTGGACGAACGGAGGCCGCGCCTACAAGGGGGTAGAGTCATAATCCTCGGTCAGGATA |
| GGGCGGTGATGCAGCAGCAGCGAGCGAAACATCTGCTGCCGCCGCCGCTCCGTCCGGCAGGAAAACAACACGCCGGT |
| GGTCTCCTCCGCGATAATCCGCACCGCCCGCAGCATCAGCTTCCTCGTTCTCCGCGCGCAGCACCTCACCCTTATCT |
| CGCTCAAATCGGCGCAGTAGGTACAGCACAGCACCACGATGTTATTCATGATCCCACAGTGCAGGGCGCTGTATCCA |
| AAGCTCATGCCGGGAACCACCGCCCCACGTGGCCATCGTACCACAAGCGCACGTAAATCAAGTGTCGACCCCTCAT |
| GAACGCGCTGGACACAAACATTACTTCCTTGGGCATGTTGTAATTCACCACTTCCCGGTACCAGATAAACCTCTGGT |
| TGAACAGGGCACCTTCCACCACCATCCTGAACCAAGAGGCCAGAACCTGCCCACCGGCTATGCACTGCAGGGAACCC |
| GGGTTGGAACAATGACAATGCAGACTCCAAGGCTCGTAACCGTGGATCATCCGGCTGCTGAAGGCATCGATGTTGGC |
| ACAACACAGACACGTGCATGCACTTTCTCATGATTAGCAGCTCTTCCCTCGTCAGGATCATATCCCAAGGAATAA |
| CCCATTCTTGAATCAACGTAAAACCCACACAGCAGGGAAGGCCTCGCACATAACTCACGTTGTGCATGGTCAGCGTG |

| DESCRIPTION OF THE SEQUENCES |
|---|
| TTGCATTCCGGAAACAGCGGATGATCCTCCAGTATCGAGGCGCGGGTCTCCTTCTCACAGGGAGGTAAAGGGTCCCT
GCTGTACGGACTGCGCCGGGACGACCGAGATCGTGTTGAGCGTAGTGTCATGGAAAAGGGAACGCCGGACGTGGTCA
TACTTCTTGAAGCAGAACCAGGTTCGCGCGTGGCAGGCCTCCTTGCGTCTGCGGTCTCGCCGTCTAGCTCGCTCCGT
GTGATAGTTGTAGTACAGCCACTCCCGCAGAGCGTCGAGGCGCACCCTGGCTTCCGGATCTATGTAGACTCCGTCTT
GCACCGCGGCCCTGATAATATCCACCACCGTAGAATAAGCAACACCCAGCCAAGCAATACACTCGCTCTGCGAGCGG
CAGACAGGAGGAGCGGGCAGAGATGGGAGAACCATGATAAAAAACTTTTTTTAAAGAATATTTTCCAATTCTTCGAA
AGTAAGATCTATCAAGTGGCAGCGCTCCCCTCCACTGGCGCGGTCAAACTCTACGGCCAAAGCACAGACAACGGCAT
TTCTAAGATGTTCCTTAATGGCGTCCAAAAGACACACCGCTCTCAAGTTGCAGTAAACTATGAATGAAAACCCATCC
GGCTGATTTTCCAATATAGACGCGCCGGCAGCGTCCACCAAACCCAGATAATTTTCTTCTCTCCAGCGGTTTACGAT
CTGTCTAAGCAAATCCCTTATATCAAGTCCGACCATGCCAAAAATCTGCTCAAGAGCGCCCTCCACCTTCATGTACA
AGCAGCGCATCATGATTGCAAAAATTCAGGTTCTTCAGAGACCTGTATAAGATTCAAAATGGGAACATTAACAAAAA
TTCCTCTGTCGCGCAGATCCCTTCGCAGGGCAAGCTGAACATAATCAGACAGGTCCGAACGGACCAGTGAGGCCAAA
TCCCCACCAGGAACCAGATCCAGAGACCCTATACTGATTATGACGCGCATACTCGGGGCTATGCTGACCAGCGTAGC
GCCGATGTAGGCGTGCTGCATGGGCGGCGAGATAAAATGCAAAGTGCTGGTTAAAAAATCAGGCAAAGCCTCGCGCA
AAAAAGCTAACACATCATAATCATGCTCATGCAGGTAGTTGCAGGTAAGCTCAGGAACCAAAACGGAATAACACACG
ATTTTCCTCTCAAACATGACTTCGCGGATACTGCGTAAAACAAAAAATTATAAATAAAAAATTAATTAAATAACTTA
AACATTGGAAGCCTGTCTCACAACAGGAAAAACCACTTTAATCAACATAAGACGGGCCACGGGCATGCCGGCATAGC
CGTAAAAAAATTGGTCCCCGTGATTAACAAGTACCACAGACAGCTCCCCGGTCATGTCGGGGGTCATCATGTGAGAC
TCTGTATACACGTCTGGATTGTGAACATCAGACAAACAAAGAAATCGAGCCACGTAGCCCGGAGGTATAATCACCCG
CAGGCGGAGGTACAGCAAAACGACCCCCATAGGAGGAATCACAAAATTAGTAGGAGAAAAAAATACATAAACACCAG
AAAAACCCTGTTGCTGAGGCAAAATAGCGCCCTCCCGATCCAAAACAACATAAAGCGCTTCCACAGGAGCAGCCATA
ACAAAGACCCGAGTCTTACCAGTAAAAGAAAAAAGATCTCTCAACGCAGCACCAGCACCAACACTTCGCAGTGTAAA
AGGCCAAGTGCCGAGAGAGTATATATAGGAATAAAAAGTGACGTAAACGGGCAAAGTCCAAAAAACGCCCAGAAAAA
CCGCACGCGAACCTACGCCCCGAAACGAAAGCCAAAAAACACTAGACACTCCCTTCCGGCGTCAACTTCCGCTTTCC
CACGCTACGTCACTTCCCCCGGTCAAACAAACTACATATCCCGAACTTCCAAGTCGCCACGCCCAAAACACCGCCTA
CACCTCCCCGCCCGCCGGCCCGCCCCCGGACCCGCCTCCCGCCCCGCGCCGCCCATCTCATTATCATATTGGCTTCA
ATCCAAAATAAGGTATATTATTGATGATG

SEQ ID NO: 2 Polynucleotide sequence encoding wild type ChAd83
CATCATCAATAATATACCTCAAACTTTTGGTGCGCGTTAATATGCAAATGAGCTGTTTGAATTTGGGGAT
GCGGGGCGCTGATTGGCTGCGGGAGCGGCGACCGTTAGGGGCGGGGCGGGTGACGTTTTGATGACGTGGC
CGTGAGGCGGAGCCGGTTTGCAAGTTCTCGTGGGAAAAGTGACGTCAAACGAGGTGTGGTTTGAACACGG
AAATACTCAATTTTCCCGCGCTCTCTGACAGGAAATGAGGTGTTTCTGGGCGGATGCAAGTGAAAACGGG
CCATTTTCGCGCGAAAACTGAATGAGGAAGTGAAAATCTGAGTAATTTCGCGTTTATGGCAGGGAGGAGT
ATTTGCCGAGGGCCGAGTAGACTTTGACCGATTACGTGGGGGTTTCGATTACCGTATTTTTCACCTAAAT
TTCCGCGTACGGTGTCAAAGTCCGGTGTTTTTACGTAGGCGTCAGCTGATCGCCAGGGTATTTAAACCTG
CGCTCACTAGTCAAGAGGCCACTCTTGAGTGCCAGCGAGTAGAGTTTTCTCCTCCGCGCCGCGAGTCAGA
TCTACACTTTGAAAGATGAGGCACTTGAGAGACCTGCCCGGTAATGTTTTCCTGGCTACTGGGAACGAGA
TTCTGGAATTGGTGGTGGACGCCATGATGGGTGACGACCCTCCCGAGCCCCCTACCCCATTTGAGGCGCC
TTCGCTGTACGATTTGTATGATCTGGAGGTGGATGTGCCCGAGAACGACCCCAACGAGGAGGCGGTGAAT
GATTTGTTTAGCGATGCCGCGCTGCTGGCTGCCGAGCAGGCTAATACGACTTTGGCTCAGACAGCGATT
CTTCTCTCCATACCCCGAGACCCGGCAGAGGTGAGAAAAAGATCCCCGAGCTTAAAGGGGAAGAGCTCGA
CCTGCGCTGCTATGAGGAATGCTTGCCTCCGAGCGATGATGAGGAGGACGAGGAGGCGATTCGAGCTGCA
GCGAACCAGGGAGTGAAAGCTGCGGGCGAAAGCTTTAGCCTGGACTGTCCTACTCTGCCCGGACACGGCT
GTAAGTCTTGTGAATTTCATCGCATGAATACTGGAGATAAGAATGTGATGTGTGCCCTGTGCTATATGAG
AGCTTACAACCATTGTGTTTACAGTAAGTGTGATTAACTTTAGTTGGGAAGGCAGAGGGTGACTGGGTGC
TGACTGGTTTATTTATGTATATGTTTTTTATGTGTAGGTCCCGTCTCTGACGCAGATGAGACCCCCACTT
CAGAGTGCATTTCATCACCCCCAGAAATTGGCGAGGAACCGCCCGAAGATATTATTCATAGACCAGTTGC
AGTGAGAGTCACCGGGCGGAGAGCAGCTGTGGAGAGTTTGGATGACTTGCTACAGGGTGGGGATGAACCT
TTGGACTTGTGTACCCGGAAACGCCCCAGGCACTAAGTGCCACACATGTGTGTTTACTTAAGGTGATGTC
AGTATTTATAGGGTGTGGAGTGCAATAAAATCCGTGTTGACTTTAAGTGCGTGGTTTATGACTCAGGGGT
GGGGACTGTGGGTATATAAGCAGGTGCAGACCTGTGTGGTCAGTTCAGAGCAGGACTCATGGAGATCTGG
ACGGTCTTGGAAGACTTTCACCAGACTAGACAGCTGCTAGAGAACTCATCGGAGGGAGTCTCTTACCTGT
GGGAGATTCTGCTTCGGTGGGCCTCTAGCTAAGCTAGTCTATAGGGCCAAGCAGGATTATAAGGATCAATT
TGAGGATATTTTGAGAGAGTGTCCTGGTATTTTTGACTCTCTCAACTTGGGCCATCAGTCTCACTTTAAC
CAGAGTATTCTGAGAGCCCTTGACTTTTCCACTCCTGGCAGAACTACCGCCGCGGTAGCCTTTTTTGCCT
TTATCCTTGACAAATGGAGTCAAGAAACCCATTTCAGCAGGGATTACCGTCTGGACTGCTTAGCAGTAGC
TTTGTGGAGAACATGGAGGTGCCAGCGCCTGAATGCAATCTTCCGGCTACTTGCCAGTACAGCCGGTAGAC
ACGCTGAGGATCCTGAGTCTCCAGTCACCCCAGGAACACCAACGCCGCCAGCAGCCGCAGCAGGAGCAGC
AGCAAGAGGAGGACCGAGAAGAGAACCCGAGAGCCGGTCTGGACCCTCCGGTGGCGGAGGAGGAGGAGTA
GCTGACTTGTTTCCCGAGCTGCGCCGGGTGCTGACTAGGTCTTCCAGTGGACGGGAGGGGGATTAAGC
GGGAGAGGCATGAGGAGACTAGTCACAGAACTGAACTGACTGTCAGTCTGATGAGCGCAGGCGCCCAGA
ATCGGTGTGGTGGCATGAGGTGCAGTCGCAGGGGATAGATGAGGTCTCGGTGATGCATGAGAAATATTCC
CTAGAACAAGTCAAGACTTGTTGGTTGGAGCCTGAGGATGATTGGGAGGTAGCCATCAGGAATTATGCCA
AGCTAGCTCTGAAGCCAGACAAGAAGTACAAGATTACCAAACTGATTAATATCAGAAATTCCTGCTACAT
TTCAGGGAATGGGGCCGAGGTGGAGATCAGTACCCAGGAGAGGGTGGCCTTCAGATGCTGCATGATGAAT
ATGTACCCGGGGGTGGTGGGCATGGAGGGAGTCACCTTTATGAACGCGAGGTTCAGGGGCGATGGGTATA
ATGGGGTGGTCTTTATGGCCAACACCAAGCTGACAGTGCACGGATGCTCCTTCTTTGGCTTCAATAACAT
GTGCATCGAGGCCTGGGGCAGTGTTTCAGTGAGGGGATGCAGTTTTTCAGCCAACTGGATGGGGGTCGTG
GGCAGAACCAAGAGCAAGGTGTCAGTGAAGAAATGCCTGTTCGAGAGGTGCCACCTGGGGGTGATGAGCG
AGGGCGAAGCCAAAGTCAAACACTGCGCCTCTACTGAGACGGGGCTGCTTTGTGCTGATCAAGGGCAATGC
CCAAGTCAAGCATAACATGATCTGTGGGGCCTCGGATGAGCGCGGCTACCAGATGCTGACCTGCGCCGGT
GGGAACAGCCATATGCTGGCCACCGTGCATGTGACCTCGCACCCCCGCAAGACATGGCCCGAGTTCGAGC
ACAACGTCATGACCCGCTGCAATGTGCACCTGGGCTCCCGCCGAGGCATGTTCATGCCCTACCAGTGCAA
CATGCAATTTGTGAAGGTGCTGCTGGAGCCCGATGCCATGTCCAGAGTGAGCCTGACGGGGGTGTTTGAC
ATGAATGTGGAGATGTGGAAAATTCTGAGATATGATGAATCAAGACCAGGTGCCGGGCCTGCAATGCG
GAGGCAAGCACGCCAGGCTTCAGCCCGTGTGTGTGGAGGTGACGGAGGACCTGCGACCCGATCATTTGGT |

-continued

| DESCRIPTION OF THE SEQUENCES |
|---|
| GTTGTCCTGCAACGGGACGGAGTTCGGCTCCAGCGGGGAAGAATCTGACTAGAGTGAGTAGTGTTTGGGG |
| GAGGTGGAGGGCCTGGATGAGGGGCAGAATGACTAAAATCTGTGTTTTTCTGCGCAGCAGCATGAGCGGA |
| AGCGCCTCCTTTGAGGGAGGGGTATTCAGCCCTTATCTGACGGGGCGTCTCCCCTCCTGGGCGGGAGTGC |
| GTCAGAATGTGATGGGATCCACGGTGGACGGCCGGCCCGTGCAGCCCGCGAACTCTTCAACCCTGACCTA |
| CGCGACCCTGAGCTCCTCGTCGTGGACGCAGCTGCCGCCGCAGCTGCTGCTTCCGCCGCCAGCGCCGTG |
| CGCGGAATGGCCCTGGGCGCCGGCTACTACAGCTCTCTGGTGGCCAACTCGAGTTCCACCAATAATCCCG |
| CCAGCCTGAACGAGGAGAAGCTGCTGCTGCTGATGGCCCAGCTCGAGGCCCTGACCCAGCGCCTGGGCGA |
| GCTGACCCAGCAGGTTGCTCAGCTGCAGGCGGAGACGCGGGCCGCGGTTGCCACGGTGAAAACCAAATAA |
| AAAATGAATCAATAAATAAACGGAGACGGTTGTTGATTTTAACACAGAGTCTTGAATCTTTATTTGATTT |
| TTCGCGCGCGGTAGGCCCTGGACCACCGGTCTCGATCATTGAGCACCCGGTGGATCTTTTCCAGGACCCG |
| GTAGAGGTGGGCTTGGATGTTGAGGTACATGGGCATGAGCCCGTCCCGGGGGTGGAGGTAGCTCCATTGC |
| AGGGCCTCGTGCTCGGGGGTGGTGTTGTAAATCACCCAGTCATAGCAGGGGCGCAGGGCGTGGTGCTGCA |
| CGATGTCCTTGAGGAGGAGACTGATGGCCACGGGCAGCCCCTTGGTGTAGGTGTTGACGAACCTGTTGAG |
| CTGGGAGGGATGCATGCGGGGGGAGATGAGATGCATCTTGGCCTGGATCTTGAGATTGGCGATGTTCCCG |
| CCCAGATCCCGCCGGGGGTTCATGTTGTGCAGGACCACCGGCACGGTGTATCCGGTGCACTTGGGGAATT |
| TGTCATGCAACTTGGAAGGGAAGGCGTGAAAGAATTTGGAGACGCCCTTGTGGCCGCCCAGGTTTTCCAT |
| GCACTCATCCATGATGATGGCGATGGGCCCGTGGGCGGCGGCCTGGGCAAAGACGTTTCGGGGGTCGGAC |
| ACATCGTAGTTGTGGTCCTGGGTGAGCTCGTCATAGGCCATTTTAATGAATTTGGGGCGGAGGGTGCCCG |
| ACTGGGGGACGAAGGTGCCCTCGATCCCGGGGGCGTAGTTGCCCTCGCAGATCTGCATCTCCCAGGCCTT |
| GAGCTCGGAGGGGGGATCATGTCCACCTGCGGGGCGATGAAAAAACGGTTTCCGGGGCGGGGGAGATG |
| AGCTGCGCCGAAAGCAGGTTCCGGAGCAGCTGGGACTTGCCGCAGCCGGTGGGGCCGTAGATGACCCCGA |
| TGACCGGCTGCAGGTGGTAGTTGAGGGAGAGACAGCTGCCGTCCTCGCGGAGGAGGGGGCCACCTCGTT |
| CATCATCTCGCGCACATGCATGTTCTCGCGCACGAGTTCCGCCAGGAGGCGCTCGCCCCCAGCGAGAGG |
| AGCTCTTGCAGCGAGGCGAAGTTTTCAGCGGCTTGAGCCCGTCGGCCATGGGCATTTTGGAGAGGGTCT |
| GTTGCAAGAGTTCCAGACGGTCCCAGAGCTCGGTGATGTGCTCTAGGGCATCTCGATCCAGCAGACCTCC |
| TCGTTTCGCGGGTTGGGCGACTGCGGGAGTAGGGCACCAGGCGATGGGCGTCCAGCGAGGCCAGGGTCC |
| GGTCCTTCCAGGGTCGCAGGGTCCGCGTCAGCGTGGTCTCCGTCACGGTGAAGGGGTGCGCGCCGGGCTG |
| GGCGCTTGCGAGGGTGCGCTTCAGGCTCATCCGGCTGGTCGGAGCACCGCTCCCGGTCGGCGCCCTGTGCG |
| TCGGCCAGGTAGCAATTGAGCATGAGTTCGTAGTTGAGCGCCTCGGCGCGTGGCCCTTGGCGCGGAGCT |
| TACCTTTGGAAGTGTGTCCGCAGACGGGACAGAGGAGGGACTTGAGGGCGTAGAGCTTGGGGGCGAGGAA |
| GACGGACTCGGGGGCGTAGGCGTCCGCGCCGCAGCTGGCGCAGACGGTCTCGCACTCCACGAGCCAGGTG |
| AGGTCGGGGCGGTCGGGGTCAAAAACGAGGTTTCCTCCGTGCTTTTTGATGCGTTTCTTACCTCTGGTCT |
| CCATGAGCTCGTGTCCCCGCTGGGTGACAAAGAGGCTGTCCGTGTCCCCGTAGACCGACTTTATGGGCCG |
| GTCCTCGAGCGGGGTGCCGCGGTCCTCGTCGTAGAGGAACCCCGCCCACTCCGAGACGAAGGCCCGGGTC |
| CAGGCCAGCACGAAGGAGGCCACGTGGGAGGGGTAGCGGTCGTTGTCCACCAGCGGGTCCACCTTCTCCA |
| GGGTATGCAAGCACATGTCCCCCTCGTCCACATCCAGGAAGGTGATTGGCTTGTAAGTGTAGGCCACGTG |
| ACCGGGGGTCCCGGCCGGGGGGGTATAAAAGGGGGCGGGCCCCTGCTCGTCCTCACTGTCTTCCGGATCG |
| CTGTCCAGGAGCGCCAGCTGTTGGGGTAGGTATTCCCTCTCGAAGGCGGGCATGACCTCGGCACTCAGGT |
| TGTCAGTTTCTAGAAACGAGGAGGATTTGATATTGACGGTGCCGTTGGAGACGCCTTTCATGAGCCCCTC |
| GTCCATCTGGTCAGAAAAGACGATCTTTTTGTTGTCGAGCTTGGTGGCGAAGGAGCCGTAGAGGGCGTTG |
| GAGAGCAGCTTGGCGATGGAGCGCATGGTCTGGTTCTTTTCCTTGTCGGCGCGCTCCTTGGCGGCGATGT |
| TGAGCTGCACGTACTCGCGCGCCACGCACTTCCATTCGGGGAAGACGGTGGTGAGCTCGTCGGGCACGAT |
| TCTGACCCGCCAGCCGCGGTTGTGCAGGGTGATGAGGTCCACGCTGGTGGCCACCTCGCCGCGCAGGGGC |
| TCGTTGGTCCAGCAGAGGCGCCCGCCCTTGCGCGAGCAGAAGGGGGGCAGCGGGTCCAGCATGAGCTCGT |
| CGGGGGGGTCGGCGTCCACGGTGAAGATGCCGGGCAGGAGCTCGGGGGTCGAAGTAGCTGATGCAGGTGCC |
| CAGATCGTCCAGCGCCGCTTGCCAGTCGCGCACGGCCAGCGCGCGCTCGTAGGGGCTGAGGGGCGTGCCC |
| CAGGGCATGGGGTGCGTGAGCGCGGAGGCGTACATGCCGCAGATGTCGTAGACGTAGAGGGGCTCCTCGA |
| GGACGCCGATGTAGGTGGGGTAGCAGCGCCCCCCGCGGATGCTGGCGCGCACGTAGTCGTACAGCTCGTG |
| CGAGGGCGCGAGGAGCCCCGTGCCGAGGTTGGAGCGTTGCGGCTTTTCGGCGCGGTAGACGATCTGGCGG |
| AAGATGGCGTGGGAGTTGGAGGAGATGGTGGGCCTCTGGAAGATGTTGAAGTGGGCGTGGGGCAGGCCGA |
| CCGAGTCCTGATGAAGTGGGCGTAGGAGTCCTGCAGCTTGGCGACGAGCTCGGCGGTGACGAGGACGTC |
| CAGGGCGCAGTAGTCGAGGGTCTCTTGGATGATGTCGTACTTGAGCTGGCCCTTCTGCTTCCACAGCTCG |
| CGGTTGAGAAGGAACTCTTCGCGGTTCCTTCCAGTACTCTTCGAGGGGGGAACCCGTCCTGATCGGCACGGT |
| AAGAGCCCACCATGTAGAACTGGTTGACGGCCTTGTAGGCGCAGCAGCCCTTCTCCACGGGGAGGGCGTA |
| AGCTTGCGCGGCCTTGCGCAGGGAGGTGTGGGTGAGGGCGAAGGTGTCGCGCACCATGACTTTGAGGAAC |
| TGGTGCTTGAAGTCGAGGTCGTCGCAGCCGCCCTGCTCCCAGAGTTGGAAGTCCGTGCGCTTCTTGTAGG |
| CGGGGTTGGGCAAAGCGAAAGTAACATCGTTGAAGAGGATCTTGCCCGCGCGGGGCATGAAGTTGCGAGT |
| GATGCGGAAAGGCTGGGGCACCTCGGCCCGGTTGTTGATGACCTGGGCGGCGAGGACGATCTCGTCGAAG |
| CCGTTGATGTTGTGCCCGACGATGTAGAGTTCCACGAATCGCGGGCAGCCCTTGACGTGGGGCAGCTTCT |
| TGAGCTCGTCGTAGGTGAGCTCGGCGGGTCGCTGAGCCCGTGCTGCTCGAGGGCCAGTCGGCGACGTG |
| GGGGTTGGCGCTGAGGAAGGAAGTCCAGAGATCCACGGCCAGGGCGGTCTGCAAGCGGTCCCGGTACTGA |
| CGGAACTGCTGGCCCACGGCCATTTTTTCGGGGGTGACGCAGTAGAAGGTGCGGGGGTCGCCGTGCCAGC |
| GGTCCCACTTGAGTTGGAGGGCGAGGTCGTGGGCGAGCTCGACGAGCGGCGGGTCCCCGGAGAGTTTCAT |
| GACCAGCATGAAGGGGACGAGCTGCTTGCCGAAGGACCCCATCCAGGTGTAGGTTTCCACATCGTAGGTG |
| AGGAAGAGCCTTTCGGTGCGAGGATGCGAGCCGATGGGAAGAACTGGATCTCCTGCCACCAGTTGGAGG |
| AATGGCTGTTGATGTGATGAAGTAGAAATGCCGACGGCGCGCCGAGCACTCGTGCTTGTGTTTATACAA |
| GCGTCCGCAGTGCTCGCAACGCTGCACGGGATGCACGTGTGCACGAGCTGTACCTGGGTTCCTTTGACG |
| AGGAATTTCAGTGGGCAGTGGAGCGCTGGCGCTGCATCTGGTGCTGTACTACGTCCTGGCCATCGGCGT |
| GGCCATCGTCTGCCTCGATGGTGGTCATGCTGACGAGCCCGCGCGGGAGGCAGGTCCAGACCTCGGCTCG |
| GACGGGTCGGAGAGCGAGGACGAGGGCGCGCAGGCCGGAGCTGTCCAGGGTCCTGAGACGCTGCGGAGTC |
| AGGTCAGTGGGCAGCGGCGGCGCGCGGTTGACTTGCAGGAGCTTTTCCAGGGCGCGCGGGAGGTCCAGAT |
| GGTACTTGATCTCCACGGCGCCGTTGGTGGCGACGTCCACGGCTTGCAGGGTCCGTGCCCCTGGGGCGC |
| CACCACCGTGCCCCGTTTCTTCTTGGGCGGCGGCGGCTCCATGCTTAGAAGCGGCGGCGAGGACGCGCGC |
| CGGGCGGCAGGGGCGGCTCGGGGCCCGGAGGCAGGGGCGGCAGGGGCACGTCGGCCGCGCGCGGGCAG |
| GTTCTGGTACTGCGCCCGGAGAAGACTGGCGTGAGCGACGACGCGACGGTTGACGTCCTGGATCTGACGC |
| CTCTGGGTGAAGGCCACGGGACCCGTGAGTTTGAACCTGAAAGAGAGTTCGACAGAATCAATTTCGGTAT |
| CGTTGACGGCGGCCTGCCGCAGGATCTCTTGCACGTCGCCCGAGTTGTCCTGGTAGGCGATCTCGGTCAT |

| DESCRIPTION OF THE SEQUENCES |
|---|
| GAACTGCTCGATCTCCTCCTCCTGAAGGTCTCCGCGGCCGGCGCGCTCGACGGTGGCCGCGAGGTCGTTG |
| GAGATGCGGCCCATGAGCTGCGAGAAGGCGTTCATGCCGGCCTCGTTCCAGACGCGGCTGTAGACCACGG |
| CTCCGTTGGGGTCGCGCGCGCGCATGACCACCTGGGCGAGGTTAAGCTCGACGTGGCGCGTGAAGACCGC |
| GTAGTTGCAGAGGCGCTGGTAGAGGTAGTTGAGCGTGGTGGCGATGTGCTCGGTGACGAAGAAGTACATG |
| ATCCAGCGGCGGAGCGGCATCTCGCTGACGTCGCCCAGGGCTTCCAAGCGCTCCATGGTCTCGTAGAAGT |
| CCACGGCGAAGTTGAAAAACTGGGAGTTGCGCGCCGAGACGGTCAACTCCTCCTCCAGAAGACGGATGAG |
| CTCGGCGATGGTGGCGCGCACCTCGCGCTCGAAGGCCCCGGGGGGCTCCTCTTCTTCCATCTCCTCCTCC |
| TCTTCCTCCTCCACTAACATCTCTTCTACTTCCTCCTCAGGAGGCGGCGGCGGGGAGGGGCCCTGCGTC |
| GCCGGCGGCGCACGGGCAGACGGTCGATGAAGCGCTCGATGGTCTCCCCGCGCCGGCGACGCATGGTCTC |
| GGTGACGGCGCGCCCGTCCTCGCGGGGCCGCAGCGTGAAGACGCCGCCGCGCATCTCCAGGTGGCCGCCG |
| GGGGGGTCTCCGTTGGGCAGGGAGAGGGCGCTGACGATGCATCTTATCAATTGGCCCGTAGGGACTCCGC |
| GCAAGGACCTGAGCGTCTCGAGATCCACGGGATCCGAAAACCGCTGAACGAAGGCTTCGAGCCAGTCGCA |
| GTCGCAAGGTAGGCTGAGCCCGGTTTCTTGTTCTTGGGTATTTGGTCGGGAGGCGGGCGGGCGATGCTG |
| CTGGTGATGAAGTTGAAGTAGGCGGTCCTGAGACGGCGGATGGTGGCGAGGAGCACCAGGTCCTTGGGCC |
| CGGCTTGCTGGATGCGCAGACGGTCGGCCATGCCCCAGGCGTGGTCCTGACACCTGGCGAGGTCCTTGTA |
| GTAGTCCTGCATGAGCCGCTCTACGGGCACGTCCTCCTCGCCCGCGCGGCCGTGCATGCGCGTGAGCCCG |
| AACCCGCGCTGCGGCTGGACGAGCGCCAGGTCGGCGACGACGCGCTCGGCGAGGATGGCCTGCTGGATCT |
| GGGTGAGGGTGGTCTGGAAGTCGTCGAAGTCGACGAAGCGGTGGTAGGCTCCGGTGTTGATGGTGTAGGA |
| GCAGTTGGCCATGACGGACCAGTTGACGGTCTGGTGGCCGGGCGCACGAGCTCGTGGTACTTGAGGCGC |
| GAGTAGGCGCGCGTGTCGAAGATGTAGTCGTTGCAGGTGCGCACGAGGTACTGGTATCCGACGAGGAAGT |
| GCGGCGGCGGCTGGCGGTAGAGCGGCCATCGCTCGGTGGCGGGGGCGCCGGGCGCGAGGTCCTCGAGCAT |
| GAGGCGGTGGTAGCCGTAGATGTACCTGGACATCCAGGTGATGCCGGCGGCGGTGGTGGAGGCGCGCGGG |
| AACTCGCGGACGCGGTTCCAGATGTTGCGCAGCGGCAGGAAGTAGTTCATGGTGGCCGCGGTCTGGCCCG |
| TGAGGCGCGCGCAGTCGTGGATGCTCTAGACATACGGGCAAAAACGAAAGCGGTCAGCGGCTCGACTCCG |
| TGGCCTGGAGGCTAAGCGAACGGGTTGGGCTGCGCGTGTACCCCGGTTCGAATCTCGAATCAGGCTGGAG |
| CCGCAGCTAACGTGGTACTGGCACTCCCGTCTCGACCCAAGCCTGCTAACGAAACCTCCAGGATACGGAG |
| GCGGGTCGTTTTTTGGCCTTGGTCGCTGGTCATGAAAAACTAGTAAGCGCGGAAAGCGGCCGCCCGCGAT |
| GGCTCGCTGCCGTAGTCTGGAGAAAGAATCGCCAGGGTTGCGTTGCGGTGTGCCCCGGTTCGAGCCTCAG |
| CGCTCGGTGCCGGCCGGATTCCGCGGCTAACGTGGGCGTGGCTGCCCCGTCGTTTCCAAGACCCCTTAGC |
| CAGCCGACTTCTCCAGTTACGGAGCGAGCCCCTCTTTTTCTTGTGTTTTTGCCAGATGCATCCCGTACTG |
| CGGCAGATGCGCCCCCACCCTCCACCACAACCGCCCCTACCGCAGCAGCAGCAACAGCCGGCGCTTCTGC |
| CCCCGCCCCAGCAGCAGCAGCCAGCCATCACCGCGGCGGCCGCCGTGAGCGAGCCGGCGTTCAGTATGA |
| CCTGGCCTTGGAAGAGGGCGAGGGGCTGGCGCGGCTGGGGGCGTCGTCGCCGGAGCGGCACCCGCGCGTG |
| CAGATGAAAAGGGACGCTCGCGAGGCCTACGTGCCCAAGCAGAACCTGTTCAGAGACAGGAGCGGCGAGG |
| AGCCCGAGGAGATGCGCGCCTCCCGCTTCCACGCGGGGCGGGAGCTGCGGCGCGGCCTGGACCGAAAGCG |
| GGTGCTGAGGGACGAGGATTTCGAGGCGGACGAGCTGACGGGGATCAGCCCCGCGCGCGCGCACGTGGCC |
| GCGGCCAACCTGGTCACGGCGTACGAGCAGACCGTGAAGGAGGAGAGCAACTTTCAAAAATCCTTCAACA |
| ACCACGTGCGCACGCTGATCGCGCGCGAGGAGGTGACCCTGGGCCTGATGCACCTGTGGGACCTGCTGGA |
| GGCCATCGTGCAGAACCCCACGAGCAAGCCGCTGACGGCGCAGCTGTTTCTGGTGGTGCAGCACAGTCGG |
| GACAACGAGACGTTCAGGGAGGCGCTGCTGAATATCACCGAGCCCGTGGACCGCGCTGGCTCCTGGACCTGG |
| TGAACATTCTGCAGAGCATCGTGGTGCAGGAGCGCGGGCTGCCGCTGTCCGGAAGCTGGCGGCCGCATCAA |
| CTTCTCGGTGCTGAGCCTGGGCAAGTACTACGCTAGGAAGATCTACAAGACCCCGTACGTGCCCATAGAC |
| AAGGAGGTGAAGATCGACGGGTTTTACATGCGCATGACCCTGAAAGTGCTGACCCTGAGCGACGATCTGG |
| GGGTGTACCGCAACGACAGGATGCACCGCGCGGTGAGCGCCAGCCGCCGGCGCGAGCTGAGCGACCAGGA |
| GCTGATGCACAGCCTGCAGCGGGCCCTGACCGGGGCCGGGACCGAGGGGGAGAGCTACTTTGACATGGGC |
| GCGGACCTGCGCTGGCAGCCCAGCCGCCGGGCCTTGGAAGCTGCCGGCGGCGTGCCCTACGTGGAGGAGG |
| TGGACGATGAGGAGGAGGAGGGCGAGTACCTGGAAGACTGATGGCGCGACCGTATTTTTGCTAGATGCAG |
| CAACAGCCACCGCCGCCTCCTGATCCCGCGATGCGGGCGGCGCTGCAGAGCCAGCCGTCCGGCATTAACT |
| CCTCGGACGATTGGACCCAGGCCATGCAACGCATCATGGCGCTGACGAAGCCTGACAATCCCGAAGCCTTTAG |
| ACAGCAGCCTCAGGCCAACCGGCTCTCGGCCATCCTGGAGGCCGTGGTGCCCTCGCGCTCGAACCCCACG |
| CACGAGAAGGTGCTGGCCATCGTGAACGCGCTGGTGGAGAACAAGGCCATCGCGGCGACGAGGCCGGGC |
| TGGTGTACAACGCGCTGCTGGAGCGCGTGGCCCGCTACAACAGCACCAACGTGCAGACGAACCTGGACCG |
| CATGGTGACCGACGTGCGCGAGGCGGTGTCGCAGCGCGAGCGGTTCCACCGCGAGTCGAACCTGGGCTCC |
| ATGGTGGCGCTGAACGCCTTCCTGAGCACGCAGCCCGCCAACGTGCCCCGGGGCCAGGAGGACTACACCA |
| ACTTCATCAGCGCGCTGCGGCTGATGGTGGCCGAGGTGCCCCAGAGCGAGGTGTACCAGTCGGGCCGGA |
| CTACTTCTTCCAGACCAGTCGCCAGGGCTTGCAGACCGTGAACCTGAGCCAGGCTTTCAAGAACTTGCAG |
| GGACTGTGGGGCGTGCAGGCCCCGGTCGGGGACCGCGGCGCAGCTGTCGAGCCTGCTGACGCCGAACTCGC |
| GCCTGCTGCTGCTGCTGGTGGCGCCCTTCACGGACAGCGGCAGCGTGAGCGCGACTCGTACCTGGGCTA |
| CCTGCTTAACCTGTACCGCGAGGCCATCGGGCAGGCGCACGTGGACGAGCAGACCTACCAGGAGATCACC |
| CACGTGAGCCGCGCGCTGGGCCAGGAGGACCCGGGCAACCTGGAGGCCACCCTGAACTTCCTGCTGACCA |
| ACCGGTCGCAGAAGATCCCGCCCCAGTACGCGCTGACGCACCGAGGAGGAGCGCATCCTGCGCTACGTGCA |
| GCAGAGCGTGGGCTGTTCCTGATGCAGGAGGGGCCACGCCCAGCGCCGCGCTCGACATGCGCGCGCGC |
| AACATGGAGCCCAGCATGTACGCCCGCAACCGCCCGTTCATCAATAAGCTGATGGACTACTTGCATCGGG |
| CGGCCGCCATGAACTCGGACTACTTTACCAACGCCATCTTGAACCCGCACTGGCTCCCGCCGCCCGGGTT |
| CTACACGGGCGAGTACGACATGCCCGACCCCAACGACGGGTTCCTGTGGGATGACGTGGACAGCAGCGTG |
| TTCTCGCCGCGTCCCACCACCACCGTGTGGAAGAAAGAGGGCGGGGACCGGCGGCCGTCCTCGGCGCTGT |
| CCGGTCGCGCGGGTGCTGCCGCGGCGGTGCCCGAGGCCGCCAGCCCCTTCCGAGCCTGCCCTTTTCGCT |
| GAACAGCGTGCGCAGCAGCGAGCTGGGTCGGCTGACGCGGCCGCGCCTGCTGGGCGAGGAGGAGTACCTG |
| AACGACTCCTTGTTGAGGCCCGAGCGCGAAAAGAACTTCCCCAATAACGGGATAGAGAGCCTGGTGGACA |
| AGATGAGCCGCTGGAAGACGTACGCGCACGAGCACAGGGACGAGCCCCGAGCTAGCAGCGCAGGCACCCG |
| TAGACGCCAGCGGCACGACAGGCAGCGGGGTCTGGTGTGGGACGATGAGGATTCCGCCGACAGCGAGCGC |
| GTGTTGGACTTGGGTGGGAGTGGTGGTGGTAACCCGTTCGCTCACTTGCGCCCCCGTATCGGCGCCTGA |
| TGTAAGAATCTGAAAAATAAAAAACGGTACTCACCAAGGCCATGGCGACCAGCGTGCGTTCTTCTCTGTT |
| GTTTGTAGTAGTATGATGAGGCGCGTGTACCCGGAGGGTCCTCCTCCCTCGTACGAGAGCGTGATGCAGC |
| AGGCGGTGGCGGCGGCGATGCAGCCCCGCTGGAGGCGCCTTACGTGCCCCGCGGTACCTGGCGCCTAC |
| GGAGGGGCGGAACAGCATTCGTTACTCGGAGCTGGCACCCTTGTACGATACCACCCGGTTGTACCTGGTG |
| GACAACAAGTCGGCGGACATCGCCTCGCTGAACTACCAGAACGACCACAGCAACTTCCTGACCACCGTGG |

DESCRIPTION OF THE SEQUENCES

```
TGCAGAACAACGATTTCACCCCCACGGAGGCCAGCACCCAGACCATCAACTTTGACGAGCGCTCGCGGTG
GGGCGGCCAGCTGAAAACCATCATGCACACCAACATGCCCAACGTGAACGAGTTCATGTACAGCAACAAG
TTCAAGGCGCGGGTGATGGTCTCGCGCAAGACCCCCAACGGGGTCACAGTAACAGATGGTAGTCAGGACG
AGCTGACCTACGAGTGGGTGGAGTTTGAGCTGCCCGAGGGCAACTTCTCGGTGACCATGACCATCGATCT
GATGAACAACGCCATCATCGACAACTACTTGGCGGTGGGGCGGCAGAACGGGGTGCTGGAGAGCGACATC
GGCGTGAAGTTCGACACGCGCAACTTCCGGCTGGGCTGGGACCCCGTGACCGAGCTGGTGATGCCGGGCG
TGTACACCAACGAGGCCTTCCACCCCGACATCGTCCTGCTGCCCGGCTGCGGCGTGGACTTCACCGAGAG
CCGCCTCAGCAACCTGCTGGGCATCCGCAAGCGGCAGCCCTTCCAGGAGGGCTTCCAGATCCTGTACGAG
GACCTGGAGGGGGGCAACATCCCCGCGCTCTTGGATGTCGAAGCCTACGAGAAAAGCAAGGAGGATAGCA
CCGCCGTGGCTACCGCCGCGACTGTGGCAGATGCCACTGTCACCAGGGGCGATACATTCGCCACCCAGGC
GGAGGAAGCAGCCGCCCTAGCGGCGACCGATGATAGTGAAAGTAAGATAGTTATCAAGCCGGTGGAGAAG
GACAGCAAGGACAGGAGCTACAACGTTCTATCGGATGGAAAGAACACCGCCTACCGCAGCTGGTACCTGG
CCTACAACTACGGCGACCCCGAGAAGGGCGTGCGCTCCTGGACGCTGCTCACCACCTCGGACGTCACCTG
CGGCGTGGAGCAAGTCTACTGGTCGCTGCCCGACATGATGCAAGACCCGGTCACCTTCCGCTCCACGCGT
CAAGTTAGCAACTACCCGGTGGTGGGCGCCGAGCTCCTGCCCGTCTACTCCAAGAGCTTCTTCAACGAGC
AGGCCGTCTACTCGCAGCAGCTGCGCGCCTTCACCTCGCTCACGCACGTCTTCAACCGCTTCCCCGAGAA
CCAGATCCTCGTCCGCCCGCCCGCGCCCACCATTACCACCGTCAGTGAAAACGTTCCTGCTCTCACAGAT
CACGGGACCCTGCCGCTGCGCAGCAGTATCCGGGGAGTCCAGCGCGTGACCGTCACTGACGCCAGACGCC
GCACCTGCCCCTACGTCTACAAGGCCCTGGGCGTAGTCGCGCGCGCGTCCTCTCGAGCCGCACCTTCTA
AAAAATGTCCATTCTCATCTCGCCCAGTAATAACACCGGTTGGGGCCTGCGCGCCCAGCAAGATGTAC
GGAGGCGCTCGCCAACGCTCCACGCAACACCCCGTGCGCGTGCGCGGGCACTTCCGCGCTCCCTGGGGCG
CCCTCAAGGGTCGCGTGCGCTCGCGCACCACCGTCGACGACGTGATCGACCAGGTGGTGGCCGACGCGCG
CAACTACACGCCCGCCGCCGCGCCCGCCTCCACCGTGGACGCCGTCATCGACAGCGTGGTGGCCGACGCG
CGCCGGTACGCCCGCGCCAAGAGCCGGCGGCGGCGCATCGCCCGGCGGCACCGGAGCCACCCCCGCCATGC
GCGCGGCGCGAGCCTTGCTGCGCAGGGCCAGGCGCACGGGACGCAGGGCCATGCTCAGGGCGGCCAGACG
CGCGGCCTCCGGCAGCAGCAGCGCCGGCAGGACCCGCAGACGCGCGGCCACGGCGGCGGCGGCGGCCATC
GCCAGCATGTCCCGCCCGCGGCGCGGCAACGTGTACTGGGTGCGCGACGCCGCCACCGGTGTGCGCGTGC
CCGTGCGCACCCGCCCCCCTCGCACTTGAAGATGCTGACTTCGCGATGTTGATGTGTCCCAGCGGCGAGG
AGGATGTCCAAGCGCAAATACAAGGAAGAGATGCTCCAGGTCATCGCGCCTGAGATCTACGGCCCCGCGG
CGGCGGTGAAGGAGGAAAGAAAGCCCCGCAAACTGAAGCGGGTCAAAAAGGACAAAAAGGAGGAGGAAGA
TGTGGACGGACTGGTGGAGTTTGTGCGCGAGTTCGCCCCCCGGCGGCGCGTGCAGTGGCGCGGGCGGAAA
GTGAAACCGGTGCTGCGGCCCGGCACCACGGTGGTCTTCACGCCCGGCGAGCGTTCCGGCTCCGCCTCCA
AGCGCTCCTACGACGAGGTGTACGGGACGAGGACATCCTCGAGCAGGCGGCCGAGCGTCTGGGCGAGTT
TGCTTACGGCAAGCGCAGCCGCCCCGCGCCCTTGAAAGAGGAGGCGGTGTCCATCCCGCTGGACCACGGC
AACCCCACGCCGAGCCTGAAGCCGGTGACCCTGCAGCAGGTGCTGCCGAGCGCGGCGCCGCGCCGGGGCT
TCAAGCGCGAGGGCGGCGAGGATCTGTACCCGACCATGCGCTGATGGTGCCCAAGCGCCAGAAGCTGGA
GGACGTGCTGGAGCACATGAAGGTGGACCCCGAGGTGCAGCCCGAGGTCAAGGTGCGGCCCATCAAGCAG
GTGGCCCCGGGCCTGGGCGTGCAGACCGTGGACATCAAGATCCCCACGGAGCCCATGGAAACGCAGACCG
AGCCCGTGAAGCCCAGCACCAGCACCATGGAGGTGCAGACGGATCCCTGGATGCCGGCGCCGGCTTCCAC
CACCACTCGCCGAAGACGCAAGTACGGCGCGGCCAGCCTGCTGATGCCCAACTACGCGCTGCATCCTTCC
ATCATCCCACGCCGGGCTACCGCGGCACGCGCTTCTACCGCGGCTACAGCAGCCGCCGCAAGACCACCA
CCCGCCGCCGCCGTCGCCGCACCCGCCGCAGCACCACCGCGACTTCCGCCGCCGCCTTGGTGCGGAGAGT
GTACCGCAGCGGGCGTGAGCCTCTGACCCTGCCGCGCGCGCGCTACCACCCGAGCATCGCCATTTAACTC
TGCCGTCGCCTCCTTGCAGATATGGCCCTCACATGCCGCTCCGCGTCCCCATTACGGGCTACCGAGGAA
GAAAGCCGCGCCGTAGAAGGCTGACGGGGAACGGGCTGCGTCGCCATCACCACCGGCGGCGGCGCGCCAT
CAGCAAGCGGTTGGGGGGAGGCTTCCTGCCCGCGCTGATCCCCATCATCGCCGCGGCGATCGGGGCGATC
CCCGGCATAGCTTCCGTGGCGGTGCAGGCCTCTCAGCGCCACTGAGACACAGCTTGGAAAATTTGTAATA
AAAAAATGGACTGACGCTCCTGGTCCTGTGATGTGTGTTTTTAGATGGAAGACATCAATTTTTCGTCCCT
GGCACCGCGACACGGCACGCGGCCGTTTATGGGCACCTGGAGCGACATCGGCAACAGCCAACTGAACGGG
GGCGCCTTCAATTGGAGCAGTCTCTGGAGCGGGCTTAAGAATTTCGGGTCCACGCTCAAAACCTATGGCA
ACAAGGCGTGGAACAGCAGCACAGGGCAGGCGCTGAGGGAAAAGCTGAAAGAGCAGAACTTCCAGCAGAA
GGTGGTCGATGGCCTGGCCTCGGGCATCAACGGGGTGGTGGACCTGGCCAACCAGGCCGTGCAGAAACAG
ATCAACAGCCGCCTGGACGCGGTCCCGCCCGCGGGGTCCGTGGAGATGCCCCAGGTGGAGGAGGAGCTGC
CTCCCCTGGACAAGCGCGGCGACAAGCGACCGCGTCCCGACGCGGAGGAGACGCTGCTGACGCACACGGA
CGAGCCGCCCCCGTACGAGGAGGCGGTGAAACTGGGTCTGCCCACCACGCGGCCCGTGGCGCCTCTGGCC
ACCGGGGTGCTGAAACCCAGCAGCAGCAGCAGCCAGCCCGCGACCCTGGACTTGCCTCCACCTCGCCCCT
CCACAGTGGCTAAGCCCCTGCCGCCGGTGGCCGTCGCGTCGCGCGCCCCCCGAGGCCGCCCCCAGGCGAA
CTGGCAGAGCACTCTGAACAGCATCGTGGGTCTGGGAGTGCAGAGTGTGAAGCGCCGCCGCTGCTATTAA
AAGACACTGTAGCGCTTAACTTGCTTGTCTGTGTATATGTATGTCCGCCGACCAGAAGGAGGAGGAAG
AGGCGCGTCGCCGAGTTGCAAGATGGCCACCCCATCGATGCTGCCCCAGTGGGCGTACATGCACATCGCC
GGACAGGACGCTTCGGAGTACCTGAGTCCGGGTCTGGTGCAGTTCGCCGGCGCCACAGACACCTACTTCA
GTCTGGGGAACAAGTTTAGGAACCCCACGGTGGCACCCACGCACGATGTGACCACCGACCGCAGCCAGCG
GCTGACGCTGCGCTTCGTGCCCGTGGACCGCGAGGACAACACCTACTCGTACAAAGTGCGCTACACGCTG
GCCGTGGGCGACAACCGCGTGCTGGACATGGCCAGCACCTACTTTGACATCCGCGGCGTGCTGGATCGGG
GCCCCAGCTTCAAACCCTACTCCGGCACCGCCTACAACAGCCTGGCTCCCAAGGGAGCGCCCAACACCTC
ACAGTGGATAACCAAAGACAATGGAACTGATAAGCACATACAGTTTTGGAAATGCTCCAGTCAGAGGATTG
GACATTACAGAAGAGGGTCTCCAAATAGGAACCGATGAGTCAGGGGGTGAAAGCAAGAAAATTTTTGCAG
ACAAAAACCTATCAGCCTGAACCTCAGCTTGGAGATGAGGAATGGCATGATACTATTGGAGCTGAAGACAA
GTATGGAGGCAGAGCGCTTAAACCTGCCACCAACATGAAACCCTGCTATGGGTCTTTCGCCAAGCCAACT
AATGCTAAGGGAGGTCAGGCTAAAAGCAGAACCAAGGACGATGGCACTACTGAGCCTGATATTGACATGG
CCTTCTTTGACGATCGCAGTCAGCAAGCTAGTTTCAGTCCAGAACTTGTTTTGTATACTGAGAATGTCGA
TCTGGACACCCCGGATACCCACATTATTTACAAACCTGGCACTGATGAAACAAGTTCTTCTTTCAACTTG
GGTCAGCAGTCCATGCCCAACAGACCCAACTACATTGGCTTCAGAGACAACTTTATCGGGCTCATGTACT
ACAACAGCACTGGCAATATGGGTGTACTGGCCGGTCAGGCCTCCCAGCTGAATGCTGTGGTGGACTTGCA
GGACAGAAACACTGAACTGTCCTACCAGCTCTTGCTTGACTCTCTGGGTGACAGAACCAGGTATTTCAGT
ATGTGGAATCAGGCGGTGGACAGCTATGACCCCGATGTGCGCATTATTGAAAATCACGGTGTGGAGGATG
AACTCCCCAACTATTGCTTCCCTTTGAATGGTGTGGGCTTTACAGATACATTCCAGGGAATTAAGGTTAA
```

| DESCRIPTION OF THE SEQUENCES |
|---|
| AACTACAAATAACGGAACAGCAAATGCTACAGAGTGGGAATCTGATACCTCTGTCAATAATGCTAATGAG |
| ATTGCCAAGGGCAATCCTTTCGCCATGGAGATCAACATCCAGGCCAACCTGTGGCGGAACTTCCTCTACG |
| CGAACGTGGCGCTGTACCTGCCCGACTCCTACAAGTACACGCCGGCCAACATCACGCTGCCCACCAACAC |
| CAACACCTACGATTACATGAACGGCCGCGTGGTGGCGCCCTCGCTGGTGGACGCCTACATCAACATCGGG |
| GCGCGCTGGTCGCTGGACCCCATGGACAACGTCAACCCCTTCAACCACCACCGCAACGCGGGCCTGCGCT |
| ACCGCTCCATGCTCCTGGGCAACGGGCGCTACGTGCCCTTCCACATCCAGGTGCCCCAAAAGTTTTTCGC |
| CATCAAGAGCCTTCCTGCTCCTGCCCGGGTCCTACACCTACGAGTGGAACTTCCGCAAGGACGTCAACATG |
| ATCCTGCAGAGCTCCCTCGGCAACGACCTGCGCACGGACGGGGCCTCCATCGCCTTCACCAGCATCAACC |
| TCTACGCCACCTTCTTCCCCATGGCGCACAACACCGCCTCCACGCTCGAGGCCATGCTGCGCAACGACAC |
| CAACGACCAGTCCTTCAACGACTACCTCTCGGCGGCCAACATGCTCTACCCCATCCCGGCCAACGCCACC |
| AACGTGCCCATCTCCATCCCCTCGCGCAACTGGGCCGCCTTCCGCGGATGGTCCTTCACGCGCCTCAAGA |
| CCCGCGAGACGCCCTCGCTCGGCTCCGGGTTCGACCCCTACTTCGTCTACTCGGGCTCCATCCCCTACCT |
| CGACGGCACCTTCTACCTCAACCACACCTTCAAGAAGGTCTCCATCACCTTCGACTCCTCCGTCAGCTGG |
| CCCGGCAACGACCGCCTCCTGACGCCCAACGAGTTCGAAATCAAGCGCACCGTCGACGGAGAGGGGTACA |
| ACGTGGCCCAGTGCAACATGACCAAGGACTGGTTCCTGGTCCAGATGCTGGCCCACTACAACATCGGCTA |
| CCAGGGCTTCTACGTGCCCGAGGGCTACAAGGACCGCATGTACTCCTTCTTCCGCAACTTCCAGCCCATG |
| AGCCGCCAGGTCGTGGACGAGGTCAACTACAAGGACTACCAGGCCGTCACCCTGGCCTACCAGCACAACA |
| ACTCGGGCTTCGTCGGCTACCTCGCGCCCACCATGCGCCAGGGCCAGCCCTACCCCGCCAACTACCCCTA |
| CCCGCTCATCGGCAAGAGCGCCGTCGCCAGCGTCACCCAGAAAAAGTTCCTCTGCGACCGGGTCATGTGG |
| CGCATCCCCTTCTCCAGCAACTTCATGTCCATGGGCGCTTCCACCGACCTCGGCCAGAACATGCTCTACG |
| CCAACTCCGCCCACGCGCTAGACATGAATTTCGAAGTCGACCCCATGGATGAGTCCACCCTTCTCTATGT |
| TGTCTTCGAAGTCTTCGACGTCGTCCGAGTGCACCAGCCCCACCGCGGCGTCATCGAGGCCGTCTACCTG |
| CGCACGCCCTTCTCGGCCGGCAACGCCACCACCTAAGCCTCTTGCTTCTTGCAAGATGACGGCCTGTGGC |
| TCCGGCGAGCAGGAGCTCAGGGCCATCTCCGCGACCTGGGCTGCGGCCCTACTTCCTGGGCACCTTCG |
| ACAAGCGCTTCCCGGGATTCATGGCCCCGCACAAGCTGGCCTGCGCCATCGTCAACACGGCCGGCCGCGA |
| GACCGGGGGCGAGCACTGGCTGGCCTTCGCCTGGAACCCGCGCACCCACACCTGCTACCTCTTCGACCCC |
| TTCGGGTTCTCGGACGAGCGCCTCAAGCAGATCTACCAGTTCGAGTACGAGGGCCTGCTGCGCCGCAGCG |
| CCCTGGCCACCGAGGACCGCTGCGTCACCCTGGAAAAGTCCACCCAGACCGTGCAGGGTCCGCGCTCGGC |
| CGCCTGCGGGCTCTTCTGCTGCATGTTCCTGCACGCCTTCGTGCACTGGCCCGACCGCCCCATGGACAAG |
| AACCCCACCATGAACTTGCTGACGGGGGTGCCCAACGGCATGCTCCAGTCGCCCCAGGTGGAACCCACCC |
| TGCGCCGCAACCAGGAGGCGCTCTACCGCTTCCTCAACGCCCACTCCGCCTACTTTCGCTCCCACCGCGC |
| GCGCATGGAGAAGGCCACCGCCTTCGACCGCATGAATCAAGACATGTAAACTGTGTGTATGTGAATGCTT |
| TATTCATAATAAACAGCACATGTTTATGCCACCTTCTCTGAGGCTCTGACTTTATTTAGAAATCGAAGGG |
| GTTCTGCCGGCTCTCGGCGTGCCCCGCGGGCAGGGATACGTTGCGGAACTGGTACTTGGGCAGCCACTTG |
| AACTCGGGGATCAGCAGCTTCGGCACGGGGAGGTCGGGGAACGAGTCGCTCCACAGCTTGCGCGTGAGTT |
| GCAGGGCGCCCAGCAGGTCGGGCGCGGATATCTTGAAATCACAGTTGGGACCCGCGTTCTGCGCGCAGAGTTG |
| GTTGCGGTACACGGGGTTGCAGCACTGGAACACCATCAGGGCGGGTGCTTCACGCTCGCCAGCACCGTC |
| GCGTCGGTGATGCCCTCCACGTCCAGATCCTCGGCGTTGGCCATCCCGAAGGGGGTCATCTTGCAGGTCT |
| GCCGCCCATGCTGGGCACGCAGCCGGGCTTGTGGTTGCAATCGCAGTGCAGGGGGATCAGCATCATCTG |
| GGCCTGCTCGGAGCTCATGCCCGGGTACATGGCCTTCATGAAAGCCTCCAGCTGGCGGAAGGCCTGCTGC |
| GCCTTGCCGCCCTCGGTGAAGAAGACCCCGCAGGACTTGCTAGAGAACTGGTTGGTGGCGCAGCCGGCGT |
| CGTGCACGCAGCAGCGCGCGTCGTTGTTGGCCAGCTGCACCACGCTGCGCCCCAGCGGTTCTGGGTGAT |
| CTTGGCCCGGTCGGGGTTCTCCTTCAGCGCGCGCTGCCCGTTCTCGCTCGCCACATCCATCTCGATCGTG |
| TGCTCCTTCTGGATCATCACGGTCCCGTGCAGGCACCGCAGCTTGCCCTCGGCTTCGGTGCATCCGTGCA |
| GCCACAGCGCGCAGCCGGTGCACTCCCAGTTCTTGTGGGCGATCTGGGAGTGCGAGTGCACGAAGCCCTG |
| CAGGAAGCGGCCCATCATCGCGGTCAGGGTCTTGTTGCTGGTGAAGGTCAGCGGGATGCCGCGGTGCTCC |
| TCGTTCACATACAGGTGGCAGATGCGGCGGTACACCTCGCCCTGCTCGGGCATCAGCTGGAAGGCGGACT |
| TCAGGTCGCTCTCCACGCGGTACCGCTCCATCAGCAGCGTCATGACTTCCATGCCCTTCTCCCAGGCCGA |
| AACGATCGGCAGGCTCAGGGGGTTCTTCACCGTTGTCATCTTAGTCGCCGCCGCCAGGTCAGGGGGTCG |
| TTCTCGTCCAGGGTCTCAAACACTCGCTTGCCGTCCTTCTCGGTGATGCGCACGGGGGGAAAGCTGAAGC |
| CCACGGCCGCCAGCTCCTCCTCGGCCTGCCTTTCGTCCTCGCTGTCCTGGCTGATGTCTTGCAAAGGCAC |
| ATGCTTGGTCTTGCGGGGTTTCTTTTTGGGCGGCAGAGGCGGCGGCGGAGACGTGCTGGGCGAGCGCGAG |
| TTCTCGCTCACCACGACTATTTCTTCTTCTTGGCCGTCGTCCGAGACCACGCGGCGGTAGGCATGCCTCT |
| TCTGGGGCAGAGGCGGAGGCGACGGGCTCTCGCGGTTCGGCGGGCGGCTGGCAGAGCCCCTTCCGCGTTC |
| GGGGGTGCGCTCCTGGCGGCGCTGCTCTGACTGACTTCCTCCGCGGCCGGCCATTGTGTTCCTAGGGA |
| GCAAGCATGGAGACTCAGCCATCGTCGCCAACATCGCCATCTGCCCCGCCGCCGCCGACGAGAACCAGC |
| AGCAGCAGAATGAAAGCTTAACCGCCCCGCCGCCAGCCCCACCTCCGACGCCGCGGCCCCAGACATGCA |
| AGAGATGGAGGAATCCATCGAGATTGACCTGGGCTACGTGACGCCGCGGAGCACGAGGAGGAGCTGGCA |
| GCGCGCTTTTCAGCCCCGGAAGAGAACCACCAAGAGCAGCCAGAGCAGGAAGCAGAGAGCGAGCAGAGCC |
| AGGCTGGGCTCGAGCATGGCGACTACCTGAGCGGGCAGAGGACGTGCTCATCAAGCATCTGGCCCGCCA |
| ATGCATCATCGTCAAGGATGCGCTGCTCGACCGCGCCGAGGTGCCCCTCAGCGTGGCGGAGCTCAGCGC |
| GCCTACGAGCGCAACCTCTTCTCGCGCGCGTGCCCCCAAGCGCCAGCCCAACGGCACCTGCGAGCCCA |
| ACCCGCGCCTCAACTTCTACCCGGTCTTCGCGGTGCCCGAGGCCCTGGCCACCTACCACCTCTTTTTCAA |
| GAACCAAAGGATCCCCGTCTCCTGCCGCGCCAACCGCACCCGCGCCGACGCCCTGCTCAACCTGGGCCCC |
| GGCGCCCGCCTACCTGATATCGCCTCCTTGGAAGAGGTTCCCAAGATCTTCGAGGGTCTGGGCAGCGACG |
| AGACTCGGGCCGCGAACGCTCTGCAAGGAAGCGGAGAGGAGCATGACCACCACGCGCCTGGTGGAGTT |
| GGAAGGCGACAACGCGCGCCTGGCGGTCCTCAAGCGCACGGTCGAGCTGACCCACTTCGCCTACCCGGCG |
| CTCAACCTGCCCCCCAAGGTCATGAGCGCCGTCATGACCAGGTGCTCATCAAGCGCGCCTCGCCCCTCT |
| CGGAGGAGGAGATGCAGGACCCCGAGAGCTCGGACGAGGGCAAGCCCGTGGTCAGCGACGAGCAGCTGGC |
| GCGCTGGCTGGGAGCGAGTAGCACCCCCAGAGCCTGGAAGAGCGGCGCAAGCTCATGATGGCCGTGGTC |
| CTGGTGACCGTGGAGCTGGAGTGTCTGCGCCGCTTCTTCGCCGACGGGAGACCCTGCGCAAGGTCGAGG |
| AGAACCTGCACTACCTCTTCAGGCACGGGTTCGTGCGCCAGGCCTGCAAGATCTCCAACGTGGAGCTGAC |
| CAACCTGGTCTCCTACATGGGCATCCTGCACGAGAACCGCCTGGGGCAGAACGTGCTGCACACCACCCTG |
| CGCGGGGAGGCCCGCCGCGACTACATCCGCGACTGCGTCTACCTGTACCTCTGCCACACCCTGGCAGACGG |
| GCATGGGCGTGTGGCAGCAGTGCCTGGAGGAGCAGAACCTGAAAGAGCTCTGCAAGCTCCTGCAGAAGAA |
| CCTGAAGGCCCTGTGGACCGGGTTCGACGAGCGCACCACCGCCTCGGACCTGGCCGACCTCATCTTCCCC |
| GAGCGCCTGCGCGCTGACGCTGCGCAACGGGCTGCCCGACTTTATGAGCCAAAGCATGTTGCAAAACTTTC |

-continued

| DESCRIPTION OF THE SEQUENCES |
|---|
| GCTCTTTCATCCTCGAACGCTCCGGGATCCTGCCCGCCACCTGCTCCGCGCTGCCCTCGGACTTCGTGCC |
| GCTGACCTTCCGCGAGTGCCCCCCGCCGCTCTGGAGCCACTGCTACCTGCTGCGTCTGGCCAACTACCTG |
| GCCTACCACTCGGACGTGATCGAGGACGTCAGCGGCGAGGGTCTGCTCGAGTGCCACTGCCGCTGCAACC |
| TCTGCACGCCGCACCGCTCCCTGGCCTGCAACCCCCAGCTGCTGAGCGAGACCCAGATCATCGGCACCTT |
| CGAGTTGCAAGGCCCCGGCGAGGAGGGCAAGGGGGGTCTGAAACTCACCCCGGGGCTGTGGACCTCGGCC |
| TACTTGCGCAAGTTCGTGCCCGAGGACTACCATCCCTTCGAGATCAGGTTCTACGAGGACCAATCCCAGC |
| CGCCCAAGGCCGAGCTGTCGGCCTGCGTCATCACCCAGGGGGCCATCCTGGCCCAATTGCAAGCCATCCA |
| GAAATCCCGCCAAGAATTTCTGCTGAAAAAGGGCCACGGGGTCTACTTGGACCCCCAGACCGGAGAGGAG |
| CTCAACCCCAGCTTCCCCCAGGATGCCCAGAGGAAGCAGCAAGAAGCTGAAAGTGGAGCTGCCGCTGCCG |
| CCGGAGGATTTGGAGGAAGACTGGGAGAGCAGTCAGGCAGAGGAGGAGGAGATGGAAGACTGGGACAGCA |
| CTCAGGCAGAGGAGGACAGCCTGCAAGACAGTCTGGAAGACGAGGTGGAGGAGGAGGCAGAGGAAGAAGC |
| AGCCGCCGCCAGACCGTCGTCCTCGGCGGAGAAAGCAAGCAGCACGGATACCATCTCCGCTCCGGGTCGG |
| GGTCTCGGCGGCCGGGCCCACAGTAGGTGGGACGAGACCGGGCGCTTCCCGAACCCCACCACCCAGACCG |
| GTAAGAAGGAGCGGCAGGGATACAAGTCCTGGCGGGGGCACAAAAACGCCATCGTCCTGCTTGCAAGC |
| CTGCGGGGCAACATCTCCTTCACCCGGCGCTACCTGCTCTTCCACCGCGGGGTGAACTTCCCCGCAAC |
| ATCTTGCATTACTACCGTCACCTCCACAGCCCCTACTACTGTTTCCAAGAAGAGGCAGAAACCCAGCAGC |
| AGCAGAAAACCAGCAGCAGCTAGAAAATCCACAGCGGCGGCGGCGGCAGGTGGACTGAGGATCGCGGCGA |
| ACGAGCCGGCGCAGACCCGGGAGCTGAGGAACCGGATCTTTCCCACCCTCTATGCCATCTTCCAGCAGAG |
| TCGGGGGCAGGAGCAGGAACTGAAAGTCAAGAACCGTTCTCTGCGCTCGCTCACCCGCAGTTGTCTGTAT |
| CACAAGAGCGAAGACCAACTTCAGCGCACTCTCGAGGAGCGCCGAGGCTCTCTTCAACAAGTACTGCGCGC |
| TCACTCTTAAAGAGTAGCCCGCGCCCGCCCACACACGGAAAAAGGCGGGAATTACGTCACCACCTGCGCC |
| CTTCGCCCGACCATCATCATGAGCAAAGAGATTCCCACGCCTTACATGTGGAGCTACCAGCCCCAGATGG |
| GCCTGGCCGCCGGCGCCGCCCAGGACTACTCCACCCGCATGAACTGGCTCAGTGCCGGGCCCGCGATGAT |
| CTCACGGGTGAATGACATCCGCGCCCGCCGAAACCAGATACTCCTAGAACAGTCAGCGATCACCGCCACG |
| CCCCGCCATCACCTTAATCCGCGTAATTGGCCCGCCGCCCTGGTGTACCAGGAAATTCCCCAGCCCACGA |
| CCGTACTACTTCCGCGAGACGCCCAGGCCGAAGTCCAGCTGACTAACTCAGGTGTCCAGCTGGCCGGCGG |
| CGCCGCCCTGTGTCGTCACCGCCCCGCTCAGGGTATAAAGCGGCTGGTGATCCGAGGCAGAGGCACACAG |
| CTCAACGACGAGGTGGTGAGCTCTTCGCTGGGTCTGCGACCTGACGGAGTCTTCCAACTCGCCGGATCGG |
| GGGAGATCTTCCTTCACGCCTCGTCAGGCCGTCCTGACTTTGGAGAGTTCGTCCTCGCAGCCCCGCTCGGG |
| TGGCATCGGCACTCTCCAGTTCGTGGAGGAGTTCACTCCCTCGGTCTACTTCAACCCCTTCTCCGGCTCC |
| CCCGGCCACTACCCGGACGAGTTCATCCCGAACTTCGACGCCATCAGCGAGTCGGTGGACGGCTACGATT |
| GAATGTCCCATGGTGGCGCGGCTGACCTAGCTCGGCTTCGACACCTGGACCACTGCCGCCGCTTCCGCTG |
| CTTCGCTCGGGATCTCGCCGAGTTTGCCTACTTTGAGCTGCCCGAGGAGCACCCTCAGGGCCCGGCCCAC |
| GGAGTGCGGATCATCGTCGAAGGGGGCCTCGACTCCCACCTGCTTGGATCTTCAGCCAGCGTCCGATCC |
| TGGTCGAGCGCGAGCAAGGACAGACCCGTCTGACCCTGTACTGCATCTGCAACCACCCCGGCCTGCATGA |
| AAGTCTTTGTTGTCTGCTGTGTACTGAGTATAATAAAAGCTGAGATCAGCGACTACTCCGGACTTCCGTG |
| TGTTCCTGAATCCATCAACCAGTCCCTGTTCTTCACCGGGAACGAGACCGAGCTCCAGCTCCAGTGTAAG |
| CCCCACAAGAAGTACCTCACCTGGCTGTTCCAGGGCTCCCCGATCGCCGTTGTCAACCACTGCGACAACG |
| ACGGAGTCCTGCTGAGCGGCCCTGCCAACCTTACTTTTTCCACCCGCAGAAGCAAGCTCCAGCTCTTCCA |
| ACCCTTCCTCCCCGGGACCTATCAGTGCGTCTCGGGACCCTGCCATCACACCTTCCACCTGATCCCGAAT |
| ACCACAGCGTCGCTCCCCGCTACTAACAACCAAACTACCCACCAACGCCACCGTCGCGACCTTTCCTCTG |
| AATCTAATACCACTACCGGAGGTGAGCTCCGAGGTCGACCAACCTCTGGGATTTACTACGGCCCCTGGGA |
| GGTGGTGGGGTTAATAGCGCTAGGCCTAGTTGTGGGTGGGCTTTTGGCTCTCTGCTACCTATACCTCCCT |
| TGCTGTTCGTACTTAGTGGTGCTGTGTTGCTGGTTTAAGAAATGGGGCAGATCACCCTAGTGAGCTGCGG |
| TGTGCTGGTGGCGGTGGTGCTTTCGATTGTGGGACTGGGCGGCGCGGCTGTAGTGAAGGAGAAGGCCGAT |
| CCCTGCTTGCATTTCAATCCCGACAAATGCCAGCTGAGTTTTCAGCCCGATGGCAATCGGTGCGCGGTGC |
| TGATCAAGTGCGGATGGGAATGCGAGAACGTGAGAATCGAGTACAATAACAAGACTCGGAACAATACTCT |
| CGCGTCCGTGTGGCAGCCCGGGGACCCCGAGTGGTACACCGTCTCTGTCCCCGGTGCTGACGGCTCCCCG |
| CGCACCGTGAATAATACTTTCATTTTTGCGCACATGTGCAGACAGCGGTCATGTGGATGAGCAAGCAGTACG |
| ATATGTGGCCCCCCACGAAGGAGAACATCGTGGTCTTCTCCATCGCTTACAGCCTGTGCACGGTGCTAAT |
| CACCGCTATCGTGTGCCTGAGCATTCACATGCTCATCGCTATTCGCCCCAGAAATAATGCCGAAAAAGAG |
| AAACAGCCATAACACGTTTTTTCACACACCTTGTTTTACAGACAATGCGTCTGTTAAATTTTTAAACA |
| TTGTGCTCAGTATTGCTTATGCCTCTGGCTATGCAAACATACAGAAAACCCTCTATGTAGGATCTGATGA |
| TACACTAGAGGGTACCCAATCACAAGCTAGGGTTTCATGGTATTTTTATAAAAGCTCAGATAATCCTATT |
| ACTCTTTGCAAAGGTGATCAGGGGCGGACAACAAAGCCGCCTATCACATTTAGCTGTACCAGAACAAATC |
| TCACGCTTTTCTCAATTACAAAACAATATGCTGGTATTTATTACAGTACAAACTTTCATAGTGGGCAAGA |
| TAAATATTATACTGTTAAGGTAGAAAATCCTACCACTCCTAGAACTACCACCACCACCACCACCACCACC |
| ACTACTGCGAAGCCCACTAAACCTAAAACTACCAAGAAAACCACTGTGAAAACTACAACTAGAACCACCA |
| CAACTACAGAAACCACCACCAGCACAACACTTGCTGCAACTACACACACACACTGAGCTAACCTTACA |
| GACCACTAATGATTTGATAGCCCTGTTGCAAAAGGGGGATAACAGCACCACTTCCAATGAGGAGATACCC |
| AAATCCATGATTGGCATTATTGTTGCTGTAGTGGTGTGCATGTTGATCATCGCCTTGTCATGGTGTACT |
| ATGCCTTCTGCTACAGAAAGCACAGACTGAACGACAAGCTGGAACACTTACTAAGTGTTGAATTTTAATT |
| TTTTAGAACCATGAAGATCCTAGGCCTTTTAGTTTTTTCTATCATTACCTCTGCTCTATGCAATTCTGAC |
| AATGAGGACGTTACTGTCGTTGTCGGATCAAATTATACACTGAAAGGTCCAGCGAAGGGTATGCTTTCGT |
| GGTATTGCTGGTTTGGAACTGACACTGATCAAACTGAGCTTTGCAATGCAATGAAAGGTCAAATACCAAC |
| CTCAAAAATTAAACATAAATGCAATGGTACTGACTTAGTACTACTCAATATCACGAAATCATATGCTGGC |
| AGCTATTCATGCCCTGGAGATGATGCTGAGAACATGATTTTTTACAAAGTAACTGTTGTTGATCCCACTA |
| CTCCACCACCCACCACCACAACTACTCACACCACACACACAGAACAAACACCAGAGGCAGCAGAAGCAGA |
| GTTGGCCTTCCAGGTTCACGGAGATTCCTTTGCTGTCAATACCCCTACACCCGATCATCGGTGTCCGGGG |
| CTGCTAGTCAGCGGCATTGTCGGTGTGCTTTCGGGATTAGCAGTCATAATCATCTGCATGTTCATTTTTG |
| CTTGCTGCTATAGAAGGCTTTACCGACAAAAATCAGACCCACTGCTGAAACTCTATGTTTAATTTTTTCC |
| AGAGCCATGAAGGCAGTTAGCGCTCTAGTTTTTTGTTCTTTGATTGGCATTGTTTTTGCAATCCTATTA |
| CTAGAGTTAGCTTTATTAAAGATGTGAATGTTACTGAGGGGGCAATGTGACACTGGTAGGTGTAGAGGG |
| TGCTAAAACACCACCTGGACAAAATACCACCTTGGGTGGAAAGATATTTGCAATTGGAGTGTCACTGTG |
| TACACATGTGAGGGAGTTAATCTTACCATTGTCAATGCCACCTCAGCTCAAAATGGTAGAATTCAAGGAC |
| AAAGTGTTAGTGTGACCAGTGATGGGTATTTTACCCAACATACTTTTATCTATGACGTTAAAGTCATACC |
| ACTGCCTACGCCTAGCCCACCTAGCACCACTACACAAACAACCCACACTACACAGACAACCACATACAGT |

DESCRIPTION OF THE SEQUENCES

```
ACATCAAATCAGCCTACCACCACTACAGCAGCAGAGGTTGCCAGTCGTCTGGAGTTCAAGTGGCATTTT
TGTTGTTGCCCCCATCTAGCAGTCCCACTGCTATTACCAATGAGCAGACTACTGCATTTTTGTCCACTGT
CGAGAGCCACACCACAGCTACCTCCAGTGCCTTCTCTAGCACCGCCAATCTCTCCTCGCTTTCCTCTACA
CCAATCAGTCCCGCTACTACTACTACCCCCGCTATTCTTCCCACTCCCCTGAAGCAAACAGACGGCGGCA
TGCAATGGCAGATCACCCTGCTCATTGTGATCGGGTTGGTCATCCTAGCCGTGTTGCTCTACTACATCTT
CTGCCGCCGCATTCCCAACGCGCACCGCAAGCCGGTCTACAAGCCCATCATTGTCGGGCAGCCGGAGCCG
CTTCAGGTGGAAGGGGGTCTAAGGAATCTTCTCTTCTCTTTTACAGTATGGTGATTGAACTATGATTCCT
AGACAATTCTTGATCACTATTCTTATCTGCCTCCTCCAAGTCTGTGCCACCCTCGCTCTGGTGGCCAACG
CCAGTCCAGACTGTATTGGGCCTTCGCCTCCTACGTGCTCTTTGCCTTCATCACCTGCATCTGCTGCTG
TAGCATAGTCTGCCTGCTTATCACCTTCTTCCAGTTCATTGACTGGATCTTTGTGCGCATCGCCTACCTG
CGCCACCACCCCCAGTACCGCGACCAGCGAGTGGCGCAGCTGCTCAGGCTCCTCTGATAAGCATGCGGGC
TCTGCTACTTCTCGCGCTTCTGCTGTTAGTGCTCCCCCGTCCCGTTGACCCCCGGCCCCCCACTCAGTCC
CCCGAGGAGGTCCGCAAATGCAAATTCCAAGAACCCTGGAAATTCCTCAAATGCTACCGCCAAAAATCAG
ACATGCATCCCAGCTGGATCATGATCATTGGGATCGTGAACATTCTGGCCTGCACCCTCATCTCCTTTGT
GATTTACCCCTGCTTTGACTTTGGTTGGAACTCGCCAGAGGCGCTCTATCTCCCGCCTGAACCTGACACA
CCACCACAGCAACCTCAGGCACACGCACTACCACCACCACAGCCTAGGCCACAATACATGCCCATATTAG
ACTATGAGGCCGAGCCACAGCGACCCATGCTCCCCGCTATTAGTTACTTCAATCTAACCGGCGGAGATGA
CTGACCCACTGGCCAACAACAACGTCAACGACCTTCTCCTGGACATGGACGGCCGCGCCTCGGAGCAGCG
ACTCGCCCAACTTCGCATTCGCCAGCAGCAGGAGAGAGCCGTCAAGGAGCTGCAGGACGGCATAGCCATC
CACCAGTGCAAGAAAGGCATCTTCTGCCTGGTGAAACAGGCCAAGATCTCCTACGAGGTCACCCAGACCG
ACCATCGCCTCTCCTACGAGCTCCTGCAGCAGCGCCAGAAGTTCACCTGCCTGGTCGGAGTCAACCCCAT
CGTCATCACCCAGCAGTCGGGCGATACCAAGGGGTGCATCCACTGCTCCTGCGACTCCCCGACTGCGTC
CACACTCTGATCAAGACCCTCTGCGGCCTCCGCGACCTCCTCCCCATGAACTAATCACCCACTTATCCAG
TGAAATAAAAAAATAATCATTTGATTTGAAATAAAGATACAATCATATATTGATGATTTGAGTTTAACAAA
ATAAAGAATCACTTACTTGAAATCTGATACCAGGTCTCTGTCCATATTTTCTGCCAACACCACCTCACTC
CCCTCTTCCCAGCTCTGGTACTGCAGGCCCCGGCGGGCTGCAAACTTCCTCCACACGCTGAAGGGGATGT
CAAATTCCTCCTGCCCCTCAATCTTCATTTTATCTTCTATCAGATGTCCAAAAAGCGCGTCCGGGTGGAT
GATGACTTCGACCCCGTCTACCCCTACGATGCAGACAACGCACCGACCGTGCCCTTCATCAACCCCCCCT
TCGTCTCTTCAGATGGATTCCAAGAGAAGCCCCTGGGGGTGTTGTCCCTGCGACTGGCCGACCCCGTCAC
CACCAAGAACGGGGAAATCACCCTCAAGCTGGGAGAGGGGGTGGACCTCGACTCCTCGGGAAAACTCATC
TCCAACACGGCCACCAAGGCCGCTGCCCCTCTCAGTTTTTCCAACAACACCATTTCCCTTAACATGGATC
ACCCCTTTTACACTAAAGATGGAAAATTAGCCTTACAAGTTTCTCCACCATTAAATATACTGAGAACAAG
CATTCTAAACACACTAGCTTTAGGTTTTGGATCAGGTTTAGGACTCCGTGGCTCTGCCTTGGCAGTACAG
TTAGTCTCTCCACTTACATTTGATACTGATGGAAACATAAAGCTTACCTTAGACAGAGGTTTGCATGTTA
CAACAGGAGATGCAATTGAAAGCAACATAAGCTGGGCTAAAGGTTTAAAATTTGAAGATGGAGCCATAGC
AACCAACATTGGAAATGGGTTAGAGTTTGGAAGCAGTAGTACAGAAACAGGTGTCGATGATGCTTACCCA
ATCCAAGTTAAACTTGGATCTGGCCTTAGCTTTGACAGTACAGGAGCCATAATGGCTGGTAACAAAGAAG
ACGATAAACTCACTTTGTGGACAACACCTGATCCATCACCAAACTGTCAAATACTCGCAGAAAATGATGC
AAAACTAACACTTTGCTTGACTAAATGTGGTAGTCAAATACTGGCCACTGTGTCAGTCTTAGTTGTAGGA
AGTGGAAACCTAAACCCCATTACTGGCCACCGTAAGCAGTGCTCAGGTGTTTCTACGTTTTGATGCAAACG
GTGTTCTTTTAACAGAACATTCTACACTAAAAAAAATACTGGGGGTATAGGCAGGGAGATAGCATAGATGG
CACTCCATATGTCAATGCTGTAGGATTCATGCCCAATTTAAAAGCTTATCCAAAGTCACAAAGTTCTACT
ACTAAAAATAATATAGTAGGGCAAGTATACATGAATGGAGATGTTTCAAAACCTATGCTTCTCACTATAA
CCCTCAATGGTACTGATGACAGCAACAGTACATATTCAATGTCATTTTCATACACCTGGACTAATGGAAG
CTATGTTGGAGCAACATTTGGAGCTAACTCTTATACCTTCTCCTACATCGCCCAAGAATGAATACTGTAT
CCCACCCTGCATGCCCAACCCTCCCCCACCTCTGTCTATATGGAAAACTCTGAAACACAAAATAAAATAA
AGTTCAAGTGTTTTATTGATTCAACAGTTTTACAGGATTCGAGCAGTTATTTTCCTCCACCCTCCCAGG
ACATGGAATACACCACCCTCTCCCCCCGCACAGCCTTGAACATCTGAATGCCATTGGTGATGGACATGCT
TTTGGTCTCCACGTTCCACACAGTTTCAGAGCGAGCCAGTCTCGGGTCGGTCAGGGAGATGAAACCCTCC
GGGCACTCCCGCATCTGCACCTCACAGCTCAACAGCTGAGGATTGTCCTCGGTGGTCGGGATCACGGTTA
TCTGGAAGAAGCAGAAGAGCGGCGGTGGGAATCATAGTCCGCGAACGGGATCGGCCGGTGGTGTCGCATC
AGGCCCCGCAGCAGTCGCTGCCGCCGCCGCTCCGTCAAGCTGCTGCTCAGGGGGTCCGGGTCCAGGGACT
CCCTCAGCATGATGCCCACGGCCCTCAGCATCAGTCGTCTGGTGCCGCGGGCGCAGCAGCGCATGCGGAT
CTCGCTCAGGTCGCTGCAGTACGTGCAACACAGGACCACCAGGTTGTTCAACAGTCCATAGTTCAACACG
CTCCAGCCGAAACTCATCGCGGGAAGGATGCTACCCACGTGGCCGTCGTACCAGATCCTCAGGTAAATCA
AGTGGCGCCCCCTCCAGAACACGCTGCCCATGTACATGATCTCCTTGGGCATGTGGCGGTTCACCACCTC
CCGGTACCACATCACCCTCTGGTTGAACATGCAGCCCCGGATGATCCTGCGGAACCACAGGGCCAGCACC
GCCCCGCCCGCCATGCAGCGAAGAGACCCGGGTCCCGGCAATGGCAATGGAGGACCCACCGCTCGTACC
CGTGGATCATCTGGGAGCTGAACAAGTCTATGTTGGCACAGCACAGGCACACGCTCATGCATCTCTTCAG
CACTCTCAGCTCCTCGGGGTCAAAACCATATCCCAGGGCACGGGAAACTCTTGCAGGACAGCGAAGCCC
GCAGAACAGGGCAATCCTCGCACATAACTTACATTGTGCATGGACAGGGTATCGCAATCAGGCAGCACCG
GGTGATCCTCCACCAGAGAAGCGCGGGTCTCGGTCTCCTCACAGCGTGGTAAGGGGGCCGGCCGATACGG
GTGATGGCGGGACGCGGCTGATCGTGTTCGCGACCGTGTCATGATGCAGTTGCTTTCGGACATTTTCGTA
CTTGCTGAAGCAGAACCTGGTCCGGGCGCTGCACACCGATCGCCGGCGGCGGTCTCGGCGCTTGGAACGC
TCGGTGTTGAAGTTGTAAAACAGCCACTCTCTCAGACCGTGCAGCAGATCTAGGGCCTCAGGAGTGATGA
AGATCCCATCATGCCTGATGGCTCTGATCACATCGACCCACCGTGGAATGGGCCAGACCCAGCCAGATGAT
GCAATTTTGTTGGGTTTCGGTGACGGCGGGGAGGGAAGAACAGGAAGAACCATGATTAACTTTTAATCC
AAACGGTCTCGGAGCACTTCAAAATGAAGGTCGCGGAGATGGCACCTCTCGCCCCCGCTGTGTTGGTGGA
AAATAACAGCCAGGTCAAAGGTGATACGGTTCTCGAGATGTTCCACGGTGGCTTCCAGCAAAGCCTCCAC
GCGCACATCCAGAAACAAGACAATAGCGAAAGCGGGAGGGTTCTCTAATTCCTCAATCATCATGTTACAC
TCCTGCACCATCCCCAGATAATTTTCATTTTTCCAGCCTTGAATGATTCGAACTAGTTCCTGAGGTAAAT
CCAAGCCAGCCATGATAAAGAGCTCGCGCAGAGCGCCCTCCACCGGCATTCTTAAGCACACCCTCATAAT
TCCAAGATATTCTGCTCCTGGTTCACCTGCAGCAGATTGACAAGCGGGATATCAAAATCTCTGCCGCGAT
CCCTGAGCTCCTCCCTCAGCAATAACTGTAAGTACTCTTTCATATCCTCTCCGAAATTTTTAGCCATAGG
ACCCCCAGGAATAAGAGAAGGGCAAGCCACATTACAGATAAACCGAAGTCCCCCCCAGTGAGCATTGCCA
AATGTAAGATTGAAATAAGCATGCTGGCTAGACCCGGTGATATCTTCCAGATAACTGGACAGAAAATCGG
GCAAGCAATTTTTAAGAAAATCAACAAAAGAAAAATCTTCCAGGTGCACGTTTAGGGCCTCGGGAACAAC
```

| DESCRIPTION OF THE SEQUENCES |
|---|
| GATGGAGTAAGTGCAAGGGGTGCGTTCCAGCATGGTTAGTTAGCTGATCTGTAAAAAAACAAAAAATAAA
ACATTAAACCATGCTAGCCTGGCGAACAGGTGGGTAAATCGTTCTCTCCAGCACCAGGCAGGCCACGGGG
TCTCCGGCGCGACCCTCGTAAAAATTGTCGCTATGATTGAAAACCATCACAGAGAGACGTTCCCGGTGGC
CGGCGTGAATGATTCGAGAAGAAGCATACACCCCCGGAACATTGGAGTCCGTGAGTGAAAAAAAGCGGCC
GAGGAAGCAATGAGGCACTACAACGCTCACTCTCAAGTCCAGCAAAGCGATGCCATGCGGATGAAGCACA
AAATTTTCAGGTGCGTAAAAAATGTAATTACTCCCCTCCTGCACAGGCAGCGAAGCTCCCGATCCCTCCA
GATACACATACAAAGCCTCAGCGTCCATAGCTTACCGAGCGGCAGCAGCAGCGGCACACAACAGGCGCAA
GAGTCAGAGAAAAGACTGAGCTCTAACCTGTCCGCCCGCTCTCTGCTCAATATATAGCCCCAGATCTACA
CTGACGTAAAGGCCAAAGTCTAAAAATACCCGCCAAATAATCACACACGCCCAGCACACGCCCAGAAACC
GGTGACACACTCAAAAAAATACGCGCACTTCCTCAAACGCCCAAACTGCCGTCATTTCCGGGTTCCCACG
CTACGTCATCAAAACACGACTTTCAAATTCCGTCGACCGTTAAAAACGTCACCCGCCCCGCCCCTAACGG
TCGCCGCTCCCGCAGCCAATCAGCGCCCCGCATCCCCAAATTCAAACAGCTCATTTGCATATTAACGCGC
ACCAAAAGTTTGAGGTATATTATTGATGATG

SEQ ID NO: 3 Polynucleotide sequence encoding the CASI promoter
GGAGTTCCGCGTTACATAACTTACGGTAAATGGCCCGCCTGGCTGACCGCCCAACGACCCCCGCCCATTGACGTCAA
TAATGACGTATGTTCCCATAGTAACGCCAATAGGGACTTTCCATTGACGTCAATGGGTGGAGTATTTACGGTAAACT
GCCCACTTGGCAGTACATCAAGTGTATCATATGCCAAGTACGCCCCCTATTGACGTCAATGACGGTAAATGGCCCGC
CTGGCATTATGCCCAGTACATGACCTTATGGGACTTTCCTACTTGGCAGTACATCTACGTATTAGTCATCGCTATTA
CCATGGTCGAGGTGAGCCCCACGTTCTGCTTCACTCTCCCCATCTCCCCCCCCTCCCCACCCCCAATTTTGTATTTA
TTTATTTTTTAATTATTTTGTGCAGCGATGGGGGCGGGGGGGGGGGGGGCGCGCGCCAGGCGGGGCGGGGCGGGGC
GAGGGGCGGGGCGGGGCGAGGCGGAGAGGTGCGGCGGCAGCCAATCAGAGCGGCGCGCTCCGAAAGTTTCCTTTTAT
GGCGAGGCGGCGGCGGCGGCCCTATAAAAAGCGAAGCGCTCCCTATCAGTGATAGAGATCTCCCTATCAGTGAT
AGAGATCGTCGACGAGCTCGCGGCGGGCGGGAGTCGCTGCGCGCTGCCTTCGCCCCGTCCCCGCTCCGCCGCCGCC
TCGCGCCGCCCGCCCCGGCTCTGACTGACCGCGTTACTAAAACAGGTAAGTCCGGCCTCCGCGCCGGGTTTGGCGC
CTCCCGCGGGCGCCCCCTCCTCACGGCGAGCGCTGCCACGTCAGCGAAGGGCGCAGCGAGCGTCCTGATCCTTCC
GCCCGGACGCTCAGGACAGCGGCCCGCTGCTCATAAGACTCGGCCTTAGAACCCCAGTATCAGCAGAAGGACATTTT
AGGACGGGACTTGGGTGACTCTAGGGCACTGGTTTTCTTTCCAGAGAGCGGAACAGGCGAGGAAAAGTAGTCCCTTC
TCGGCGATTCTGCGGAGGGATCTCCGTGGGGCGGTGAACGCCGATGATGCCTCTACTAACCATGTTCATGTTTTCTT
TTTTTTTCTACAGGTCCTGGGTGACGAACAG SEQ ID NO: 4 - Polynucleotide sequence encoding ChAd155/RSV
CATCATCAATAATATACCTTATTTTGGATTGAAGCCAATATGATAATGAGATGGGCGGCGCGGGGCGG
GGCGCGGGGCGGGAGGCGGGTTTGGGGGCGGGCCGGCGGGCGGGCGGTGTGGCGGAAGTGGACTTT
GTAAGTGTGGCGGATGTGACTTGCTAGTGCCGGGCGCGGTAAAAGTGACGTTTTCCGTGCGCGACAAC
GCCCCCGGGAAGTGACATTTTTCCCGCGGTTTTTACCGGATGTTGTAGTGAATTTGGGCGTAACCAAGT
AAGATTTGGCCATTTTCGCGGGAAAACTGAAACGGGGAAGTGAAATCTGATTAATTTTGCGTTAGTCA
TACCGCGTAATATTTGTCTAGGGCCGAGGGACTTTGGCCGATTACGTGGAGGACTCGCCCAGGTGTTTT
TTGAGGTGAATTTCCGCGTTCCGGGTCAAAGTCTGCGTTTTATTATTATAGGATATCCCATTGCATACG
TTGTATCCATATCATAATATGTACATTTATATTGGCTCATGTCCAACATTACCGCCATGTTGACATTGAT
TATTGACTAGTTATTAATAGTAATCAATTACGGGGTCATTAGTTCATAGCCCATATATGGAGTTCCGCG
TTACATAACTTACGGTAAATGGCCCGCCTGGCTGACCGCCCAACGACCCCCGCCCATTGACGTCAATA
ATGACGTATGTTCCCATAGTAACGCCAATAGGGACTTTCCATTGACGTCAATGGGTGGAGTATTTACG
GTAAACTGCCCACTTGGCAGTACATCAAGTGTATCATATGCCAAGTACGCCCCCTATTGACGTCAATG
ACGGTAAATGGCCCGCCTGGCATTATGCCCAGTACATGACCTTATGGGACTTTCCTACTTGGCAGTACA
TCTACGTATTAGTCATCGCTATTACCATGGTGATGCGGTTTTGGCAGTACATCAATGGGCGTGGATAGC
GGTTTGACTCACGGGGATTTCCAAGTCTCCACCCCATTGACGTCAATGGGAGTTTGTTTTGGCACCAAA
ATCAACGGGACTTTCCAAAATGTCGTAACAACTCCGCCCCATTGACGCAAATGGGCGGTAGGCGTGTA
CGGTGGGAGGTCTATATAAGCAGAGCTCTCCCTATCAGTGATAGAGATCTCCCTATCAGTGATAGAGA
TCGTCGACGAGCTCGTTTAGTGAACCGTCAGATCGCCTGGAGACGCCATCCACGCTGTTTTGACCTCCA
TAGAAGACACCGGGACCGATCCAGCCTCCGCGGCCGGGAACGGTGCATTGGAACGCGGATTCCCCGT
GCCAAGAGTGAGATCTTCCGTTTATCTAGGTACCAGATATCGCCACCATGGAACTGCTGATCCTGAAG
GCCAACGCCATCACCACCATCCTGACCGCCGTGACCTTCTGCTTCGCCAGCGGCCAGAACATCACCGA
GGAATTCTACCAGAGCACCTGTAGCGCCGTGAGCAAGGGCTACCTGAGCGCCCTGAGAACCGGCTGGT
ACACCAGCGTGATCACCATCGAGCTGAGCAACATCAAAGAAAACAAGTGCAACGGCACCGACGCCAA
AGTGAAGCTGATCAAGCAGGAACTGGACAAGTACAAGAACGCCGTGACCGAGCTGCAGCTGCTGATG
CAGAGCACCCCCGCCACCAACAACCGGGCCAGACGGGAGCTGCCCCGGTTCATGAACTACACCCTGA
ACAACGCCAAAAAGACCAACGTGACCCTGAGCAAGAAGCGGAAGCGGCGGTTCCTGGGCTTTCTGCT
GGGCGTGGGCAGCGCCATTGCCAGCGGCGTGGCCGTGTCTAAGGTGCTGCACCTGGAAGGCGAAGTG
AACAAGATCAAGAGCGCCCTGCTGAGCACCAACAAGGCCGTGGTGTCCCTGAGCAACGGCGTGAGCG
TGCTGACCAGCAAGGTGCTGGATCTGAAGAACTACATCGACAAGCAGCTGCTGCCCATCGTGAACAAG
CAGAGCTGCAGCATCAGCAACATCGAGACAGTGATCGAGTTCCAGCAGAAGAACAACCGGCTGCTGG
AAATCACCCGGGAGTTCAGCGTGAACGCCGGCGTGACCACCCCTGTGTCCACCTACATGCTGACCAAC
AGCGAGCTGCTGAGCCTGATCAACGACATGCCCATCACCAACGACCAGAAAAAGCTGATGAGCAACA
ACGTGCAGATCGTGCGGCAGCAGAGCTACTCCATCATGTCCATCATCAAAGAAGAGGTGCTGGCCTAC
GTGGTGCAGCTGCCCCTGTACGGCGTGATCGACACCCCCTGCTGGAAGCTGCACACCAGCCCCCTGTG
CACCACCAACACCAAAGAGGGCAGCAACATCTGCCTGACCCGGACCGACAGAGGCTGGTACTGCGAC
AACGCCGGCAGCGTGTCATTCTTTCCACAGGCCGAGACATGCAAGGTGCAGAGCAACCGGGTGTTCTG
CGACACCATGAACAGCCTGACCCTGCCCTCCGAAGTGAACCTGTGCAACGTGGACATCTTCAACCCCA
AGTACGACTGCAAGATCATGACCTCCAAGACCGACGTGTCCAGCTCCGTGATCACCTCCCTGGGCGCC
ATCGTGTCCTGCTACGGCAAGACCAAGTGCACCGCCAGCAACAAGAACCGGGGCATCATCAAGACCTT
CAGCAACGGCTGCGACTACGTGTCCAACAAGGGGGTGGACACCGTGTCCGTGGGCAACACCCTGTACT
ACGTGAACAAACAGGAAGGCAAGAGCCTGTACGTGAAGGGCGAGCCCATCATCAACTTCTACGACCC
CCTGGTGTTCCCCAGCGACGAGTTCGACGCCAGCATCAGCCAGGTGAACGAGAAGATCAACCAGAGC
CTGGCCTTCATCCGGAAGTCCGACGAGCTGCTGCACAATGTGAATGCCGGCAAGTCCACCACCAACCG
GAAGCGGAGAGCCCCTGTGAAGCAGACCCTGAACTTCGACCTGCTGAAGCTGGCCGGCGACGTGGAG
AGCAATCCCGGCCCTATGGGCCCTGAGCAAAGTGAAACTGAACGATACACTGAACAAGGACCAGCTGC |

DESCRIPTION OF THE SEQUENCES

```
TGTCCAGCAGCAAGTACACCATCCAGCGGAGCACCGGCGACAGCATCGATACCCCCAACTACGACGT
GCAGAAGCACATCAACAAGCTGTGCGCATGCTGCTGATCACAGAGGACGCCAACCACAAGTTCACC
GGCCTGATCGGCATGCTGTACGCCATGAGCCGGCTGGGCCGGAGGACACCATCAAGATCCTGCGGG
ACGCCGGCTACCACGTGAAGGCCAATGGCGTGGACGTGACCACACACCGGCAGGACATCAACGGCAA
AGAAATGAAGTTCGAGGTGCTGACCCTGGCCAGCCTGACCACCGAGATCCAGATCAATATCGAGATCG
AGAGCCGGAAGTCCTACAAGAAAATGCTGAAAGAAATGGGCGAGGTGGCCCCCGAGTACAGACACGA
CAGCCCCGACTGCGGCATGATCATCCTGTGTATCGCCGCCCTGGTGATCACAAAGCTGGCCGCTGGCG
ACAGATCTGGCCTGACAGCCGTGATCAGACGGGCCAACAATGTGCTGAAGAACGAGATGAAGCGGTA
CAAGGGCCTGCTGCCCAAGGACATTGCCAACAGCTTCTACGAGGTGTTCGAGAAGTACCCCCACTTCA
TCGACGTGTTCGTGCACTTCGGCATTGCCCAGAGCAGCACCAGAGGCGGCTCCAGAGTGGAGGGCATC
TTCGCCGGCCTGTTCATGAACGCCTACGGCGCTGGCCAGGTGATGCTGAGATGGGGCGTGCTGGCCAA
GAGCGTGAAGAACATCATGCTGGGCCACGCCAGCGTGCAGGCCGAGATGGAACAGGTGGTGGAGGTG
TACGAGTACGCCCAGAAGCTGGGCGGAGAGGCCGGCTTCTACCACATCCTGAACAACCCTAAGGCCTC
CCTGCTGTCCCTGACCCAGTTCCCCCACTTCTCCAGCGTGGTGCTGGGAAATGCCGCCGGACTGGGCAT
CATGGGCGAGTACCGGGGCACCCCCAGAAACCAGGACCTGTACGACGCCGCCAAGGCCTACGCCGAG
CAGCTGAAAGAAAACGGCGTGATCAACTACAGCGTGCTGGACCTGACCGCTGAGGAACTGGAAGCCA
TCAAGCACCAGCTGAACCCCAAGGACAACGACGTGGAGCTGGGAGGCGGAGGATCTGGCGGCGGAGG
CATGAGCAGACGGAACCCCTGCAAGTTCGAGATCCGGGCCACTGCCTGAACGGCAAGCGGTGCCAC
TTCAGCCACAACTACTTCGAGTGGCCCCCTCATGCTCTGCTGGTGCGGCAGAACTTCATGCTGAACCGG
ATCCTGAAGTCCATGGACAAGAGCATCGACACCCTGAGCGAGATCAGCGGACCGCCCAAGCTGGACA
GAACCGAGGAATATGCCCTGGGCGTGGTGGGAGTGCTGGAAAGCTACATCGGCTCCATCAACAACAT
CACAAAGCAGAGCGCCTGCGTGGCCATGAGCAAGCTGCTGACAGAGCTGAACAGCGACGACATCAAG
AAGCTGAGGGACAACGAGGAACTGAACAGCCCCAAGATCCGGGTGTACAACACCGTGATCAGCTACA
TTGAGAGCAACCGCAAGAACAACAAGCAGACCATCCATCTGCTGAAGCGGCTGCCCGCCGACGTGCT
GAAAAAGACCATCAAGAACACCCTGGACATCCACAAGTCCATCACCATCAACAATCCCAAAGAAAGC
ACCGTGTCGACACCAACGATCACGCCAAGAACAACGACACCACCTGATGAGCGGCCGCGATCTGCTG
TGCCTTCTAGTTGCCAGCCATCTGTTGTTTGCCCCTCCCCCGTGCCTTCCTTGACCCTGGAAGGTGCCAC
TCCCACTGTCCTTTCCTAATAAAATGAGGAAATTGCATCGCATTGTCTGAGTAGGTGTCATTCTATTCT
GGGGGGTGGGGTGGGGCAGGACAGCAAGGGGGAGGATTGGGAAGACAATAGCAGGCATGCTGGGGA
TGCGGTGGGCTCTATGCCGATCAGCGATCGCTGAGGTGGGTGAGTGGGCGTGGCCTGGGGTGGTCAT
GAAAATATATAAGTTGGGGGTCTTAGGGTCTCTTTATTTGTGTTGCAGAGACCGCCGGAGCCATGAGC
GGGGAGCAGCAGCAGCAGTAGCAGCAGCGCCTTGGATGGCGACATCGTGAGCCCTTATTTGACGA
CGCGGATGCCCCACTGGGCCGGGGTGCGTCAGAATGTGATGGGCTCCAGCATCGACGGCCGACCCGTC
CTGCCCGCAAATTCCGCCACGCTGACCTATGCGACCGTCGCGGGACGCCGTTGGACGCCACCGCCGC
CGCCGCCGCCACCGCAGCCGCCTCGGCCGTGCGCAGCCTGGCCACGGACTTTGCATTCCTGGGACCAC
TGGCGACAGGGGCTACTTCTCGGGCGTGCTGCCGCCGTTCGCGATGACAAGCTGACCGCCCTGCTG
GCGCAGTTGGATGCGCTTACTCGGGAACTGGGTGACCTTTCTCAGCAGGTCATGGCCCTGCGCCAGCA
GGTCTCCTCCCTGCAAGCTGGCGGGAATGCTTCTCCCACAAATGCCGTTTAAGATAAATAAAACCAGA
CTCTGTTTGGATTAAAGAAAAGTAGCAAGTGCATTGCTCTCTTTATTTCATAATTTTCCGCGCGCGATA
GGCCCTAGACCAGCGTTCTCGGTCGTTGAGGGTGCGGTGTATCTTCTCCAGGACGTGGTAGAGGTGGC
TCTGGACGTTGAGATACATGGGCATGAGCCCGTCCCGGGGGTGGAGGTAGCACCACTGCAGAGCTTCA
TGCTCCGGGGTGGTGTTGTAGATGATCCAGTCGTAGCAGGAGCGCTGGGCATGGTGCCTAAAAATGTC
CTTCAGCAGCAGGCCGATGGCCAGGGGAGGCCCTTGGTGTAAGTGTTTACAAAACGGTTAAGTTGGG
AAGGGTGCATTCGGGGAGAGATGATGTGCATCTTGGACTGTATTTTTAGATTGGCGATGTTTCCGCCCA
GATCCCTTCTGGGATTCATGTTGTGCAGGACCACCAGTACAGTGTCCGGTGCACTTGGGGAATTTGT
CATGCAGCTTAGAGGGAAAAGCGTGGAAGAACTTGGAGACGCCTTTGTGGCCTCCCAGATTTTCCATG
CATTCGTCCATGATGATGGCAATGGGCCCGCGGGAGGCAGCTTGGGCAAAGATATTTCTGGGGTCGCT
GACGTCGTAGTTGTGTTCCAGGGTGAGGTCGTCATAGGCCATTTTTACAAAGCGCGGGCGGAGGGTGC
CCGACTGGGGGATGATGGTCCCCTCTGGCCCTGGGGCGTAGTTGCCCTCGCAGATCTGCATTTCCCAG
GCCTTAATCTCGGAGGGGGGAATCATATCCACCTGCGGGCGATGAAGAAAACGGTTTCCGGAGCCG
GGGAGATTAACTGGGATGAGAGCAGGTTTCTAAGCAGCTGTGATTTTCCACAACCGGTGGGCCCATAA
ATAACACCTATAACCGGTTGCAGCTGGTAGTTTAGAGAGCTGCAGCTGCCGTCGTCCCGGAGGAGGGG
GGCCACCTCGTTGAGCATGTCCCTGACGCGCATGTTCTCCCCGACCAGATCCGCCAGAAGGCGCTCGC
CGCCCAGGGACAGCAGCTCTTGCAAGGAAGCAAAGTTTTTTCAGCGGCTTGAGGCCGTCCGCCGTGGGC
ATGTTTTTCAGGGTCTGGCTCAGCAGCTCCAGGCGGTCCCAGAGCTCGGTGACGTGCTCTACGGCATCT
CTATCCAGCATATCTCCTCGTTTCGCGGGTTGGGGCGACTTTCGCTGTAGGGCACCAAGCGGTGGTCGT
CCAGCGGGGCCAGAGTCATGTCCTTCCATGGGCACAGGTCCTCGTCAGGGTGGTCTGGGTCACGGTG
AAGGGGTGCGCTCCGGGCTGAGCGCTTGCCAAGGTGCGCTTGAGGCTGGTTCTGCTGGTGCTGAAGCG
CTGCCGGTCTTCGCCCTGCGCGTCGGCCAGGTAGCATTTGACCATGGTGTCATAGTCCAGCCCCTCCGC
GGCGTGTCCCTTGGCGCGCAGCTTGCCCTTGGAGGTGGCGCCGCACGAGGGGCAGAGCAGGCTCTTGA
GCGCGTAGAGCTTGGGGGCGAGGAAGACCGATTCGGGGGAGTAGGCGTCCGCCGCCAGACCCCGCA
CACGGTCTCGCACTCCACCAGCCAGGTGAGCTCGGGGCGCGCCGGGTCAAAAACCAGGTTTCCCCCAT
GCTTTTTGATGCGTTTCTTACCTCGGGTCTCCATGAGGTGGTGTCCCCGCTCGGTGACGAAGAGGCTGT
CCGTGTCTCCGTAGACCGACTTGAGGGGTCTTTTCTCCAGGGGGTCCCTCGGTCTTCCTCGTAGAGGA
ACTCGGACCACTCTGAGACGAAGGCCCGCGTCCAGGCCAGGACGAAGGAGGCTATGTGGGAGGGGTA
GCGGTCGTTGTCCACTAGGGGGTCCACCTTCTCCAAGGTGTGAAGACACATGTCGCCTTCCTCGGCGTC
CAGGAAGGTGATTGGCTTGTAGGTGTAGGCCACGTGACCGGGGGTTCCTGACGGGGGGTATAAAAG
GGGGTGGGGCGCGCTCGTCGTCACTCTCTTCCGCATCGCTGTCTGCGAGGGCCAGCTGCTGGGGTGA
GTATTCCCTCTCGAAGGCGGGCATGACCTCCGCGCTGAGGTTGTCAGTTTCCAAAAACGAGGAGGATT
TGATGTTCACCTGTCCCGAGGTGATACCTTTGAGGGTACCCGCGTCCATCTGGTCAGAAAACACGATCT
TTTTATTGTCCAGCTTGGTGGCGAACACCGTAGAGGGCGTTGGAGAGCAGCTTGGCGATGGAGCGC
AGGGTCTGGTTCTTGTCCCTGTCGGCGCGCTCCTTGGCCGCGATGTTGAGCTGCACGTACTCGCGCGCG
ACGCAGCGCCACTCGGGAAGACGGTGGTGCGCTCGTCGGGCACCAGGCGCACGCGCCAGCCGCGGT
TGTGCAGGGTGACCAGGTCCACGCTGGTGGCGACCTCGCCGCGCAGGCGCTCGTTGGTCCAGCAGAGA
CGGCCGCCCTTGCGCGAGCAGAAGGGGGGCAGGGGTCGAGCTGGGTCTCGTCCGGGGGTCCGCGT
CCACGGTGAAAACCCCGGGCGCAGGCGCGCGTCGAAGTAGTCTATCTTGCAACCTTGCATGTCCAGC
GCCTGCTGCCAGTCGCGGGCGGCGAGCGCGCGCTCGTAGGGGTTGAGCGGCGGGCCCAGGGCATGG
```

| DESCRIPTION OF THE SEQUENCES |
|---|
| GGTGGGTGAGTGCGGAGGCGTACATGCCGCAGATGTCATAGACGTAGAGGGGCTCCCGCAGGACCCC |
| GATGTAGGTGGGGTAGCAGCGGCCGCCGCGGATGCTGGCGCGCACGTAGTCATACAGCTCGTGCGAG |
| GGGGCGAGGAGGTCGGGGCCCAGGTTGGTGCGGGCGGGGCGCTCCGCGCGGAAGACGATCTGCCTGA |
| AGATGGCATGCGAGTTGGAAGAGATGGTGGGGCGCTGGAAGACGTTGAAGCTGGCGTCCTGCAGGCC |
| GACGGCGTCGCGCACGAAGGAGGCGTAGGAGTCGCGCAGCTTGTGTACCAGCTCGGCGGTGACCTGC |
| ACGTCGAGCGCGCAGTAGTCGAGGGTCTCGCGGATGATGTCATATTTAGCCTGCCCCTTCTTTTTCCAC |
| AGCTCGCGGTTGAGGACAAACTCTTCGCGGTCTTTCCAGTACTCTTGGATCGGGAAACCGTCCGGTTCC |
| GAACGGTAAGAGCCTAGCATGTAGAACTGGTTGACGGCCTGGTAGGCGCAGCAGCCCTTCTCCACGGG |
| GAGGGCGTAGGCCTGCGCGGCCTTGCGGAGCGAGGTGTGGGTCAGGGCGAAGGTGTCCCTGACCATG |
| ACTTTGAGGTACTGGTGCTTGAAGTCGGAGTCGTCGCAGCCGCCCCGCTCCCAGAGCGAGAAGTCGGT |
| GCGCTTCTTGGAGCGGGGGTTGGGCAGAGCGAAGGTGACATCGTTGAAGAGGATTTTGCCCGCGCGG |
| GGCATGAAGTTGCGGGTGATGCGGAAGGGCCCCGGCACTTCAGAGCGGTTGTTGATGACCTGGCGG |
| CGAGCACGATCTCGTCGAAGCCGTTGATGTTGTGGCCCACGATGTAGAGTTCCAGGAAGCGGGGCCGG |
| CCCTTTACGGTGGGCAGCTTCTTTAGCTCTTCGTAGGTGAGCTCCTCGGGCGAGGCGAGGCCGTGCTCG |
| GCCAGGGCCCAGTCCGCGAGGTGCGGGTTGTCTCTGAGGAAGGACTTCCAGAGGTCGCGGGCCAGGA |
| GGGTCTGCAGGCGGTCTCTGAAGGTCCTGAACTGGCGGCCCACGGCCATTTTTTCGGGGGTGATGCAG |
| TAGAAGGTGAGGGGGTCTTGCTGCCAGCGGTCCCAGTCGAGCTGCAGGGCGAGGTCGCGCGCGGCGG |
| TGACCAGGCGCTCGTCGCCCCCGAATTTCATGACCAGCATGAAGGGCACGAGCTGCTTTCCGAAGGCC |
| CCCATCCAAGTGTAGGTCTCTACATCGTAGGTGACAAAGAGGCGCTCCGTGCGAGGATGCGAGCCGAT |
| CGGGAAGAACTGGATCTCCCGCCACCAGTTGGAGGAGTGGCTGTTGATGTGGTGGAAGTAGAAGTCCC |
| GTCGCCGGGCCGAACACTCGTGCTGGCTTTTGTAAAAGCGAGCGCAGTACTGGCAGCGCTGCACGGGC |
| TGTACCTCATGCACGAGATGCACCTTTCGCCCGCGCACGAGGAAGCCGAGGGGAAATCTGAGCCCCCC |
| GCCTGGCTCGCGGCATGGCTGGTTCTCTTCTACTTTGGATGCGTGTCCGTCTCCGTCTGGCTCCTCGAG |
| GGGTGTTACGGTGGAGCGGACCACCACGCCGCGCGAGCCGCAGGTCCAGATATCGGCGCGCGGCGGT |
| CGGAGTTTGATGACGACATCGCGCAGCTGGGAGCTGTCCATGGTCTGGAGCTCCCGCGGCGGCGGCAG |
| GTCAGCCGGGAGTTCTTGCAGGTTCACCTCGCAGAGTCGGGCCAGGGCGCGGGGCAGGTCTAGGTGGT |
| ACCTGATCTCTAGGGGCGTGTTGGTGGCGGCGTCGATGGCTTGCAGGAGCCCGCAGCCCCGGGGGGCG |
| ACGACGGTGCCCCGCGGGGTGGTGGTGGTGGCGGTGCAGCTCAGAAGCGGTGCCGCGGGCGGGC |
| CCCCGGAGGTAGGGGGGCTCCGGTCCCGCGGGCAGGGCGGCAGCGGCACGTCGGCGTGGAGCGCG |
| GGCAGGAGTTGGTGCTGTGCCCGGAGGTTGCTGGCGAAGGCGACGACGCGGCGGTTGATCTCCTGGAT |
| CTGGCGCCTCTGCGTGAAGACGACGGGCCCGGTGAGCTTGAACCTGAAAGAGAGTTCGACAGAATCA |
| ATCTCGGTGTCATTGACCGCGGCCTGGCGCAGGATCTCCTGCACGTCTCCCGAGTTGTCTTGGTAGGCG |
| ATCTCGGCCATGAACTGCTCGATCTCTTCCTCCTGGAGGTCTCCGCGTCCGGCGCGTTCCACGGTGGCC |
| GCCAGGTCGTTGGAGATGCGCCCCATGAGCTGCGAGAAGGCGTTGAGTCCGCCCTCGTTCCAGACTCG |
| GCTGTAGACCACGCCCCCCTGGTCATCGCGGGCGCGCATGACCACCTGCGCGAGGTTGAGCTCCACGT |
| GCCGCGCGAAGACGGCGTAGTTGCGCAGACGCTGGAAGAGGTAGTTGAGGGTGGTGGCGGTGCTC |
| GGCCACGAAGAAGTTCATGACCCAGCGGCGCAACGTGGATTCGTTGATGTCCCCCAAGGCCTCCAGCC |
| GTTCCATGGCCTCGTAGAAGTCCACGGCGAAGTTGAAAAACTGGGAGTTGCGCGCCGACACGGTCAAC |
| TCCTCCTCCAGAAGACGGATGAGCTCGGCGACGGTGTCGCGCACCTCGCGCTCGAAGGCTATGGGGAT |
| CTCTTCCTCCGCTAGCATCACCACCTCCTCCTCTTCCTCCTCTTCTGGCACTTCCATGATGGCTTCCTCCT |
| CTTCGGGGGTGGCGGCGGCGGCGGTGGGGGAGGGGGCGCTCTGCGCCGGCGGCGGCACCGGGAG |
| GCGGTCCACGAAGCGCGCGATCATCTCCCCGCGGCGGCGGCGCATGGTCTCGGTGACGGCGCGGCCGT |
| TCTCCCGGGGGCGCAGTTGGAAGACGCCGCCGGACATCTGGTGCTGGGGCGGGTGGCCGTGAGGCAG |
| CGAGACGGCGCTGACGATGCATCTCAACAATTGCTGCGTAGGTACGCCGCCGAGGGACCTGAGGGAG |
| TCCATATCCACCGGATCCGAAAACCTTTCGAGGAAGGCGTCTAACCAGTCGCAGTCGCAAGGTAGGCT |
| GAGCACCGTGGCGGGCGGCGGGGGGTGGGGGAGTGTCTGGCGGAGGTGCTGCTGATGATGTAATTG |
| AAGTAGGCGGACTTGACACGGCGGATGGTCGACAGGAGCACCATGTCCTTGGGTCCGGCCTGCTGGAT |
| GCGGAGGCGGTCGGCTATGCCCCAGGCTTCGTTCTGGCATCGGCGCAGGTCCTTGTAGTAGTCTTGCAT |
| GAGCCTTTCCACCGGCACCTCTTCTCCTTCCTCTTCTGCTTCTTCCATGTCTGCTTCGGCCCTCGGGGCGG |
| CGCCGCGCCCCCTGCCCCCCATGCGCGTGACCCCGAACCCCCTGAGCGGTTGGAGCAGGGCCAGGTC |
| GGCGACGACGCGCTCGGCCAGGATGGCCTGCTGCACCTGCGTGAGGGTGGTTTGGAAGTCATCCAAGT |
| CCACGAAGCGGTGGTAGGCGCCCGTGTTGATGGTGTAGGTGCAGTTGGCCATGACGGACCAGTTGACG |
| GTCTGGTGGCCCGGTTGCGACATCTCGGTGTACCTGAGTCGCGAGCTGAGGCGCGGGAGTCGAAGACGTA |
| GTCGTTGCAAGTCCGCACCAGGTACTGGTAGCCCACCAGGAAGTGCGCGGCGGCTGGCGGTAGAGG |
| GGCCAGCGCAGGGTGGCGGGGGCTCCGGGGGCCAGGTCTTCCAGCATGAGGCGGTGGTAGGCGTAGA |
| TGTACCTGGACATCCAGGTGATACCCGCGGCGGTGGTGGAGGCGCGCGGGAAGTCGCGCACCCGGTTC |
| CAGATGTTGCGCAGGGGCAGAAAGTGCTCCATGGTAGGCGTGCTCTGTCCAGTCAGACGCGCAGTC |
| GTTGATACTCTAGACCAGGGAAAACGAAAGCCGGTCAGCGGGCACTCTTCCGTGGTCTGGTGAATAGA |
| TCGCAAGGGTATCATGGCGGAGGGCCTCGGTTCGAGCCCGGGTCCGGGCCGGACGGTCCGCCATGAT |
| CCACGCGGTTACCGCCCGCGTGTCGAACCCAGGTGTGCGACGTCAGACAACGGTGGAGTGTTCCTTTT |
| GGCGTTTTTCTGGCCGGGCGCCGGCGCCGCGTAAGAGACTAAGCCGCGAAAGCGAAAGCAGTAAGTG |
| GCTCGCTCCCCGTAGCCGGAGGGATCCTTGCTAAGGGTTGCGTTGCGGCGAACCCCGGTTCGAATCCC |
| GTACTCGGGCCGGCCGGACCCGCGGCTAAGGTGTTGGATTGGCCTCCCCCTCGTATAAAGACCCCGCT |
| TGCGGATTGACTCCGGACACGGGACGAGCCCCTTTTATTTTTGCTTTCCCCAGATGCATCCGGTGCTG |
| CGGCAGATGCGCCCCCCGCCCCAGCAGCAGCAACAACACCAGCAAGAGCGGCAGCAACAGCAGCGGG |
| AGTCATGCAGGGCCCCCTCACCCACCCTCGGCGGGCCGGCCACCTCGGCGTCCGCGGCCGTGTCTGGC |
| GCCTGCGGCGGCGCGGGGGGCCGGCTGACGACCCCGAGGAGCCCCGCGGCGCAGGGCCAGACACT |
| ACCTGGACCTGGAGGAGGCGAGGGCCTGGCGCGGCTGGGGCGCCGTCTCCCGAGCGCCACCCGCG |
| GGTGCAGCTGAAGCGCGACTCGCGCGAGGCGTACGTGCCTCGGCAGAACCTGTTCAGGGACCGCGCG |
| GGCGAGGAGCCCGAGGAGATGCGGGACAGGAGGTTCAGCGCAGGGCGGGAGCTGCGGCAGGGGCTG |
| AACCGCGAGCGGCTGCTGCGCGAGGAGGACTTTGAGCCCGACGCGGGGGATCAGCCCCGCGC |
| GCGCGCACGTGGCGGCCGCCGACCTGGTGACGGCGTACGAGCAGACGGTGAACCAGGAGATCAACTT |
| CCAAAAGAGTTTCAACAACCACGTGCGCACGCTGGTGGCGCGCGAGGAGGTGACCATCGGGCTGATG |
| CACCTGTGGGACTTTGTAAGCGCGCTGGTGCAGAACCCCAACAGCAAGCCTCTGACGGCGCAGCTGTT |
| CCTGATAGTGCAGCACAGCAGGGACAACGAGGCGTTTAGGGACGCGCTGCTGAACATCACCGAGCCC |
| GAGGGTCGGTGGCTGCTGGACCTGATTAACATCCTGCAGAGCATAGTGGTGCAGGAGCGCAGCCTGA |
| GCCTGGCCGACAAGGTGGCGGCCATCAACTACTCGATGCTGAGCCTGGGCAAGTTTTACGCGCGCAAG |

-continued

DESCRIPTION OF THE SEQUENCES

```
ATCTACCAGACGCCGTACGTGCCCATAGACAAGGAGGTGAAGATCGACGGTTTTTACATGCGCATGGC
GCTGAAGGTGCTCACCCTGAGCGACGACCTGGGCGTGTACCGCAACGAGCGCATCCACAAGGCCGTG
AGCGTGAGCCGGCGGCGCGAGCTGAGCGACCGCGAGCTGATGCACAGCCTGCAGCGGGCGCTGGCGG
GCGCCGGCAGCGGCGACAGGGAGGCGGAGTCCTACTTCGATGCGGGGCGGACCTGCGCTGGGCGCC
CAGCCGGCGGGCCCTGGAGGCCGCGGGGGTCCGCGAGGACTATGACGAGGACGGCGAGGAGGATGA
GGAGTACGAGCTAGAGGAGGGCGAGTACCTGGACTAAACCGCGGGTGGTGTTTCCGGTAGATGCAAG
ACCCGAACGTGGTGGACCCGGCGCTGCGGGCGGCTCTGCAGAGCCAGCCGTCCGGCCTTAACTCCTCA
GACGACTGGCGACAGGTCATGGACCGCATCATGTCGCTGACGGCGCGTAACCCGGACGCGTTCCGGCA
GCAGCCGCAGGCCAACAGGCTCTCCGCCATCCTGGAGGCGGTGGTGCCTGCGCGCTGAACCCCACGC
ACGAGAAGGTGCTGGCCATAGTGAACGCGCTGGCCGAGAACAGGGCCATCCGCCCGGACGAGGCCGG
GCTGGTGTACGACGCGCTGCTGCAGCGCGTGGCCCGCTACAACAGCGGCAACGTGCAGACCAACCTG
GACCGGCTGGTGGGGGACGTGCGCGAGGCGGTGGCGCAGCGCGAGCGCGCGGATCGGCAGGGCAACC
TGGGCTCCATGGTGGCGCTGAATGCCTTCCTGAGCACGCAGCCGGCCAACGTGCCGCGGGGGCAGGA
AGACTACACCAACTTTGTGAGCGCGCTGCGGCTGATGGTGACCGAGACCCCCAGAGCGAGGTGTACC
AGTCGGGCCCGGACTACTTCTTCCAGACCAGCAGACAGGGCCTGCAGACGGTGAACCTGAGCCAGGCT
TTCAAGAACCTGCGGGGGCTGTGGGGCGTGAAGGCGCCCACCGGCGACCGGGCGACGGTGTCCAGCC
TGCTGACGCCCAACTCGCGCCTGCTGCTGCTGCTGATCGCGCCGTTCACGGACAGCGGCAGCGTGTCC
CGGGACACCTACCTGGGGCACCTGCTGACCCTGTACCGCGAGGCCATCGGGCAGGCGCAGGTGGACG
AGCACACCTTCCAGGAGATCACCAGCGTGAGCCGCGCGCTGGGGCAGGAGGACACGAGCAGCCTGGA
GGCGACTCTGAACTACCTGCTGACCAACCGGCGGCAGAAGATTCCCTCGCTGCACAGCCTGACCTCCG
AGGAGGAGCGCATCTTGCGCTACGTGCAGCAGAGCGTGAGCCTGAACCTGATGCGCGACGGGGTGAC
GCCCAGCGTGGCGCTGGACATGACCGCGCGCAACATGGAACCGGGCATGTACGCCGCGCACCGGCCT
TACATCAACCGCCTGATGGACTACCTGCATCGCGCGGCGGCCGTGAACCCCGAGTACTTTACCAACGC
CATCCTGAACCCGCACTGGCTCCCGCCCCGGGTTCTACAGCGGGGCTTCGAGGTCCCGGAGACCA
ACGATGGCTTCCTGTGGGACGACATGGACGACAGCGTGTTCTCCCCGCGGCCGCAGGCGCTGGCGGAA
GCGTCCCTGCTGCGTCCCAAGAAGGAGGAGGAGGAGGAGGCGAGTCGCCGCCGCGGCAGCAGCGGCG
TGGCTTCTCTGTCCGAGCTGGGGCGGCAGCCGCCGCGCGCCCCGGGTCCCTGGGCGGCAGCCCCTTT
CCGAGCCTGGTGGGGTCTCTGCACAGCGAGCGCACCACCCGCCCTCGGCTGCTGGGCGAGGACGAGTA
CCTGAATAACTCCCTGCTGCAGCCGGTGCGGGAGAAAAACCTGCCTCCCGCCTTCCCCAACAACGGGA
TAGAGAGCCTGGTGGACAAGATGAGCAGATGGAAGACCTATGCGCAGGAGCACAGGGACGCGCCTGC
GCTCCGGCCGCCCACGCGGCGCCAGCGCCACGACCGGCAGCGGGGCTGGTGTGGGATGACGAGGAC
TCCGCGGACGATAGCAGCGTGCTGGACCTGGGAGGGAGCGGCAACCCGTTCGCGCACCTGCGCCCCC
GCCTGGGGAGGATGTTTTAAAAAAAAAAAAAAAAAAGCAAGAAGCATGATGCAAAAATTAAATAAAA
CTCACCAAGGCCATGGCGACCGAGCGTTGGTTTCTTGTGTTCCCTTCAGTATGCGGCGCGCGGCGATGT
ACCAGGAGGGACCTCCTCCCTCTTACGAGAGCGTGGTGGGCGCGGCGGCGGCGGCGCCCTCTTCTCCC
TTTGCGTCGCAGCTGCTGGAGCCGCCGTACGTGCCTCCGCGCTACCTGCGGCCTACGGGGGGAGAAA
CAGCATCCGTTACTCGGAGCTGGCGCCCCTGTTCGACACCACCCGGGTGTACCTGGTGGACAACAAGT
CGGCGGACGTGGCCTCCCTGAACTACCAGAACGACCACAGCAATTTTTTTGACCACGGTCATCCAGAAC
AATGACTACAGCCCGAGCGAGGCCAGCACCCAGACCATCAATCTGGATGACCGGTCGCACTGGGGCG
GCGACCTGAAAACCATCCTGCACACCAACATGCCCAACGTGAACGAGTTCATGTTCACCAATAAGTTC
AAGGCGCGGGTGATGGTGTCGCGCTCGCACACCAAGGAAGACCGGGTGGAGCTGAAGTACGAGTGGG
TGGAGTTCGAGCTGCCAGAGGGCAACTACTCCGAGACCATGACCATTGACCTGATGAACAACGCGATC
GTGGAGCACTATCTGAAAGTGGGCAGGCAGAACGGGGTCCTGGAGAGCGACATCGGGGTCAAGTTCG
ACACCAGGAACTTCCGCCTGGGGCTGGACCCCGTGACCGGGCTGGTTATGCCCGGGGTGTACACCAAC
GAGGCCTTCCATCCCGACATCATCCTGCTGCCCGGCTGCGGGTTGGACTTCACTTACAGCCGCCTGAG
CAACCTCCTGGGCATCCGCAAGCGGCAGCCCTTCCAGGAGGGCTTCAGGATCACCTACGAGGACCTGG
AGGGGGGCAACATCCCCGCGCTCCTCGATGTGGAGGCCTACCAGGATAGCTTGAAGGAAAATGAGGC
GGGACAGGAGGATACCGCCCCGCCGCCTCCGCCGCCGCCGAGCAGGGCGAGGATGCTGCTGACACC
GCGGCCGCGGACGGGGCAGAGGCCGACCCCGCTATGGTGGTGGACGGTCCCGAGCAGGAGGAGGACA
TGAATGACAGTGCGGTGCGCGGAGACACCCTTCGTCACCCGGGGGGAGGAAAAGCAAGCGGAGGCCGA
GGCCGCGGCCGAGGAAAAGCAACTGGCGGCAGCAGCGGCGGCGGCGGCGTTGGCCGCGGCGGAGGC
TGAGTCTGAGGGGACCAAGCCCGCCAAGGAGCCCGTGATTAAGCCCCTGACCGAAGATAGCAAGAAG
CGCAGTTACAACCTGCTCAAGGACAGCACCAACAACCGCGTACCGCAGCTGGTACCTGGCCTACAACTA
CGGCGACCCGTCGACGGGGGTGCGCTCCTGGACCCTGCTGTGCACGCCGGACGTGACCTGCGGCTCGG
AGCAGGTGTACTGGTCGCTGCCCGACATGATGCAAGACCCCGTGACCTTCCGCTCCACGCGGCAGGTC
AGCAACTTCCCGGTGGTGGGCGCCGAGCTGCTGCCCGTGCACTCCAAGAGCTTCTACAACGACCAGGC
CGTCTACTCCCAGCTCATCCGCCAGTTCACCTCTCTGACCCACGTGTTCAATCGCTTTCCTGAGAACCA
GATTCTGGCGCGCCCGCCCGCCCCACCATCACCACCGTCAGTGAAAACGTTCCTGCTCTCACAGATC
ACGGGACGCTACCGCTGCGCAACAGCATCGGAGGAGTCCAGCGAGTGACCGTTACTGACGCCAGACG
CCGCACCTGCCCCTACGTTTACAAGGCCTTGGGCATAGTCTCGCCGCGCGTCCTTTCCAGCCGCACTTT
TTGAGCAACACCACCATCATGTCCATCCTGATCTCACCCAGCAATAACTCCGGCTGGGGACTGCTGCG
CGCGCCCAGCAAGATGTTCGGAGGGGCGAGGAAGCGTTCCGAGCAGCACCCCGTGCGTGCGCGGG
CACTTCCGCGCCCCTGGGGAGCGCACAAACGCGGCCGCGCGGGGCGCACCACCGTGGACGACGCCA
TCGACTCGGTGGTGGAGCAGGCGCGCAACTACAGGCCCGGTCTCTACCGTGGACGCGGCCATCCAG
ACCGTGGTGCGGGCGCGCGGCGGTACGCCAAGCTGAAGAGCCGCCGGAAGCGCGTGGCCCGCCGCC
ACCGCCGCCGACCCGGGGCCGCGCCAAACGCGCCAGCCCTGCTTCGCCGGGCCAAGCGCAC
GGGCGCCGCGCCGCCATGAGGGCCGCGCGCCGCTTGGCCGCCGGCATCACCGCCGCCACCATGGCCC
CCCGTACCCGAAGACGCGCGGCCGCCGCCGCCGCCGCCGCCATCAGTGACATGGCCAGCAGGCGCCG
GGGCAACGTGTACTGGGTGCGCGACTCGGTGACCGGCACGCGCGTGCCCGTGCGCTTCCGCCCCCCGC
GGACTTGAGATGATGTGAAAAAACAACACTGAGTCTCCTGCTGTTGTGTATCCCAGCGGCGGCGGC
GCGCGCAGCGTCATGTCCAAGCGCAAAATCAAAGAAGAGATGCTCCAGGTCGTCGCGCCGGAGATCT
ATGGGCCCCGAAGAAGGAAGAGCAGGATTCGAAGCCCGCAAGATAAAGCGGGTCAAAAAGAAAA
AGAAAGATGATGACGATGCCGATGGGGAGGTGGAGTTCCTGCGCGCCACGGCGCCCAGGCGCCCGGT
GCAGTGAAGGGCCGGCGCGTAAAGCGCGTCCTGCGCCCCGGCACCGCGGTGGTCTTCACGCCCGGC
GAGCGCTCCACCCGGACTTTCAAGCGCGTCTATGACGAGGTGTACGGCGACGAAGACCTGCTGGAGCA
GGCCAACGAGCGCTTCGGAGAGTTTGCTTACGGGAAGCGTCAGCGGGCGCTGGGGAAGGAGGACCTG
CTGGCGCTGCCGCTGGACCAGGGCAACCCCACCCCCAGTCTGAAGCCCGTGACCCTGCAGCAGGTGCT
```

DESCRIPTION OF THE SEQUENCES

```
GCCGAGCAGCGCACCCTCCGAGGCGAAGCGGGGTCTGAAGCGCGAGGGCGGCGACCTGGCGCCCACC
GTGCAGCTCATGGTGCCCAAGCGGCAGAGGCTGGAGGATGTGCTGGAGAAAATGAAAGTAGACCCCG
GTCTGCAGCCGGACATCAGGGTCCGCCCCATCAAGCAGGTGGCGCCGGGCCTCGGCGTGCAGACCGTG
GACGTGGTCATCCCCACCGGCAACTCCCCCGCCGCCGCCACCACTACCGCTGCCTCCACGGACATGGA
GACACAGACCGATCCCGCCGCAGCCGCAGCCGCAGCCGCCGCCGCGACCTCCTCGGCGGAGGTGCAG
ACGGACCCCTGGCTGCCGCCGGCGATGTCAGCTCCCCGCGCGCGTCGCGGGCGCAGGAAGTACGGCG
CCGCCAACGCGCTCCTGCCCGAGTACGCCTTGCATCCTTCCATCGCGCCCACCCCCGGCTACCGAGGCT
ATACCTACCGCCCGCGAAGAGCCAAGGGGTTCCACCCGCCGTCCCCGCCGACGCGCCGCCGCCACCACC
CGCCGCCGCCGCCGCAGACGCCAGCCCGCACTGGCTCCAGTCTCCGTGAGGAAAGTGGCGCGCGACG
GACACACCCTGGTGCTGCCCAGGGCGCGCTACCACCCCAGCATCGTTTAAAAGCCTGTTGTGGTTCTTG
CAGATATGGCCCTCACTTGCCGCCTCCGTTTCCCGGTGCCGGGATACCGAGGAGGAAGATCGCGCCGC
AGGAGGGGTCTGGCCGGCCGCGGCCTGAGCGGAGGCAGCCGCCGCGCACCGGCGGCGACGCGCCA
CCAGCCGACGCATGCGCGGCGGGGTGCTGCCCCTGTTAATCCCCCTGATCGCCGCGGCGATCGGCGCC
GTGCCCGGGATCGCCTCCGTGGCCTTGCAAGCGTCCCAGAGGCATTGACAGACTTGCAAACTTGCAAA
TATGGAAAAAAAAACCCCAATAAAAAAGTCTAGACTCTCACGCTCGCTTGGTCCTGTGACTATTTTGT
AGAATGGAAGACATCAACTTTGCGTCGCTGGCCCCGCGTCACGGCTCGCGCCCGTTCCTGGGACACTG
GAACGATATCGGCACCAGCAACATGAGCGGTGGCGCCTTCAGTTGGGGCTCTCTGTGGAGCGGCATTA
AAAGTATCGGGTCTGCCGTTAAAAATTACGGCTCCCGGGCCTGGAACAGCAGCACGGGCCAGATGTTG
AGAGACAAGTTGAAAGAGCAGAACTTCCAGCAGAAGGTGGTGGAGGGCCTGGCCTCCGGCATCAACG
GGGTGGTGGACCTGGCCAACCAGGCCGTGCAGAATAAGATCAACAGCAGACTGGACCCCCGGCCGCC
GGTGGAGGAGGTGCCGCCGGCGCTGGAGACGGTGTCCCCGATGGGCGTGGCGAGAAGCGCCCGCGG
CCCGATAGGGAAGAGACCACTCTGGTCACGCAGACCGATGAGCCGCCCCGTATGAGGAGGCCCTGA
AGCAAGGTCTGCCCACCACGCGGCCCATCGCGCCCATGGCCACCGGGGTGGTGGGCCGCCACACCCCC
GCCACGCTGGACTTGCCTCCGCCCGCCGATGTGCCGCAGCAGCAGAGGCGGCACAGCCGGGCCCGC
CCGCGACCGCCTCCCGTTCCTCCGCCGGTCCTCTGCCGCGCGGCCAGCGGCCCCGCGGGGGGGTC
GCGAGGCACGGCAACTGGCAGAGCACGCTGAACAGCATCGTGGGTCTGGGGGTGCGGTCCGTGAAGC
GCCGCCGATGCTACTGAATAGCTTAGCTAACGTGTTGTATGTGTATGCGCCCTATGTCGCCGCCAGA
GGAGCTGCTGAGTCGCCGCCGTTCGCGCGCCCACCACCACCGCCACTCCGCCCCTCAAGATGGCGACC
CCATCGATGATGCCGCAGTGGTCGTACATGCACATCTCGGGCCAGGACGCCTCGGAGTACCTGAGCCC
CGGGCTGGTGCAGTTCGCCCGCGCCACCGAGAGCTACTTCAGCCTGAGTAACAAGTTTAGGAACCCCA
CGGTGGCGCCCACGCACGATGTGACCACCGACCGGTCTCAGCGCCTGACGCTGCGGTTCATTCCCGTG
GACCGCGAGGACACCGCGTACTCGTACAAGGCGCGGTTCACCCTGGCCGTGGGCGACAACCGCGTGCT
GGACATGGCCTCCACCTACTTTGACATCCGCGGGTGCTGGACCGGGGTCCCACTTTCAAGCCCTACTC
TGGCACCGCCTACAACTCCCTGGCCCCCAAGGGCGCTCCCAACTCCTGCGAGTGGGAGCAAGAGGAA
ACTCAGGCAGTTGAAGAAGCAGCAGAAGAGGAAGAAGAAGATGCTGACGGTCAAGCTGAGGAAGAG
CAAGCAGCTACCAAAAAGACTCATGTATATGCTCAGGCTCCCCTTTCTGGCGAAAAAATTAGTAAAGA
TGGTCTGCAAATAGGAACGGACGCTACAGCTACAGAACAAAAACCTATTTATGCAGACCCTACATTCC
AGCCCGAACCCCAAATCGGGGAGTCCCAGTGGAATGAGGCAGATGCTACAGTCGCCGGCGGTAGAGT
GCTAAAGAAATCTACTCCCATGAAACCATGCTATGGTTCCTATGCAAGACCCACAAATGCTAATGGAG
GTCAGGGTGTACTAACGGCAAATGCCCAGGGACAGCTAGAATCTCAGGTTGAAATGCAATTCTTTTCA
ACTTCTGAAAACGCCCGTAACGAGGCTAACAACATTCAGCCCAAATTGGTGCTGTATAGTGAGGATGT
GCACATGGAGACCCCGGATACGCACCTTTCTTACAAGCCCGCAAAAAGCGATGACAATTCAAAAATCA
TGCTGGGTCAGCAGTCCATGCCCAACAGACCTAATTACATCGGCTTCAGAGACAACTTTATCGGCCTC
ATGTATTACAATAGCACTGGCAACATGGGAGTGCTTGCAGGTCAGGCCTCTCAGTTGAATGCAGTGGT
GGACTTGCAAGACAGAAACACAGAACTGTCCTACCAGCTCTTGCTTGATTCCATGGGTGACAGAACCA
GATACTTTTCCATGTGGAATCAGGCAGTGGACAGTTATGACCCAGATGTTAGAATTATTGAAAATCAT
GGAACTGAAGACGAGCTCCCCAACTATTGTTTCCCTCTGGGTGGCATAGGGGTAACTGACACTTACCA
GGCTGTTAAAACCAACAATGGCAATAACGGGGGCCAGGTGACTTGGACAAAAGATGAAACTTTTGCA
GATCGCAATGAAATAGGGGTGGGAAACAATTTCGCTATGGAGATCAACCTCAGTGCCAACCTGTGGA
GAAACTTCCTGTACTCCAACGTGGCGCTGTACCTACCAGACAAGCTTAAGTACAACCCCTCCAATGTG
GACATCTCTGACAACCCCAACACCTACGATTACATGAACAAGCGAGTGGTGGCCCCGGGGCTGGTGGA
CTGCTACATCAACCTGGGCGCGCGCTGGTCGCTGGACTACATGGACAACGTCAACCCCTTCAACCACC
ACCGCAATGCGGGCCTGCGCTACCGCTCCATGCTCCTGGGCAACGGGCGCTACGTGCCCTTCCACATC
CAGGTGCCCCAGAAGTTCTTTGCCATCAAGAACCTCCTCCTCCTGCCGGGCTCCTACACCTACGAGTGG
AACTTCAGGAAGGATGTCAACATGGTCCTCCAGAGCTCTCTGGGTAACGATCTCAGGGTGGACGGGGC
CAGCATCAAGTTCGAGAGCATCTGCCTCTACGCCACCTTCTTCCCCATGGCCCACAACACGGCCTCCAC
GCTCGAGGCCATGCTCAGGAACGACACCAACGACCAGTCCTTCAATGACTACCTCTCCGCCGCCAACA
TGCTCTACCCCATACCCGCCAACGCCACCAACGTCCCCATCTCCATCCCCTCGCGCAACTGGGCGGCCT
TCCGCGGCTGGGCCTTCACCCGCCTCAAGACCAAGGAGACCCCCTCCCTGGGCTCGGGATTCGACCCC
TACTACACCTACTCGGGCTCCATTCCCTACCTGGACGGCACCTTCTACCTCAACCACACTTTCAAGAAG
GTCTCGGTCACCTTCGACTCCTCGGTCAGCTGGCCGGGCAACGACGTCTGCTCACCCCCCAACGAGTTC
GAGATCAAGCGCTCGGTCGACGGGGAGGGCTACAACGTGGCCCAGTGCAACATGACCAAGGACTGGT
TCCTGGTCCAGATGCTGGCCAACTACAACATCGGCTACCAGGGCTTCTACATCCCAGAGAGCTACAAG
GACAGGATGTACTCCTTCTTCAGGAACTTCCAGCCCATGAGCCGGCAGGTGGTGGACCAGACCAAGTA
CAAGGACTACCAGGAGGTGGGCATCATCCACCAGCACAACAACTCGGGCTTCGTGGGCTACCTCGCCC
CCACCATGCGCGAGGGACAGGCCTACCCCGCCAACTTCCCCTATCCGCTCATAGGCAAGACCGCGGTC
GACAGCATCACCCAGAAAAAGTTCCTCTGCGACCGCACCCTCTGGCGCATCCCCTTCTCCAGCAACTTC
ATGTCCATGGGTGCGCTCTCGGACCTGGGCCAGAACTTGCTCTACGCCAACTCCGCCCACGCCCTCGA
CATGACCTTCGAGGTCGACCCCATGGACGAGCCCACCCTTCTCTATGTTCTGTTCGAAGTCTTTGACGT
GGTCCGGGTCCACCAGCCGCACCGCGGCGTCATCGAGACCGTGTACCTGCGTACGCCCTTCTCGGCCG
GCAACGCCACCACCTAAAGAAGCAAGCCGCAGTCATCGCCGCTGCATGCCGTCGGGTTCCACCGAGC
AAGAGCTCAGGGCCATCGTCAGAGACCTGGGATGCGGGCCCTATTTTTTGGGCACCTTCGACAAGCGC
TTCCCTGGCTTTGTCTCCCCACACAAGCTGGCCTGCGCCATCGTCAACACGGCCGGCCGCGAGACCGG
GGGCGTGCACTGGCTGGCCTTCGCCTGGAACCCGCGCTCCAAAACATGCTTCCTCTTTGACCCCTTCGG
CTTTTCGGACCAGCGGCTCAAGCAAATCTACGAGTTCGAGTACGAGGGCTTGCTGCGTCGCAGCGCCA
TCGCCTCCTCGCCCGACCGCTGCGTCACCCTCGAAAAGTCCACCCAGACCGTGCAGGGGCCCGACTCG
GCCGCCTGCGGTCTCTTCTGCTGCATGTTTCTGCACGCCTTTGTGCACTGGCCTCAGAGTCCCATGGAC
```

DESCRIPTION OF THE SEQUENCES

```
CGCAACCCCACCATGAACTTGCTGACGGGGGTGCCCAACTCCATGCTCCAGAGCCCCCAGGTCGAGCC
CACCCTGCGCCGCAACCAGGAGCAGCTCTACAGCTTCCTGGAGCGCCACTCGCCTTACTTCCGCCGCC
ACAGCGCACAGATCAGGAGGGCCACCTCCTTCTGCCACTTGCAAGAGATGCAAGAAGGGTAATAACG
ATGTACACACTTTTTTTCTCAATAAATGGCATCTTTTTATTTATACAAGCTCTCTGGGGTATTCATTTCC
CACCACCACCCGCCGTTGTCGCCATCTGGCTCTATTTAGAAATCGAAAGGGTTCTGCCGGGAGTCGCC
GTGCGCCACGGGCAGGGACACGTTGCGATACTGGTAGCGGGTGCCCCACTTGAACTCGGGCACCACCA
GGCGAGGCAGCTCGGGGAAGTTTTCGCTCCACAGGCTGCGGGTCAGCACCAGCGCGTTCATCAGGTCG
GGCGCCGAGATCTTGAAGTCGCAGTTGGGGCGCCGCCCTGCGCGCGCGAGTTGCGGTACACCGGGTT
GCAGCACTGGAACACCAACAGCGCCGGGTGCTTCACGCTGGCCAGCACGCTGCGGTCGGAGATCAGC
TCGGCGTCCAGGTCCTCCGCGTTGCTCAGCGCGAACGGGGTCATCTTGGGCACTTGCCGCCCCAGGAA
GGGCGCGTGCCCCGGTTTCGAGTTGCAGTCGCAGCGCAGCGGGATCAGCAGGTGCCCGTGCCCGGACT
CGGCGTTGGGGTACAGCGCGCGCATGAAGGCCTGCATCTGGCGGAAGGCCATCTGGGCCTTGGCGCCC
TCCGAGAAGAACATGCCGCAGGACTTGCCCGAGAACTGGTTTGCGGGGCAGCTGGCGTCGTGCAGGC
AGCAGCGCGCGTCGGTGTTGGCGATCTGCACCACGTTGCGCCCCCACCGGTTCTTCACGATCTTGGCCT
TGGACGATTGCTCCTTCAGCGCGCGCTGCCCGTTCTCGCTGGTCACATCCATCTCGATCACATGTTCCT
TGTTCACCATGCTGCTGCCGTGCAGACACTTCAGCTCGCCCTCCGTCTCGGTGCAGCGGTGCTGCCACA
GCGCGCAGCCCGTGGGCTCGAAAGACTTGTAGGTCACCTCCGCGAAGGACTGCAGGTACCCCTGCAAA
AAGCGGCCCATCATGGTCACGAAGGTCTTGTTGCTGCTGAAGGTCAGCTGCAGCCCGCGGTGCTCCTC
GTTCAGCCAGGTCTTGCACACGGCCGCCAGCGCCTCCACCTGGTCGGGCAGCATCTTGAAGTTCACCTT
CAGCTCATTCTCCACGTGGTACTTGTCCATCAGCGTGCGCGCCGCCTCCATGCCCTTCTCCCAGGCCGA
CACCAGCGGCAGGCTCACGGGGTTCTTCACCATCACCGTGGCCGCCGCCTCCGCCGCGCTTTCGCTTTC
CGCCCCGCTGTTCTCTTCCTCTTCCTCCTCTTCCTCGCCGCCGCCCACTCGCAGCCCCGCACCACGGGG
TCGTCTTCCTGCAGGCGCTGCACCTTGCGCTTGCCGTTGCGCCCCTGCTTGATGCGCACGGGCGGGTTG
CTGAAGCCCACCATCACCAGCGCGGCCTCTTCTTGCTCGTCCTCGCTGTCCAGAATGACCTCCGGGGAG
GGGGGGTTGGTCATCCTCAGTACCGAGGCACGCTTCTTTTTTCTTCCTGGGGGCGTTCGCCAGCTCCGCG
GCTGCGGCCGCTGCCGAGGTCGAAGGCCGAGGGCTGGGCGTGCGCGGCACCAGCGCGTCCTGCGAGC
CGTCCTCGTCCTCCTCGGACTCGAGACGGAGGCGGGCCCGCTTCTTCGGGGGCGCGCGGGGCGGCGGA
GGCGGCGGCGGCGACGGAGACGGGGACGAGACATCGTCCGGGGTGGGTGGACGGCGGGCCGCGCCG
CGTCCGCGCTCGGGGGTGGTCTCGCGCTGGTCCTCTTCCCGACTGGCCATCTCCCACTGCTCCTTCTCCT
ATAGGCAGAAAGAGATCATGGAGTCTCTCATGCGAGTCGAGAAGGAGGAGGACAGCCTAACCGCCCC
CTCTGAGCCCTCCACCACCGCCGCCACCACCGCCAATGCCGCCGCGACGACGCGCCCACCGAGACCA
CCGCCAGTACCACCCTCCCCAGCGACGCACCCCCGCTCGAGAATGAAGTGCTGATCGAGCAGGACCCG
GGTTTTGTGAGCGGAGAGGAGGATGAGGTGGATGAGAAGGAGAAGGAGGAGGTCGCCGCCTCAGTGC
CAAAAGAGGATAAAAAGCAAGACCAGGACGACGCAGATAAGGATGAGACAGCAGTCGGGCGGGGA
ACGGAAGCCATGATGCTGATGACGGCTACCTAGACGTGGGAGACGACGTGCTGCTTAAGCACCTGCAC
CGCCAGTGCGTCATCGTCTGCGACGCGCTGCAGGAGCGCTGCGAAGTGCCCCTGGACGTGGCGGAGGT
CAGCCGCGCCTACGAGCGGCACCTCTTCGCGCCGCACGTGCCCCCCAAGCGCCGGGAGAACGGCACCT
GCGAGCCCAACCCGCGTCTCAACTTCTACCCGGTCTTCGCGGTACCCGAGGTGCTGGCCACCTACCAC
ATCTTTTTCCAAAACTGCAAGATCCCCCTCTCCTGCCGCGCCAACCGCACCCGCGCCGACAAAACCCTG
ACCCTGCGGCAGGGCGCCCACATACCTGATATCGCCTCTCTGGAGGAAGTGCCCAAGATCTTCGAGGG
TCTCGGTCGCGACGAGAAACGGGCGGCGAACGCTCTGCACGGAGACAGCGAAAACGAGAGTCACTCG
GGGGTGCTGGTGGAGCTCGAGGGCGACAACGCGCGCCTGGCCGTACTCAAGCGCAGCATAGAGGTCA
CCCACTTTGCCTACCCGGCGCTCAACCTGCCCCCCAAGGTCATGAGTGTGGTCATGGGCGAGCTCATC
ATGCGCCGCGCCCAGCCCCTGGCCGCGGATGCAAACTTGCAAGAGTCCTCCGAGGAAGGCCTGCCCGC
GGTCAGCGACGAGCAGCTGGCGCGCTGGCTGGAGACCCGCGACCCCGCAGCTGGAGGAGCGGCGC
AAGCTCATGATGGCCGCGGTGCTGGTCACCGTGGAGCTCGAGTGTCTGCAGCGCTTCTTCGCGGACCC
CGAGATGCAGCGCAAGCTCGAGGAGACCCTGCACTACACCTTCCGCCAGGGCTACGTGCGCCAGGCCT
GCAAGATCTCCAACGTGGAGCTCTGCAACCTGGTCTCCTACCTGGGCATCCTGCACGAGAACCGCCTC
GGGCAGAACGTCCTGCACTCCACCCTCAAAGGGGAGGCGCGCCCGACTACATCCGCGACTGCGCCTA
CCTCTTCCTCTGCTACACCTGGCAGACGGCCATGGGGGTCTGGCAGCAGTGCCTGGAGGAGCGCAACC
TCAAGGAGCTGGAAAAGCTCCTCAAGCGCACCCTCAGGGACCTCTGGACGGGCTTCAACGAGCGCTCG
GTGGCCGCCGCGCTGGCGGACATCATCTTTCCCGAGCGCCTGCTCAAGACCCTGCAGCAGGGCCTGCC
CGACTTCACCAGCCAGAGCATGCTGCAGAACTTCAGGACTTTCATCCTGGAGCGCTCGGGCATCCTGC
CGGCCACTTGCTGCGCGCTGCCCAGCGACTTCGTGCCCATCAAGTACAGGGAGTGCCCGCCGCCGCTC
TGGGGCCACTGCTACCTCTTCCAGCTGGCCAACTACCTCGCCTACCACTCGGACCTCATGGAAGACGT
GAGCGGCGAGGGCCTGCTCGAGTGCCACTGCCGCTGCAACCTCTGCACGCCCCACCGCTCTCTAGTCT
GCAACCCGCAGCTGCTCAGCGAGAGTCAGATTATCGGTACCTTCGAGCTGCAGGGTCCCTCGCCTGAC
GAGAAGTCCGCGGCTCCAGGGCTGAAACTCACTCCGGGGCTGTGGACTTCCGCCTACCTACGCAAATT
TGTACCTGAGGACTACCACGCCCACGAGATCAGGTTCTACGAAGACCAATCCCGCCCGCCCAAGGCGG
AGCTCACCGCCTGCGTCATCACCCAGGGGCACATCCTGGGCCAATTGCAAGCCATCAACAAAGCCCGC
CGAGAGTTCTTGCTGAAAAAGGGTCGGGGGGTGTACCTGGACCCCCAGTCCGGCGAGGAGCTAAACC
CGCTACCCCCGCCGCCGCCCCAGCAGCGGGACCTTGCTTCCCAGGATGGCACCCAGAAAGAAGCAGC
AGCCGCCGCCGCCGCCGCAGCCATACATGCTTCTGGAGGAAGAGGAGGAGGACTGGGACAGTCAGGC
AGAGGAGGTTTCGGACGAGGAGCAGGAGGAGATGATGGAAGACTGGGAGGAGGACAGCAGCCTAGA
CGAGGAAGCTTCAGAGGCCGAAGAGGTGGCAGACGCAACACCATCGCCCTCGGTCGCAGCCCCTCG
CCGGGGCCCCTGAAATCCTCCGAACCCAGCACCAGCGCTATAACCTCCGCTCCTCCGGCGCCGGCGCC
ACCCGCCCGCAGACCCAACCGTAGATGGGACACCACAGGAACCGGGGTCGGTAAGTCCAAGTGCCCG
CCGCCGCCACCGCAGCAGCAGCAGCAGCAGCGCCAGGGCTACCGCTCGTGGCGCGGGCACAAGAACG
CCATAGTCGCCTGCTTGCAAGACTGCGGGGGCAACATCTCTTTCGCCCGCCGCTTCCTGCTATTCCACC
ACGGGGTCGCCTTTCCCCGCAATGTCCTGCATTACTACCGTCATCTCTACAGCCCCTACTGCAGCGGCG
ACCCAGAGGCGGCAGCGGCAGCGCAGGCGGCGACCACCACCTAGGAAGATATCCTCCGCGGGCAAGA
CAGCGGCAGCAGCGGCCAGGAGACCCGCGGCAGCAGCGGCGGAGCGGTGGGCGCACTGCGCCTCTC
GCCCAACGAACCCCTCTCGACCCGGGAGCTCAGACACAGGATCTTCCCCACTTTGTATGCCATCTTCCA
ACAGAGCAGAGGCCAGGAGCAGGAGCTGAAAATAAAAACAGATCTCTGCGCTCCCTCACCCGCAGC
TGTCTGTATCACAAAAGCGAAGATCAGCTTCGGCGCACGCTGGAGGACGCGGAGGCACTCTTCAGCAA
ATACTGCGCGCTCACTCTTAAAGACTAGCTCCGCGCCCTTCTCGAATTTAGGCGGGAGAAAACTACGT
CATCGCCGGCCGCCGCCCAGCCCGCCCAGCCGAGATGAGCAAAGAGATTCCCACGCCATACATGTGG
```

DESCRIPTION OF THE SEQUENCES

```
AGCTACCAGCCGCAGATGGGACTCGCGGCGGGAGCGGCCCAGGACTACTCCACCCGCATGAACTACA
TGAGCGCGGGACCCCACATGATCTCACAGGTCAACGGGATCCGCGCCCAGCGAAACCAAATACTGCT
GGAACAGGCGGCCATCACCGCCACGCCCCGCCATAATCTCAACCCCCGAAATTGGCCCGCCGCCCTCG
TGTACCAGGAAACCCCCTCCGCCACCACCGTACTACTTCCGCGTGACGCCCAGGCCGAAGTCCAGATG
ACTAACTCAGGGGCGCAGCTCGCGGGCGGCTTTCGTCACGGGGCGCGGCCGCTCCGACCAGGTATAAG
ACACCTGATGATCAGAGGCCGAGGTATCCAGCTCAACGACGAGTCGGTGAGCTCTTCGCTCGGTCTCC
GTCCGGACGGAACTTTCCAGCTCGCCGGATCCGGCCGCTCTTCGTTCACGCCCCGCCAGGCGTACCTG
ACTCTGCAGACCTCGTCCTCGGAGCCCCGCTCCGGCGGCATCGGAACCCTCCAGTTCGTGGAGGAGTT
CGTGCCCTCGGTCTACTTCAACCCCTTCTCGGGACCTCCCGGACGCTACCCCGACCAGTTCATTCCGAA
CTTTGACGCGGTGAAGGACTCGGCGGACGGCTACGACTGAATGTCAGGTGTCGAGGCAGAGCAGCTTC
GCCTGAGACACCTCGAGCACTGCCGCCGCCACAAGTGCTTCGCCCCGCGGTTCTGGTGAGTTCTGCTACT
TTCAGCTACCCGAGGAGCATACCGAGGGGCCGGCGCACGGCGTCCGCCTGACCACCCAGGGCGAGGT
TACCTGTTCCCTCATCCGGGAGTTTACCCTCCGTCCCTGCTAGTGGAGCGGGAGCGGGGTCCCTGTGT
CCTAACTATCGCCTGCAACTGCCCTAACCCTGGATTACATCAAGATCTTTGCTGTCATCTCTGTGCTGA
GTTTAATAAACGCTGAGATCAGAATCTACTGGGGCTCCTGTCGCCATCCTGTGAACGCCACCGTCTTCA
CCCACCCCGACCAGGCCCAGGCGAACCTCACCTGCGGTCTGCATCGGAGGGCCAAGAAGTACCTCACC
TGGTACTTCAACGGCACCCCCTTTGTGGTTTACAACAGCTTCGACGGGGACGGAGTCTCCCTGAAAGA
CCAGCTCTCCGGTCTCAGCTACTCCATCCACAAGAACACCACCCTCCAACTCTTCCCTCCCTACCTGCC
GGGAACCTACGAGTGCGTCACCGGCCGCTGCACCCACCTCACCCGCCTGATCGTAAACCAGAGCTTTC
CGGGAACAGATAACTCCCTCTTCCCCAGAACAGGAGGTGAGCTCAGGAAACTCCCCGGGGACCAGGG
CGGAGACGTACCTTCGACCCTTGTGGGGTTAGGATTTTTTATTACCGGGTTGCTGGCTCTTTTAATCAA
AGTTTCTTGAGATTTGTTCTTTCCTTCTACGTGTATGAACACCTCAACCTCCAATAACTCTACCCTTTC
TTCGGAATCAGGTGACTTCTCTGAAATCGGGCTTGGTGTGCTGCTTACTCTGTTGATTTTTTCCTTATC
ATACTCAGCCTTCTGTGCCTCAGGCTCGCCGCCTGCTGCGCACACATCTATATCTACTGCTGGTTGCTC
AAGTGCAGGGGTCGCCACCCAAGATGAACAGGTACATGGTCCTATCGATCCTAGGCCTGCTGGCCCTG
GCGGCCTGCAGCGCCGCCAAAAAAGAGATTACCTTTGAGGAGCCCGCTTGCAATGTAACTTTCAAGCC
CGAGGGTGACCAATGCACCACCCTCGTCAAATGCGTTACCAATCATGAGAGGCTGCGCATCGACTACA
AAAACAAAACTGGCCAGTTTGCGGTCTATAGTGTGTTTACGCCCGGAGACCCCTCTAACTACTCTGTCA
CCGTCTTCCAGGGCGGACAGTCTAAGATATTCAATTACACTTTCCCTTTTTATGAGTTATGCGATGCGG
TCATGTACATGTCAAAACAGTACAACCTGTGGCCTCCCTCTCCCAGGCGTGTGTGGAAAATACTGGG
TCTTACTGCTGTATGGCTTTCGCAATCACTACGCTCGCTCTAATCTGCACGGTGCTATACATAAAATTC
AGGCAGAGGCGAATCTTTATCGATGAAAAGAAAATGCCTTGATCGCTAACACCGGCTTTCTATCTGCA
GAATGAATGCAATCACCTCCCTACTAATCACCACCACCCTCCTTGCGATTGCCCATGGGTTGACACGA
ATCGAAGTGCCAGTGGGGTCCAATGTCACCATGGTGGGCCCCGCCGGCAATTCCACCCTCATGTGGGA
AAAATTTGTCCGCAATCAATGGGTTCATTTCTGCTCTAACCGAATCAGTATCAAGCCCAGAGCCATCTG
CGATGGGCAAAATCTAACTCTGATCAATGTGCAAATGATGAGTGCTGGGTACTATTACGGGCAGCGGG
GAGAAATCATTAATTACTGGCGACCCCACAAGGACTACATGCTGCATGTAGTCGAGGCACTTCCCACT
ACCACCCCCACTACCACCTCTCCCACCACCACCACCACTACTACTACTACTACTACTACTACTACTACT
ACCACTACCGCTGCCCGCCATACCCGCAAAAGCACCATGATTAGCACAAAGCCCCCTCGTGCTCACTC
CCACGCCGGCGGGCCCATCGGTGCGACCTCAGAAACCACCGAGCTTTGCTTCTGCCAATGCACTAACG
CCAGCGCTCATGAACTGTTCGACCTGGAGAATGAGGATGTCCAGCAGAGCTTCCGCTTGCCTGACCCAG
GAGGCTGTGGAGCCCGTTGCCCTGAAGCAGATCGGTGATTCAATAATTGACTCTTCTTCTTTTGCCACT
CCCGAATACCCTCCCGATTCTACTTTCCACATCACGGGTACCAAAGACCCTAACCTCTCTTTCTACCTG
ATGCTGCTGCTCTGTATCTCTGTGGTCTCTTCCGCGCTGATGTTACTGGGGATGTTCTGCTGCCTGATCT
GCCGCAGAAAGAGAAAAGCTCGCTCTCAGGGCCAACCACTGATGCCCTTTCCCCTACCCCCCGGATTTT
GCAGATAACAAGATATGAGCTCGCTGCTGACACTAACCGCTTTACTAGCCTGCGCTCTAACCCTTGTCG
CTTGCGACTCGAGATTCCACAATGTCACAGCTGTGGCAGGAGAAAATGTTACTTTCAACTCCACGGCC
GATACCCAGTGGTCGTGGAGTGGCTCAGGTAGCTACTTAACTATCTGCAATAGCTCCACTTCCCCCGGC
ATATCCCAACCAAGTACCAATGCAATGCCAGCCTGTTCACCCTCATCAACGCTTCCACCCTGGACAAT
GGACTCTATGTAGGCTATGTACCCTTTGGTGGGCAAGGAAAGACCCACGCTTACAACCTGGAAGTTCG
CCAGCCCAGAACCACTACCCAAGCTTCTCCCACCACCACCACCACCACCATCACCAGCAGCAGCA
GCAGCAGCAGCCACAGCAGCAGCAGCAGATTATTGACTTTGGTTTTGGCCAGCTCATCTGCCGCTACC
CAGGCCATCTACAGCTCTGTGCCCAGAAACCACTCAGATCCACCGCCCAGAAACGACCACCGCCACCAC
CCTACACACCTCCAGCGATCAGATGCCGACCAACATCACCCCCTTGGCTCTTCAAATGGACTTCAA
GCCCCACTCCAAAACCAGTGGATGCGGCCGAGGTCTCCGCCCTCGTCAATGACTGGGCGGGGCTGGGA
ATGTGGTGGTTCGCCATAGGCATGATGGCGCTCTGCCTGCTTCTGCTCTGGCTCATCTGCTGCCTCCAC
CGCAGGCGAGCCAGACCCCCCATCTATAGACCCATCATTGTCCTGAACCCCGATAATGATGGGATCCA
TAGATTGGATGGCCTGAAAAACCTACTTTTTTCTTTTACAGTATGATAAATTGAGACATGCCTCGCATT
TTCTTGTACATGTTCCTTCTCCCACCTTTTCTGGGGTGTTCTACGCTGGCCGCTGTGTCTCACCTGGAGG
TAGACTGCCTCTCACCCTTCACTGTCTACCTGCTTTACGGATTGGTCACCCTCACTCTCATCTGCAGCCT
AATCACAGTAATCATCGCCTTCATCCAGTGCATTGATTACATCTGTGTGCGCCTCGCCATACTTCAGACA
CCACCCGCAGTACCGAGACAGGAACATTGCCCAACTTCTAAGACTGCTCTAATCATGCATAAGACTGT
GATCTGCCTTCTGATCCTCTGCATCCTGCCCACCCTCACCTCCTGCCAGTACACCACAAAATCTCCGCG
CAAAAGACATGCCTCCTGCCGCTTCACCCAACTGTGGAATATACCCAAATGCTACAACGAAAAGAGCG
AGCTCTCCGAAGCTTGGCTGTATGGGGTCATCTGTGTCTTAGTTTTCTGCAGCACTGTCTTTGCCCTCAT
AATCTACCCCTACTTTGATTTGGGATGGAACGCGATCGATGCCATGATGAATTACCCCACCTTTCCCGCACC
CGAGATAATTCCACTGCGACAAGTTGTACCCGTTGTCGTTAATCAACGCCCCCCATCCCCTACGCCCAC
TGAAATCAGCTACTTTAACCTAACAGGCGGAGATGACTGACGCCCTAGATCTAGAAATGGACGGCATC
AGTACCGAGCAGCGTCCTAGAGAGGCGCAGGCAGGCGGCTGAGCAAGAGCGCCTCAATCAGGAGC
TCCGAGATCTCGTTAACCTGCACCAGTGCAAAAGAGGCATCTTTTGTCTGGTAAAGCAGGCCAAAGTC
ACCTACGAGAAGACCGGCAACAGCCACCGCCTCAGTTACAAATTGCCCACCCAGCGCCAGAAGCTGG
TGCTCATGGTGGGTGAGAATCCCATCACCGTCACCCAGCACTCGGTAGAGACCGAGGGGTGTCTGCAC
TCCCCCTGTCGGGGTCCAGAAGACCTCTGCACCCTGGTAAAGACCCTGTGCGGTCTCAGAGATTTAGT
CCCCTTTAACTAATCAAACACTGGAATCAATAAAAAGAATCACTTACTTAAAATCAGACAGCAGGTCT
CTGTCCAGTTTATTCAGCAGCACCTCCTTCCCCTCCTCCCAACTCTGGTACTCCAAACGCCTTCTGGCG
GCAAACTTCCTCCACACCCTGAAGGGAATGTCAGATTCTTGCTCCTGTCCCTCCGCACCCACTATCTTC
ATGTTGTTGCAGATGAAGCGCACCAAAACGTCTGACGAGAGCTTCAACCCCGTGTACCCCTATGACAC
```

-continued

| DESCRIPTION OF THE SEQUENCES |
| --- |

GGAAAGCGGCCCTCCCTCCGTCCCTTTCCTCACCCCTCCCTTCGTGTCTCCCGATGGATTCCAAGAAAG
TCCCCCCGGGGTCCTGTCTCTGAACCTGGCCGAGCCCCTGGTCACTTCCCACGGCATGCTCGCCCTGAA
AATGGGAAGTGGCCTCTCCCTGGACGACGCTGGCAACCTCACCTCTCAAGATATCACCACCGCTAGCC
CTCCCCTCAAAAAAACCAAGACCAACCTCAGCCTAGAAACCTCATCCCCCCTAACTGTGAGCACCTCA
GGCGCCCTCACCGTAGCAGCCGCCGCTCCCCTGGCGGTGGCCGGCACCTCCCTCACCATGCAATCAGA
GGCCCCCCTGACAGTACAGGATGCAAAACTCACCCTGGCCACCAAAGGCCCCCTGACCGTGTCTGAAG
GCAAACTGGCCTTGCAAACATCGGCCCCGCTGACGGCCGCTGACAGCAGCACCCTCACAGTCAGTGCC
ACACCACCCCTTAGCACAAGCAATGGCAGCTTGGGTATTGACATGCAAGCCCCCATTTACACCACCAA
TGGAAAACTAGGACTTAACTTTGGCGCTCCCCTGCATGTGGTAGACAGCCTAAATGCACTGACTGTAG
TTACTGGCCAAGGTCTTACGATAAACGGAACAGCCCTACAAACTAGAGTCTCAGGTGCCCTCAACTAT
GACACATCAGGAAACCTAGAATTGAGAGCTGCAGGGGGTATGCGAGTTGATGCAAATGGTCAACTTA
TCCTTGATGTAGCTTACCCATTTGATGCACAAAACAATCTCAGCCTTAGGCTTGGACAGGGACCCCTGT
TTGTTAACTCTGCCCACAACTTGGATGTTAACTACAACAGAGGCCTCTACCTGTTCACATCTGGAAATA
CCAAAAAGCTAGAAGTTAATATCAAAACAGCCAAGGGTCTCATTTATGATGACACTGCTATAGCAATC
AATGCGGGTGATGGGCTACAGTTTGACTCAGGCTCAGATACAAATCCATTAAAAACTAAACTTGGATT
AGGACTGGATTATGACTCCAGCAGAGCCATAATTGCTAAACTGGGAACTGGCCTAAGCTTTGACAACA
CAGGTGCCATCACAGTAGGCAACAAAAATGATGACAAGCTTACCTTGTGGACCACACCAGACCCATCC
CCTAACTGTAGAATCTATTCAGAGAAAGATGCTAAATTCACACTTGTTTTGACTAAATGCGGCAGTCA
GGTGTTGGCCAGCGTTTCTGTTTTATCTGTAAAAGGTAGCCTTGCGCCCATCAGTGGCACAGTAACTAG
TGCTCAGATTGTCCTCAGATTTGATGAAAATGGAGTTCTACTAAGCAATTCTTCCCTTGACCCTCAATA
CTGGAACTACAGAAAAGGTGACCTTACAGAGGGCACTGCATATACCAACGCAGTGGGATTTATGCCCA
ACCTCACAGCATACCCAAAAACACAGAGCCAAACTGCTAAAAGCAACATTGTAAGTCAGGTTTACTTG
AATGGGGACAAATCCAAACCCATGACCCTCACCATTACCCTCAATGGAACTAATGAAACAGGAGATG
CCACAGTAAGCACTTACTCCATGTCATTCTCATGGAACTGGAATGGAAGTAATTACATTAATGAAACG
TTCCAAACCAACTCCTTCACCTTCTCCTACATCGCCCAAGAATAAAAAGCATGACGCTGTTGATTTGAT
TCAATGTGTTTCTGTTTTATTTTCAAGCACAACAAAATCATTCAAGTCATTCTTCCATCTTAGCTTAATA
GACACAGTAGCTTAATAGACCCAGTAGTGCAAAGCCCCATTCTAGCTTATAACTAGTGGAGAAGTACT
CGCCTACATGGGGGTAGAGTCATAATCGTGCATCAGGATAGGGCGGTGGTGCTGCAGCAGCGCGCGA
ATAAACTGCTGCCGCCGCCGCTCCGTCCTGCAGGAATACAACATGGCAGTGGTCTCCTCAGCGATGAT
TCGCACCGCCCGCAGCATAAGGCGCCTTGTCCTCCGGGCACAGCAGCGCACCCTGATCTCACTTAAAT
CAGCACAGTAACTGCAGCACAGCACCACAATATTGTTCAAAATCCCACAGTGCAAGGCGCTGTATCCA
AAGCTCATGGCGGGGACCACAGAACCCACGTGGCCATCATACCACAAGCGCAGGTAGATTAAGTGGC
GACCCCTCATAAACACGCTGGACATAAACATTACCTCTTTTGGCATGTTGTAATTCACCACCTCCCGGT
ACCATATAAACCTCTGATTAAACATGGCGCCATCCACCACCATCCTAAACCAGCTGGCCAAAACCTGC
CCGCCGGCTATACACTGCAGGGAACCGGGACTGGAACAATGACAGTGGAGAGCCCAGGACTCGTAAC
CATGGATCATCATGCTCGTCATGATATCAATGTTGGCACAACACAGGCACACGTGCATACACTTCCTC
AGGATTACAAGCTCCTCCCGCGTTAGAACCATATCCCAGGGAACAACCCATTCCTGAATCAGCGTAAA
TCCCACACTGCAGGGAAGACCTCGCACGTAACTCACGTTGTGCATTGTCAAAGTGTTACATTCGGGCA
GCAGCGGATGATCCTCCAGTATGGTAGCGCGGGTTTCTGTCTCAAAAGGAGGTAGACGATCCCTACTG
TACGGAGTGCGCCGAGACAACCGAGATCGTGTTGGTCGTAGTGTCATGCCAAATGGAACGCCGGACGT
AGTCATATTTCCTGAAGTCTTAGATCTCTCAACGCAGCACCAGCACCAACACTTCGCAGTGTAAAAGG
CCAAGTGCCGAGAGAGTATATATAGGAATAAAAAGTGACGTAAACGGGCAAAGTCCAAAAAACGCCC
AGAAAAACCGCACGCGAACCTACGCCCCGAAACGAAAGCCAAAAAACACTAGACACTCCCTTCCGGC
GTCAACTTCCGCTTTCCCACGCTACGTCACTTGCCCCAGTCAAACAAACTACATATCCCGAACTTCCAA
GTCGCCACGCCCAAAACACCGCCTACACCTCCCCGCCCGCCGGCCCGCCCCCAAACCCGCCTCCCGCC
CCGCGCCCCGCCCCGCGCCGCCCATCTCATTATCATATTGGCTTCAATCCAAAATAAGGTATATTATTG
ATGATG

SEQ ID NO: 5 - RSV F0ΔTM-N-M2-1 amino acid sequence
MELLILKANAITTILTAVTFCFASGQNITELFYQSTCSAVSKGYLSALRTGWYTSVITIELSNIKENKCNGTDA
KVKLIKQELDKYKNAVTELQLLMQSTPATNNRARRELPRFMNYTLNNAKKTNVTLSKKRKRRFLGFLLGV
GSAIASGVAVSKVLHLEGEVNKIKSALLSTNKAVVSLSNGVSVLTSKVLDLKNYIDKQLLPIVNKQSCSISNI
ETVIEFQQKNNRLLEITREFSVNAGVTTPVSTYMLTNSELLSLNDMPITNDQKKLMSNNVQIVRQQSYSIMSI
IKEEVLAYVVQLPLYGVIDTPCWKLHTSPLCTTNTKEGSNICLTRTDRGWYCDNAGSVSFFPQAETCKVQS
NRVFCDTMNSLTLPSEVNLCNVDIFNPKYDCKIMTSKTDVSSSVITSLGAIVSCYGKTKCTASNKNRGIIKTF
SNGCDYVSNKGVDTVSVGNTLYYVNKQEGKSLYVKGEPIINFYDPLVFPSDEFDASISQVNEKINQSLAFIR
KSDELLHNVNAGKSTTNRKRRAPVKQTLNFDLLKLAGDVESNPGPMALSKVKLNDTLNKDQLLSSSKYTI
QRSTGDSIDTPNYDVQKHINKLCGMLLITEDANHKFTGLIGMLYAMSRLGREDTIKILRDAGYHVKANGVD
VTTHRQDINGKEMKFEVLTLASLTTEIQINIEIESRKSYKKMLKEMGEVAPLYRHDSPDCGMIILCIAALVIT
KLAAGDRSGLTAVIRRANNVLKNEMKRYKGLLPKDIANS
FYEVFEKYPHFIDVFVHFGIAQSSTRGGSRVEGIFAGLFMNAYGAGQVMLRWGVLAKSVKNIMLGHASVQ
AEMEQVVEVYLYAQKLGGEAGFYHILNNPKASLLSLTQFPHFSSVVLGNAAGLGIMGEYRGTPRNQDLYD
AAKAYAEQLKENGVINYSVLDLTAEELEAIKHQLNPKDNDVELGGGGSGGGGMSRRNPCKFEIRGHCLNG
KRCHFSHNYFEWPPHALLVRQNFMLNRILKSMDKSIDTLSEISGAAELDRTELYALGVVGVLESYIGSINNIT
KQSACVAMSKLLTELNSDDIKKLRDNEELNSPKIRVYNTVISYIESNRKNNKQTIHLLKRLPADVLKKTIKN
TLDIHKSITINNPKESTVSDTNDHAKNNDTT SEQ ID NO: 6 Polynucleotide sequence encoding the enhanced hCMV promoter
CCATTGCATACGTTGTATCCATATCATAATATGTACATTTATATTGGCTCATGTCCAACATTACCGCCATGTTG
ACATTGATTATTGACTAGTTATTAATAGTAATCAATTACGGGGTCATTAGTTCATAGCCCATATATGGAGTTCC
GCGTTACATAACTTACGGTAAATGGCCCGCCTGGCTGACCGCCCAACGACCCCCGCCCATTGACGTCAATAATG
ACGTATGTTCCCATAGTAACGCCAATAGGGACTTTCCATTGACGTCAATGGGTGGAGTATTTACGGTAAACTGC
CCACTTGGCAGTACATCAAGTGTATCATATGCCAAGTACGCCCCCTATTGACGTCAATGACGGTAAATGGCCCG
CCTGGCATTATGCCCAGTACATGACCTTATGGGACTTTCCTACTTGGCAGTACATCTACGTATTAGTCATCGCT
ATTACCATGGTGATGCGGTTTTGGCAGTACATCAATGGGCGTGGATAGCGGTTTGACTCACGGGGATTTCCAAG
TCTCCACCCCATTGACGTCAATGGGAGTTTGTTTTGGCACCAAAATCAACGGGACTTTCCAAAATGTCGTAACA
ACTCCGCCCCATTGACGCAAATGGGCGGTAGGCGTGTACGGTGGGAGGTCTATATAAGGCGAAGCGCTCCCTAT

| DESCRIPTION OF THE SEQUENCES |
|---|
| CAGTGATAGAGATCTCCCTATCAGTGATAGAGATCGTCGACGAGCTCGCGGCGGGCGGGAGTCGCTGCGCGCTG<br>CCTTCGCCCCGTGCCCCGCTCCGCCGCCGCCTCGCGCCGCCCGCCCCGGCTCTGACTGACCGCGTTACTAAAAC<br>AGGTAAGTCCGGCCTCCGCGCCGGGTTTTGGCGCCTCCCGCGGCGCCCCCCTCCTCACGGCGAGCGCTGCCAC<br>GTCAGACGAAGGGCGCAGCGAGCGTCCTGATCCTTCCGCCCGGACGCTCAGGACAGCGGCCCGCTGCTCATAAG<br>ACTCGGCCTTAGAACCCCAGTATCAGCAGAAGGACATTTTAGGACGGGACTTGGGTGACTCTAGGGCACTGGTT<br>TTCTTTCCAGAGAGCGGAACAGGCGAGGAAAAGTAGTCCCTTCTCGGCGATTCTGCGGAGGGATCTCCGTGGGG<br>CGGTGAACGCCGATGATGCCTCTACTAACCATGTTCATGTTTTCTTTTTTTTCTACAGGTCCTGGGTGACGAA<br>CAG<br><br>SEQ ID NO: 7 Polynucleotide sequence encoding the hCMV NM2 bghpolyA<br>cassette<br>CCATTGCATACGTTGTATCCATATCATAATATGTACATTTATATTGGCTCATGTCCAACATTACCGCCATGTTG<br>ACATTGATTATTGACTAGTTATTAATAGTAATCAATTACGGGGTCATTAGTTCATAGCCCATATATGGAGTTCC<br>GCGTTACATAACTTACGGTAAATGGCCCGCCTGGCTGACCGCCCAACGACCCCCGCCCATTGACGTCAATAATG<br>ACGTATGTTCCCATAGTAACGCCAATAGGGACTTTCCATTGACGTCAATGGGTGGAGTATTTACGGTAAACTGC<br>CCACTTGGCAGTACATCAAGTGTATCATATGCCAAGTACGCCCCCTATTGACGTCAATGACGGTAAATGGCCCG<br>CCTGGCATTATGCCCAGTACATGACCTTATGGGACTTTCCTACTTGGCAGTACATCTACGTATTAGTCATCGCT<br>ATTACCATGGTGATGCGGTTTTGGCAGTACATCAATGGGCGTGGATAGCGGTTTGACTCACGGGGATTTCCAAG<br>TCTCCACCCCATTGACGTCAATGGGAGTTTGTTTTGGCACCAAAATCAACGGGACTTTCCAAAATGTCGTAACA<br>ACTCCGCCCCATTGACGCAAATGGGCGGTAGGCGTGTACGGTGGGAGGTCTATATAAGCAGCTCTCCCTATC<br>AGTGATAGAGATCTCCCTATCAGTGATAGAGATCGTCGACGAGCTCGTTTAGTGAACCGTCAGATCGCCTGGAG<br>ACGCCATCCACGCTGTTTTGACCTCCATAGAAGACACCGGGACCGATCCAGCCTCCGCGGCCGGGAACGGTGCA<br>TTGGAACGCGGATTCCCCGTGCCAAGAGTGAGATCTTCCGTTTATCTAGGTACCAGATATCGCCACCATGGCCC<br>*TGAGCAAAGTGAAACTGAACGATACACTGAACAAGGACCAGCTGCTGTCCAGCAGCAAGTACACCATCCAGCGG<br>AGCACCGGCGACAGCATCGATACCCCCAACTACGACGTGCAGAAGCACATCAACAAGCTGTGCGGCATGCTGCT<br>GATCACAGAGGACGCCAACCACAAGTTCACCGGCCTGATCGGCATGCTGTACGCCATGAGCCGGCTGGGCCGGG<br>AGGACACCATCAAGATCCTGCGGGACGCCGGCTACCACGTGAAGGCCAATGGCGTGGACGTGACCACACACCGG<br>CAGGACATCAACGGCAAAGAAATGAAGTTCGAGGTGCTGACCCTGGCCAGCCTGACCACCGAGATCCAGATCAA<br>TATCGAGATCGAGAGCCGGAAGTCCTACAAGAAAATGCTGAAAGAAATGGGCGAGGTGGCCCCCGAGTACAGAC<br>ACGACAGCCCCGACTGCGGCATGATCATCCTGTGTATCGCCGCCCTGGTGATCACAAAGCTGGCCGCTGGCGAC<br>AGATCTGGCCTGACAGCCGTGATCAGACGGGCCAACAATGTGCTGAAGAACGAGATGAAGCGGTACAAGGGCCT<br>GCTGCCCAAGGACATTGCCAACAGCTTCTACGAGGTGTTCGAGAAGTACCCCCACTTCATCGACGTGTTCGTGC<br>ACTTCGGCATTGCCCAGAGCAGCACCAGAGGCGGCTCCAGAGTGGAGGGCATCTTCGCCGGCCTGTTCATGAAC<br>GCCTACGGCGCTGGCCAGGTGATGCTGAGATGGGGCGTGCTGGCCAAGAGCGTGAAGAACATCATGCTGGGCCA<br>CGCCAGCGTGCAGGCCGAGATGGAACAGGTGGTGGAGGTGTACGAGTACGCCCAGAAGCTGGGCGGAGAGGCCG<br>GCTTCTACCACATCCTGAACAACCCTAAGGCCTCCCTGCTGTCCCTGACCCAGTTCCCCCACTTCTCCAGCGTG<br>GTGCTGGGAAATGCCGCCGGACTGGGCATCATGGGCGAGTACCGGGGCACCCCCAGAAACCAGGACCTGTACGA<br>CGCCGCCAAGGCCTACGCCGAGCAGCTGAAAGAAAACGGCGTGATCAACTACAGCGTGCTGGACCTGACCGCTG<br>AGGAACTGGAAGCCATCAAGCACCAGCTGAACCCCAAGGACAACGACGTGGAGCTGGGGAGGCGGAGGATCTGGC<br>GGCGGAGGCATGAGCAGACGGAACCCCTGCAAGTTCGAGATCCGGGGCCACTGCCTGAACGGCAAGCGGTGCCA<br>CTTCAGCCACAACTACTTCGAGTGGCCCCCTCATGCTCTGCTGGTGCGGCAGAACTTCATGCTGAACCGGATCC<br>TGAAGTCCATGGACAAGAGCATCGACACCCTGAGCGAGATCAGCGGAGCCGCCGAGCTGGACAGAACCGAGGAA<br>TATGCCCTGGGCGTGGTGGGAGTGCTGGAAAGCTACATCGGCTCCATCAACAACATCACAAAGCAGAGCGCCTG<br>CGTGGCCATGAGCAAGCTGCTGACAGAGCTGAACAGCGACGACATCAAGAAGCTGAGGGACAACGAGGAACTGA<br>ACAGCCCCAAGATCCGGGTGTACAACACCGTGATCAGCTACATTGAGAGCAACCGCAAGAACAACAAGCAGACC<br>ATCCATCTGCTGAAGCGGCTGCCCGCCGACGTGCTGAAAAAGACCATCAAGAACACCCTGGACATCCACAAGTC<br>CATCACCATCAACAATCCCAAAGAAAGCACCGTGTCTGACACCAACGATCACGCCAAGAACAACGACACCACCT<br>GATGAGCGGCCGCGATCTGCTGTGCCTTCTAGTTGCCAGCCATCTGTTGTTTGCCCCTCCCCCGTGCCTTCCTT*<br>*GACCCTGGAAGGTGCCACTCCCACTGTCCTTTCCTAATAAAATGAGGAAATTGCATCGCATTGTCTGAGTAGGT*<br><u>*GTCATTCTATTCTGGGGGGTGGGGTGGGGCAGGACAGCAAGGGGGAGGATTGGGAAGACAATAGCAGGCATGCT*</u><br><u>*GGGGATGCGGTGGGCTCTATGG*</u><br>CMV Promoter sequence: bold<br>Transgene sequence NM2: Italic<br>bghpolyA PolyA signal: italic + underline<br><br>SEQ ID NO: 8 NM2 protein sequence<br>MALSKVKLNDTLNKDQLLSSSKYTIQRSTGDSIDTPNYDVQKHINKLCGMLLITEDANHKFTGLIGMLYAMSRL<br>GREDTIKILRDAGYHVKANGVDVTTHRQDINGKEMKFEVLTLASLTTEIQINIEIESRKSYKKMLKEMGEVAPE<br>YRHDSPDCGMIILCIAALVITKLAAGDRSGLTAVIRRANNVLKNEMKRYKGLLPKDIANSFYEVFEKYPHFIDV<br>FVHFGIAQSSTRGGSRVEGIFAGLFMNAYGAGQVMLRWGVLAKSVKNIMLGHASVQAEMEQVVEVYEYAQKLGG<br>EAGFYHILNNPKASLLSLTQFPHFSSVVLGNAAGLGIMGEYRGTPRNQDLYDAAKAYAEQLKENGVINYSVLDL<br>TAEELEAIKHQLNPKDNDVELGGGGSGGGGMSRRNPCKFEIRGHCLNGKRCHFSHNYFEWPPHALLVRQNFMLN<br>RILKSMDKSIDTLSEISGAAELDRTEEYALGVVGVLESYIGSINNITKQSACVAMSKLLTELNSDDIKKLRDNE<br>ELNSPKIRVYNTVISYIESNRKNNKQTIHLLKRLPADVLKKTIKNTLDIHKSITINNPKESTVSDTNDHAKNND<br>TT<br><br>SEQ ID NO: 9 Polynucleotide sequence encoding the hCMV F0 WPRE bghpolyA<br>cassette<br>CCATTGCATACGTTGTATCCATATCATAATATGTACATTTATATTGGCTCATGTCCAACATTACCGCCATGTTG<br>ACATTGATTATTGACTAGTTATTAATAGTAATCAATTACGGGGTCATTAGTTCATAGCCCATATATGGAGTTCC<br>GCGTTACATAACTTACGGTAAATGGCCCGCCTGGCTGACCGCCCAACGACCCCCGCCCATTGACGTCAATAATG<br>ACGTATGTTCCCATAGTAACGCCAATAGGGACTTTCCATTGACGTCAATGGGTGGAGTATTTACGGTAAACTGC<br>CCACTTGGCAGTACATCAAGTGTATCATATGCCAAGTACGCCCCCTATTGACGTCAATGACGGTAAATGGCCCG<br>CCTGGCATTATGCCCAGTACATGACCTTATGGGACTTTCCTACTTGGCAGTACATCTACGTATTAGTCATCGCT<br>ATTACCATGGTGATGCGGTTTTGGCAGTACATCAATGGGCGTGGATAGCGGTTTGACTCACGGGGATTTCCAAG |

DESCRIPTION OF THE SEQUENCES

TCTCCACCCCATTGACGTCAATGGGAGTTTGTTTTGGCACCAAAATCAACGGGACTTTCCAAAATGTCGTAACA
ACTCCGCCCCATTGACGCAAATGGGCGGTAGGCGTGTACGGTGGGAGGTCTATATAAGGCGAAGCGCTCCCTAT
CAGTGATAGAGATCTCCCTATCAGTGATAGAGATCGTCGAGTGAACCGTCGGGCGGGAGTGAGCAAGGGCTACC
CCTTCGCCCCGTGCCCCGCTCCGCCGCCGCCTCGCGCCGCCCGCCCCGGCTCTGACTGACCGCGTTACTAAAAC
AGGTAAGTCCGGCCTCCGCGCCGGGTTTTGGCGCCTCCCGCGGGCGCCCCCTCCTCACGGCGAGCGCTGCCAC
GTCAGACGAAGGGCGCAGCGAGCGTCCTGATCCTTCCGCCCGGACGCTCAGGACAGCGGCCCGCTGCTCATAAG
ACTCGGCCTTAGAACCCCAGTATCAGCAGAAGGACATTTTAGGACGGGACTTGGGTGACTCTAGGGCACTGGTT
TTCTTTCCAGAGAGCGGAACAGGCGAGGAAAAGTAGTCCCTTCTCGGCGATTCTGCGGAGGGATCTCCGTGGGG
CGGTGAACGCCGATGATGCCTACTAACCATGTTCATGTTTTCTTTTTTTTCTACAGGTCCTGGGTGACGAA
CAGGATATCGCCACCATGGAACTGCTGATCCTGAAGGCCAACGCCATCACCACCATCCTGACCGCCGTGACCTT
CTGCTTCGCCAGCGGCCAGAACATCACCGAGGAATTCTACCAGAGCACCTGTAGCGCCGTGAGCAAGGGCTACC
TGAGCGCCCTGAGAACCGGCTGGTACACCAGCGTGATCACCATCGAGCTGAGCAACATCAAAGAAAACAAGTGC
AACGGCACCGACGCCAAAGTGAAGCTGATCAAGCAGGAACTGGACAAGTACAAGAACGCCGTGACCGAGCTGCA
GCTGCTGATGCAGAGCACCCCCGCCACCAACAACCGGGCCAGACGGGAGCTGCCCCGGTTCATGAACTACACCC
TGAACAACGCCAAAAAGACCAACGTGACCCTGAGCAAGAAGCGGAAGCGGCGGTTCCTGGGCTTTCTGCTGGGC
GTGGGCAGCGCCATTGCCAGCGGCGTGGCCGTGTCTAAGGTGCTGCACCTGGAAGGCGAAGTGAACAAGATCAA
GAGCGCCCTGCTGAGCACCAACAAGGCCGTGGTGTCCCTGAGCAACGGCGTGAGCGTGCTGACCAGCAAGGTGC
TGGATCTGAAGAACTACATCGACAAGCAGCTGCTGCCCATCGTGAACAAGCAGAGCTGCAGCATCAGCAACATC
GAGACAGTGATCGAGTTCCAGCAGAAGAACAACCGGCTGCTGGAAATCACCCGGGAGTTCAGCGTGAACGCCGG
CGTGACCACCCCTGTGTCCACCTACATGCTGACCAACAGCGAGCTGTCTGAGCCTGATCAACGACATGCCCATCA
CCAACGACCAGAAAAAGCTGATGAGCAACAACGTGCAGATCGTGCGGCAGCAGAGCTACTCCATCATGTCCATC
ATCAAAGAAGAGGTGCTGGCCTACGTGGTGCAGCTGCCCCTGTACGGCGTGATCGACACCCCTGCTGGAAGCT
GCACACCAGCCCCCTGTGCACCACCAACACCAAAGAGGGCAGCAACATCTGCCTGACCCGGACCGACAGAGGCT
GGTACTGCGACAACGCCGGCAGCGTGTCATTCTTTCCACAGGCCGAGACATGCAAGGTGCAGAGCAACCGGGTG
TTCTGCGACACCATGAACAGCCTGACCCTGCCCTCCGAAGTGAACCTGTGCAACGTGGACATCTTCAACCCCAA
GTACGACTGCAAGATCATGACCTCCAAGACCGACGTGTCCAGCTCCGTGATCACCTCCCTGGGCGCCATCGTGT
CCTGCTACGGCAAGACCAAGTGCACCGCCAGCAACAAGAACCGGGGCATCATCAAGACCTTCAGCAACGGCTGC
GACTACGTGTCCAACAAGGGGGTGGACACCGTGTCCGTGGGCAACACCCTGTACTACGTGAACAAACAGGAAGG
CAAGAGCCTGTACGTGAAGGGCGAGCCCATCATCAACTTCTACGACCCCCTGGTGTTCCCCAGCGACGAGTTCG
ACGCCAGCATCAGCCAGGTGAACGAGAAGATCAACCAGAGCCTGGCCTTCATCCGGAAGTCCGACGAGCTGCTG
CACAATGTGAATGCCGGCAAGTCCACCACCAACTGATGAGCGGCCATCTAATCAACCTCTGGATTACAAAATTT
GTGAAAGATTGACTGGTATTCTTAACTATGTTGCTCCTTTTACGCTATGTGGATACGCTGCTTTAATGCCTTTG
TATCATGCTATTGCTTCCCGTATGGCTTTCATTTTCTCCTCCTTGTATAAATCCTGGTTGCTGTCTCTTTATGA
GGAGTTGTGGCCCGTTGTCAGGCAACGTGGCGTGGTGTGCACTGTGTTTGCTGACGCAACCCCCACTGGTTGGG
GCATTGCCACCACCTGTCAGCTCCTTTCCGGGACTTTCGCTTTCCCCCTCCCTATTGCCACGGCGGAACTCATC
GCCGCCTGCCTTGCCCGCTGCTGGACAGGGGCTCGGCTGTTGGGCACTGACAATTCCGTGGTGTTGTCGGGGAA
ATCATCGTCCTTTCCTTGGCTGCTCGCCTGTGTTGCCACCTGGATTCTGCGCGGGACGTCCTTCTGCTACGTCC
CTTCGGCCCTCAATCCAGCGGACCTTCCTTCCCGCGGCCTGCTGCCGGCTCTGCGGCCTCTTCCGCGTCTTCGC
CTTCGCCCTCAGACGAGTCGGATCTCCCTTTGGGCCGCCTCCCCGCCTGCGGCCGCGATCTG*CTGTGCCTTCTA*
*GTTGCCAGCCATCTGTTGTTTGCCCCTCCCCCGTGCCTTCCTTGACCCTGGAAGGTGCCACTCCCACTGTCCTT*
*TCCTAATAAAATGAGGAAATTGCATCGCATTGTCTGAGTAGGTGTCATTCTATTCTGGGGGGTGGGGTGGGGCA*
*GGACAGCAAGGGGGAGGATTGGGAAGACAATAGCAGGCATGCTGGGGATGCGGTGGGCTCTATGG*

Enhanced CMV Promoter sequence: bold
Transgene sequence F0: Italic
WPREsequence: underlined bold
bghpolyA PolyA signal: italic + underline SEQ ID NO: 10 F0 protein sequence
MELLILKANAITTILTAVTFCFASGQNITEEFYQSTCSAVSKGYLSALRTGWYTSVITIELSNIKENKCNGTDA
KVKLIKQELDKYKNAVTELQLLMQSTPATNNRARRELPRFMNYTLNNAKKTNVTLSKKRKRRFLGFLLGVGSAI
ASGVAVSKVLHLEGEVNKIKSALLSTNKAVVSLSNGVSVLTSKVLDLKNYIDKQLLPIVNKQSCSISNIETVIE
FQQKNNRLLEITREFSVNAGVTTPVSTYMLTNSELLSLINDMPITNDQKKLMSNNVQIVRQQSYSIMSIIKEEV
LAYVVQLPLYGVIDTPCWKLHTSPLCTTNTKEGSNICLTRTDRGWYCDNAGSVSFFPQAETCKVQSNRVFCDTM
NSLTLPSEVNLCNVDIFNPKYDCKIMTSKTDVSSSVITSLGAIVSCYGKTKCTASNKNRGIIKTFSNGCDYVSN
KGVDTVSVGNTLYYVNKQEGKSLYVKGEPIINFYDPLVFPSDEFDASISQVNEKINQSLAFIRKSDELLHNVNA
GKSTTN SEQ ID NO: 11 Amino acid sequence of a flexible linker
Gly-Gly-Gly-Ser-Gly-Gly-Gly SEQ ID NO: 12 Amino acid sequence of a flexible linker
Gly-Gly-Gly-Gly-Ser-Gly-Gly-Gly-Gly

The invention claimed is:

1. A simian adenoviral vector comprising two expression cassettes, wherein each expression cassette comprises a transgene and a promoter, wherein the first expression cassette is inserted in the E1 region of the simian adenoviral vector, and the second expression cassette is inserted in a region of the adenoviral vector that is compatible with vector replication; the transgene of the first and second expression cassettes comprise a respiratory syncytial virus antigen; and the first expression cassette and/or the second expression cassette comprises an enhanced human CMV promoter having a nucleic acid sequence having at least about 90% sequence identity to SEQ ID NO:6.

2. The simian adenoviral vector of claim 1, wherein the respiratory syncytial antigen is selected from one or more of the fusion (F) protein, the attachment (G) protein, the matrix (M2) protein and the nucleoprotein (N).

3. The simian adenoviral vector of claim 2, wherein at least one respiratory syncytial antigen is a fusion (F) protein.

4. The simian adenoviral vector of claim 1, wherein the second expression cassette is inserted in the E3 region, between the stop codons of L5 and E4 (the "HE1" region) or between the end of the ITR and the cap site of E4 mRNA (the "HE2" region) of the simian adenoviral vector.

5. The simian adenoviral vector of claim 4, wherein the second expression cassette is inserted in the E3 region of the simian adenoviral vector.

6. The simian adenoviral vector of claim 4, wherein the second expression cassette is inserted in the HE1 region of the simian adenoviral vector.

7. The simian adenoviral vector of claim 4, wherein the second expression cassette is inserted in the HE2 region of the simian adenoviral vector.

8. The simian adenoviral vector of claim 1, wherein the vector is a chimpanzee adenoviral vector.

9. The simian adenoviral vector of claim 1, wherein the vector is an adenovirus.

10. The simian adenoviral vector of claim 1, wherein the enhanced hCMV promoter has a nucleic acid sequence having at least about 96% sequence identity to SEQ ID NO: 6.

11. The simian adenoviral vector of claim 1, wherein the promoter comprises the nucleic acid sequence of SEQ ID NO: 6.

12. The simian adenoviral vector of claim 1, wherein the first and second expression cassettes comprise different promoters.

13. The simian adenoviral vector of claim 1, wherein the adenoviral vector is capable of infecting a mammalian cell.

14. The simian adenoviral vector of claim 1, wherein the first and/or the second expression cassette further comprises a posttranscriptional regulatory element.

15. The simian adenoviral vector of claim 14, wherein the posttranscriptional regulatory element is a Woodchuck Hepatitis Postranscriptional Regulatory Element.

16. A composition comprising the simian adenoviral vector of claim 1 and a pharmaceutically acceptable excipient.

17. A method of inducing an immune response against respiratory syncytial virus in a subject in need thereof comprising administering an immunologically effective amount of the simian adenoviral vector of claim 1 to the subject.

18. The method of claim 17, wherein the simian adenoviral vector is a vaccine component.

* * * * *